(12) United States Patent
Zhan et al.

(10) Patent No.: US 12,428,466 B2
(45) Date of Patent: Sep. 30, 2025

(54) IL4/IL13 RECEPTOR MOLECULE FOR VETERINARY USE

(71) Applicant: Elanco US Inc., Greenfield, IN (US)

(72) Inventors: Hangjun Zhan, Foster City, CA (US); Lam Nguyen, Union City, CA (US); Fawn Qian, Burlingame, CA (US); Shyr Jiann Li, Millbrae, CA (US)

(73) Assignee: Elanco US Inc., Greenfield, IN (US)

( * ) Notice: Subject to any disclaimer, the term of this patent is extended or adjusted under 35 U.S.C. 154(b) by 1103 days.

(21) Appl. No.: 17/287,756

(22) PCT Filed: Oct. 24, 2019

(86) PCT No.: PCT/US2019/057922
§ 371 (c)(1),
(2) Date: Apr. 22, 2021

(87) PCT Pub. No.: WO2020/086886
PCT Pub. Date: Apr. 30, 2020

(65) Prior Publication Data
US 2021/0395340 A1 Dec. 23, 2021

Related U.S. Application Data

(60) Provisional application No. 62/750,782, filed on Oct. 25, 2018.

(51) Int. Cl.
*C07K 14/715* (2006.01)
*A61K 38/17* (2006.01)
*A61K 45/06* (2006.01)
*G01N 33/68* (2006.01)

(52) U.S. Cl.
CPC ...... *C07K 14/7155* (2013.01); *A61K 38/1793* (2013.01); *A61K 45/06* (2013.01); *G01N 33/6869* (2013.01); *C07K 2319/30* (2013.01); *C07K 2319/32* (2013.01); *G01N 2333/5406* (2013.01); *G01N 2333/5437* (2013.01)

(58) Field of Classification Search
CPC ............ C07K 14/7155; C07K 2319/30; C07K 2317/526; C07K 16/00; C07K 2319/32; A61K 38/1793; A61K 45/06; A61K 38/00; G01N 33/6869; G01N 2333/5406; G01N 2333/5437; G01N 33/5041
See application file for complete search history.

(56) References Cited

U.S. PATENT DOCUMENTS

| | | | |
|---|---|---|---|
| 5,599,905 A | 2/1997 | Mosley et al. |
| 5,705,154 A | 1/1998 | Dalie et al. |
| 5,844,099 A | 12/1998 | Stahl et al. |
| 6,846,486 B1 | 1/2005 | Skurkovich et al. |
| 7,078,494 B1 | 7/2006 | Collins et al. |
| 7,186,809 B2 | 3/2007 | Pluenneke |
| 7,229,962 B2 | 6/2007 | Chung et al. |
| 7,253,264 B1 | 8/2007 | Lauffer et al. |
| 7,378,275 B2 | 5/2008 | Mccall et al. |
| 7,410,781 B2 | 8/2008 | Karow et al. |
| 8,216,805 B2 | 7/2012 | Carter et al. |
| 8,722,618 B2 | 5/2014 | Jacobs et al. |
| 2003/0104567 A1 | 6/2003 | Stahl et al. |
| 2005/0032164 A1 | 2/2005 | Watson et al. |
| 2005/0191730 A1* | 9/2005 | Karow .................... A61P 35/00 435/325 |
| 2008/0287665 A1 | 11/2008 | Mccall et al. |
| 2009/0156421 A1 | 6/2009 | Yang et al. |
| 2010/0278827 A1 | 11/2010 | Chung et al. |
| 2011/0151515 A1 | 6/2011 | Heifetz et al. |
| 2013/0089893 A1 | 4/2013 | Hogarth et al. |
| 2014/0056920 A1 | 2/2014 | Ardeleanu et al. |
| 2014/0255407 A1 | 9/2014 | Koenig |
| 2015/0056162 A1 | 2/2015 | Garcia et al. |
| 2018/0134766 A1* | 5/2018 | Larson .................. C07K 16/00 |
| 2020/0048325 A1 | 2/2020 | Zhan et al. |
| 2021/0395340 A1 | 12/2021 | Zhan et al. |

FOREIGN PATENT DOCUMENTS

| | | |
|---|---|---|
| EP | 1723173 B1 | 5/2008 |
| EP | 2674440 A2 | 12/2013 |
| JP | 2007161724 A | 6/2007 |
| WO | 1998023289 A1 | 6/1998 |
| WO | 2008073463 A2 | 6/2008 |
| WO | 2017019949 A1 | 2/2017 |

(Continued)

OTHER PUBLICATIONS

Arima K, Sato K, Tanaka G, Kanaji S, Terada T, Honjo E, Kuroki R, Matsuo Y, Izuhara K. Characterization of the interaction between interleukin-13 and interleukin-13 receptors. J Biol Chem. Jul. 1, 2005;280(26):24915-22. doi: 10.1074/jbc.M502571200. Epub May 3, 2005. PMID: 15870068. (Year: 2005).*
Kraich M, Klein M, Patiño E, Harrer H, Nickel J, Sebald W, Mueller TD. A modular interface of IL-4 allows for scalable affinity without affecting specificity for the IL-4 receptor. BMC Biol. Apr. 26, 2006;4:13. doi: 10.1186/1741-7007-4-13. PMID: 16640778; PMCID: PMC1479839. (Year: 2006).*
Janeway CA Jr, Travers P, Walport M, et al. Immunobiology: The Immune System in Health and Disease. 5thedition. New York: Garland Science; 2001. Section Structural variation in immunoglobulin constant regions. (Year: 2001).*

(Continued)

*Primary Examiner* — Hong Sang
*Assistant Examiner* — Carol Ann Chase
(74) *Attorney, Agent, or Firm* — McBee, Moore & Vanik IP, LLC

(57) ABSTRACT

Provided are various embodiments relating to IL13R/IL4R heterodimeric proteins derived from companion animal species and that bind to IL13 and/or IL4. Such heterodimeric proteins can be used in methods to treat IL13 and/or IL4-induced conditions in companion animals, such as canines, felines, and equines.

18 Claims, 3 Drawing Sheets
Specification includes a Sequence Listing.

(56) References Cited

FOREIGN PATENT DOCUMENTS

| WO | 2018064190 | A1 | 4/2018 |
|---|---|---|---|
| WO | 2018195388 | A1 | 10/2018 |
| WO | 2020086886 | A1 | 4/2020 |
| WO | 2021216899 | A1 | 10/2021 |

OTHER PUBLICATIONS

Vadnais, M.L., Criscitiello, M.F. and Smider, V.V. (2017). Antibodies from Other Species. In Protein Therapeutics (eds T. Vaughan, J. Osbourn and B. Jallal). https://doi.org/10.1002/9783527699124.ch4 (Year: 2017).*
Gonzales AJ, Humphrey WR, Messamore JE, Fleck TJ, Fici GJ, Shelly JA, Teel JF, Bammert GF, Dunham SA, Fuller TE, McCall RB. Interleukin-31: its role in canine pruritus and naturally occurring canine atopic dermatitis. Vet Dermatol. Feb. 2013;24(1):48-53. e11-2. doi: 10.1111/j. 1365-3164.2012.01098. (Year: 2013).*
Elliott et al., "Antiparallel Conformation of Knob and Hole Aglycosylated Half-Antibody Homodimers Is Mediated by a CH2—CH3 Hydrophobic Interaction," J. Mol. Biol., vol. 426, 2014, pp. 1947-1957.
International Search Report and Written Opinion in PCT/US2019/057922, dated Jan. 29, 2020, 12 pages.
Ridgway et al., "'Knobs-into-holes' engineering of antibody CH3 domains for heavy chain heterodimerization," Protein Engineering, vol. 9, No. 7, 1996, pp. 167-621.
Andrews et al., "IL-4 Receptor α Is an Important Modulator of IL-4 and IL-3 Receptor Binding: Implications for the Development of Therapeutic Targets," J Immunol, (2006), vol. 176(12): 7456-61, 6 pages.
Bork, Peer, "Powers and Pitfalls in Sequence Analysis: The 70% Hurdle," Genome Research, (2000), vol. 10: 398-400.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., (1990), vol. 111: 2129-2138.
Colman, P.M., "Effects of amino acid sequence changes on antibody-antigen interactions," Res Immunol., (1994), vol. 145(1): 33-6.
Database UniProt [Online] Nov. 30, 2010, Database accession No. E2QZ78, 3 pages.
Database UniProt [Online] Jul. 27, 2011, Database accession No. F6BUHR5, 2 pages.
Database UniProt [Online] May 1, 2013, Database accession No. M3XOTO, 2 pages.
Extended European Search Report for Application No. 18788175.0, dated Nov. 27, 2020, 9 pages.
Extended European Search Report for Application No. 19875949.0, dated Jun. 15, 2022, 15 pages.
Hoffman et al., "Efficacy and Safety of Rilonacept (Interleukin-1 Trap) in Patients with Cryopyrin-Associated Periodic Syndromes," Arthritis & Rheumatism, (2008), vol. 58, No. 8: 2443-2452.
International Search Report for PCT/US2018/028507, dated Jul. 17, 2018, 15 pages.
International Search Report for PCT/US2021/28679, dated Oct. 4, 2021, 14 pages.
Kasaian et al., "Therapeutic activity of an interleukin-4/interleukin-13 dual antagonist on oxazolone-induced colitis in mice," Immunology, (2014), vol. 143: 416-427.
Laporte et al., "Molecular and structural basis of cytokine receptor pleiotropy in the Interleukin-4/13 system," Cell, (2008), vol. 132(2): 259-272, 25 pages.
Lupardus et al., "Molecular basis for shared cytokine recognition revealed in the structure of an unusually high affinity complex between IL-13 and IL-13Rα2," Structure, (2010), vol. 18(3): 332-342, 22 pages.
Mckenzie et al., "Decoy Receptors in the Regulation of T Helper Cell Type 2 Responses," J. Exp. Med., (2003), vol. 197, No. 6: 675-679, 5 pages.
Miosge et al., "Comparison of predicted and actual consequences of missense mutations," Proc Natl Acad Sci USA, (2015), vol. 112, No. 37: E5189-98.
Oh et al., "Investigational therapeutics targeting the IL-4/IL-13/STAT-6 pathway for the treatment of asthma," Eur Respir Rev, (2010), vol. 19, No. 115: 46-54, 9 pages.
Press Release, Kindred Bio, "Kindred Biosciences Announces Positive Results from Pilot Field Efficacy Study of its IL-4/IL-13 Sink Molecule Being Developed for the Treatment of Atopic Dermatitis in Dogs," (2020), 4 pages.
Skolnick et al., "From genes to protein structure and function: novel applications of computational approaches in the genomic era," Trends Biotechnol., (2000), vol. 18, No. 1: 34-39.
Takizawa et al., "Constitutive high-expression of interleukin-4/13A and GATA-3 in gill and skin of salmonid fishes suggest that these tissues form Th2-skewed immune environments," Molecular Immunology, (2011), vol. 48: 1360-1368.
Tanaka et al., "Association analysis of non-synonymous polymorphisms of interleukin-4 receptor-α and Interleukin-13 genes in canine atopic dermatitis," J. Vet. Med. Sci., (2020), vol. 82(9): 1253-1259.
Tang et al., "Expression and Characterization of Recombinant Canine IL-13 Receptor α2 Protein and its Biological Activity In Vitro," Mol. Immun., (2003), vol. 39: 719-727.
Tang et al., "Recombinant canine IL-13 receptor α2-Fc fusion protein inhibits canine allergen-specific-IgE production in vitro by peripheral blood mononuclear cells from allergic dogs," Veterinary Immunology and Immunopathology, (2001), vol. 83: 115-122.
Tang, Liang, "Molecular cloning of canine IL-13 receptor α chain (α1 and α2) cDNAs and detection of corresponding mRNAs in canine tissues," Veterinary Immunology and Immunopathology, (2001), vol. 79: 181-195.

\* cited by examiner

IL4/IL13 RECEPTOR MOLECULE FOR VETERINARY USE

This application is a national phase entry of International Patent Application No. PCT/US2019/057922, filed Oct. 24, 2019, which claims the benefit of U.S. Provisional Application No. 62/750,782, filed Oct. 25, 2018, each of which is incorporated by reference herein in its entirety for any purpose.

FIELD

This present disclosure relates to heterodimeric proteins comprising interleukin 4 receptor and interleukin 13 receptor fragments derived from companion animal species that bind to IL4 and/or IL13 of a companion animal species, for example, canine IL4 and canine IL13. The present disclosure also relates to methods of using the heterodimeric proteins, for example, for treating IL4 and/or IL13-induced conditions or reducing IL4 and/or IL13 signaling activity in cells, for instance in companion animals, such as canines, felines, and equines.

SEQUENCE LISTING

The present application is filed with a Sequence Listing in electronic format. The Sequence Listing is provided as a file entitled "2019-10-24_01157-0027-00PCT_ST25.txt" created on Oct. 25, 2019, which is 334 kilobytes in size. The information in the electronic format of the sequence listing is incorporated herein by reference in its entirety.

BACKGROUND

Interleukin 4 (IL4) is a cytokine promoting differentiation of naïve helper T cells to Th2 cells. Interleukin 13 (IL13) has similar effects on immune cells. Both IL4 and IL13 play important roles in T cell-mediated immune responses that are directly associated with allergy, for example, atopic dermatitis and asthma. It is generally understood that IL4 can form a signaling complex either with heterodimeric receptors IL4 receptor subunit alpha (IL4R) and γc or IL4R and IL13 receptor subunit alpha-1 (IL13R). IL13 can form a signaling complex with heterodimeric receptors IL4Ra and IL13Ra1. Extracellular domains of IL4Ra or IL13Ra1 may bind to IL4 and/or IL13 and reduce the free concentrations of the cytokines, thus diminishing the clinical signs and symptoms associated with dermatitis, asthma and other disorders.

Companion species animals, such as cats, dogs, and horses, suffer from many allergic diseases similar to human allergic diseases, including atopic dermatitis and asthma. There remains a need, therefore, for methods and compounds that can be used specifically to bind companion animal IL4 and/or IL13 for treating IL4/IL13-induced conditions and for reducing IL4/IL13 signaling activity.

SUMMARY

Embodiment 1. A heterodimeric protein comprising:
a) a first contiguous polypeptide comprising at least one IL13R extracellular domain (ECD) and a first Fc polypeptide, and
b) a second contiguous polypeptide comprising at least one IL4R ECD and a second Fc polypeptide,
wherein the IL13R ECD and/or the IL4R ECD are derived from a companion animal species.

Embodiment 2. The heterodimeric protein of embodiment 1, wherein the first contiguous polypeptide and/or the second contiguous polypeptide comprises one, two, three, or four IL4R ECDs and/or one, two, three, or four IL13R ECDs.

Embodiment 3. The heterodimeric protein of any one of the preceding embodiments, wherein the first contiguous polypeptide and/or the second contiguous polypeptide further comprises at least one binding partner other than IL4R ECD or IL13R ECD.

Embodiment 4. The heterodimeric protein of embodiment 3, wherein the at least one binding partner comprises IL5, IL6, IL17, IL22, IL31, LFA-1, TNF-α, TSLP, and/or IgE.

Embodiment 5. The heterodimeric protein of any one of the preceding embodiments, wherein the heterodimeric protein binds to IL13 and/or IL4 with a dissociation constant (Kd) of less than $5\times10^{-6}$ M, less than $1\times10^{-6}$ M, less than $5\times10^{-7}$ M, less than $1\times10^{-7}$ M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, or less than $1\times10^{-12}$ M, as measured by biolayer interferometry.

Embodiment 6. The heterodimeric protein of any one of the preceding embodiments, wherein the heterodimeric protein reduces IL13 and/or IL4 signaling in a companion animal species.

Embodiment 7. The heterodimeric protein of any one of the preceding embodiments, wherein the companion animal species is canine, feline, or equine.

Embodiment 8. The heterodimeric protein of any one of the preceding embodiments, wherein the amino acid sequence of the at least one IL13R ECD is at least 85% identical, at least 90% identical, at least 95% identical, or at least 98% identical to the amino acid sequence of SEQ ID NO: 22, SEQ ID NO: 24, SEQ ID NO: 26, SEQ ID NO: 32, SEQ ID NO: 34, or SEQ ID NO: 36.

Embodiment 9. The heterodimeric protein of any one of the preceding embodiments, wherein the amino acid sequence of the at least one IL13R ECD comprises a cysteine at a position corresponding to position 18 of SEQ ID NO: 22, corresponding to position 18 of SEQ ID NO: 24, or corresponding to position 18 of SEQ ID NO: 26.

Embodiment 10. The heterodimeric protein of any one of the preceding embodiments, wherein the amino acid sequence of the at least one IL13R ECD comprises a cysteine at position 18 of SEQ ID NO: 22, at position 18 of SEQ ID NO: 24, at position 18 of SEQ ID NO: 26, at position 15 of SEQ ID NO: 32, at position 15 of SEQ ID NO: 34, or at position 15 of SEQ ID NO: 36.

Embodiment 11. The heterodimeric protein of any one of the preceding embodiments, wherein the at least one IL13R ECD comprises an amino acid sequence selected from SEQ ID NO: 22, SEQ ID NO: 24, SEQ ID NO: 26, SEQ ID NO: 32, SEQ ID NO: 34, and SEQ ID NO: 36.

Embodiment 12. The heterodimeric protein of any one of the preceding embodiments, wherein the amino acid sequence of the at least one IL4R ECD is at least 85% identical, at least 90% identical, at least 95% identical, or at least 98% identical to the amino acid sequence of SEQ ID NO: 23, SEQ ID NO: 25, SEQ ID NO: 27, SEQ ID NO: 33, SEQ ID NO: 35, or SEQ ID NO: 37.

Embodiment 13. The heterodimeric protein of any one of the preceding embodiments, wherein the at least one IL4R ECD comprises an amino acid sequence selected from SEQ ID NO: 23, SEQ ID NO: 25, SEQ ID NO: 27, SEQ ID NO: 33, SEQ ID NO: 35, and SEQ ID NO: 37.

Embodiment 14. The heterodimeric protein of any one of the preceding embodiments, wherein the first Fc polypeptide and/or the second Fc polypeptide is:
- a) a canine IgG-A, IgG-B, IgG-C, or IgG-D Fc polypeptide;
- b) a feline IgG1a, IgG1b, or IgG2 Fc polypeptide; and/or
- c) an equine IgG1, IgG2, IgG3, IgG4, IgG5, IgG6, or IgG7 Fc polypeptide.

Embodiment 15. The heterodimeric protein of any one of the preceding embodiments, wherein the first Fc polypeptide or the second Fc polypeptide comprises a knob mutation.

Embodiment 16. The heterodimeric protein of any one of the preceding embodiments, wherein the first Fc polypeptide or the second Fc polypeptide comprises a hole mutation.

Embodiment 17. The heterodimeric protein of any one of the preceding embodiments, wherein the first Fc polypeptide or the second Fc polypeptide comprises:
- a) an amino acid substitution at a position corresponding to position 138 of SEQ ID NO: 38, position 137 of SEQ ID NO: 39, position 137 of SEQ ID NO: 40, or position 138 of SEQ ID NO: 41; and/or
- b) an amino acid substitution at a position corresponding to position 154 of SEQ ID NO: 42, SEQ ID NO: 43, SEQ ID NO: 44, SEQ ID NO: 45, or SEQ ID NO: 46; and/or
- c) an amino acid substitution at a position corresponding to position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 18. The heterodimeric protein of any one of the preceding embodiments, wherein the first Fc polypeptide or the second Fc polypeptide comprises:
- a) a tryptophan at a position corresponding to position 138 of SEQ ID NO: 38, position 137 of SEQ ID NO: 39, position 137 of SEQ ID NO: 40, or position 138 of SEQ ID NO: 41; and/or
- b) a tryptophan at a position corresponding to position 154 of SEQ ID NO: 42, SEQ ID NO: 43, SEQ ID NO: 44, SEQ ID NO: 45, or SEQ ID NO: 46; and/or
- c) a tryptophan at a position corresponding to position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 19. The heterodimeric protein of any one of the preceding embodiments, wherein the first Fc polypeptide or the second Fc polypeptide comprises:
- a) an amino acid substitution at position 138 of SEQ ID NO: 38, position 137 of SEQ ID NO: 39, position 137 of SEQ ID NO: 40, or position 138 of SEQ ID NO: 41; and/or
- b) an amino acid substitution at position 154 of SEQ ID NO: 42, SEQ ID NO: 43, SEQ ID NO: 44, SEQ ID NO: 45, or SEQ ID NO: 46; and/or
- c) an amino acid substitution at position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 20. The heterodimeric protein of any one of the preceding embodiments, wherein the first Fc polypeptide or the second Fc polypeptide comprises:
- a) a tryptophan at position 138 of SEQ ID NO: 38, position 137 of SEQ ID NO: 39, position 137 of SEQ ID NO: 40, or position 138 of SEQ ID NO: 41; and/or
- b) a tryptophan at position 154 of SEQ ID NO: 42, SEQ ID NO: 43, SEQ ID NO: 44, SEQ ID NO: 45, or SEQ ID NO: 46; and/or
- c) a tryptophan at position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 21. The heterodimeric protein of any one of the preceding embodiments, wherein the first Fc polypeptide or the second Fc polypeptide comprises:
- a) an amino acid substitution at a position corresponding to position 138 and/or position 140 and/or position 181 of SEQ ID NO: 38, position 137 and/or position 139 and/or position 180 of SEQ ID NO: 39, position 137 and/or position 139 and/or position 180 of SEQ ID NO: 40, or position 138 and/or position 140 and/or position 181 of SEQ ID NO: 41; and/or
- b) an amino acid substitution at a position corresponding to position 154 and/or position 156 and/or position 197 of SEQ ID NO: 42, SEQ ID NO: 43, SEQ ID NO: 44, SEQ ID NO: 45, or SEQ ID NO: 46; and/or
- c) an amino acid substitution at a position corresponding to position 130 and/or position 132 and/or position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 22. The heterodimeric protein of any one of the preceding embodiments, wherein the first Fc polypeptide or the second Fc polypeptide comprises:
- a) a serine at a position corresponding to position 138 and/or an alanine at a position corresponding to position 140 and/or a threonine at a position corresponding to position 181 of SEQ ID NO: 38, a serine at a position corresponding to position 137 and/or an alanine at a position corresponding to position 139 and/or a threonine at a position corresponding to position 180 of SEQ ID NO: 39, a serine at a position corresponding to position 137 and/or an alanine at a position corresponding to position 139 and/or a threonine at a position corresponding to position 180 of SEQ ID NO: 40, or a serine at a position corresponding to position 138 and/or an alanine at a position corresponding to position 140 and/or a threonine at a position corresponding to position 181 of SEQ ID NO: 41; and/or
- b) a serine at a position corresponding to position 154 and/or an alanine at a position corresponding to position 156 and/or a threonine at a position corresponding to position 197 of SEQ ID NO: 42, SEQ ID NO: 43, SEQ ID NO: 44, SEQ ID NO: 45, or SEQ ID NO: 46; and/or
- c) a serine at a position corresponding to position 130 and/or an alanine at a position corresponding to position 132 and/or a threonine at a position corresponding to position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 23. The heterodimeric protein of any one of the preceding embodiments, wherein the first Fc polypeptide or the second Fc polypeptide comprises:
- a) an amino acid substitution at position 138 and/or position 140 and/or position 181 of SEQ ID NO: 38, position 137 and/or position 139 and/or position 180 of SEQ ID NO: 39, position 137 and/or position 139 and/or position 180 of SEQ ID NO: 40, or position 138 and/or position 140 and/or position 181 of SEQ ID NO: 41; and/or
- b) an amino acid substitution at position 154 and/or position 156 and/or position 197 of SEQ ID NO: 42, SEQ ID NO: 43, SEQ ID NO: 44, SEQ ID NO: 45, or SEQ ID NO: 46; and/or c) an amino acid substitution at position 130 and/or position 132 and/or position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 24. The heterodimeric protein of any one of the preceding embodiments, wherein the first Fc polypeptide or the second Fc polypeptide comprises:
  a) a serine at position 138 and/or an alanine at position 140 and/or a threonine at position 181 of SEQ ID NO: 38, a serine at position 137 and/or an alanine at position 139 and/or a threonine at position 180 of SEQ ID NO: 39, a serine at position 137 and/or an alanine at position 139 and/or a threonine at position 180 of SEQ ID NO: 40, or a serine at position 138 and/or an alanine at position 140 and/or a threonine at position 181 of SEQ ID NO: 41; and/or
  b) a serine at position 154 and/or an alanine at position 156 and/or a threonine at position 197 of SEQ ID NO: 42, SEQ ID NO: 43, SEQ ID NO: 44, SEQ ID NO: 45, or SEQ ID NO: 46; and/or
  c) a serine at position 130 and/or an alanine at position 132 and/or a threonine at position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment 25. The heterodimeric protein of any one of the preceding embodiments, wherein the first Fc polypeptide or the second Fc polypeptide comprises the amino acid sequence of SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, or SEQ ID NO: 101.

Embodiment 26. The heterodimeric protein of any one of the preceding embodiments, wherein the first contiguous polypeptide comprises the amino acid sequence of SEQ ID NO: 103, SEQ ID NO: 105, SEQ ID NO: 107, SEQ ID NO: 109, SEQ ID NO: 111, or SEQ ID NO: 113.

Embodiment 27. The heterodimeric protein of any one of the preceding embodiments, wherein the second contiguous polypeptide comprises the amino acid sequence of SEQ ID NO: 102, SEQ ID NO: 104, SEQ ID NO: 106, SEQ ID NO: 108, SEQ ID NO: 110, or SEQ ID NO: 112.

Embodiment 28. An isolated nucleic acid encoding: a) the first contiguous polypeptide of any one of embodiments 1 to 27; b) the second contiguous polypeptide of any one of embodiments 1 to 27; or c) the first contiguous polypeptide and the second contiguous polypeptide of any one of embodiments 1 to 27.

Embodiment 29. A host cell comprising the nucleic acid of embodiment 28.

Embodiment 30. A host cell expressing: a) the first contiguous polypeptide of any one of embodiments 1 to 27; b) the second contiguous polypeptide of any one of embodiments 1 to 27; or c) the first contiguous polypeptide and the second contiguous polypeptide of any one of embodiments 1 to 27.

Embodiment 31. A method comprising culturing the host cell of embodiment 29 or embodiment 30 and isolating the first contiguous polypeptide, or the second contiguous polypeptide, or the first contiguous polypeptide and the second contiguous polypeptide.

Embodiment 32. A pharmaceutical composition comprising the heterodimeric protein of any one of embodiments 1 to 27 and a pharmaceutically acceptable carrier.

Embodiment 33. A method of treating a companion animal species having an IL13 and/or IL4-induced condition, the method comprising administering to the companion animal species a therapeutically effective amount of the heterodimeric protein of any one of embodiments 1 to 27 or the pharmaceutical composition of embodiment 32.

Embodiment 34. The method of embodiment 33, wherein the companion animal species is canine, feline, or equine.

Embodiment 35. The method of embodiment 33 or embodiment 34, wherein the IL13 and/or IL4-induced condition is a pruritic or allergic condition, such as atopic dermatitis, pruritus, asthma, psoriasis, scleroderma, or eczema.

Embodiment 36. The method of any one of embodiments 33 to 35, wherein the heterodimeric protein or the pharmaceutical composition is administered parenterally.

Embodiment 37. The method of any one of embodiments 33 to 36, wherein the heterodimeric protein or the pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 38. The method of any one of embodiments 33 to 37, wherein the method further comprises administering a Jak inhibitor, a PI3K inhibitor, an AKT inhibitor, or a MAPK inhibitor.

Embodiment 39. The method of any one of embodiments 33 to 38, wherein the method further comprises administering one or more antibodies selected from an anti-IL17 antibody, an anti-IL31 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11α antibody, anti-IL6R antibody, anti-α4-Intergrin antibody, an anti-IL12 antibody, an anti-IL1β antibody, and an anti-BlyS antibody.

Embodiment 40. A method of reducing IL13 and/or IL4 signaling activity in a cell, the method comprising exposing the cell to the heterodimeric protein of any one of embodiments 1 to 27 or the pharmaceutical composition of embodiment 32 under conditions permissive for binding of the heterodimeric protein to IL13 and/or IL4, thereby (a) reducing binding of IL/4 and/or IL-13 to native IL13 receptor and/or native IL-4 receptor and reducing IL13- and/or IL-4-mediated signaling.

Embodiment 41. The method of embodiment 40, wherein the cell is exposed to the heterodimeric protein or the pharmaceutical composition ex vivo.

Embodiment 42. The method of embodiment 41, wherein the cell is exposed to the heterodimeric protein or the pharmaceutical composition in vivo.

Embodiment 43. The method of any one of embodiments 40 to 42, wherein the cell is a canine cell, a feline cell, or an equine cell.

Embodiment 44. A method for detecting IL13 or IL4 in a sample from a companion animal species comprising contacting the sample with the heterodimeric protein of any one of embodiments 1 to 27 or the pharmaceutical composition of embodiment 32 under conditions permissive for binding of the heterodimeric protein to IL13 and/or IL4, and detecting whether a complex is formed between the heterodimeric protein and IL13 and/or IL4 in the sample.

Embodiment 45. The method of embodiment 44, wherein the sample is a biological sample obtained from a canine, a feline, or an equine.

DESCRIPTION OF CERTAIN SEQUENCES

Figure 1:
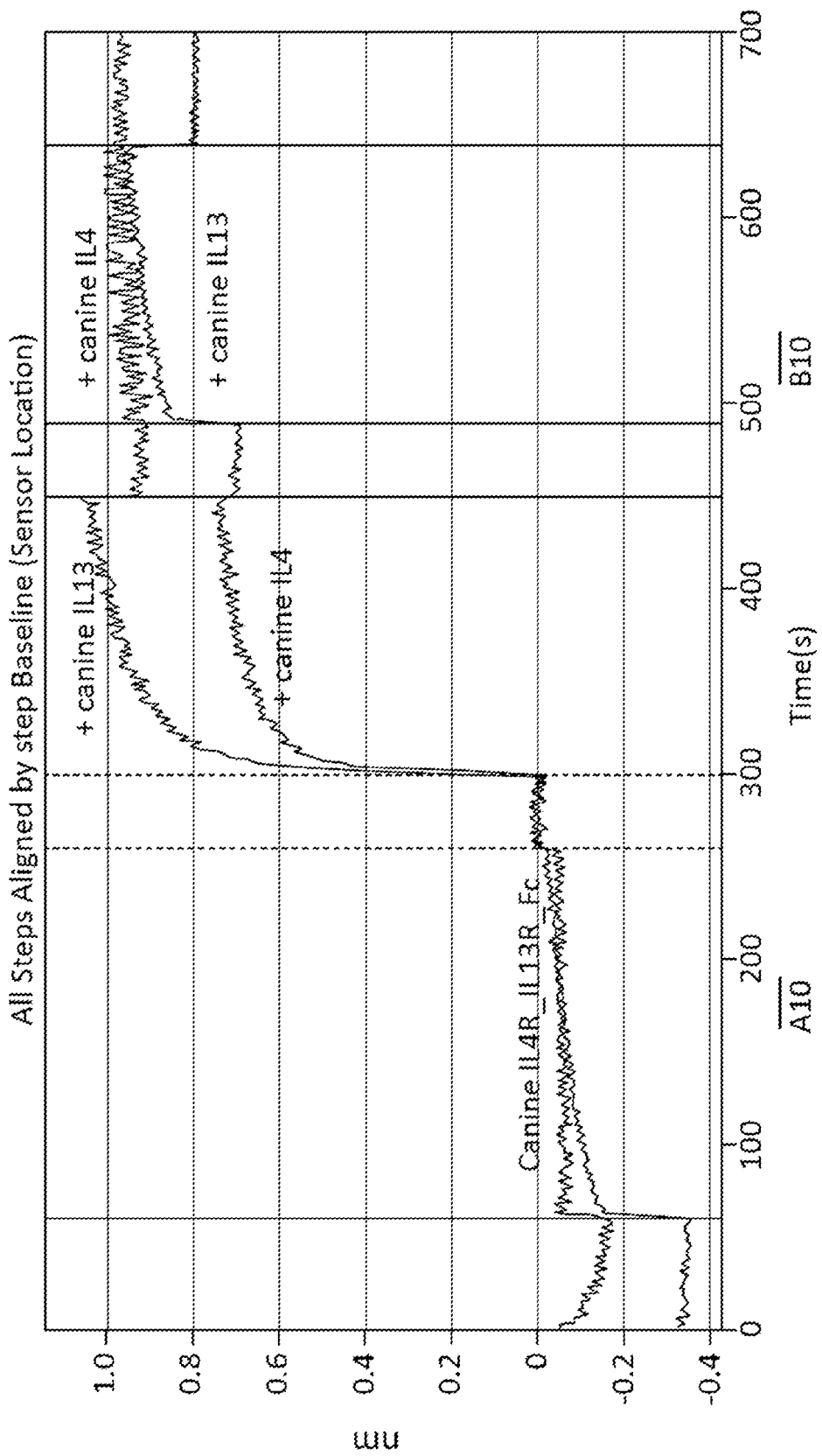
FIG. 1 is a graph of canine IL4RECD-IL13RECD-Fc sequential binding to canine IL4 and IL13 or canine IL13 and IL4 using concentrations of 30 μg/mL of IL4 and IL13 in PBS.

Table 1 provides a listing of certain sequences referenced herein.

TABLE 1

Description of Certain Sequences

| SEQ ID NO: | SEQUENCE | DESCRIPTION |
|---|---|---|
| 1 | MGLTSQLIPTLVCLLALTSTFVHGHNFNITIKEII KMLNILTARNDSCMELTVDVFTAPKNTSDKEIFCR AATVLRQIYTHNCSNRYLRGLYRNLSSMANKTCSM NEIKKSTLKDFLERLKVIMQKKYYRH | *Canis lupus* interleukin-4 precursor |
| 2 | MDLTSQLIPALVCLLAFTSTFVHGQNFNNTLKEII KILNILTARNDSCMELTMDVLAAPKNTSDKEIFCR ATTVLRQIYTHHNCSTKFLKGLDRNLSSMANRTCS VNEVKKCTLKDFLERLKAIMQKKYSKH | *Felis catus* interleukin-4 precursor |
| 3 | MGLTYQLIPALVCLLACTSNFIQGCKYDITLQEII KTLNNLTDGKGKNSCMELTVADAFAGPKNTDGKEI CRAAKVLQQLYKRHDRSLIKECLSGLDRNLKGMAN GTCCTVNEAKKSTLKDFLERLKTIMKEKYSKC | *Equus caballus* interleukin-4 precursor |
| 4 | MALWLTVVIALTCLGGLASPSPVTPSPTLKELIEE LVNITQNQASLCNGSMVWSVNLTAGMYCAALESLI NVSDCSAIQRTQRMLKALCSQKPAAGQISSERSRD TKIEVIQLVKNLLTYVRGVYRHGNFR | *Canis lupus* interleukin-13 precursor |
| 5 | MWFLDSTRQSGDQGGRRHTWPIKATARGQGHKPLS LGQPTCPLLAPPVLALGSMALWLTVVIALTCLGGL ASPGPHSRRELKELIEELVNITQNQVSLCNGSMVW SVNLTTGMYCAALESLINVSDCTAIQRTQRMLKAL CTQKPSAGQTASERSRDTKIEVIQLVKNLLNHLRR NFRHGNFK | *Felis catus* interleukin-13 precursor |
| 6 | MALWLTAVIALACLGGLASPAPLPSSMALKELIKE LVNITQNQAPLCNGSMVWSVNLTADTYCRALESLS NVSTCSAIQNTRKMLTKLCPHQLSAGQVSSERARD TKIEVIVLVKDLLKNLRKIFHGGKHVDA | *Equus caballus* interleukin-13 precursor |
| 7 | MGRLCSGLTFPVSCLVLVWVASSGSVKVLHEPSCF SDYISTSVCQWKMDHPTNCSAELRLSYQLDFMGSE NHTCVPENREDSVCVCSMPIDDAVEADVYQLDLWA GQQLLWSGSFQPSKHVKPRTPGNLTVHPNISHTWL LMWTNPYPTENHLHSELTYMVNVSNDNDPEDFKVY NVTYMGPTLRLAASTLKSGASYSARVRAWAQTYNS TWSDWSPSTTWLNYYEPWEQHLPLGVSISCLVILA ICLSCYFSIIKIKKGWWDQIPNPAHSPLVAIVIQD SQVSLWGKRSRGQEPAKCPHWKTCLTKLLPCLLEH GLGREEESPKTAKNGPLQGPGKPAWCPVEVSKTIL WPESISVVQCVELSEAPVDNEEEEEVEEDKRSLCP SLEGSGGSFQEGREGIVARLTESLFLDLLGGENGG FCPQGLEESCLPPPSGSVGAQMPWAQFPRAGPRAA PEGPEQPRRPESALQASPTQSAGSSAFPEPPPVVT DNPAYRSFGSFLGQSSDPGDGSDPELADRPGEAD PGIPSAPQPPEPPAALQPEPESWEQILRQSVLQHR AAPAPGPGPGSGYREFTCAVKQGSAPDAGGPGFGP SGEAGYKAFCSLLPGGATCPGTSGGEAGSGEGGYK PFQSLIPGCPGAPTPVPVPLFTFGLDTEPPGSPQD SLGAGSSPEHLGVEPAGKEEDSRKTLLAPEQATDP LRDDLASSIVYSALTCHLCGHLKQWHDQEERGKAH IVPSPCCGCCCGDRSSLLLSPLRAPNVLPGGVLLE ASLSPASLVPSGVSKEGKSSPFSQPASSSAQSSSQ TPKKLAVLSTEPTCMSAS | *Canis lupus* interleukin-4 receptor subunit alpha |

TABLE 1-continued

Description of Certain Sequences

| SEQ ID NO: | SEQUENCE | DESCRIPTION |
|---|---|---|
| 8 | MGRLCSGLTFPVSCLILMWAAGSGSVKVLRAPTCF SDYFSTSVCQWNMDAPTNCSAELRLSYQLNFMGSE NRTCVPENGEGAACACSMLMDDFVEADVYQLHLWA GTQLLWSGSFKPSSHVKPRAPGNLTVHPNVSHTWL LRWSNPYPPENHLHAELTYMVNISSEDDPTDVSVC ASGFLCHLLGLRRVETGAPGARLPPWLCAPRPRRV PGSQCAVISCCRWVLIALTSRGGRWRLTPGLRSQT RYVSVAEGLFGATPRVLCPGTQAGLASAAREQMSP DPSAFHSIDYEPWEQHLPLGVSISCLVILAVCLSC YLSVIKIKKEWWDQIPNPAHSHLVAIVIQDPQVSL WGKRSRGQEPAKCPHWKTCLRKLLPCLLEHGMERK EDPSKIARNGPSQCSGKSAWCPVEVSKTILWPESI SVVRCVELLEAPVESEEEEEEEDKGSFCPSPVNL EDSFQEGREGIAARLTESLFMDLLGVEKGGFGPQG SLESWFPPPSGSAGAQMPWAEFPGPGPQEASPQGK EQPFDPRSDPLATLPQSPASPTFPETPPVVTDNPA YRSFGTFQGRSSGPGECDSGPELAGRLGEADPGIP AAPQPSEPPSALQPEAETWEQILRQRVLQHRGAPA PAPGSGYREFVCAVRQGSTQDSGVGDFGPSEEAGY KAFSSLLTSGAVCPESGGEAGSGDGGYKPFQSLTP GCPGAPAPVPVPLFTFGLDAEPPHCPQDSPLPGSS PEPAGKAQDSHKTPPAPEQAADPLRDDLASGIVYS ALTCHLCGHLKQCHGQEEGGEAHPVASPCCGCCCG DRSSPLVSPLRAPDPLPGGVPLEASLSPASPAPLA VSEEGPPSLCFQPALSHAHSSSQTPKKVAMLSPEP TCTMAS | *Felis catus* interleukin-4 receptor subunit alpha |
| 9 | MGCLCPGLTLPVSCLILVWAAGSGSVKVLHLTACF SDYISASTCEWKMDRPTNCSAQLRLSYQLNDEFSD NLTCIPENREDEVCVCRMLMDNIVSEDVYELDLWA GNQLLWNSSFKPSRHVKPRAPQNLTVHAISHTWLL TWSNPYPLKNHLWSELTYLVNISKEDDPTDFKIYN VTYMDPTLRVTASTLKSRATYSARVKARAQNYNST WSEWSPSTTWHNYYEQPLEQRLPLGVSISCVVILA ICLSCYFSIIKIKKEWWDQIPNPAHSPLVAIVLQD SQVSLWGKQSRGQEPAKCPRWKTCLTKLLPCLLEH GLQKEEDSSKTVRNGPFQSPGKSAWHTVEVNHTIL RPEIISVVPCVELCEAQVESEEEEVEEDRGSFCPS PESSGSGFQEGREGVAARLTESLFLGLLGAENGAL GESCLLPPLGSAHMPWARISSAGPQEAASQGEEQP LNPESNPLATLTQSPGSLAFTEAPAVVADNPAYRS FSNSLSQPRGPGELDSDPQLAEHLGQVDPSIPSAP QPSEPPTALQPEPETWEQMLRQSVLQQGAAPAPAS APTGGYREFAQAVKQGGGAAGSGPSGEAGYKAFSS LLAGSAVCPGQSGVEASSGEGGYRPYESPDPGAPA PVPVPLFTFGLDVEPPHSPQNSLLPGGSPELPGPE PTVKGEDPRKPLLSAQQATDSLRDDLGSGIVYSAL TCHLCGHLKQCHGQEEHGEAHTVASPCCGCCCGDR SSPPVSPVRALDPPPGGVPLEAGLSLASLGSLGLS EERKPSLFFQPAPGNAQSSSQTPLTVAMLSTGPTC TSAS | *Equus caballus* interleukin-4 receptor subunit alpha |
| 10 | MERPARLCGLWALLLCAAGGRGGGVAAPTETQPPV TNLSVSVENLCTVIWTWDPPEGASPNCTLRYFSHF DNKQDKKIAPETHRSKEVPLNERICLQVGSQCSTN ESDNPSILVEKCTPPPEGDPESAVTELQCVWHNLS YMKCTWLPGRNTSPDTNYTLYYWHSSLGKILQCED IYREGQHIGCSFALTNLKDSSFEQHSVQIVVKDNA GKIRPSFNIVPLTSHVKPDPPHIKRLFFQNGNLYV QWKNPQNFYSRCLSYQVEVNNSQTETNDIFYVEEA KCQNSEFEGNLEGTICFMVPGVLPDTLNTVRIRVR TNKLCYEDDKLWSNWSQAMSIGENTDPTFYITMLL ATPVIVAGAIIVLLLYLKRLKIIIFPPIPDPGKIF KEMFGDQNDDTLHWRKYDIYEKQTKEETDSVVLIE NLKKASQ | *Canis lupus* interleukin-13 receptor subunit alpha-1 |
| 11 | MMTKCSSDRNVFKRKWFLFPASQYTFRPIHQARPC EVPAVHLEPSPPWEVGLGLLNLESEFRKLGLRGRR LAAAPPDSRAEAASQTQPPVTNLSVSVENLCTVIW TWDPPEGASPNCTLRYFSHFDNKQDKKIAPETHRS KEVPLNERICLQVGSQCSTNESDNPSILVEKCTPP PEGDPESAVTELQCVWHNLSYMKCTWLPGRNTSPD TNYTLYYWHSSLGKILQCENIYREGQHIGCSFALT NLKDSSFEQHSVQIVVKDNAGKIRPSFNIVPLTSH | *Felis catus* interleukin-13 receptor subunit alpha-1 |

TABLE 1-continued

Description of Certain Sequences

| SEQ ID NO: | SEQUENCE | DESCRIPTION |
|---|---|---|
| | VKPDPPHIKRLFFQNGNLYVQWKNPQNFYSRCLSY QVEVNNSQTETHDIFYVEEAKCQNSEFEGNLEGTI CFMVPGILPDTLNTVRIRVRTNKLCYEDDRLWSNW SQAMSIGENTDPTFYITMLLATPVIVAGAIIVLLL YLKRLKIIIFPPIPDPGKIFKEMFGDQNDDSLHWK KYDIYEKQTKEETDSVVLIENASQ | |
| 12 | MYFLCLIWTESQPPVTNLSVSVENLCTVIWTWNPP EGVSPNCSLWYFSHFGNKQDKKIAPETHRSKEVPL NERICLQVGSQCSTNESDNPSILVEKCISPPEGDP ESAVTELQCVWHNLSYMKCTWLPGKNASPDTNYTL YYWHSSLGKILQCEDIYREGQHIGCSFALTEVKDS IFEQHSVQIMVKDNAGKIRPFFNIVPLTSHVKPDP PHIKKLFFQNGDLYVQWKNPQNFYSRCLSYQVEVN NSQTETRDIFSVEEAKCQNPEFEGDLEGTICFMVP GVLPDTVNTVRIRVKTNKLCYEDDKLWSNWSQAMS IGKKADPTFYIAMLLIIPVIVAGAIIVLLLYLKRL KIIMFPPIPDPGKIFKEMFGDQNDDTLHWKKYDIY EKQTKEETDSVVLIENLKRASQ | Equus caballus interleukin-13 receptor subunit alpha-1 |
| 13 | TETQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ CVWHNLSYMKCTWLPGRNTSPDTNYTLYYWHSSLG KILQCEDIYREGQHIGCSFALTNLKDSSFEQHSVQ IVVKDNAGKIRPSFNIVPLTSHVKPDPPHIKRLFF QNGNLYVQWKNPQNFYSRCLSYQVEVNNSQTETND IFYVEEAKCQNSEFEGNLEGTICFMVPGVLPDTLN TVRIRVRTNKLCYEDDKLWSNWSQAMSIGENTDPT GGGGSGSGSVKVLHEPSCFSDYISTSVCQWKMDHPT NCSAELRLSYQLDFMGSENHTCVPENREDSVCVCS MPIDDAVEADVYQLDLWAGQQLLWSGSFQPSKHVK PRTPGNLTVHPNISHTWLLMWTNPYPTENHLHSEL TYMVNVSNDNDPEDFKVYNVTYMGPTLRLAASILK SGASYSARVRAWAQTYNSTWSDWSPSTTWLNYYEP KRENGRVPRPPDCPKCPAPEMLGGPSVFIFPPKPK DILLIARTPEVTCVVVDLDPEDPEVQISWFVDGKQ MQTAKTQPREEQFNGTYRVVSVLPIGHQDWLKGKQ FTCKVNNKALPSPIERTISKARGQAHQPSVYVLPP SREELSKNTVSLTCLIKDFFPPDIDVEWQSNGQQE PESKYRTTPPQLDEDGSYFLYSKLSVDKSRWQRGD TFICAVMHEALHNHYTQESLSHSPGK | Exemplary Canis lupus IL13RECD-IL4RECD-IgGA Fc (without signal sequence) |
| 14 | SGSVKVLHEPSCFSDYISTSVCQWKMDHPTNCSAE LRLSYQLDFMGSENHTCVPENREDSVCVCSMPIDD AVEADVYQLDLWAGQQLLWSGSFQPSKHVKPRTPG NLTVHPNISHTWLLMWTNPYPTENHLHSELTYMVN VSNDNDPEDFKVYNVTYMGPTLRLAASTLKSGASY SARVRAWAQTYNSTWSDWSPSTTWLNYYEPGGGSG TETQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ CVWHNLSYMKCTWLPGRNTSPDTNYTLYYWHSSLG KILQCEDIYREGQHIGCSFALTNLKDSSFEQHSVQ IVVKDNAGKIRPSFNIVPLTSHVKPDPPHIKRLFF QNGNLYVQWKNPQNFYSRCLSYQVEVNNSQTETND IFYVEEAKCQNSEFEGNLEGTICFMVPGVLPDTLN TVRIRVRTNKLCYEDDKLWSNWSQAMSIGENTDPT FNECRCTDTPPCPVPEPLGGPSVLIFPPKPKDILR ITRTPEVTCVVLDLGREDPEVQISWFVDGKEVHTA KTQSREQQFNGTYRVVSVLPIEHQDWLTGKEFKCR VNHIDLPSPIERTISKARGRAHKPSVYVLPPSPKE LSSSDTVSITCLIKDFYPPDIDVEWQSNGQQEPER KHRMTPPQLDEDGSYFLYSKLSVDKSRWQQGDPFT CAVMHETLQNHYTDLSLSHSPGK | Exemplary canine IL4RECD-IL13RECD-IgGA Fc (without signal sequence) |
| 15 | SGSVKVLHEPSCFSDYISTSVCQWKMDHPTNCSAE LRLSYQLDFMGSENHTCVPENREDSVCVCSMPIDD AVEADVYQLDLWAGQQLLWSGSFQPSKHVKPRITG NLTVHPNISHTWLLMWTNPYPTENHLHSELTYMVN VSNDNDPEDFKVYNVTYMGPTLRLAASTLKSGASY SARVRAWAQTYNSTWSDWSPSTTWLNYYEPGGGSG TETQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ | Exemplary canine IL4RECD-IL13RECD-IgGB Fc (without signal sequence) |

TABLE 1-continued

Description of Certain Sequences

| SEQ ID NO: | SEQUENCE | DESCRIPTION |
|---|---|---|
| | CVWHNLSYMKCTWLPGRNTSPDTNYTLYYWHSSLG<br>KILQCEDIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETND<br>IFYVEEAKCQNSEFEGNLEGTICFMVPGVLPDTLN<br>TVRIRVRTNKLCYEDDKLWSNWSQAMSIGENTDPT<br>PKRENGRVPRPPDCPKCPAPEMLGGPSVFIFPPKP<br>KDTLLIARTPEVTCVVVDLDPEDPEVQISWFVDGK<br>QMQTAKTQPREEQFNGTYRVVSVLPIGHQDWLKGK<br>QFTCKVNNKALPSPIERTISKARGQAHQPSVYVLP<br>PSREELSKNTVSLTCLIKDFFPPDIDVEWQSNGQQ<br>EPESKYRTTPPQLDEDGSYFLYSKLSVDKSRWQRG<br>DTFICAVMHEALHNHYTQESLSHSPGK | |
| 16 | SGSVKVLHEPSCFSDYISTSVCQWKMDHPTNCSAE<br>LRLSYQLDFMGSENHTCVPENREDSVCVCSMPIDD<br>AVEADVYQLDLWAGQQLLWSGSFQPSKHVKPRTPG<br>NLTVHPNISHTWLLMWTNPYPTENHLHSELTYMVN<br>VSNDNDPEDFKVYNVTYMGPTLRLAASTLKSGASY<br>SARVRAWAQTYNSTWSDWSPSTTWLNYYEPGGGSG<br>TETQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCEDIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETND<br>IFYVEEAKCQNSEFEGNLEGTICFMVPGVLPDTLN<br>TVRIRVRTNKLCYEDDKLWSNWSQAMSIGENTDPT<br>AKECECKCNCNNCPCPGCGLLGGPSVFIFPPKPKD<br>ILVTARTPTVTCVVVDLDPENPEVQISWFVDSKQV<br>QTANTQPREEQSNGTYRVVSVLPIGHQDWLSGKQF<br>KCKVNNKALPSPIEEIISKTPGQAHQPNVYVLPPS<br>RDEMSKNTVTLTCLVKDFFPPEIDVEWQSNGQQEP<br>ESKYRMTPPQLDEDGSYFLYSKLSVDKSRWQRGDT<br>FICAVMHEALHNHYTQISLSHSPGK | Exemplary canine<br>IL4RECD-IL13RECD-<br>IgGC (without signal<br>sequence) |
| 17 | SGSVKVLHEPSCFSDYISTSVCQWKMDHPTNCSAE<br>LRLSYQLDFMGSENHTCVPENREDSVCVCSMPIDD<br>AVEADVYQLDLWAGQQLLWSGSFQPSKHVKPRTPG<br>NLTVHPNISHTWLLMWTNPYPTENHLHSELTYMVN<br>VSNDNDPEDFKVYNVTYMGPTLRLAASTLKSGASY<br>SARVRAWAQTYNSTWSDWSPSTTWLNYYEPGGGSG<br>TETQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCEDIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETND<br>IFYVEEAKCQNSEFEGNLEGTICFMVPGVLPDTLN<br>TVRIRVRTNKLCYEDDKLWSNWSQAMSIGENTDPT<br>PKESTCKCISPCPVPESLGGPSVFIFPPKPKDILR<br>ITRTPEITCVVLDLGREDPEVQISWFVDGKEVHTA<br>KTQPREQQFNSTYRVVSVLPIEHQDWLTGKEFKCR<br>VNHIGLPSPIERTISKARGQAHQPSVYVLPPSPKE<br>LSSSDTVTLTCLIKDFFPPEIDVEWQSNGQPEPES<br>KYHTTAPQLDEDGSYFLYSKLSVDKSRWQQGDTFT<br>CAVMHEALQNHYTDLSLSHSPGK | Exemplary canine<br>IL4RECD-IL13RECD-<br>IgGD Fc (without signal<br>sequence) |
| 18 | SGSVKVLRAPTCFSDYFSTSVCQWNMDAPTNCSAE<br>LRLSYQLNFMGSENRTCVPENGEGAACACSMLMDD<br>FVEADVYQLHLWAGTQLLWSGSFKPSSHVKPRAPG<br>NLTVHPNVSHTWLLRWSNPYPPENHLHAELTYMVN<br>ISSEDDPTDVSVCASGFLCHLLGLRRVETGAPGAR<br>LPPWLCAPRPRRVPGSQCAVISCCRWVLIALTSRG<br>GRWRLTPGLRSQTRYVSVAEGLFGATPRVLCPGTQ<br>AGLASAAREQMSPDPSAFHSIDYEPGGGSGSQTQP<br>PVTNLSVSVENLCTVIWTWDPPEGASPNCTLRYFS<br>HFDNKQDKKIAPETHRSKEVPLNERICLQVGSQCS<br>TNESDNPSILVEKCTPPPEGDPESAVTELQCVWHN<br>LSYMKCTWLPGRNTSPDTNYTLYYWHSSLGKILQC<br>ENIYREGQHIGCSFALTNLKDSSFEQHSVQIVVKD | Exemplary Feline<br>IL4RECD-IL13RECD<br>(without signal sequence) |

TABLE 1-continued

Description of Certain Sequences

| SEQ ID NO: | SEQUENCE | DESCRIPTION |
|---|---|---|
| | NAGKIRPSFNIVPLTSHVKPDPPHIKRLFFQNGNL YVQWKNPQNFYSRCLSYQVEVNNSQTETHDIFYVE EAKCQNSEFEGNLEGTICFMVPGILPDTLNTVRIR VRTNKLCYEDDRLWSNWSQAMSIGENTDPT | |
| 19 | SGSVKVLHLTACFSDYISASTCEWKMDRPINCSAQ LRLSYQLNDEFSDNLTCIPENREDEVCVCRMLMDN IVSEDVYELDLWAGNQLLWNSSFKPSRHVKPRAPQ NLTVHAISHTWLLTWSNPYPLKNHLWSELTYLVNI SKEDDPTDFKIYNVTYMDPTLRVTASTLKSRATYS ARVKARAQNYNSTWSEWSPSTTWHNYYEQPGGGSG TESQPPVTNLSVSVENLCTVIWTWNPPEGVSPNCS LWYFSHFGNKQDKKIAPETHRSKEVPLNERICLQV GSQCSTNESDNPSILVEKCISPPEGDPESAVTELQ CVWHNLSYMKCTWLPGKNASPDTNYTLYYWHSSLG KILQCEDIYREGQHIGCSFALTEVKDSIFEQHSVQ IMVKDNAGKIRPFFNIVPLTSHVKPDPPHIKKLFF QNGDLYVQWKNPQNFYSRCLSYQVEVNNSQTETRD IFSVEEAKCQNPEFEGDLEGTICFMVPGVLPDTVN TVRIRVKTNKLCYEDDKLWSNWSQAMSIGKKADPT | Exemplary equine IL4RECD-IL13RECD (without signal sequence) |
| 20 | MAVLGLLFCLVTFPSCVLSTETQPPVTNLSVSVEN LCTVIWTWDPPEGASPNCTLRYFSHFDNKQDKKIA PETHRSKEVPLNERICLQVGSQCSTNESDNPSILV EKCTPPPEGDPESAVTELQCVWHNLSYMKCTWLPG RNTSPDTNYTLYYWHSSLGKILQCEDIYREGQHIG CSFALTNLKDSSFEQHSVQIVVKDNAGKIRPSFNI VPLTSHVKPDPPHIKRLFFQNGNLYVQWKNPQNFY SRCLSYQVEVNNSQTETNDIFYVEEAKCQNSEFEG NLEGTICFMVPGVLPDTLNTVRIRVRTNKLCYEDD KLWSNWSQAMSIGENTDPTGGGSGSGSVKVLHEPS CFSDYISTSVCQWKMDHPTNCSAELRLSYQLDFMG SENHTCVPENREDSVCVCSMPIDDAVEADVYQLDL WAGQQLLWSGSFQPSKHVKPRTPGNLTVHPNISHT WLLMWTNPYPTENHLHSELTYMVNVSNDNDPEDFK VYNVTYMGPTLRLAASTLKSGASYSARVRAWAQTY NSTWSDWSPSTTWLNYYEPKRENGRVPRPPDCPKC PAPEMLGGPSVFIFPPKPKDTLLIARTPEVTCVVV DLDPEDPEVQISWFVDGKQMQTAKTQPREEQFNGT YRVVSVLPIGHQDWLKGKQFTCKVNNKALPSPIER TISKARGQAHQPSVYVLPPSREELSKNTVSLTCLI KDFFPPDIDVEWQSNGQQEPESKYRTTPPQLDEDG SYFLYSKLSVDKSRWQRGDTFICAVMHEALHNHYT QESLSHSPGK | Exemplary canine IL13RECD-IL4RECD-IgGB Fc (with signal sequence) |
| 21 | MAVLGLLFCLVTFPSCVLSSGSVKVLHEPSCFSDY ISTSVCQWKMDHPTNCSAELRLSYQLDFMGSENHT CVPENREDSVCVCSMPIDDAVEADVYQLDLWAGQQ LLWSGSFQPSKHVKPRTPGNLTVHPNISHTWLLMW TNPYPTENHLHSELTYMVNVSNDNDPEDFKVYNVT YMGPTLRLAASTLKSGASYSARVRAWAQTYNSTWS DWSPSTTWLNYYEPGGGSGTETQPPVTNLSVSVEN LCTVIWTWDPPEGASPNCTLRYFSHFDNKQDKKIA PETHRSKEVPLNERICLQVGSQCSTNESDNPSILV EKCTPPPEGDPESAVTELQCVWHNLSYMKCTWLPG RNTSPDTNYTLYYWHSSLGKILQCEDIYREGQHIG CSFALTNLKDSSFEQHSVQIVVKDNAGKIRPSFNI VPLTSHVKPDPPHIKRLFFQNGNLYVQWKNPQNFY SRCLSYQVEVNNSQTETNDIFYVEEAKCQNSEFEG NLEGTICFMVPGVLPDTLNTVRIRVRTNKLCYEDD KLWSNWSQAMSIGENTDPTPKRENGRVPRPPDCPK CPAPEMLGGPSVFIFPPKPKDTLLIARTPEVTCVV VDLDPEDPEVQISWFVDGKQMQTAKTQPREEQFNG TYRVVSVLPIGHQDWLKGKQFTCKVNNKALPSPIE RTISKARGQAHQPSVYVLPPSREELSKNTVSLTCL IKDFFPPDIDVEWQSNGQQEPESKYRTTPPQLDED GSYFLYSKLSVDKSRWQRGDTFICAVMHEALHNHY TQESLSHSPGK | Exemplary canine IL4RECD-IL13RECD-IgGB Fc (with signal sequence) |
| 22 | TETQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ CVWHNLSYMKCTWLPGRNTSPDTNYTLYYWHSSLG KILQCEDIYREGQHIGCSFALTNLKDSSFEQHSVQ IVVKDNAGKIRPSFNIVPLTSHVKPDPPHIKRLFF | Exemplary canine IL13R extracellular domain (without signal sequence) |

TABLE 1-continued

Description of Certain Sequences

| SEQ ID NO: | SEQUENCE | DESCRIPTION |
|---|---|---|
|  | QNGNLYVQWKNPQNFYSRCLSYQVEVNNSQTETND<br>IFYVEEAKCQNSEFEGNLEGTICFMVPGVLPDTLN<br>TVRIRVRTNKLCYEDDKLWSNWSQAMSIGENTDPT |  |
| 23 | SGSVKVLHEPSCFSDYISTSVCQWKMDHPTNCSAE<br>LRLSYQLDFMGSENHTCVPENREDSVCVCSMPIDD<br>AVEADVYQLDLWAGQQLLWSGSFQPSKHVKPRTPG<br>NLTVHPNISHTWLLMWTNPYPTENHLHSELTYMVN<br>VSNDNDPEDFKVYNVTYMGPTLRLAASTLKSGASY<br>SARVRAWAQTYNSTWSDWSPSTTWLNYYEP | Exemplary canine IL4R extracellular domain (ECD; without signal sequence) |
| 24 | SQTQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCENIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETHD<br>IFYVEEAKCQNSEFEGNLEGTICFMVPGILPDTLN<br>TVRIRVRTNKLCYEDDRLWSNWSQAMSIGENTDPT | Exemplary feline IL13R extracellular domain (ECD; without signal sequence) |
| 25 | SGSVKVLRAPTCFSDYFSTSVCQWNMDAPTNCSAE<br>LRLSYQLNFMGSENRTCVPENGEGAACACSMLMDD<br>FVEADVYQLHLWAGTQLLWSGSFKPSSHVKPRAPG<br>NLTVHPNVSHTWLLRWSNPYPPENHLHAELTYMVN<br>ISSEDDPTDVSVCASGFLCHLLGLRRVETGAPGAR<br>LPPWLCAPRPRRVPGSQCAVISCCRWVLIALTSRG<br>GRWRLTPGLRSQTRYVSVAEGLFGATPRVLCPGTQ<br>AGLASAAREQMSPDPSAFHSIDYEP | Exemplary feline IL4R extracellular domain (ECD; without signal sequence) |
| 26 | TESQPPVTNLSVSVENLCTVIWTWNPPEGVSPNCS<br>LWYFSHFGNKQDKKIAPETHRSKEVPLNERICLQV<br>GSQCSTNESDNPSILVEKCISPPEGDPESAVTELQ<br>CVWHNLSYMKCTWLPGKNASPDTNYTLYYWHSSLG<br>KILQCEDIYREGQHIGCSFALTEVKDSIFEQHSVQ<br>IMVKDNAGKIRPFFNIVPLTSHVKPDPPHIKKLFF<br>QNGDLYVQWKNPQNFYSRCLSYQVEVNNSQTETRD<br>IFSVEEAKCQNPEFEGDLEGTICFMVPGVLPDTVN<br>TVRIRVKTNKLCYEDDKLWSNWSQAMSIGKKADPT | Exemplary equine IL13R extracellular domain (ECD; without signal sequence) |
| 27 | SGSVKVLHLTACFSDYISASTCEWKMDRPTNCSAQ<br>LRLSYQLNDEFSDNLICIPENREDEVCVCRMLMDN<br>IVSEDVYELDLWAGNQLLWNSSFKPSRHVKPRAPQ<br>NLTVHAISHTWLLTWSNPYPLKNHLWSELTYLVNI<br>SKEDDPTDFKIYNVTYMDPTLRVTASTLKSRATYS<br>ARVKARAQNYNSTWSEWSPSTTWHNYYEQP | Exemplary equine IL4R extracellular domain (ECD; without signal sequence) |
| 28 | SQTQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCENIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETHD<br>IFYVEEAKCQNSEFEGNLEGTICFMVPGILPDTLN<br>TVRIRVRTNKLCYEDDRLWSNWSQAMSIGENTDPT<br>GGGSGSSGSVKVLRAPTCFSDYFSTSVCQWNMDAP<br>TNCSAELRLSYQLNFMGSENRTCVPENGEGAACAC<br>SMLMDDFVEADVYQLHLWAGTQLLWSGSFKPSSHV<br>KPRAPGNLTVHPNVSHTWLLRWSNPYPPENHLHAE<br>LTYMVNISSEDDPTDVSVCASGFLCHLLGLRRVET<br>GAPGARLPPWLCAPRPRRVPGSQCAVISCCRWVLI<br>ALTSRGGRWRLTPGLRSQTRYVSVAEGLFGATPRV<br>LCPGTQAGLASAAREQMSPDPSAFHSIDYEPSPKT<br>ASTIESKTGECPKCPVPEIPGAPSVFIFPPKPKDT<br>LSISRTPEVTCLVVDLGPDDSNVQITWFVDNTEMH<br>TAKTRPREEQFNSTYRVVSVLPILHQDWLKGKEFK<br>CKVNSKSLPSAMERTISKAKGQPHEPQVYVLPPTQ<br>EELSENKVSVTCLIKGFHPPDIAVEWEITGQPEPE<br>NNYQTTPPQLDSDGTYFLYSRLSVDRSHWQRGNTY<br>TCSVSHEALHSHHTQKSLTQSPGK | Exemplary feline IL13RECD-IL4RECD-IgG2 Fc (without signal sequence) |

TABLE 1-continued

Description of Certain Sequences

| SEQ ID NO: | SEQUENCE | DESCRIPTION |
|---|---|---|
| 29 | SGSVKVLRAPTCFSDYFSTSVCQWNMDAPTNCSAE LRLSYQLNFMGSENRTCVPENGEGAACACSMLMDD FVEADVYQLHLWAGTQLLWSGSFKPSSHVKPRAPG NLTVHPNVSHTWLLRWSNPYPPENHLHAELTYMVN ISSEDDPTDVSVCASGFLCHLLGLRRVETGAPGAR LPPWLCAPRPRRVPGSQCAVISCCRWVLIALTSRG GRWRLTPGLRSQTRYVSVAEGLFGATPRVLCPGTQ AGLASAAREQMSPDPSAFHSIDYEPGGGSGSSQTQ PPVTNLSVSVENLCTVIWTWDPPEGASPNCTLRYF SHFDNKQDKKIAPETHRSKEVPLNERICLQVGSQC STNESDNPSILVEKCTPPPEGDPESAVTELQCVWH NLSYMKCTWLPGRNTSPDTNYTLYYWHSSLGKILQ CENIYREGQHIGCSFALTNLKDSSFEQHSVQIVVK DNAGKIRPSFNIVPLTSHVKPDPPHIKRLFFQNGN LYVQWKNPQNFYSRCLSYQVEVNNSQTETHDIFYV EEAKCQNSEFEGNLEGTICFMVPGILPDTLNTVRI RVRTNKLCYEDDRLWSNWSQAMSIGENTDPTSPKT ASTIESKTGECPKCPVPEIPGAPSVFIFPPKPKDT LSISRTPEVTCLVVDLGPDDSNVQITWFVDNTEMH TAKTRPREEQFNSTYRVVSVLPILHQDWLKGKEFK CKVNSKSLPSAMERTISKAKGQPHEPQVYVLPPTQ EELSENKVSVTCLIKGFHPPDIAVEWEITGQPEPE NNYQTTPPQLDSDGTYFLYSRLSVDRSHWQRGNTY TCSVSHEALHSHHTQKSLTQSPGK | Exemplary feline IL4RECD-IL13RECD-IgG2 (without signal sequence) |
| 30 | TESQPPVTNLSVSVENLCTVIWTWNPPEGVSPNCS LWYFSHFGNKQDKKIAPETHRSKEVPLNERICLQV GSQCSTNESDNPSILVEKCISPPEGDPESAVTELQ CVWHNLSYMKCTWLPGKNASPDTNYTLYYWHSSLG KILQCEDIYREGQHIGCSFALTEVKDSIFEQHSVQ IMVKDNAGKIRPFFNIVPLTSHVKPDPPHIKKLFF QNGDLYVQWKNPQNFYSRCLSYQVEVNNSQTETRD IFSVEEAKCQNPEFEGDLEGTICFMVPGVLPDTVN TVRIRVKTNKLCYEDDKLWSNWSQAMSIGKKADPT GGGSGSSGSVKVLHLTACFSDYISASTCEWKMDRP TNCSAQLRLSYQLNDEFSDNLTCIPENREDEVCVC RMLMDNIVSEDVYELDLWAGNQLLWNSSFKPSRHV KPRAPQNLTVHAISHTWLLTWSNPYPLKNHLWSEL TYLVNISKEDDPTDFKIYNVTYMDPTLRVTASILK SRATYSARVKARAQNYNSTWSEWSPSTTWHNYYEQ PDMSKCPKCPAPELLGGPSVFIFPPNPKDTLMISR TPVVTCVVVNLSDQYPDVQFSWYVDNTEVHSAITK QREAQFNSTYRVVSVLPIQHQDWLSGKEFKCSVTN VGVPQPISRAISRGKGPSRVPQVYVLPPHPDELAK SKVSVTCLVKDFYPPDISVEWQSNRWPELEGKYST TPAQLDGDGSYFLYSKLSLETSRWQQVESFTCAVM HEALHNHYTKTDISESLGK | Exemplary equine IL13RECD-IL4RECD-IgG2 Fc (without signal sequence) |
| 31 | SGSVKVLHLTACFSDYISASTCEWKMDRPTNCSAQ LRLSYQLNDEFSDNLICIPENREDEVCVCRMLMDN IVSEDVYELDLWAGNQLLWNSSFKPSRHVKPRAPQ NLTVHAISHTWLLTWSNPYPLKNHLWSELTYLVNI SKEDDPTDFKIYNVTYMDPTLRVTASTLKSRATYS ARVKARAQNYNSTWSEWSPSTTWHNYYEQPGGGSG STESQPPVTNLSVSVENLCTVIWTWNPPEGVSPNC SLWYFSHFGNKQDKKIAPETHRSKEVPLNERICLQ VGSQCSTNESDNPSILVEKCISPPEGDPESAVTEL QCVWHNLSYMKCTWLPGKNASPDTNYTLYYWHSSL GKILQCEDIYREGQHIGCSFALTEVKDSIFEQHSV QIMVKDNAGKIRPFFNIVPLTSHVKPDPPHIKKLF FQNGDLYVQWKNPQNFYSRCLSYQVEVNNSQTETR DIFSVEEAKCQNPEFEGDLEGTICFMVPGVLPDTV NTVRIRVKTNKLCYEDDKLWSNWSQAMSIGKKADP TDMSKCPKCPAPELLGGPSVFIFPPNPKDTLMISR TPVVTCVVVNLSDQYPDVQFSWYVDNTEVHSAITK QREAQFNSTYRVVSVLPIQHQDWLSGKEFKCSVTN VGVPQPISRAISRGKGPSRVPQVYVLPPHPDELAK SKVSVTCLVKDFYPPDISVEWQSNRWPELEGKYST TPAQLDGDGSYFLYSKLSLETSRWQQVESFTCAVM HEALHNHYTKTDISESLGK | Exemplary equine IL4RECD-IL13RECD-IgG2 Fc (without signal sequence) |
| 32 | QPPVTNLSVSVENLCTVIWTWDPPEGASPNCTLRY FSHFDNKQDKKIAPETHRSKEVPLNERICLQVGSQ CSTNESDNPSILVEKCTPPPEGDPESAVTELQCVW | Exemplary canine mini-IL13R ECD |

TABLE 1-continued

Description of Certain Sequences

| SEQ ID NO: | SEQUENCE | DESCRIPTION |
|---|---|---|
| | HNLSYMKCTWLPGRNTSPDTNYTLYYWHSSLGKIL QCEDIYREGQHIGCSFALTNLKDSSFEQHSVQIVV KDNAGKIRPSFNIVPLTSHVKPDPPHIKRLFFQNG NLYVQWKNPQNFYSRCLSYQVEVNNSQTETNDIFY VEEAKCQNSEFEGNLEGTICFMVPGVLPDTLNTVR IRVRTNKLCYEDDKLWSNWSQAMSI | |
| 33 | KVLHEPSCFSDYISTSVCQWKMDHPTNCSAELRLS YQLDFMGSENHTCVPENREDSVCVCSMPIDDAVEA DVYQLDLWAGQQLLWSGSFQPSKHVKPRTPGNLTV HPNISHTWLLMWTNPYPTENHLHSELTYMVNVSND NDPEDFKVYNVTYMGPTLRLAASTLKSGASYSARV RAWAQTYNS | Exemplary canine mini-IL4R ECD |
| 34 | QPPVTNLSVSVENLCTVIWTWDPPEGASPNCTLRY FSHFDNKQDKKIAPETHRSKEVPLNERICLQVGSQ CSTNESDNPSILVEKCTPPPEGDPESAVTELQCVW HNLSYMKCTWLPGRNTSPDTNYTLYYWHSSLGKIL QCENIYREGQHIGCSFALTNLKDSSFEQHSVQIVV KDNAGKIRPSFNIVPLTSHVKPDPPHIKRLFFQNG NLYVQWKNPQNFYSRCLSYQVEVNNSQTETHDIFY VEEAKCQNSEFEGNLEGTICFMVPGILPDTLNTVR IRVRTNKLCYEDDRLWSNWSQAMSI | Exemplary feline mini-IL13R ECD |
| 35 | KVLRAPTCFSDYFSTSVCQWNMDAPTNCSAELRLS YQLNFMGSENRTCVPENGEGAACACSMLMDDFVEA DVYQLHLWAGTQLLWSGSFKPSSHVKPRAPGNLTV HPNVSHTWLLRWSNPYPPENHLHAELTYMVNISSE DDPTDVSVCASGFLCHLLGLRRVETGAPGARLPPW LCAPRPRRVPGSQCAVISCCRWVLIALTSRGGRWR LTPGLRSQTRYVSVAEGLFGATPRVLCPGTQAGLA SAAREQMSPDPSAFHSIDYEP | Exemplary feline mini-IL4R ECD |
| 36 | QPPVINLSVSVENLCTVIWTWNPPEGVSPNCSLWY FSHFGNKQDKKIAPETHRSKEVPLNERICLQVGSQ CSTNESDNPSILVEKCISPPEGDPESAVTELQCVW HNLSYMKCTWLPGKNASPDTNYTLYYWHSSLGKIL QCEDIYREGQHIGCSFALTEVKDSIFEQHSVQIMV KDNAGKIRPFFNIVPLTSHVKPDPPHIKKLFFQNG DLYVQWKNPQNFYSRCLSYQVEVNNSQTETRDIFS VEEAKCQNPEFEGDLEGTICFMVPGVLPDTVNTVR IRVKTNKLCYEDDKLWSNWSQAMSI | Exemplary equine mini-IL13R ECD |
| 37 | KVLHLTACFSDYISASTCEWKMDRPTNCSAQLRLS YQLNDEFSDNLTCIPENREDEVCVCRMLMDNIVSE DVYELDLWAGNQLLWNSSFKPSRHVKPRAPQNLTV HAISHTWLLTWSNPYPLKNHLWSELTYLVNISKED DPTDFKIYNVTYMDPTLRVTASTLKSRATYSARVK ARAQNYNSTWSEWSPSTTWHNYYEQP | Exemplary equine mini-IL4R ECD |
| 38 | PVPEPLGGPSVLIFPPKPKDILRITRTPEVTCVVL DLGREDPEVQISWFVDGKEVHTAKTQSREQQFNGT YRVVSVLPIEHQDWLTGKEFKCRVNHIDLPSPIER TISKARGRAHKPSVYVLPPSPKELSSSDTVSITCL IKDFYPPDIDVEWQSNGQQEPERKHRMTPPQLDED GSYFLYSKLSVDKSRWQQGDPFICAVMHETLQNHY TDLSLSHSPGK | Exemplary wild-type canine IgG-A Fc |
| 39 | PAPEMLGGPSVFIFPPKPKDTLLIARTPEVTCVVV DLDPEDPEVQISWFVDGKQMQTAKTQPREEQFNGT YRVVSVLPIGHQDWLKGKQFTCKVNNKALPSPIER TISKARGQAHQPSVYVLPPSREELSKNTVSLTCLI KDFFPPDIDVEWQSNGQQEPESKYRTTPPQLDEDG SYFLYSKLSVDKSRWQRGDTFICAVMHEALHNHYT QESLSHSPGK | Exemplary wild-type canine IgG-B Fc |
| 40 | PGCGLLGGPSVFIFPPKPKDILVTARTPTVTCVVV DLDPENPEVQISWFVDSKQVQTANTQPREEQSNGT YRVVSVLPIGHQDWLSGKQFKCKVNNKALPSPIEE IISKTPGQAHQPNVYVLPPSRDEMSKNTVTLTCLV KDFFPPEIDVEWQSNGQQEPESKYRMTPPQLDEDG SYFLYSKLSVDKSRWQRGDTFICAVMHEALHNHYT QISLSHSPGK | Exemplary wild-type canine IgG-C Fc |

TABLE 1-continued

Description of Certain Sequences

| SEQ ID NO: | SEQUENCE | DESCRIPTION |
|---|---|---|
| 41 | PVPESLGGPSVFIFPPKPKDILRITRTPEITCVVL DLGREDPEVQISWFVDGKEVHTAKTQPREQQFNST YRVVSVLPIEHQDWLTGKEFKCRVNHIGLPSPIER TISKARGQAHQPSVYVLPPSPKELSSSDTVTLTCL IKDFFPPEIDVEWQSNGQPEPESKYHTTAPQLDED GSYFLYSKLSVDKSRWQQGDTFTCAVMHEALQNHY TDLSLSHSPGK | Exemplary wild-type canine IgG-D Fc |
| 42 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVTCLIKSFHPPDIAVEWEITGQP EPENNYRTTPPQLDSDGTYFVYSKLSVDRSHWQRG NTYTCSVSHEALHSHHTQKSLTQSPGK | Exemplary wild-type feline IgG1a Fc |
| 43 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVTCLIKSFHPPDIAVEWEITGQP EPENNYRTTPPQLDSDGTYFVYSKLSVDRSHWQRG NTYTCSVSHEALHSHHTQKSLTQSPGK | Exemplary wild-type feline IgG1a Fc |
| 44 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVTCLIEGFYPSDIAVEWEITGQP EPENNYRTTPPQLDSDGTYFLYSRLSVDRSRWQRG NTYTCSVSHEALHSHHTQKSLTQSPGK | Exemplary wild-type feline IgG1b Fc |
| 45 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVTCLIEGFYPSDIAVEWEITGQP EPENNYRTTPPQLDSDGTYFLYSRLSVDRSRWQRG NTYTCSVSHEALHSHHTQKSLTQSPGK | Exemplary wild-type feline IgG1b Fc |
| 46 | PKTASTIESKTGEGPKCPVPEIPGAPSVFIFPPKP KDTLSISRTPEVTCLVVDLGPDDSNVQITWFVDNT EMHTAKTRPREEQFNSTYRVVSVLPILHQDWLKGK EFKCKVNSKSLPSAMERTISKAKGQPHEPQVYVLP PTQEELSENKVSVTCLIKGFHPPDIAVEWEITGQP EPENNYQTTPPQLDSDGTYFLYSRLSVDRSHWQRG NTYTCSVSHEALHSHHTQKSLTQSPGK | Exemplary wild-type feline IgG2 Fc |
| 47 | GPSVFIFPPNPKDTLMITRTPEVTCVVVDVSQENP DVKFNWYMDGVEVRTATTRPKEEQFNSTYRVVSVL RIQHQDWLSGKEFKCKVNNQALPQPIERTITKTKG RSQEPQVYVLAPHPDELSKSKVSVTCLVKDFYPPE INIEWQSNGQPELETKYSTTQAQQDSDGSYFLYSK LSVDRNRWQQGTTFTCGVMHEALHNHYTQKNVSKN PGK | Exemplary wild-type equine IgG1 Fc |
| 48 | GPSVFIFPPNPKDALMISRTPVVTCVVVNLSDQYP DVQFSWYVDNTEVHSAITKQREAQFNSTYRVVSVL PIQHQDWLSGKEFKCSVTNVGVPQPISRAISRGKG PSRVPQVYVLPPHPDELAKSKVSVTCLVKDFYPPD ISVEWQSNRWPELEGKYSTTPAQLDGDGSYFLYSK LSLETSRWQQVESFTCAVMHEALHNHFTKTDISES LGK | Exemplary wild-type equine IgG2 Fc |
| 49 | GPSVFIFPPKPKDVLMITRMPEVTCLVVDVSHDSS DVLFTWYVDGTEVKTAKTMPNEEQNNSTYRVVSVL RIQHQDWLNGKKFKCKVNNQALPAPVERTISKATG QTRVPQVYVLAPHPDELSKNKVSVTCLVKDFYPPD ITVEWQSNEHPEPEGKYRTTEAQKDSDGSYFLYSK LTVEKDRWQQGTTFTCVVMHEALHNHVMQKNISKN PGK | Exemplary wild-type equine IgG3 Fc |

TABLE 1-continued

Description of Certain Sequences

| SEQ ID NO: | SEQUENCE | DESCRIPTION |
|---|---|---|
| 50 | GPSVFIFPPKPKDVLMISRTPTVTCVVVDVGHDFP DVQFNWYVDGVETHTATTEPKQEQFNSTYRVVSVL PIQHKDWLSGKEFKCKVNNKALPAPVERTISAPTG QPREPQVYVLAPHRDELSKNKVSVTCLVKDFYPPD IDIEWKSNGQPEPETKYSTTPAQLDSDGSYFLYSK LIVETNRWQQGTTFTCAVMHEALHNHYTEKSVSKS PGK | Exemplary wild-type equine IgG4 Fc |
| 51 | GPSVFIFPPKPKDVLMISRKPEVTCVVVDLGHDDP DVQFTWFVDGVETHTATTEPKEEQFNSTYRVVSVL PIQHQDWLSGKEFKCSVTSKALPAPVERTISKAKG QLRVPQVYVLAPHPDELAKNTVSVTCLVKDFYPPE IDVEWQSNEHPEPEGKYSTTPAQLNSDGSYFLYSK LSVETSRWKQGESFTCGVMHEAVENHYTQKNVSHS PGK | Exemplary wild-type equine IgG5 Fc |
| 52 | GRPSVFIFPPNPKDTLMISRTPEVTCVVVDVSQE NPDVKFNWYVDGVEAHTATTKAKEKQDNSTYRVV SVLPIQHQDWRRGKEFKCKVNNRALPAPVERTIT KAKGELQDPKVYILAPHREEVTKNTVSVTCLVKD FYPPDINVEWQSNEEPEPEVKYSTTPAQLDGDGS YFLYSKLTVETDRWEQGESFTCVVMHEAIRHTYR QKSITNFPGK | Exemplary wild-type equine IgG6 Fc |
| 53 | GPSVFIFPPKPKDVLMISRTPTVTCVVVDVGHDFP DVQFNWYVDGVETHTATTEPKQEQNNSTYRVVSIL AIQHKDWLSGKEFKCKVNNQALPAPVQKTISKPTG QPREPQVYVLAPHPDELSKNKVSVTCLVKDFYPPD IDIEWKSNGQPEPETKYSTTPAQLDGDGSYFLYSK LIVETNRWQQGTTFTCAVMHEALHNHYTEKSVSKS PGK | Exemplary wild-type equine IgG7 Fc |
| 54 | PVPEPLGGPSVLIFPPKPKDILRITRTPEVTCVVL DLGREDPEVQISWFVDGKEVHTAKTQSREQQFNGT YRVVSVLPIEHQDWLTGKEFKCRVNHIDLPSPIER TISKARGRAHKPSVYVLPPSPKELSSSDTVSIWCL IKDFYPPDIDVEWQSNGQQEPERKHRMTPPQLDED GSYFLYSKLSVDKSRWQQGDPFTCAVMHETLQNHY TDLSLSHSPGK | Exemplary variant canine IgG-A Fc Heterodimer knob T(138)W |
| 55 | PAPEMLGGPSVFIFPPKPKDTLLIARTPEVTCVVV DLDPEDPEVQISWFVDGKQMQTAKTQPREEQFNGT YRVVSVLPIGHQDWLKGKQFTCKVNNKALPSPIER TISKARGQAHQPSVYVLPPSREELSKNTVSLWCLI KDFFPPDIDVEWQSNGQQEPESKYRTTPPQLDEDG SYFLYSKLSVDKSRWQRGDTFICAVMHEALHNHYT QESLSHSPGK | Exemplary variant canine IgG-B Fc Heterodimer knob T(137)W |
| 56 | PGCGLLGGPSVFIFPPKPKDILVTARTPTVTCVVV DLDPENPEVQISWFVDGKQVQTANTQPREEQSNGT YRVVSVLPIGHQDWLSGKQFKCKVNNKALPSPIEE IISKIPGQAHQPNVYVLPPSRDEMSKNTVTLWCLV KDFFPPEIDVEWQSNGQQEPESKYRMTPPQLDEDG SYFLYSKLSVDKSRWQRGDTFICAVMHEALHNHYT QISLSHSPGK | Exemplary variant canine IgG-C Fc Heterodimer knob T(137)W |
| 57 | PVPESLGGPSVFIFPPKPKDILRITRTPEITCVVL DLGREDPEVQISWFVDGKEVHTAKTQPREQQFNST YRVVSVLPIEHQDWLTGKEFKCRVNHIGLPSPIER TISKARGQAHQPSVYVLPPSPKELSSSDTVTLWCL IKDFFPPEIDVEWQSNGQPEPESKYHTTAPQLDED GSYFLYSKLSVDKSRWQQGDTFTCAVMHEALQNHY TDLSLSHSPGK | Exemplary variant canine IgG-D Fc Heterodimer knob T(138)W |
| 58 | PVPEPLGGPSVLIFPPKPKDILRITRTPEVPCVVL DLGREDPEVQISWFVDGKEVHTAKTQSREQQFNGT YRVVSVLPIEHQDWLTGKEFKCRVNHIDLPSPIER TISKARGRAHKPSVYVLPPSPKELSSSDTVSISCA IKDFYPPDIDVEWQSNGQQEPERKHRMTPPQLDED GSYFLYSKLSVDKSRWQQGDPFTCAVMHETLQNHY TDLSLSHSPGK | Exemplary variant canine IgG-A Fc Heterodimer hole T(138)S L(140)A |

TABLE 1-continued

Description of Certain Sequences

| SEQ ID NO: | SEQUENCE | DESCRIPTION |
|---|---|---|
| 59 | PAPEMLGGPSVFIFPPKPKDTLLIARTPEVTCVVV DLDPEDPEVQISWFVDGKQMQTAKTQPREEQFNGT YRVVSVLPIGHQDWLKGKQFTCKVNNKALPSPIER TISKARGQAHQPSVYVLPPSREELSKNIVSLSCAI KDFFPPDIDVEWQSNGQQEPESKYRTTPPQLDEDG SYFLYSKLSVDKSRWQRGDTFICAVMHEALHNHYT QESLSHSPGK | Exemplary variant canine IgG-B Fc Heterodimer hole T(137)S L(139)A |
| 60 | PGCGLLGGPSVFIFPPKPKDILVTARTPTVTCVVV DLDPENPEVQISWFVDSKQVQTANTQPREEQSNGT YRVVSVLPIGHQDWLSGKQFKCKVNNKALPSPIEE IISKTPGQAHQPNVYVLPPSRDEMSKNTVTLSCAV KDFFPPEIDVEWQSNGQQEPESKYRMTPPQLDEDG SYFLYSKLSVDKSRWQRGDTFICAVMHEALHNHYT QISLSHSPGK | Exemplary variant canine IgG-C Fc Heterodimer hole T(137)S L(139)A |
| 61 | PVPESLGGPSVFIFPPKPKDILRITRTPEITCVVL DLGREDPEVQISWFVDGKEVHTAKTQPREQQFNST YRVVSVLPIEHQDWLTGKEFKCRVNHIGLPSPIER TISKARGQAHQPSVYVLPPSPKELSSSDTVTLSCA IKDFFPPEIDVEWQSNGQQEPEPESKYHTTAPQLDED GSYFLYSKLSVDKSRWQQGDTFTCAVMHEALQNHY TDLSLSHSPGK | Exemplary variant canine IgG-D Fc Heterodimer hole T(138)S L(140)A |
| 62 | PVPEPLGGPSVLIFPPKPKDILRITRTPEVTCVVL DLGREDPEVQISWFVDGKEVHTAKTQSREQQFNGT YRVVSVLPIEHQDWLTGKEFKCRVNHIDLPSPIER TISKARGRAHKPSVYVLPPSPKELSSSDTVSISCA IKDFYPPDIDVEWQSNGQQEPERKHRMTPPQLDED GSYFLTSKLSVDKSRWQQGDPFTCAVMHETLQNHY TDLSLSHSPGK | Exemplary variant canine IgG-A Fc Heterodimer hole T(138)S L(140)A Y(181)T |
| 63 | PAPEMLGGPSVFIFPPKPKDTLLIARTPEVTCVVV DLDPEDPEVQISWFVDGKQMQTAKTQPREEQFNGT YRVVSVLPIGHQDWLKGKQFTCKVNNKALPSPIER TISKARGQAHQPSVYVLPPSREELSKNTVSLSCAI KDFFPPDIDVEWQSNGQQEPESKYRTTPPQLDEDG SYFLTSKLSVDKSRWQRGDTFICAVMHEALHNHYT QESLSHSPGK | Exemplary variant canine IgG-B Fc Heterodimer hole T(137)S L(139)A Y(180)T |
| 64 | PGCGLLGGPSVFIFPPKPKDILVTARTPTVTCVVV DLDPENPEVQISWFVDSKQVQTANTQPREEQSNGT YRVVSVLPIGHQDWLSGKQFKCKVNNKALPSPIEE IISKIPGQAHQPNVYVLPPSRDEMSKNTVTLSCAV KDFFPPEIDVEWQSNGQQEPESKYRMTPPQLDEDG SYFLTSKLSVDKSRWQRGDTFICAVMHEALHNHYT QISLSHSPGK | Exemplary variant canine IgG-C Fc Heterodimer hole T(137)S L(139)A Y(180)T |
| 65 | PVPESLGGPSVFIFPPKPKDILRITRTPEITCVVL DLGREDPEVQISWFVDGKEVHTAKTQPREQQFNST YRVVSVLPIEHQDWLTGKEFKCRVNHIGLPSPIER TISKARGQAHQPSVYVLPPSPKELSSSDTVTLSCA IKDFFPPEIDVEWQSNGQQEPEPESKYHTTAPQLDED GSYFLTSKLSVDKSRWQQGDTFTCAVMHEALQNHY TDLSLSHSPGK | Exemplary variant canine IgG-D Fc Heterodimer hole T(138)S L(140)A Y(181)T |
| 66 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVWCLIKSFHPPDIAVEWEITGQP EPENNYRTTPPQLDSDGTYFVYSKLSVDRSHWQRG NTYTCSVSHEALHSHHTQKSLTQSPGK | Exemplary variant feline IgG1a Fc Heterodimer knob T(154)W |
| 67 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVWCLIKSFHPPDIAVEWEITGQP EPENNYRTTPPQLDSDGTYFVYSKLSVDRSHWQRG NTYTCSVSHEALHSHHTQKSLTQSPGK | Exemplary variant feline IgG1a Fc Heterodimer knob T(154)W |

TABLE 1-continued

Description of Certain Sequences

| SEQ ID NO: | SEQUENCE | DESCRIPTION |
|---|---|---|
| 68 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVWCLIEGFYPSDIAVEWEITGQP EPENNYRTTPPQLDSDGTYFLYSRLSVDRSRWQRG NTYTCSVSHEALHSHHTQKSLTQSPGK | Exemplary variant feline IgG1b Fc Heterodimer knob T(154)W |
| 69 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVWCLIEGFYPSDIAVEWEITGQP EPENNYRTTPPQLDSDGTYFLYSRLSVDRSRWQRG NTYTCSVSHEALHSHHTQKSLTQSPGK | Exemplary variant feline IgG1b Fc Heterodimer knob T(154)W |
| 70 | PKTASTIESKTGEGPKCPVPEIPGAPSVFIFPPKP KDTLSISRTPEVTCLVVDLGPDDSNVQITWFVDNT EMHTAKTRPREEQFNSTYRVVSVLPILHQDWLKGK EFKCKVNSKSLPSAMERTISKAKGQPHEPQVYVLP PTQEELSENKVSVWCLIKGFHPPDIAVEWEITGQP EPENNYQTTPPQLDSDGTYFLYSRLSVDRSHWQRG NTYTCSVSHEALHSHHTQKSLTQSPGK | Exemplary variant feline IgG2 Fc Heterodimer knob T(154)W |
| 71 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVSCAIKSFHPPDIAVEWEITGQP EPENNYRTTPPQLDSDGTYFVYSKLSVDRSHWQRG NTYTCSVSHEALHSHHTQKSLTQSPGK | Exemplary variant feline IgG1a Fc Heterodimer hole T(154)S L(156)A |
| 72 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVSCAIKSFHPPDIAVEWEITGQP EPENNYRTTPPQLDSDGTYFVYSKLSVDRSHWQRG NTYTCSVSHEALHSHHTQKSLTQSPGK | Exemplary variant feline IgG1a Fc Heterodimer hole T(154)S L(156)A |
| 73 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVSCAIEGFYPSDIAVEWEITGQP EPENNYRTTPPQLDSDGTYFLYSRLSVDRSRWQRG NTYTCSVSHEALHSHHTQKSLTQSPGK | Exemplary variant feline IgG1b Fc Heterodimer hole T(154)S L(156)A |
| 74 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVSCAIEGFYPSDIAVEWEITGQP EPENNYRTTPPQLDSDGTYFLYSRLSVDRSRWQRG NTYTCSVSHEALHSHHTQKSLTQSPGK | Exemplary variant feline IgG1b Fc Heterodimer hole T(154)S L(156)A |
| 75 | PKTASTIESKTGEGPKCPVPEIPGAPSVFIFPPKP KDTLSISRTPEVTCLVVDLGPDDSNVQITWFVDNT EMHTAKTRPREEQFNSTYRVVSVLPILHQDWLKGK EFKCKVNSKSLPSAMERTISKAKGQPHEPQVYVLP PTQEELSENKVSVSCAIKGFHPPDIAVEWEITGQP EPENNYQTTPPQLDSDGTYFLYSRLSVDRSHWQRG NTYTCSVSHEALHSHHTQKSLTQSPGK | Exemplary variant feline IgG2 Fc Heterodimer hole T(154)S L(156)A |
| 76 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVSCAIKSFHPPDIAVEWEITGQP EPENNYRTTPPQLDSDGTYFTSKLSVDRSHWQRG NTYTCSVSHEALHSHHTQKSLTQSPGK | Exemplary variant feline IgG1a Fc Heterodimer hole T(154)S L(156)A Y(197)T |

TABLE 1-continued

Description of Certain Sequences

| SEQ ID NO: | SEQUENCE | DESCRIPTION |
|---|---|---|
| 77 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKAKGQPHEPQVYVLP PAQEELSENKVSVSCAIKSFHPPDIAVEWEITGQP EPENNYRTTPPQLDSDGTYFVTSKLSVDRSHWQRG NTYTCSVSHEALHSHHTQKSLTQSPGK | Exemplary variant feline IgG1a Fc Heterodimer hole T(154)S L(156)A Y(197)T |
| 78 | RKTDHPPGPKPCDCPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVSCAIEGFYPSDIAVEWEITGQP EPENNYRTTPPQLDSDGTYFLTSRLSVDRSRWQRG NTYTCSVSHEALHSHHTQKSLTQSPGK | Exemplary variant feline IgG1b Fc Heterodimer hole T(154)S L(156)A Y(197)T |
| 79 | RKTDHPPGPKTGEGPKCPPPEMLGGPSIFIFPPKP KDTLSISRTPEVTCLVVDLGPDDSDVQITWFVDNT QVYTAKTSPREEQFNSTYRVVSVLPILHQDWLKGK EFKCKVNSKSLPSPIERTISKDKGQPHEPQVYVLP PAQEELSENKVSVSCAIEGFYPSDIAVEWEITGQP EPENNYRTTPPQLDSDGTYFLTSRLSVDRSRWQRG NTYTCSVSHEALHSHHTQKSLTQSPGK | Exemplary variant feline IgG1b Fc Heterodimer hole T(154)S L(156)A Y(197)T |
| 80 | PKTASTIESKTGEGPKCPVPEIPGAPSVFIFPPKP KDTLSISRTPEVTCLVVDLGPDDSNVQITWFVDNT EMHTAKTRPREEQFNSTYRVVSVLPILHQDWLKGK EFKCKVNSKSLPSAMERTISKAKGQPHEPQVYVLP PTQEELSENKVSVSCAIKGFHPPDIAVEWEITGQP EPENNYQTTPPQLDSDGTYFLTSRLSVDRSHWQRG NTYTCSVSHEALHSHHTQKSLTQSPGK | Exemplary variant feline IgG2 Fc Heterodimer hole T(154)S L(156)A Y(197)T |
| 81 | GPSVFIFPPNPKDTLMITRTPEVTCVVVDVSQENP DVKFNWYMDGVEVRTATTRPKEEQFNSTYRVVSVL RIQHQDWLSGKEFKCKVNNQALPQPIERTITKTKG RSQEPQVYVLAPHPDELSKSKVSVWCLVKDFYPPE INIEWQSNGQPELETKYSTTQAQQDSDGSYFLYSK LSVDRNRWQQGTTFTCGVMHEALHNHYTQKNVSKN PGK | Exemplary variant equine IgG1 Fc Heterodimer knob T(130)W |
| 82 | GPSVFIFPPNPKDALMISRTPVVTCVVVNLSDQYP DVQFSWYVDNTEVHSAITKQREAQFNSTYRVVSVL PIQHQDWLSGKEFKCSVINVGVPQPISRAISRGKG PSRVPQVYVLPPHPDELAKSKVSVWCLVKDFYPPD ISVEWQSNRWPELEGKYSTTPAQLDGDGSYFLYSK LSLETSRWQQVESFTCAVMHEALHNHFIKTDISES LGK | Exemplary variant equine IgG2 Fc Heterodimer knob T(130)W |
| 83 | GPSVFIFPPKPKDVLMITRMPEVTCLVVDVSHDSS DVLFTWYVDGTEVKTAKTMPNEEQNNSTYRVVSVL RIQHQDWLNGKKFKCKVNNQALPAPVERTISKATG QTRVPQVYVLAPHPDELSKNKVSVWCLVKDFYPPD ITVEWQSNEHPEPEGKYRTTEAQKDSDGSYFLYSK LTVEKDRWQQGTTFTCVVMHEALHNHVMQKNISKN PGK | Exemplary variant equine IgG3 Fc Heterodimer knob T(130)W |
| 84 | GPSVFIFPPKPKDVLMISRTPTVTCVVVDVGHDFP DVQFNWYVDGVETHTATTEPKQEQFNSTYRVVSVL PIQHKDWLSGKEFKCKVNNKALPAPVERTISAPTG QPREPQVYVLAPHRDELSKNKVSVWCLVKDFYPPD IDIEWKSNGQPEPETKYSTTPAQLDSDGSYFLYSK LTVETNRWQQGTTFTCAVMHEALHNHYTEKSVSKS PGK | Exemplary variant equine IgG4 Fc Heterodimer knob T(130)W |
| 85 | GPSVFIFPPKPKDVLMISRKPEVTCVVVDLGHDDP DVQFTWFVDGVETHTATTEPKEEQFNSTYRVVSVL PIQHQDWLSGKEFKCSVTSKALPAPVERTISKAKG QLRVPQVYVLAPHPDELAKNTVSVWCLVKDFYPPE IDVEWQSNEHPEPEGKYSTTPAQLNSDGSYFLYSK LSVETSRWKQGESFTCGVMHEAVENHYTQKNVSHS PGK | Exemplary variant equine IgG5 Fc Heterodimer knob T(130)W |

TABLE 1-continued

Description of Certain Sequences

| SEQ ID NO: | SEQUENCE | DESCRIPTION |
|---|---|---|
| 86 | RPSVFIFPPNPKDTLMISRTPEVTCVVVDVSQENP DVKFNWYVDGVEAHTATTKAKEKQDNSTYRVVSVL PIQHQDWRRGKEFKCKVNNRALPAPVERTITKAKG ELQDPKVYILAPHREEVTKNTVSVWCLVKDFYPPD INVEWQSNEEPEPEVKYSTTPAQLDGDGSYFLYSK LTVETDRWEQGESFTCVVMHEAIRHTYRQKSITNF PGK | Exemplary variant equine IgG6 Fc Heterodimer knob T(130)W |
| 87 | GPSVFIFPPKPKDVLMISRTPTVTCVVVDVGHDFP DVQFNWYVDGVETHTATTEPKQEQNNSTYRVVSIL AIQHKDWLSGKEFKCKVNNQALPAPVQKTISKPTG QPREPQVYVLAPHPDELSKNKVSVWCLVKDFYPPD IDIEWKSNGQPEPETKYSTTPAQLDGDGSYFLYSK LTVETNRWQQGTTFTCAVMHEALHNHYTEKSVSKS PGK | Exemplary variant equine IgG7 Fc Heterodimer knob T(130)W |
| 88 | GPSVFIFPPNPKDTLMITRTPEVTCVVVDVSQENP DVKFNWYMDGVEVRTATTRPKEEQFNSTYRVVSVL RIQHQDWLSGKEFKCKVNNQALPQPIERTITKTKG RSQEPQVYVLAPHPDELSKSKVSVSCAVKDFYPPE INIEWSNGQPELETKYSTTQAQQDSDGSYFLYSK LSVDRNRWQQGTTFTCGVMHEALHNHYTQKNVSKN PGK | Exemplary variant equine IgG1 Fc Heterodimer hole T(130)S L(132)A |
| 89 | GPSVFIFPPNPKDALMISRTPVVTCVVVNLSDQYP DVQFSWYVDNTEVHSAITKQREAQFNSTYRVVSVL PIQHQDWLSGKEFKCSVINVGVPQPISRAISRGKG PSRVPQVYVLPPHPDELAKSKVSVSCAVKDFYPPD ISVEWQSNRWPELEGKYSTTPAQLDGDGSYFLYSK LSLETSRWQQVESFTCAVMHEALHNHFIKTDISES LGK | Exemplary variant equine IgG2 Fc Heterodimer hole T(130)S L(132)A |
| 90 | GPSVFIFPPKPKDVLMITRMPEVTCLVVDVSHDSS DVLFTWYVDGTEVKTAKTMPNEEQNNSTYRVVSVL RIQHQDWLNGKKFKCKVNNQALPAPVERTISKATG QTRVPQVYVLAPHPDELSKNKVSVSCAVKDFYPPD ITVEWQSNEHPEPEGKYRTTEAQKDSDGSYFLYSK LTVEKDRWQQGTTFTCVVMHEALHNHVMQKNISKN PGK | Exemplary variant equine IgG3 Fc Heterodimer hole T(130)S L(132)A |
| 91 | GPSVFIFPPKPKDVLMISRTPTVTCVVVDVGHDFP DVQFNWYVDGVETHTATTEPKQEQFNSTYRVVSVL PIQHKDWLSGKEFKCKVNNKALPAPVERTISAPTG QPREPQVYVLAPHRDELSKNKVSVSCAVKDFYPPD IDIEWKSNGQPEPETKYSTTPAQLDSDGSYFLYSK LTVETNRWQQGTTFACAVMHEALHNHYTEKSVSKS PGK | Exemplary variant equine IgG4 Fc Heterodimer hole T(130)S L(132)A |
| 92 | GPSVFIFPPKPKDVLMISRKPEVTCVVVDLGHDDP DVQFTWFVDGVETHTATTEPKEEQFNSTYRVVSVL PIQHQDWLSGKEFKCSVTSKALPAPVERTISKAKG QLRVPQVYVLAPHPDELAKNTVSVSCAVKDFYPPE IDVEWQSNEHPEPEGKYSTTPAQLNSDGSYFLYSK LSVETSRWKQGESFTCGVMHEAVENHYTQKNVSHS PGK | Exemplary variant equine IgG5 Fc Heterodimer hole T(130)S L(132)A |
| 93 | RPSVFIFPPNPKDTLMISRTPEVTCVVVDVSQEN PDVKFNWYVDGVEAHTATTKAKEKQDNSTYRVVS VLPIQHQDWRRGKEFKCKVNNRALPAPVERTITK AKGELQDPKVYILAPHREEVTKNTVSVSCAVKDF YPPDINVEWQSNEEPEPEVKYSTTPAQLDGDGSY FLYSKLTVETDRWEQGESFTCVVMHEAIRHTYRQ KSITNFPGK | Exemplary variant equine IgG6 Fc Heterodimer hole T(130)S L(132)A |
| 94 | GPSVFIFPPKPKDVLMISRTPTVTCVVVDVGHDFP DVQFNWYVDGVETHTATTEPKQEQNNSTYRVVSIL AIQHKDWLSGKEFKCKVNNQALPAPVQKTISKPTG QPREPQVYVLAPHPDELSKNKVSVSCAVKDFYPPD IDIEWKSNGQPEPETKYSTTPAQLDGDGSYFLYSK LTVETNRWQQGTTFTCAVMHEALHNHYTEKSVSKS PGK | Exemplary variant equine IgG7 Fc Heterodimer hole T(130)S L(132)A |
| 95 | GPSVFIFPPNPKDTLMITRTPEVTCVVVDVSQENP DVKFNWYMDGVEVRTATTRPKEEQFNSTYRVVSVL | Exemplary variant equine IgG1 Fc |

TABLE 1-continued

Description of Certain Sequences

| SEQ ID NO: | SEQUENCE | DESCRIPTION |
|---|---|---|
|  | RIQHQDWLSGKEFKCKVNNQALPQPIERTITKTKG RSQEPQVYVLAPHPDELSKSKVSVSCAVKDFYPPE INIEWQSNGQPELETKYSTTQAQQ<u>D</u>S<u>D</u>GSYFLTSK LSVDRNRWQQGTTFTCGVMHEALHNHYTQKNV<u>S</u>KN PGK | Heterodimer hole T(130)S L(132)A Y(173)T |
| 96 | GPSVFIFPPNPKDALMISRTPVVTCVVVNLSDQYP DVQFSWYVDNTEVHSAITKQREAQFNSTYRVVSVL PIQHQDWLSGKEFKCSVTNVGVPQPISRAISRGKG PSRVPQVYVLPPHPDELAKSKVSVSCAVKDFYPPD ISVEWQSNRWPELEGKYSTTPAQL<u>D</u>G<u>D</u>GSYFLTSK LSLETSRWQQVESFTCAVMHEALHNHFIKTDI<u>S</u>ES LGK | Exemplary variant equine IgG2 Fc Heterodimer hole T(130)S L(132)A Y(173)T |
| 97 | GPSVFIFPPKPKDVLMITRMPEVTCLVVDVSHDSS DVLFTWYVDGTEVKTAKTMPNEEQNNSTYRVVSVL RIQHQDWLNGKKFKCKVNNQALPAPVERTISKATG QTRVPQVYVLAPHPDELSKNKVSVSCAVKDFYPPD ITVEWQSNEHPEPEGKYRTTEAQK<u>D</u>S<u>D</u>GSYFLTSK LTVEKDRWQQGTTFTCVVMHEALHNHVMQKNI<u>S</u>KN PGK | Exemplary variant equine IgG3 Fc Heterodimer hole T(130)S L(132)A Y(173)T |
| 98 | GPSVFIFPPKPKDVLMISRTPTVTCVVVDVGHDFP DVQFNWYVDGVETHTATTEPKQEQFNSTYRVVSVL PIQHKDWLSGKEFKCKVNNKALPAPVERTISAPTG QPREPQVYVLAPHRDELSKNKVSVSCAVKDFYPPD IDIEWKSNGQPEPETKYSTTPAQL<u>D</u>S<u>D</u>GSYFLTSK LTVETNRWQQGTTFTCVVMHEALHNHYTEKSV<u>S</u>KS PGK | Exemplary variant equine IgG4 Fc Heterodimer hole T(130)S L(132)A Y(173)T |
| 99 | GPSVFIFPPKPKDVLMISRKPEVTCVVVDLGHDDP DVQFTWFVDGVETHTATTEPKEEQFNSTYRVVSVL PIQHQDWLSGKEFKCSVTSKALPAPVERTISKAKG QLRVPQVYVLAPHPDELAKNTVSVSCAVKDFYPPE IDVEWQSNEHPEPEGKYSTTPAQL<u>N</u>S<u>D</u>GSYFLTSK LSVETSRWQGESFTCGVMHEAVENHYTQKNV<u>S</u>HS PGK | Exemplary variant equine IgG5 Fc Heterodimer hole T(130)S L(132)A Y(173)T |
| 100 | RPSVFIFPPNPKDTLMISRTPEVTCVVVDVSQENP DVKFNWYVDGVEAHTATTKAKEK<u>Q</u>DNSTYRVVSVL PIQHQDWRRGKEFKCKVNNRALPAPVERTITKAKG ELQDPKVYILAPHREEVTKNTVSVSCAVKDFYPPD INVEWQSNEEPEPEVKYSTTPAQL<u>D</u>G<u>D</u>GSYFLTSK LTVETDRWEQESFTCVVMHEAIRHTYRQKSI<u>T</u>NF PGK | Exemplary variant equine IgG6 Fc Heterodimer hole T(130)S L(132)A Y(173)T |
| 101 | GPSVFIFPPKPKDVLMISRTPTVTCVVVDVGHDFP DVQFNWYVDGVETHTATTEPKQEQNNSTYRVVSIL AIQHKDWLSGKEFKCKVNNQALPAPVQKTISKPTG QPREPQVYVLAPHPDELSKNKVSVSCAVKDFYPPD IDIEWKSNGQPEPETKYSTTPAQL<u>D</u>G<u>D</u>GSYFLTSK LTVETNRWQQGTTFTCVVMHEALHNHYTEKSV<u>S</u>KS PGK | Exemplary variant equine IgG7 Fc Heterodimer hole T(130)S L(132)A Y(173)T |
| 102 | SGSVKVLHEPSCFSDYISTSVCQWKMDHPTNCSAE LRLSYQLDFMGSENHTCVPENREDSVCVCSMPIDD AVEADVYQLDLWAGQQLLWSGSFQPSKHVKPRTPG NLTVHPNISHTWLLMWTNPYPTENHLHSELTYMVN VSNDNDPEDFKVYNVTYMGPTLRLAASTLKSGASY SARVRAWAQTYNSTWSDWSPSITWLNYYEP*GGGSG GGGSGGGGSGGGGSGGGGSG*PAPEMLGGPSVFIFP PKPKDTLLIARTPEVTCVVVDLDPEDPEVQISWFV DGKQMQTAKTQPREEQFNGTYRVVSVLPIGHQDWL KGKQFTCKVNNKALPSPIERTISKARGQAHQPSVY VLPPSREELSKNTVSLWCLIKDFFPPDIDVEWQSN GQQEPESKYRTTPPQL<u>D</u>EDGSYFLYSKLSVDKSRW QRGDTFICAVMHEALHNHYTQESLSHSPGK | Canine IL4R ECD canine IgG-B Fc knob |
| 103 | TETQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ CVWHNLSYMKCTWLPGRNTSPDTNYTLYYWHSSLG KILQCEDIYREGQHIGCSFALTNLKDSSFEQHSVQ IVVKDNAGKIRPSFNIVPLTSHVKPDDPHIKRLFF QNGNLYVQWKNPQNFYSRCLSYQVEVNNSQTETND | Canine IL13R ECD canine IgG-B Fc hole |

TABLE 1-continued

Description of Certain Sequences

| SEQ ID NO: | SEQUENCE | DESCRIPTION |
|---|---|---|
| | IFYVEEAKCQNSEFEGNLEGTICFMVPGVLPDTLN<br>TVRIRVRTNKLCYEDDKLWSNWSQAMSIGENTDPT<br>*GGGSGGGGSGGGGSGGGGSGGGGSGGGGSG*PAPEMLGGPS<br>VFIFPPKPKDTLLIARTPEVTCVVVDLDPEDPEVQ<br>ISWFVDGKQMQTAKTQPREEQFNGTYRVVSVLPIG<br>HQDWLKGKQFTCKVNNKALPSPIERTISKARGQAH<br>QPSVYVLPPSREELSKNTVSL<u>SCA</u>IKDFFPPDIDV<br>EWQSNGQQEPESKYRTTPPQL<u>D</u>EDGSYFL<u>T</u>SKLSV<br>DKSRWQRGDTFICAVMHEALHNHYTQESL<u>S</u>HSPGK | |
| 104 | SGSVKVLHEPSCFSDYISTSVCQWKMDHPTNCSAE<br>LRLSYQLDFMGSENHTCVPENREDSVCVCSMPIDD<br>AVEADVYQLDLWAGQQLLWSGSFQPSKHVKPRTPG<br>NLTVHPNISHTWLLMWTNPYPTENHLHSELTYMVN<br>VSNDNDPEDFKVYNVTYMGPTLRLAASTLKSGASY<br>SARVRAWAQTYNSTWSDWSPSTTWLNYYEP*GGGSG<br>GGGSGGGGSGGGGSGGGGSG*PAPEMLGGPSVFIFP<br>PKPKDTLLIARTPEVTCVVVDLDPEDPEVQISWFV<br>DGKQMQTAKTQPREEQFNGTYRVVSVLPIGHQDWL<br>KGKQFTCKVNNKALPSPIERTISKARGQAHPSVY<br>VLPPSREELSKNTVSL<u>SCA</u>IKDFFPPDIDVEWQSN<br>GQQEPESKYRTTPPQL<u>D</u>EDGSYFL<u>T</u>SKLSVDKSRW<br>QRGDTFICAVMHEALHNHYTQESL<u>S</u>HSPGK | Canine IL4R ECD canine IgG-B Fc hole |
| 105 | TETQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCEDIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETND<br>IFYVEEAKCQNSEFEGNLEGTICFMVPGVLPDTLN<br>TVRIRVRTNKLCYEDDKLWSNWSQAMSIGENTDPT<br>*GGGSGGGGSGGGGSGGGGSGGGGSG*PAPEMLGGPS<br>VFIFPPKPKDTLLIARTPEVTCVVVDLDPEDPEVQ<br>ISWFVDGKQMQTAKTQPREEQFNGTYRVVSVLPIG<br>HQDWLKGKQFTCKVNNKALPSPIERTISKARGQAH<br>QPSVYVLPPSREELSKNTVSL<u>W</u>CLIKDFFPPDIDV<br>EWQSNGQQEPESKYRTTPPQL<u>D</u>EDGSYFLYSKLSV<br>DKSRWQRGDTFICAVMHEALHNHYTQESLSHSPGK | Canine IL13R ECD canine IgG-B Fc knob |
| 106 | SGSVKVLRAPTCFSDYFSTSVCQWNMDAPTNCSAE<br>LRLSYQLNFMGSENRTCVPENGEGAACACSMLMDD<br>FVEADVYQLHLWAGTQLLWSGSFKPSSHVKPRAPG<br>NLTVHPNVSHTWLLRWSNPYPPENHLHAELTYMVN<br>ISSEDDPTDVSVCASGFLCHLLGLRRVETGAPGAR<br>LPPWLCAPRPRRVPGSQCAVISCCRWVLIALTSRG<br>GRWRLTPGLRSQTRYVSVAEGLFGATPRVLCPGTQ<br>AGLASAAREQMSPDPSAFHSIDYEP*GGGSGGGGSG<br>GGGSGGGGSGGGGSG*PKTASTIESKTGEGPKCPVP<br>EIPGAPSVFIFPPKPKDTLSISRTPEVTCLVVDLG<br>PDDSNVQITWFVDNTEMHTAKTRPREEQFNSTYRV<br>VSVLPILHQDWLKGKEFKCKVNSKSLPSAMERTIS<br>KAKGQPHEPQVYVLPPTQEELSENKVSV<u>W</u>CLIKGF<br>HPPDIAVEWEITGQPEPENNYQTTPPQL<u>D</u>SDGTYF<br>LYSRLSVDRSHWQRGNTYTCSVSHEALHSHHTQKS<br>LTQSPGK | Feline IL4R ECD feline IgG-2 Fc knob |
| 107 | SQTQPPVTNLSVSVENLCTVIWTWDPPEGASPNCT<br>LRYFSHFDNKQDKKIAPETHRSKEVPLNERICLQV<br>GSQCSTNESDNPSILVEKCTPPPEGDPESAVTELQ<br>CVWHNLSYMKCTWLPGRNTSPDTNYTLYYWHSSLG<br>KILQCENIYREGQHIGCSFALTNLKDSSFEQHSVQ<br>IVVKDNAGKIRPSFNIVPLTSHVKPDPPHIKRLFF<br>QNGNLYVQWKNPQNFYSRCLSYQVEVNNSQTETHD<br>IFYVEEAKCQNSEFEGNLEGTICFMVPGILPDTLN<br>TVRIRVRTNKLCYEDDRLWSNWSQAMSIGENTDPT<br>*GGGSGGGGSGGGGSGGGGSGGGGSG*PKTASTIESK<br>TGEGPKCPVPEIPGAPSVFIFPPKPKDTLSISRTP<br>EVTCLVVDLGPDDSNVQITWFVDNTEMHTAKTRPR<br>EEQFNSTYRVVSVLPILHQDWLKGKEFKCKVNSKS<br>LPSAMERTISKAKGQPHEPQVYVLPPTQEELSENK<br>VSV<u>SCA</u>IKGFHPPDIAVEWEITGQPEPENNYQTTP<br>PQL<u>D</u>SDGTYFL<u>T</u>SRLSVDRSHWQRGNTYTCSVSHE<br>ALHSHHTQKSLTQSPGK | Feline IL13R ECD feline IgG-2 Fc hole |

| SEQ ID NO: | SEQUENCE | DESCRIPTION |
|---|---|---|
| 108 | SGSVKVLRAPTCFSDYFSTSVCQWNMDAPTNCSAE LRLSYQLNFMGSENRTCVPENGEGAACACSMLMDD FVEADVYQLHLWAGTQLLWSGSFKPSSHVKPRAPG NLTVHPNVSHTWLLRWSNPYPPENHLHAELTYMVN ISSEDDPTDVSVCASGFLCHLLGLRRVETGAPGAR LPPWLCAPRPRRVPGSQCAVISCCRWVLIALTSRG GRWRLTPGLRSQTRYVSVAEGLFGATPRVLCPGTQ AGLASAAREQMSPDPSAFHSIDYEP*GGGGSGGGGSG GGGSGGGGSGGGGSG*PKTASTIESKTGEGPKCPVP EIPGAPSVFIFPPKPKDTLSISRTPEVTCLVVDLG PDDSNVQITWFVDNTEMHTAKTRPREEQFNSTYRV VSVLPILHQDWLKGKEFKCKVNSKSLPSAMERTIS KAKGQPHEPQVYVLPPTQEELSENKVSVSCAIKGF HPPDIAVEWEITGQPEPENNYQTTPPQLD̄SDGTYF LTSRLSVDRSHWQRGNTYTCSVSHEALHSHHTQKS LTQSPGK | Feline IL4R ECD feline IgG-2 Fc hole |
| 109 | SQTQPPVTNLSVSVENLCTVIWTWDPPEGASPNCT LRYFSHFDNKQDKKIAPETHRSKEVPLNERICLQV GSQCSTNESDNPSILVEKCTPPPEGDPESAVTELQ CVWHNLSYMKCTWLPGRNTSPDTNYTLYYWHSSLG KILQCENIYREGQHIGCSFALTNLKDSSFEQHSVQ IVVKDNAGKIRPSFNIVPLTSHVKPDDPPHIKRLFF QNGNLYVQWKNPQNFYSRCLSYQVEVNNSQTETHD IFYVEEA

TABLE 1-continued

Description of Certain Sequences

| SEQ ID NO: | SEQUENCE | DESCRIPTION |
|---|---|---|
| | AITKQREAQFNSTYRVVSVLPIQHQDWLSGKEFKC SVTNVGVPQPISRAISRGKGPSRVPQVYVLPPHPD ELAKSKVSVSCAVKDFYPPDISVEWQSNRWPELEG KYSTTPAQLDGDGSYFLTSKLSLETSRWQQVESFT CAVMHEALHNHFTKTDISESLGK | |
| 113 | TESQPPVTNLSVSVENLCTVIWTWNPPEGVSPNCS LWYFSHFGNKQDKKIAPETHRSKEVPLNERICLQV GSQCSTNESDNPSILVEKCISPPEGDPESAVTELQ CVWHNLSYMKCTWLPGKNASPDTNYTLYYWHSSLG KILQCEDIYREGQHIGCSFALTEVKDSIFEQHSVQ IMVKDNAGKIRPFFNIVPLTSHVKPDPPHIKKLFF QNGDLYVQWKNPQNFYSRCLSYQVEVNNSQTETRD IFSVEEAKCQNPEFEGDLEGTICFMVPGVLPDTVN TVRIRVKTNKLCYEDDKLWSNWSQAMSIGKKADPT *GGGSGGGSGGGSGGGSGGGSGGGSG*PSVFIFPPN PKDALMISRTPVVTCVVVNLSDQYPDVQFSWYVDN TEVHSAITKQREAQFNSTYRVVSVLPIQHQDWLSG KEFKCSVTNVGVPQPISRAISRGKGPSRVPQVYVL PPHPDELAKSKVSVWCLVKDFYPPDISVEWQSNRW PELEGKYSTTPAQLDGDGSYFLYSKLSLETSRWQQ VESFTCAVMHEALHNHFTKTDISESLGK | Equine IL13R ECD equine IgG-2 Fc knob |

DESCRIPTION OF THE EMBODIMENTS

IL13R/IL4R heterodimeric proteins that bind canine IL13 and/or IL4, feline IL13 and/or IL4, and/or equine IL13 and/or IL4 are provided. In some embodiments, the IL13R/IL4R heterodimeric protein comprises a first contiguous polypeptide comprising an extracellular domain of an IL13R polypeptide and an Fc polypeptide and a second contiguous polypeptide comprising an extracellular domain of an IL4R polypeptide and an Fc polypeptide. Methods of producing or purifying IL13R/IL4R heterodimeric proteins and contiguous polypeptides are also provided. Methods of treatment using IL13R/IL4R heterodimeric proteins to bind IL13 and/or IL4 and inhibit IL13- and/or IL-4-mediated signaling are provided. Such methods include, but are not limited to, methods of treating IL13- and/or IL4-induced conditions in companion animal species. Methods of detecting IL13 and/or IL4 in a sample from a companion animal species are also provided.

For the convenience of the reader, the following definitions of terms used herein are provided.

As used herein, numerical terms such as Kd are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary IL13R/IL4R Heterodimeric Proteins

Novel IL13R/IL4R heterodimeric proteins are provided, for example, heterodimeric proteins that bind canine IL13 and/or IL4, feline IL13 and/or IL4, and/or equine IL13 and/or IL4.

"Amino acid sequence," means a sequence of amino acids residues in a peptide or protein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "contiguous polypeptide" herein is used to mean an uninterrupted sequence of amino acids. A contiguous polypeptide is typically translated from a single continuous DNA sequence. It can be made by genetic engineering, for example, by removing the stop codon from the DNA sequence of the first protein, then appending the DNA sequence of the second protein in frame, so that the DNA sequence is expressed as a single protein, Typically, this is accomplished by cloning a cDNA into an expression vector in frame with an existing gene "IL4R," as used herein, is a polypeptide comprising the entirety or a fragment of IL4 receptor subunit alpha that bind to IL-4.

For example, "IL4R" refers to an IL4R polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, IL4R is an extracellular domain fragment that binds IL4. In some such embodiments, the IL4R may be referred to as an IL4R extracellular domain (ECD). In some embodiments, IL4R comprises the amino acid sequence of SEQ ID NO: 7, SEQ ID NO:8, SEQ ID NO: 9, SEQ ID NO: 23, SEQ ID NO: 25, SEQ ID NO: 27, SEQ ID NO: 33, SEQ ID NO: 35, or SEQ ID NO: 37.

"IL13R," as used herein, is a polypeptide comprising the entirety or a portion of IL13 receptor subunit alpha-1 that binds to IL-13.

For example, "IL13R" refers to an IL13R polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, IL13R is an extracellular domain fragment that binds IL13. In some such embodiments, the IL13R may be referred to as an IL13R extracellular domain (ECD). In some embodiments, the IL13R polypeptide comprises the amino acid sequence of SEQ ID NO: 10, SEQ ID NO: 11, SEQ ID NO: 12, SEQ ID NO: 22, SEQ ID NO: 24, SEQ ID NO: 26, SEQ ID NO: 32, SEQ ID NO: 34, or SEQ ID NO: 36.

The term "companion animal species" refers to an animal suitable to be a companion to humans. In some embodiments, a companion animal species is a small mammal, such as a canine, feline, dog, cat, horse, rabbit, ferret, guinea pig, rodent, etc. In some embodiments, a companion animal species is a farm animal, such as a horse, cow, pig, etc.

An "extracellular domain" ("ECD") is the portion of a polypeptide that extends beyond the transmembrane domain into the extracellular space. The term "extracellular domain," as used herein, may comprise a complete extracellular domain or may comprise a truncated extracellular domain missing one or more amino acids, that binds to its ligand. The composition of the extracellular domain may depend on the algorithm used to determine which amino acids are in the membrane. Different algorithms may predict, and different systems may express, different extracellular domains for a given protein.

An extracellular domain of an IL4R polypeptide may comprise a complete extracellular domain or a truncated extracellular domain of IL4R that binds IL4. As used herein, the terms "extracellular domain of an IL4R polypeptide," "IL4R ECD," and similar terms refer to an IL4R polypeptide that does not comprise a transmembrane domain or cytoplasmic domain, even if the term follows an open transitional word, such as "comprising," "comprises," and the like. In some embodiments, an extracellular domain of an IL4R polypeptide is an extracellular domain of an IL4R polypeptide derived from a companion species animal. For example, in some embodiments, an extracellular domain of an IL4R polypeptide is derived from canine IL4R, feline IL4R or equine IL4R. In some embodiments, an extracellular domain of an IL4R polypeptide comprises the amino acid sequence of SEQ ID NO: 23, SEQ ID NO: 25, or SEQ ID NO: 27, or any fragment thereof. In some embodiments, an extracellular domain of an IL4R polypeptide comprises the amino acid sequence of SEQ ID NO: 33, SEQ ID NO: 35, or SEQ ID NO: 37, or any fragment thereof.

An extracellular domain of an IL13R polypeptide may comprise a complete extracellular domain or a truncated extracellular domain of IL13R that binds IL13. As used herein, the terms "extracellular domain of an IL13R polypeptide," "IL13R ECD," and similar terms refer to an IL13R polypeptide that does not comprise a transmembrane domain or cytoplasmic domain, even if the term follows an open transitional word, such as "comprising," "comprises," and the like. In some embodiments, an extracellular domain of an IL13R polypeptide is an extracellular domain of an IL13R polypeptide derived from a companion species animal. For example, in some embodiments, an extracellular domain of an IL13R polypeptide is derived from canine IL13R, feline IL13R or equine IL13R. In some embodiments, an extracellular domain of an IL13R polypeptide comprises the amino acid sequence of SEQ ID NO: 22, SEQ ID NO: 24, or SEQ ID NO: 26, or any fragment thereof. In some embodiments, an extracellular domain of an IL13R polypeptide comprises the amino acid sequence of SEQ ID NO: 32, SEQ ID NO: 34, or SEQ ID NO: 36, or any fragment thereof.

The terms "IL13R/IL4R heterodimeric protein" and "IL4R/IL13R heterodimeric protein" are used interchangeably to refer to a heterodimeric protein comprising a first contiguous polypeptide comprising an IL13R polypeptide and a second contiguous polypeptide comprising an IL4R polypeptide.

In some embodiments, the first contiguous polypeptide and/or second contiguous polypeptide comprises an Fc polypeptide.

The IL13R/IL4R heterodimeric protein of the invention may comprise an extracellular domain of a IL13R polypeptide and/or an extracellular domain of a IL4R polypeptide, wherein the polypeptides are derived from a companion animal species. For example, a heterodimeric protein may comprise an extracellular domain of an IL4R polypeptide from a dog, cat, or horse and/or may comprise an extracellular domain of an IL13R polypeptide from a dog, cat, or horse.

"Wild-type" refers to a non-mutated version of a polypeptide that occurs in nature, or a fragment thereof. A wild-type polypeptide may be produced recombinantly. A "wildtype IL13R ECD" or a "wildtype IL4R ECD" refers to a protein having an amino acid sequence that is identical to the same portion of an extracellular domain of an IL13R or IL4R that occurs in nature.

A "variant" is a nucleic acid molecule or polypeptide that differs from a referent nucleic acid molecule or polypeptide by single or multiple amino acid substitutions, deletions, and/or additions and substantially retains at least one biological activity of the referent nucleic acid molecule or polypeptide.

A "biologically active" entity, or an entity having "biological activity," is an entity having any function related to or associated with a metabolic or physiological process, and/or having structural, regulatory, or biochemical functions of a naturally-occurring molecule. Biologically active polynucleotide fragments are those exhibiting similar activity, but not necessarily identical, to an activity of a polynucleotide of the present invention. A biologically active polypeptide or fragment thereof includes one that can participate in a biological reaction, including, but not limited to, a ligand-receptor interaction or antigen-antibody binding. The biological activity can include an improved desired activity, or a decreased undesirable activity. An entity may demonstrate biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that may be detected as unique for the polynucleotide molecule, and when it can be used as a primer in a polymerase chain reaction (PCR).

As used herein, "percent (%) amino acid sequence identity" and "homology" with respect to a nucleic acid molecule or polypeptide sequence are defined as the percentage of nucleotide or amino acid residues in a referent sequence that are identical with the nucleotide or amino acid residues in the specific nucleic acid molecule or polypeptide sequence, after aligning the sequences and introducing gaps, if necessary to achieve the maximum percent sequence identity, and not considering any conservative substitutions as part of the sequence identity. Alignment for purposes of determining percent sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

In some embodiments, a variant has at least about 50% sequence identity with the referent nucleic acid molecule or polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, deleted, at the N- or C-terminus of the polypeptide. In some embodiments, a variant has at least about 50% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 98% sequence identity with the sequence of the referent nucleic acid or polypeptide.

In some embodiments, a contiguous polypeptide comprises an extracellular domain of an IL13R polypeptide having at least 85%, at least 90%, at least 95%, at least 98% sequence identity to the amino acid sequence of SEQ ID NO: 22, SEQ ID NO: 24, SEQ ID NO: 26, SEQ ID NO: 32, SEQ ID NO: 34, or SEQ ID NO: 36. In some embodiments, a contiguous polypeptide comprises an extracellular domain of an IL4R polypeptide having at least 85%, at least 90%, at least 95%, at least 98% sequence identity to the amino acid sequence of SEQ ID NO: 23, SEQ ID NO: 25, SEQ ID NO: 27, SEQ ID NO: 33, SEQ ID NO: 35, or SEQ ID NO: 37.

As used herein, "position corresponding to position n," wherein n is any number, refers to an amino acid position of a subject polypeptide that aligns with position n of a reference polypeptide after aligning the amino acid sequences of the subject and reference polypeptides and introducing gaps. Alignment for purposes of whether a position of a subject polypeptide corresponds with position n of a reference polypeptide can be achieved in various ways that are within the skill in the art, for instance, using publicly available computer software such as BLAST, BLAST-2, CLUSTAL OMEGA, ALIGN, or MEGALIGN™ (DNASTAR) software. Those skilled in the art can determine appropriate parameters for alignment, including any parameters needed to achieve maximal alignment over the full length of two sequences being compared. In some embodiments, the subject polypeptide and the reference polypeptide are of different lengths.

In some embodiments, the contiguous polypeptide comprises an extracellular domain of an IL13R polypeptide comprising a cysteine at a position corresponding to position 18 of SEQ ID NO: 22, at a position corresponding to position 18 of SEQ ID NO: 24, or at a position corresponding to position 18 of SEQ ID NO: 26. In some embodiments, the contiguous polypeptide comprises an extracellular domain of an IL13R polypeptide comprising a cysteine at position 18 of SEQ ID NO: 22, at position 18 of SEQ ID NO: 24, at position 18 of SEQ ID NO: 26, at position 15 of SEQ ID NO: 32, at position 15 of SEQ ID NO: 34, or at position 15 of SEQ ID NO: 36.

A "point mutation" is a mutation that involves a single nucleotide or amino acid residue. The mutation may be the loss of a nucleotide or amino acid, substitution of one nucleotide or amino acid residue for another, or the insertion of an additional nucleotide or amino acid residue.

An amino acid substitution may include but is not limited to the replacement of one amino acid in a polypeptide with another amino acid. Exemplary substitutions are shown in Table 2. Amino acid substitutions may be introduced into a molecule of interest and the products screened for a desired activity, for example, retained/improved antigen binding, decreased immunogenicity, or improved ADCC or CDC or enhanced pharmacokinetics.

TABLE 2

| Original Residue | Exemplary Substitutions |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes with another class.

A "fusion partner," as used herein, refers to an additional component of an IL13R/IL4R contiguous polypeptide, such as an additional polypeptide, such as albumin, an albumin binding fragment, or a fragment of an immunoglobulin molecule. A fusion partner may comprise an oligomerization domain such as an Fc domain of a heavy chain immunoglobulin.

The term "IgX Fc" or "IgX Fc polypeptide" means the Fc region is derived from a particular antibody isotype (e.g., IgG, IgA, IgD, IgE, IgM, etc.), where "X" denotes the antibody isotype. Thus, "IgG" or "IgG Fc" denotes the Fc region of a γ chain, "IgA" or "IgA Fc" denotes the Fc region of an α chain, "IgD" or "IgD Fc" denotes the Fc region of a δ chain, "IgE" or "IgE Fc" denotes the Fc region of an ε chain, "IgM" or "IgM Fc" denotes the Fc region of a μ chain, etc.

In some embodiments, the Fc polypeptide or the IgG Fc region comprises CH1, hinge, CH2, CH3, and CL1. In some embodiments, the IgG Fc polypeptide comprises the hinge, CH2, and CH3, but does not comprise CH1 or CL. In some embodiments, the IgG Fc polypeptide comprises CH2 and CH3, but does not comprise CH1, the hinge, or CL. In some embodiments, the IgG Fc polypeptide comprises CH1, hinge, CH2, and CH3, with or without CL1.

"IgXN Fc" or "IgXN Fc polypeptide" denotes that the Fc region is derived from a particular subclass of antibody isotype (such as canine IgG subclass A, B, C, or D; feline IgG subclass 1, 2a, or 2b; or equine IgG subclass IgG1, IgG2, IgG3, IgG4, IgG5, IgG6, or IgG7, etc.), where "N" denotes the subclass.

In some embodiments, IgX or IgXN regions are derived from a companion animal, such as a dog, a cat, or a horse. In some embodiments, IgG regions are isolated from canine γ heavy chains, such as IgGA, IgGB, IgGC, or IgGD. In some instances, IgG Fc regions are isolated from feline γ heavy chains, such as IgG1a, IgG1b, or IgG2. In other instances, IgG regions are isolated from equine γ heavy chains, such as IgG1, IgG2, IgG3, IgG4, IgG5, IgG6, or IgG7. Polypeptides comprising an Fc region of IgGA, IgGB, IgGC, or IgGD may provide for higher expression levels in recombination production systems.

In some embodiments, a contiguous polypeptide comprises a first variant IgG Fc polypeptide comprising a "knob" mutation and a second variant IgG Fc polypeptide comprising a "hole" mutation. Nonlimiting exemplary knob and hole mutations are described, for example, in Merchant, A. M. et al. An efficient route to human bispecific IgG. *Nat Biotechnol*, 16(7):677-81 (1998).

A "knob" mutation," as used herein, refers to an interfacing mutation of a molecule (e.g., an Fc polypeptide) that comprises a bulky amino acid.

A "hole mutation," as used herein, refers to an interfacing mutation of a molecule (e.g., an Fc polypeptide) that comprises one or more smaller amino acids.

In some embodiments, a variant IgG Fc polypeptide comprises a knob mutation. In some embodiments, a variant IgG Fc polypeptide comprises an amino acid substitution at a position corresponding to position 138 of SEQ ID NO: 38; position 137 of SEQ ID NO: 39, position 137 of SEQ ID NO: 40; position 138 of SEQ ID NO: 41; position 154 of SEQ ID NO: 42, SEQ ID NO: 43, SEQ ID NO: 44, SEQ ID NO: 45, or SEQ ID NO: 46; or position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises an amino acid substitution at position 138 of SEQ ID NO: 38; position 137 of SEQ ID NO: 39; position 137 of SEQ ID NO: 40; position 138 of SEQ ID NO: 41; position 154 of SEQ ID NO: 42, SEQ ID NO: 43, SEQ ID NO: 44, SEQ ID NO: 45, or SEQ ID NO: 46; or position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises a tryptophan at a position corresponding to position 138 of SEQ ID NO: 38; position 137 of SEQ ID NO: 39; position 137 of SEQ ID NO: 40; position 138 of SEQ ID NO: 41, or position 154 of SEQ ID NO: 42, SEQ ID NO: 43, SEQ ID NO: 44, SEQ ID NO: 45, or SEQ ID NO: 46; or position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises a tryptophan at position 138 of SEQ ID NO: 38; position 137 of SEQ ID NO: 39; position 137 of SEQ ID NO: 40; position 138 of SEQ ID NO: 41; position 154 of SEQ ID NO: 42, SEQ ID NO: 43, SEQ ID NO: 44, SEQ ID NO: 45, or SEQ ID NO: 46; or position 130 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises the amino acid sequence of SEQ ID NO: 54, 55, 56, 57, 66, 67, 68, 69, 70, 81, 82, 83, 84, 85, 86, or 87.

In some embodiments, a variant IgG Fc polypeptide comprises a hole mutation. In some embodiments, a variant IgG Fc polypeptide comprises an amino acid substitution at a position corresponding to position 138 and/or position 140 and/or position 181 of SEQ ID NO: 38; position 137 and/or position 139 and/or position 180 of SEQ ID NO: 39; position 137 and/or position 139 and/or position 180 of SEQ ID NO: 40; position 138 and/or position 140 and/or position 181 of SEQ ID NO: 41; position 154 and/or position 156 and/or position 197 of SEQ ID NO: 42, SEQ ID NO: 43, SEQ ID NO: 44, SEQ ID NO: 45, or SEQ ID NO: 46; and/or position 130 and/or position 132 and/or position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises an amino acid substitution at position 138 and/or position 140 and/or position 181 of SEQ ID NO: 38; position 137 and/or position 139 and/or position 180 of SEQ ID NO: 39; position 137 and/or position 139 and/or position 180 of SEQ ID NO: 40; position 138 and/or position 140 and/or position 181 of SEQ ID NO: 41; position 154 and/or position 156 and/or position 197 of SEQ ID NO: 42, SEQ ID NO: 43, SEQ ID NO: 44, SEQ ID NO: 45, or SEQ ID NO: 46; or position 130 and/or position 132 and/or position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises a serine at a position corresponding to position 138 and/or an alanine at a position corresponding to position 140 and/or a threonine at a position corresponding to position 181 of SEQ ID NO: 38; a serine at a position corresponding to position 137 and/or an alanine at a position corresponding to position 139 and/or a threonine at a position corresponding to position 180 of SEQ ID NO: 39; a serine at a position corresponding to position 137 and/or an alanine at a position corresponding to position 139 and/or a threonine at a position corresponding to position 180 of SEQ ID NO: 40; a serine at a position corresponding to position 138 and/or an alanine at a position corresponding to position 140 and/or a threonine at a position corresponding to position 181 of SEQ ID NO: 41; a serine at a position corresponding to position 154 and/or an alanine at a position corresponding to position 156 and/or a threonine at a position corresponding to position 197 of SEQ ID NO: 42, SEQ ID NO: 43, SEQ ID NO: 44, SEQ ID NO: 45, or SEQ ID NO: 46; or a serine at a position corresponding to position 130 and/or an alanine at a position corresponding to position 132 and/or a threonine at a position corresponding to position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises a serine at position 138 and/or an alanine at position 140 and/or a threonine at position 181 of SEQ ID NO: 38; a serine at position 137 and/or an alanine at position 139 and/or a threonine at position 180 of SEQ ID NO: 39; a serine at position 137 and/or an alanine at position 139 and/or a threonine at position 180 of SEQ ID NO: 40; a serine at position 138 and/or an alanine at position 140 and/or a threonine at position 181 of SEQ ID NO: 41; a serine at position 154 and/or an alanine at position 156 and/or a threonine at position 197 of SEQ ID NO: 42, SEQ ID NO: 43, SEQ ID NO: 44, SEQ ID NO: 45, or SEQ ID NO: 46; or a serine at position 130 and/or an alanine at position 132 and/or a threonine at position 173 of SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, a variant IgG Fc polypeptide comprises the amino acid sequence of SEQ ID NO: 58, 59, 60, 61, 62, 63, 64, 65, 71, 72, 73, 74, 75, 76, 77, 78, 79, 80, 88, 89, 90, 91, 92, 93, 94, 95, 96, 97, 98, 99, 100, or 101.

A "signal sequence" refers to a sequence of amino acid residues or polynucleotides encoding such, which facilitates secretion of a polypeptide of interest and is typically cleaved upon export of the polypeptide to the outside of the cell surface membrane.

A "linker" refers to one or more amino acid residues that connects a first polypeptide with a second polypeptide.

In some embodiments, the linker is a glycine-rich and/or serine-rich, flexible, non-structural linker. In some embodiments, a linker comprises the amino acids G (Gly) and/or S (Ser). For example, a linker may comprise G or a repeat of G (e.g., GG, GGG, etc.); GS or a repeat of GS (e.g., GSGS (SEQ ID NO: 114), GSGSGS (SEQ ID NO: 115), etc.); GGS or a repeat of GGS (e.g., GGSGGS (SEQ ID NO: 116), GGSGGSGGS (SEQ ID NO: 117), etc.); GGGS (SEQ ID NO: 118) or a repeat of GGG-S(SEQ ID NO: 119) (e.g., GGGSGGGS (SEQ ID NO: 120), GGGSGGGSGGGS (SEQ ID NO: 121), etc.); GSS or a repeat of GSS (e.g., GSSGSS (SEQ ID NO: 122), GSSGSSGSS (SEQ ID NO: 123), etc.); or GGSS (SEQ ID NO: 124) or a repeat of GGSS (SEQ ID NO: 125) (e.g., GGSSGGSS (SEQ ID NO: 126) GGSSGGSSGGSS (SEQ ID NO: 127), etc.).

In some embodiments, the contiguous polypeptide comprises at least one linker. In some embodiments, the contiguous polypeptide comprises an optional signal sequence, and at least one optional linker. In some embodiments, the contiguous polypeptide does not comprise a signal sequence, or a linker. In some embodiments, the contiguous polypeptide is translated with a signal sequence, but the signal sequence is cleaved from the contiguous polypeptide.

In some embodiments, a heterodimeric protein comprises a) a first contiguous polypeptide comprising at least one IL13R extracellular domain (ECD) and a first Fc polypeptide and b) a second contiguous polypeptide comprising at least one IL4R ECD and a second Fc polypeptide, wherein the IL13R ECD and/or the IL4R ECD are derived from a companion animal species.

In some embodiments, a first contiguous polypeptide or a second contiguous polypeptide has the formula:

IL13R(n)-L-Fc or

IL4R(n)-L-Fc, wherein IL13R(n) is at least one IL13R extracellular domain (ECD) polypeptide derived from a companion animal species, IL4R(n) is at least one IL4R ECD polypeptide derived from a companion animal species, (n) is one, two, three, four, or more ECD polypeptides, L is an optional linker, Fc is a variant Fc polypeptide, such as a variant Fc polypeptide comprising knob or a hole mutation.

In addition, other binding partner(s) may be included in the contiguous polypeptide before, after, and/or between any one or more IL13R or IL4R ECD polypeptide(s). Other potential binding partners include: IL5, IL6, IL17, IL22, IL31, LFA-1, TNF-α, TSLP, and/or IgE.

In some embodiments, the heterodimeric protein comprises a first contiguous polypeptide comprising the amino acid sequence of SEQ ID NO: 103, SEQ ID NO: 105, SEQ ID NO: 107, SEQ ID NO: 109, SEQ ID NO: 111, or SEQ ID NO: 113.

In some embodiments, the heterodimeric protein comprises a second contiguous polypeptide comprising the amino acid sequence of SEQ ID NO: 102, SEQ ID NO: 104, SEQ ID NO: 106, SEQ ID NO: 108, SEQ ID NO: 110, or SEQ ID NO: 112.

Exemplary Expression and Production

Polynucleotide sequences that encode all or part (e.g., the extracellular domain) of a contiguous polypeptide with or without a signal sequence are provided. If a homologous signal sequence (i.e., a signal sequence of native IL-4R or IL13R) is not used in the construction of the nucleic acid molecule, then another signal sequence may be used, for example, any one of the signal sequences described in PCT/US06/02951.

Typically, nucleotide sequence encoding the polypeptide of interest, such as a contiguous polypeptide, is inserted into an expression vector, suitable for expression in a selected host cell.

A "vector" is a plasmid that can be used to transfer DNA sequences from one organism to another or to express a gene of interest. A vector typically includes an origin of replication and regulatory sequences which regulate the expression of the gene of interest, and may or may not carry a selective marker gene, such as an antibiotic resistance gene. A vector is suitable for the host cell in which it is to be expressed. A vector may be termed a "recombinant vector" when the gene of interest is present in the vector.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated."

In some embodiments, the heterodimeric protein or contiguous polypeptide is isolated using chromatography, such as size exclusion chromatography, ion exchange chromatography, protein A column chromatography, hydrophobic interaction chromatography, and CHT chromatography.

The terms "label" and "detectable label" mean a moiety attached to a IL13R/IL4R contiguous polypeptide to render it detectable. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Exemplary IL13R/IL4R Heterodimeric Proteins as Decoy Receptor Traps

The IL13R/IL4R heterodimeric proteins of the invention can function as decoy receptors for trapping IL13 and/or IL4 and inhibiting their interaction with IL13R and/or IL4R on cell surfaces. Decoy receptors, such as those of the invention, recognize their ligands with high affinity and specificity but are structurally incapable of signaling. They compete with wild-type receptors for ligand binding and participate in ligand/receptor interactions, thus modulating the activity of or the number of functioning receptors and/or the cellular activity downstream from the receptors. Decoy receptors can act as molecular traps for agonist ligands and thereby inhibit ligand-induced receptor activation.

"IL13" as used herein refers to any native IL13 that results from expression and processing of IL13 in a cell. The term includes IL13 from any vertebrate source, including mammals such as primates (e.g., humans and cynomolgus monkeys) and rodents (e.g., mice and rats), and companion animals (e.g., dogs, cats, and equine), unless otherwise indicated. The term also includes naturally occurring variants of IL13, e.g., splice variants or allelic variants.

In some embodiments, a canine IL13 comprises the amino acid sequence of SEQ ID NO: 4. In some embodiments, a feline IL13 comprises the amino acid sequence of SEQ ID NO: 5. In some embodiments, an equine IL13 comprises the amino acid sequence of SEQ ID NO: 6.

"IL4" as used herein refers to any native IL4 that results from expression and processing of IL4 in a cell. The term includes IL4 from any vertebrate source, including mammals such as primates (e.g., humans and cynomolgus monkeys) and rodents (e.g., mice and rats), and companion animals (e.g., dogs, cats, and equine), unless otherwise indicated. The term also includes naturally occurring variants of IL4, e.g., splice variants or allelic variants.

In some embodiments, a canine IL4 comprises the amino acid sequence of SEQ ID NO: 1. In some embodiments, a feline IL4 comprises the amino acid sequence of SEQ ID NO: 2. In some embodiments, an equine IL4 comprises the amino acid sequence of SEQ ID NO: 3.

The invention provides IL13R/IL4R heterodimeric proteins as therapeutic agents. The IL13R/IL4R heterodimeric proteins of the invention bind to IL13 and/or IL4, described in more detail herein, which have been demonstrated to be associated with allergic diseases. In various embodiments, IL13R/IL4R heterodimeric proteins can bind IL13 and/or IL4 with very high affinity. In various embodiments, the IL13R/IL4R heterodimeric proteins can interfere with IL13 and/or IL4 signaling.

The term "affinity" means the strength of the sum total of noncovalent interactions between a single binding site of a molecule (for example, a receptor) and its binding partner (for example, a ligand). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

The terms "$K_D$," "$K_d$," "Kd" or "Kd value" as used interchangeably to refer to the equilibrium dissociation constant of a receptor fusion-ligand interaction. In some embodiments, the $K_d$ of the fusion molecule to its ligand is measured by using biolayer interferometry assays using a biosensor, such as an Octet® System (Pall ForteBio LLC, Fremont, CA) according to the supplier's instructions. Briefly, biotinylated antigen is bound to the sensor tip and the association of fusion molecule is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "$k_{on}$" refers to the rate constant for association of a molecule X to its partner Y and the term "$k_{off}$" refers to the rate constant for dissociation of a molecule X or partner Y from the molecule X/partner Y complex.

The term "binds" to a substance is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

In some embodiments, an IL13R/IL4R heterodimeric protein binds to canine IL13 and/or IL4, feline IL13 and/or IL4, or equine IL13 and/or IL4 with a dissociation constant (Kd) of less than $5\times10^{-6}$ M, less than $1\times10^{-6}$ M, less than $5\times10^{-7}$M, less than $1\times10^{-7}$M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, or less than $1\times10^{-12}$M, as measured by biolayer interferometry. In some embodiments, an IL13R/IL4R heterodimeric protein binds to canine IL13 and/or IL4, feline IL13 and/or IL4, or equine IL13 and/or IL4 with a Kd of between $5\times10^{-6}$ M and $1\times10^{-6}$ M, between $5\times10^{-6}$ M and $5\times10^{-7}$M, between $5\times10^{-6}$ M and $1\times10^{-7}$ M, between $5\times10^{-6}$ M and $5\times10^{-8}$ M, $5\times10^{-6}$ M and $1\times10^{-8}$ M, between $5\times10^{-6}$ M and $5\times10^{-9}$ M, between $5\times10^{-6}$ M and $1\times10^{-9}$ M, between $5\times10^{-6}$ M and $5\times10^{-10}$ M, between $5\times10^{-6}$ M and $1\times10^{-10}$ M, between $5\times10^{-6}$ M and $5\times10^{-11}$M, between $5\times10^{-6}$ M and $1\times10^{-11}$ M, between $5\times10^{-6}$ M and $5\times10^{-12}$M, between $5\times10^{-6}$ M and $1\times10^{-12}$M, between $1\times10^{-6}$ M and $5\times10^{-7}$ M, between $1\times10^{-6}$ M and $1\times10^{-7}$ M, between $1\times10^{-6}$ M and $5\times10^{-8}$M, $1\times10^{-6}$ M and $1\times10^{-8}$M, between $1\times10^{-6}$ M and $5\times10^{-9}$M, between $1\times10^{-6}$ M and $1\times10^{-9}$ M, between $1\times10^{-6}$ M and $5\times10^{-10}$ M, between $1\times10^{-6}$ M and $1\times10^{-10}$ M, between $1\times10^{-6}$ M and $5\times10^{-11}$M, between $1\times10^{-6}$M and $1\times10^{-11}$M, between $1\times10^{-6}$M and $5\times10^{-12}$ M, between $1\times10^{-6}$ M and $1\times10^{-12}$M, between $5\times10^{-7}$ M and $1\times10^{-7}$ M, between $5\times10^{-7}$M and $5\times10^{-8}$M, $5\times10^{-7}$M and $1\times10^{-8}$M, between $5\times10^{-7}$M and $5\times10^{-9}$M, between $5\times10^{-7}$M and $1\times10^{-9}$ M, between $5\times10^{-7}$M and $5\times10^{-10}$ M, between $5\times10^{-7}$ M and $1\times10^{-10}$ M, between $5\times10^{-7}$M and $5\times10^{-11}$ M, between $5\times10^{-7}$ M and $1\times10^{-11}$M, between $5\times10^{-7}$ M and $5\times10^{-12}$M, between $5\times10^{-7}$M and $1\times10^{-12}$M, between $1\times10^{-7}$ M and $5\times10^{-8}$ M, $1\times10^{-7}$ M and $1\times10^{-8}$ M, between $1\times10^{-7}$ M and $5\times10^{-9}$ M, between $1\times10^{-7}$ M and $1\times10^{-9}$ M, between $1\times10^{-7}$ M and $5\times10^{-10}$ M, between $1\times10^{-7}$ M and $1\times10^{-10}$ M, between $1\times10^{-7}$ M and $5\times10^{-11}$ M, between $1\times10^{-7}$ M and $1\times10^{-11}$ M, between $1\times10^{-7}$ M and $5\times10^{-12}$ M, between $1\times10^{-7}$ M and $1\times10^{-12}$ M, between $5\times10^{-8}$M and $1\times10^{-8}$M, between $5\times10^{-8}$M and $5\times10^{-9}$M, between $5\times10^{-8}$M and $1\times10^{-9}$ M, between $5\times10^{-8}$M and $5\times10^{-10}$ M, between $5\times10^{-8}$M and $1\times10^{-10}$ M, between $5\times10^{-8}$M and $5\times10^{-11}$ M, between $5\times10^{-8}$ M and $1\times10^{-11}$ M, between $5\times10^{-8}$M and $5\times10^{-12}$M, between $5\times10^{-8}$M and $1\times10^{-12}$ M, $1\times10^{-8}$M and $5\times10^{-9}$M, between $1\times10^{-8}$M and $1\times10^{-9}$ M, between $1\times10^{-8}$M and $5\times10^{-10}$ M, between $1\times10^{-8}$ M and $1\times10^{-10}$ M, between $1\times10^{-8}$M and $5\times10^{-11}$ M, between $1\times10^{-8}$ M and $1\times10^{-11}$ M, between $1\times10^{-8}$ M and $5\times10^{-12}$M, between $1\times10^{-8}$M and $1\times10^{-12}$M, between $5\times10^{-9}$M and $1\times10^{-9}$M, between $5\times10^{-9}$ M and $5\times10^{-10}$ M, between $5\times10^{-9}$ M and $1\times10^{-10}$ M, between $5\times10^{-9}$ M and $5\times10^{-11}$M, between $5\times10^{-9}$ M and $1\times10^{-11}$ M, between $5\times10^{-9}$ M and $5\times10^{-12}$ M, between $5\times10^{-9}$ M and $1\times10^{-12}$ M, between $1\times10^{-9}$ M and $5\times10^{-10}$ M, between $1\times10^{-9}$ M and $1\times10^{-10}$ M, between $1\times10^{-9}$M and $5\times10^{-11}$ M, between $1\times10^{-9}$M and $1\times10^{-11}$ M, between $1\times10^{-9}$M and $5\times10^{-12}$ M, between $1\times10^{-9}$M and $1\times10^{-12}$ M, between $5\times10^{-10}$ M and $1\times10^{-10}$ M, between $5\times10^{-10}$ M and $5\times10^{-11}$ M, between, $1\times10^{-10}$ M and $5\times10^{-11}$ M, $1\times10^{-10}$ M and $1\times10^{-11}$ M, between $1\times10^{-10}$ M and $5\times10^{-12}$ M, between $1\times10^{-10}$ M and $1\times10^{-12}$ M, between $5\times10^{-11}$M and $1\times10^{-12}$ M, between $5\times10^{-11}$ M and $5\times10^{-12}$ M, between $5\times10^{-11}$ M and $1\times10^{-12}$ M, between $1\times10^{-11}$ M and $5\times10^{-12}$ M, or between $1\times10^{-11}$ M and $1\times10^{-12}$ M, as measured by biolayer interferometry. In some embodiments, an IL13R/IL4R heterodimeric protein binds to canine IL13 and/or IL4, feline IL13 and/or IL4, and/or equine IL13 and/or IL4.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

The term "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15% 20%, 25%, 30%, 35%, 40%, 45%, 50%, 60%, 70%, 80%, 90%, or 100% compared to the reference value.

In some embodiments, an IL13R/IL4R heterodimeric protein may reduce IL13 and/or IL4 signaling in a companion animal species by at least 10%, at least 15%, at least 20%, at least 25%, at least 30%, at least 35%, at least 40%, at least 45%, at least 50%, at least 60%, at least 70%, at least 80%, at least 90%, or 100% compared to IL13 and/or IL4 signaling in the absence of the fusion molecule. In some embodiments, signaling is measured by a reduction in IL4-dependent TF-1 cell proliferation. In some embodiments, the reduction in IL13 and/or IL4 signaling or the reduction in proliferation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where the fusion molecule is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

Exemplary Uses of IL13R/IL4R Heterodimeric Proteins and Pharmaceutical Compositions The IL13R/IL4R heterodimeric proteins or pharmaceutical compositions comprising the IL13R/IL4R heterodimeric proteins of the invention may be useful for treating an IL13- and/or IL4-induced condition. As used herein, an "IL13 or IL4-induced condition" means a disease associated with, caused by, or characterized by, elevated levels or altered distribution of IL13 or IL4. Such IL13 and/or IL4-induced conditions include, but are not limited to, a pruritic or an allergic disease. In some embodiments, the IL13- and/or IL4-induced condition is atopic dermatitis, pruritus, asthma, psoriasis, scleroderma, or eczema. An IL13- or IL4-induced condition may be exhibited in a companion animal, including, but not limited to, canine, feline, or equine.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, an IL13R/IL4R heterodimeric proteins or pharmaceutical compositions comprising it can be utilized in accordance with the methods herein to treat IL13- or IL4-induced conditions. In some embodiments, an IL13R/IL4R heterodimeric proteins or pharmaceutical compositions is administered to a companion animal, such as a canine, a feline, or equine, to treat an IL13- and IL4-induced condition.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, IL13R/IL4R heterodimeric protein or pharmaceutical composition comprising an IL13R/IL4R heterodimeric protein is administered parenterally, by subcutaneous administration, intravenous infusion, or intramuscular injection. In some embodiments, an IL13R/IL4R heterodimeric protein or pharmaceutical composition comprising an IL13R/IL4R heterodimeric protein is administered as a bolus injection or by continuous infusion over a period of time. In some embodiments, an IL13R/IL4R heterodimeric protein or pharmaceutical composition comprising an IL13R/IL4R heterodimeric protein is administered by an intramuscular, an intraperitoneal, an intracerebrospinal, a subcutaneous, an intra-arterial, an intrasynovial, an intrathecal, or an inhalation route.

An IL13R/IL4R heterodimeric protein described herein may be administered in an amount in the range of 0.1 mg/kg body weight to 100 mg/kg body weight per dose. In some embodiments, an IL13R/IL4R heterodimeric protein may be administered in an amount in the range of 0.1 mg/kg body weight to 50 mg/kg body weight per dose. In some embodiments, an IL13R/IL4R heterodimeric protein may be administered in an amount in the range of 1 mg/kg body weight to 10 mg/kg body weight per dose. In some embodiments, an IL13R/IL4R heterodimeric protein may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, or in the range of 5 mg/kg body weight to 50 mg/kg body weight.

An IL13R/IL4R heterodimeric protein or a pharmaceutical composition comprising an IL13R/IL4R heterodimeric protein can be administered to a companion animal at one time or over a series of treatments. For example, IL13R/IL4R heterodimeric protein or a pharmaceutical composition comprising an IL13R/IL4R heterodimeric protein may be administered at least once, more than once, at least twice, at least three times, at least four times, or at least five times.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the method comprises administering in combination with an IL13R/IL4R heterodimeric protein or a pharmaceutical composition comprising an IL13R/IL4R heterodimeric protein, a Jak inhibitor, a PI3K inhibitor, an AKT inhibitor, or a MAPK inhibitor. In some embodiments, the method comprises administering in combination with an IL13R/IL4R heterodimeric protein or a pharmaceutical composition comprising an IL13R/IL4R contiguous polypeptide, an anti-IL17 antibody, an anti-TNFα antibody, an anti-CD20 antibody, an anti-CD19 antibody, an anti-CD25 antibody, an anti-IL31 antibody, an anti-IL23 antibody, an anti-IgE antibody, an anti-CD11α antibody, anti-IL6R antibody, anti-α4-Intergrin antibody, an anti-IL12 antibody, an anti-IL1β antibody, or an anti-BlyS antibody.

Provided herein are methods of exposing to a cell an IL13R/IL4R heterodimeric protein or a pharmaceutical composition comprising an IL13R/IL4R heterodimeric protein under conditions permissive for binding to IL13 and/or IL4. In some embodiments, the cell is exposed to the IL13R/IL4R heterodimeric protein or pharmaceutical composition ex vivo. In some embodiments, the cell is exposed to the IL13R/IL4R heterodimeric protein or pharmaceutical composition in vivo. In some embodiments, a cell is exposed to the IL13R/IL4R heterodimeric protein. In some embodiments, a cell is exposed to the IL13R/IL4R heterodimeric protein or the pharmaceutical composition under conditions permissive for binding of the heterodimeric protein to extracellular IL13 and/or IL4. In some embodiments, a cell may be exposed in vivo to the IL13R/IL4R heterodimeric protein or the pharmaceutical composition by any one or more of the administration methods described herein, including but not limited to, intraperitoneal, intramuscular, intravenous injection into the subject. In some embodiments, a cell may be exposed ex vivo to the IL13R/IL4R heterodimeric protein or the pharmaceutical composition by exposing the cell to a culture medium comprising the heterodimeric protein or the pharmaceutical composition. In some embodiments, the permeability of the cell membrane may be affected using any number of methods understood by those of skill in the art (such as electroporating the cells or exposing the cells to a solution containing calcium chloride) before exposing the cell to a culture medium comprising the fusion molecule or the pharmaceutical composition.

In some embodiments, the exposure results in a reduction of IL13 and/or IL4 signaling function by the cell. In some embodiments, an IL13R/IL4R heterodimeric protein may reduce IL13 and/or IL4 signaling in a cell by at least 10%, at least 15%, at least 20%, at least 25%, at least 30%, at least 35%, at least 40%, at least 45%, at least 50%, at least 60%, at least 70%, at least 80%, at least 90%, or 100% compared to IL13 and/or IL4 signaling function in the absence of the IL13R/IL4R heterodimeric protein. In some embodiments, the reduction in IL13 and/or IL4 signaling and/or the reduction in TF-1 proliferation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Provided herein are methods of using the IL13R/IL4R heterodimeric protein, polypeptides and polynucleotides for detection, diagnosis and monitoring of an IL13- or IL4-induced condition. Provided herein are methods of determining whether a companion animal will respond to IL13R/IL4R heterodimeric protein therapy. In some embodiments, the method comprises detecting whether the animal has cells that express IL13 or IL4 using an IL13R/IL4R heterodimeric protein. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the IL13R/IL4R heterodimeric protein described herein are an appropriate treatment for the subject animal.

In some embodiments, the sample is a biological sample. The term "biological sample" means a quantity of a substance from a living thing or formerly living thing. In some embodiments, the biological sample is a cell or cell/tissue lysate. In some embodiments, the biological sample includes, but is not limited to, blood, (for example, whole blood), plasma, serum, urine, synovial fluid, and epithelial cells.

In some embodiments, the cells or cell/tissue lysate are contacted with an IL13R/IL4R heterodimeric protein and the binding between the IL13R/IL4R heterodimeric protein and the cell is determined. When the test cells show binding activity as compared to a reference cell of the same tissue type, it may indicate that the subject would benefit from treatment with an IL13R/IL4R heterodimeric protein. In some embodiments, the test cells are from tissue of a companion animal.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or p-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the IL13R/IL4R heterodimeric protein can be labeled with a detectable moiety including but not limited to radioisotopes, fluorescent labels, and various enzyme-substrate labels know in the art. Methods of conjugating labels to polypeptides are known in the art. In some embodiments, the IL13R/IL4R heterodimeric protein need not be labeled, and the presence thereof can be detected, for example, using an antibody that binds to the IL13R/IL4R heterodimeric protein. In some embodiments, the IL13R/IL4R heterodimeric protein can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). The anti-IL13 and IL4 antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, $^{3}$H, or any other radionuclide label, including those outlined herein) so that the cells or tissue of interest can be localized using immunoscintiography. The IL13R/IL4R heterodimeric protein may also be used as staining reagent in pathology using techniques well known in the art.

In some embodiments, a IL13R/IL4R heterodimeric protein is used for a diagnostic and a IL13R/IL4R heterodimeric protein is used as a therapeutic. In some embodiments, the first and second IL13R/IL4R heterodimeric proteins are different.

The following examples illustrate particular aspects of the disclosure and are not intended in any way to limit the disclosure.

EXAMPLES

Example 1

Expression and Purification of Canine IL4 and IL13

A nucleotide sequence encoding canine IL13 protein (SEQ ID NO: 4) was synthesized with poly-His tag on the C-terminal end and cloned into a mammalian expression vector and transfected to 293 cells or CHOS. The same method was used to clone and express a nucleotide sequence encoding canine IL4 protein (SEQ ID NO: 1) with a poly-His tag on the C-terminal end.

The supernatant containing canine IL13 protein was collected and filtered. Canine IL13 was affinity purified using Ni-NTA column (CaptivA® Protein A Affinity Resin, Repligen). The same method was used to purify canine IL4.

Example 2

Extracellular Domains of IL13R and IL4R

Extracellular domains of canine, feline, and equine IL4R that are responsible for binding canine, feline and equine IL4 and/or IL13 were identified and boundaries were defined. Full-length extracellular domains of canine IL4R, feline IL4R, and equine IL4 were identified as SEQ ID NO: 23, SEQ ID NO: 25, and SEQ ID NO: 27, respectively. Extracellular domain fragments of canine IL4R, feline IL4R, and equine IL4R postulated to retain biological activity were identified as SEQ ID NO: 33, SEQ ID NO: 35, and SEQ ID NO: 37, respectively.

Extracellular domains of canine, feline, and equine IL13R that are responsible for binding canine, feline, and equine IL4 and/or IL13 were identified and boundaries were defined. Full length extracellular domains of canine IL13R, feline IL13R, and equine IL13R were identified as SEQ ID NO: 22, SEQ ID NO: 24, and SEQ ID NO: 26, respectively. Extracellular domain fragments of canine IL13R, feline IL13R, and equine IL13R postulated to retain biological activity were identified as SEQ ID NO: 32, SEQ ID NO: 34, and SEQ ID NO: 36, respectively.

An unpaired cysteine (Cys) in canine IL13R (at position 18 of SEQ ID NO: 22), feline IL13R (at position 18 of SEQ ID NO: 24), and equine IL13R (at position 18 of SEQ ID NO: 26) was identified informatically and determined as embedded (unexposed) based on 3-D modeling. It is unlikely that the unpaired cysteine will form disulfide bonds and the likelihood of aggregation is low. Thus, site-directed mutagenesis of this Cys residue was not introduced.

Example 3

Expression and Purification of Canine IL13R/IL4R Contiguous Polypeptides from CHO Cells Nucleotide sequences encoding canine IL13R ECD/IL4R ECD contiguous polypeptides linked to an IgGB Fc polypeptide were designed with a signal sequence. For contiguous polypeptide "IL13RECD-IL4RECD-IgGB Fc" (SEQ ID NO: 20), an extracellular domain of IL13R (SEQ ID NO: 22) precedes an extracellular domain of IL4R (SEQ ID NO: 23). For contiguous polypeptide "IL4RECD-IL13RECD-IgGB Fc" (SEQ ID NO: 21), an extracellular domain of IL4R precedes an extracellular domain of IL13R.

The nucleotide sequences were synthesized chemically and inserted into an expression vector suitable for transfection into a CHO host cell. After transfection into CHO cells, the fusion proteins were secreted from the cell. For example, fusion protein was purified by single step Protein A column chromatography.

Each of IL13RECD-IL4RECD-IgGB Fc and IL4RECD-IL13RECD-IgGB Fc may be expressed and purified in a single step with a protein A column or other chromatographic methods, such as ion exchange column chromatography, hydrophobic interaction column chromatography, mixed mode column chromatography such as CHT, or multimodal mode column chromatography such as CaptoMMC. Low pH or other viral inactivation and viral removal steps can be applied. The purified protein may be admixed with excipients, and sterilized by filtration to prepare a pharmaceutical composition of the invention. The pharmaceutical composition may be administered to a dog with an atopic dermatitis or asthma in an amount sufficient to bind and/or inhibit either IL13 and/or IL4.

The vectors were then used to perform pilot-scale transfection in CHO-S cells using the FreestyleMax™ transfection reagent (Life Technologies). The supernatant was harvested by clarifying the conditioned media. Protein was purified with a single pass Protein A chromatography step and used for further investigation.

Example 4

Demonstration of IL13 and IL4 Binding Activity

This example demonstrates that both IL13RECD-IL4RECD-IgGB Fc (SEQ ID NO:20) and IL4RECD-IL13RECD-IgGB Fc (SEQ ID NO:21) bind canine IL4 and IL13 with kinetics requisite for therapeutic activity.

The binding analysis was performed using a biosensor Octet as follows. Briefly, canine IL4 (produced using 293 cells) was biotinylated. The free unreacted biotin was removed from biotinylated IL4 by extensive dialysis. Biotinylated canine IL4 was captured on streptavidin sensor tips. The IL4 association with various concentrations (12, 16, and 44 nM) of IL13RECD-IL4RECD-IgGB Fc (SEQ ID NO:20) was monitored for ninety seconds. Dissociation was monitored for 600 seconds. A buffer only blank curve was subtracted to correct for any drift. The data were fit to a 1:1 binding model using ForteBio™ data analysis software to determine the $k_{on}$, $k_{off}$, and the Kd. The buffer for dilutions and all binding steps was: 20 mM phosphate, 150 mM NaCl, pH 7.2. The Kd for IL13RECD-IL4RECD-IgGB Fc and ligand IL4 was $8 \times 10^{-11}$.

The canine IL4 association with various concentrations (40.7, and 140 nM) of IL4RECD-IL13RECD-IgGB Fc (SEQ ID NO:21) was monitored for ninety seconds. Dissociation was monitored for 600 seconds. A buffer only blank curve was subtracted to correct for any drift. The data were fit to a 1:1 binding model using ForteBio™ data analysis software to determine the $k_{on}$, $k_{off}$, and the Kd. The buffer for dilutions and all binding steps was: 20 mM phosphate, 150 mM NaCl, pH 7.2. The Kd for IL4RECD-IL13RECD-IgGB Fc and ligand IL4 was $1.1 \times 10^{-11}$.

Canine IL4 and canine IL13 with C-terminal polyHis tag was expressed and purified from 293 cells. EZ-Link NHS-LC-biotin was obtained from Thermo Scientific (Cat. #21336), and Streptavidin biosensors was obtained from ForteBio (Cat. #18-509).

Figure 2:
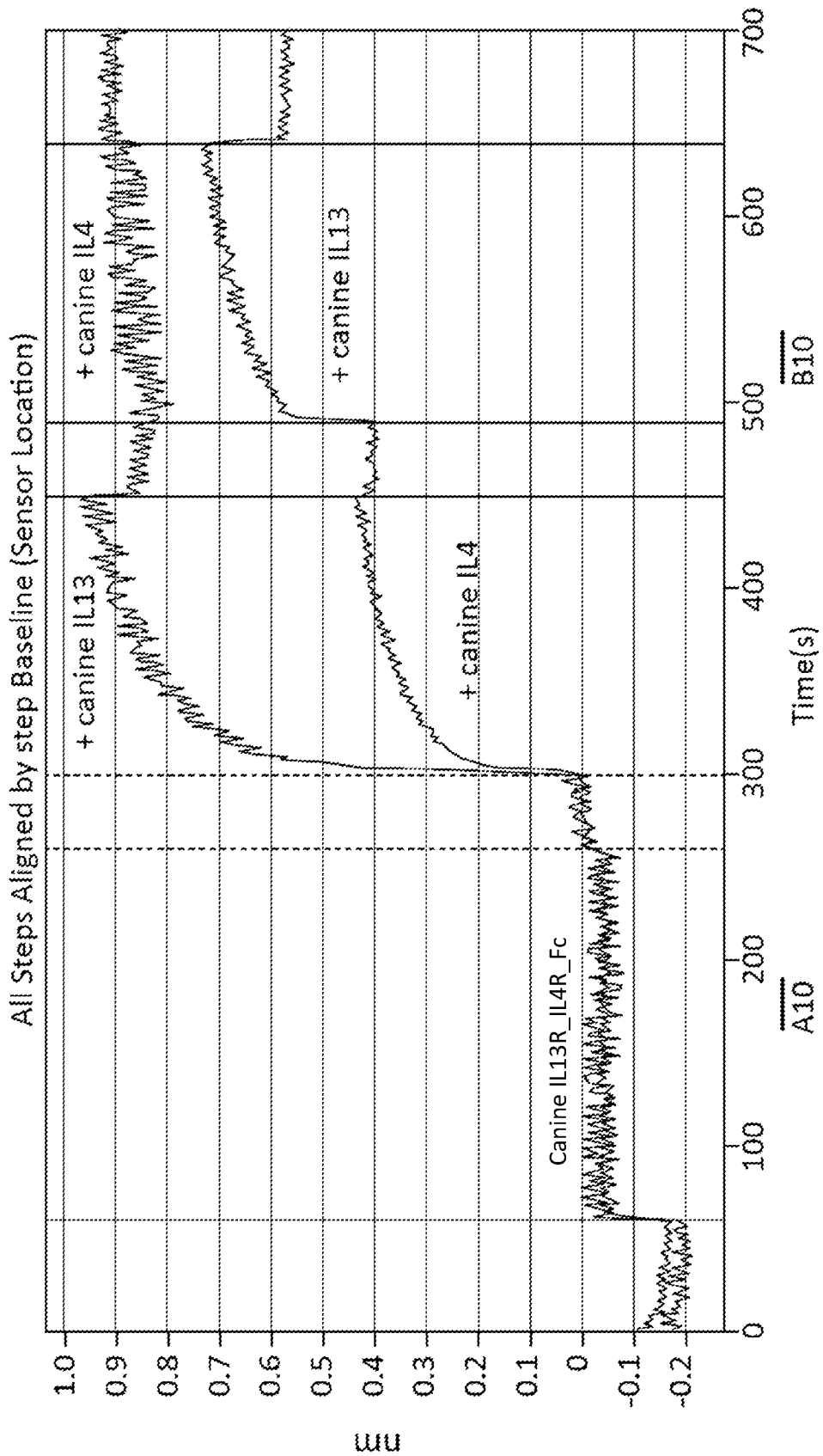
FIG. 2 is a graph of canine IL13RECD-IL4RECD-Fc sequential binding to canine IL4 and IL13 or canine IL13 and IL4 using concentrations of 30 μg/mL of IL4 and IL13 in PBS.

IL4 and IL13 sequential binding experiments with IL13R-IL4R-IgGB (SEQ ID NO:20) were performed. Biotinylated canine IL13R-IL4R-IgGB was captured on streptavidin sensor tips. Canine IL13R-IL4R-IgGB was exposed to either (1) canine IL4 followed by IL13 or (2) canine IL13 followed by IL4 using concentrations of 30 µg/mL of IL4 and IL13 in PBS (FIG. 2). The experiments demonstrated that once IL13R-IL4R-IgGB bound to IL13, it may not bind to IL4, and that once bound to IL4, its ability to bind IL13 is reduced.

IL4 and IL13 sequential binding experiments with IL4R-IL13R-IgGB (SEQ ID NO:21) were performed. Biotinylated canine IL4R-IL13R-IgGB was captured on streptavidin sensor tips. Canine IL4R-IL13R-IgGB was exposed to either (1) canine IL4 followed by IL13 or (2) canine IL13 followed by IL4 using concentrations of 30 ug/mL of IL4 and IL13 in PBS (FIG. 1). These experiments demonstrated that once IL4R-IL13R-IgGB bound to IL13, it may not bind to IL4, and that once bound to IL4, its ability to bind IL13 is reduced.

The tight binding of IL13RECD-IL4RECD-IgGB Fc and IL4RECD-IL13RECD-IgGB Fc to IL4 or IL13 is thought to be due to simultaneous binding contributions made by both IL4RECD and IL13RECD.

Example 5

Cellular Functional Activity of Canine IL4RECD-IL13RECD-Fc (SINK)

TF1 cells (ATCC cat #CRL-2003), a human Erythroleukemia cell line which expresses endogenous interleukin 4 receptors on cell surface, was used in a proliferation assay. Cells grown in RPMI1640 (Gibco, Cat #11875) supplemented with 10% Fetal Bovine Serum, heat inactivated (Sigma, Cat #2868) and 2 nM/ml Human GM-CSF (R&D System, Cat #215-GM-010) at exponential growth phase were used for the assay. Cells were washed with PBS twice and resuspended in above medium without GM-CSF. 20,000 cells per well were plated in a 96-well plate (Corning, Cat #3610). Canine IL4RECD-IL13RECD-IgGB Fc (SINK) was added at a series of dilutions followed by addition of canine IL4 (Sino Biological Inc, Cat #70021-DNAE-5) at 50 ng/ml. The cells were incubated in 37° C., 5% CO2 for 48 hours in a total volume of 100 μl. At the end of the incubation, the cells were cooled in room temperature and assayed for proliferation/variability by measuring cellular ATP content using CellTiter-Glo® Luminescent Cell Viability Assay (Promega, Cat #G7570).

In this assay, 100 μl premixed reagent A and B were added to each well. After shaking on an orbital shaker for 2 mins, the cells were lysed. Mono-oxygenation of luciferin was catalyzed by luciferase in the presence of Mg2+ and ATP that presented in cells, resulting in the generation of a luminescent signal proportional to the amount of ATP in the cells. The amount of ATP is directly proportional to the number of cells present in culture. The plate was incubated at room temperature for 10 minutes to stabilize the luminescent signal and luminescence was detected using a Synergy HT microplate reader (Biotek, Winooski, VT).

Figure 3:
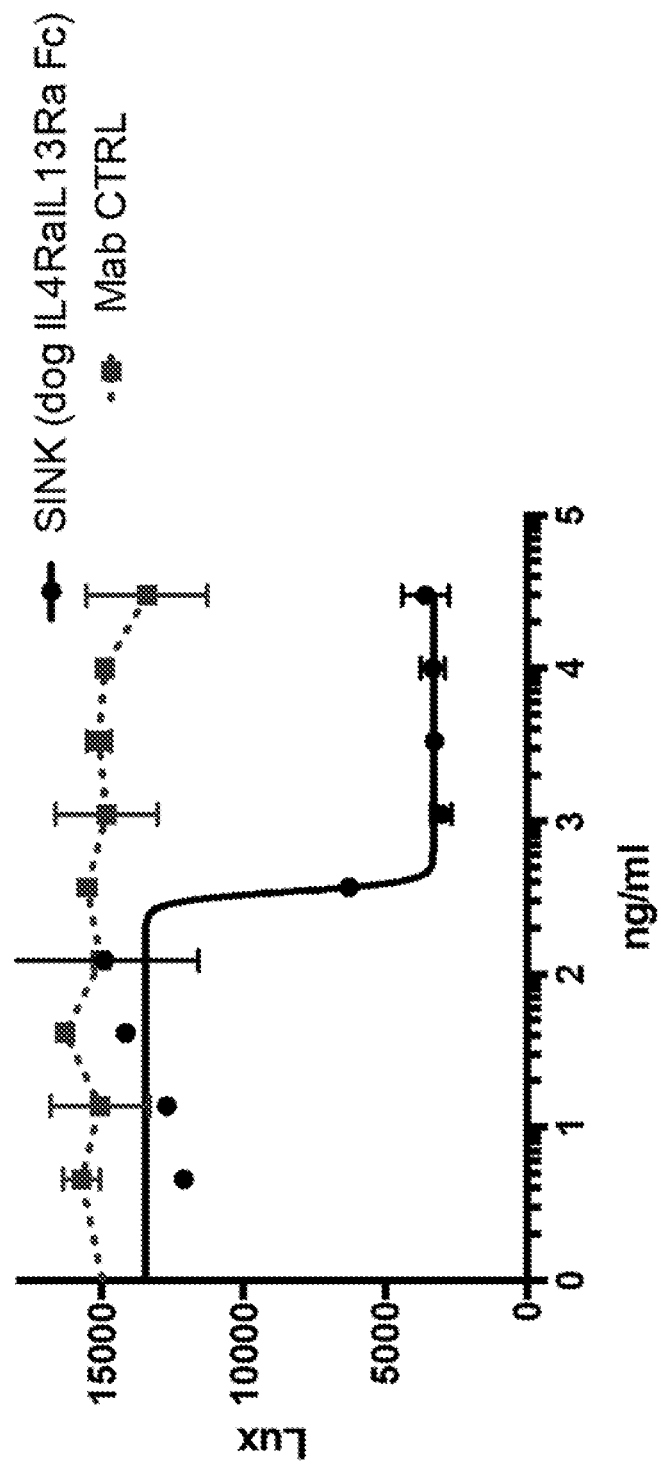
FIG. 3 is a graph of canine IL4RECD-IL13RECD-Fc neutralizing canine IL4 activity in a TF1 cell proliferation assay. Canine IL4 (50 ng/mL or 3.85 nM) was used in the assay.

The data were analyzed using 4 parameter logistic fit and IC50 is 2.0 nM. See FIG. 3.

Example 6

Canine, Feline, and Equine IgG Fc Polypeptides for IL31R and IL4R Heterodimeric Proteins Pairs of variant canine IgG Fc polypeptides, variant feline IgG Fc polypeptides, and variant equine IgG Fc polypeptides were designed such that a knob-in-hole heterodimerization approach may be used to prepare heterodimeric proteins comprising at least one IL31R ECD and at least one IL4R ECD. First, pairing of two Fc polypeptides was designed by introducing CH3 interfacing mutations so that a first Fc polypeptide comprises a bulky amino acid (knob) and a second Fc polypeptide comprises smaller amino acids in the same general location (hole).

An amino acid substitution of threonine to tryptophan at a position corresponding to position 138 of canine IgG-A (SEQ ID NO: 38), at a position corresponding to position 137 of canine IgG-B Fc (SEQ ID NO: 39), at a position corresponding to position 137 of canine IgG-C Fc (SEQ ID NO: 40), or at a position corresponding to position 138 of canine IgG-D Fc (SEQ ID NO: 41) (T138W or T137W) can be introduced as a knob. Examples of amino acid sequences of a first variant canine IgG-A, IgG-B, IgG-C, and IgG-D Fc polypeptide comprising a knob mutation are SEQ ID NO: 54, SEQ ID NO: 55, SEQ ID NO: 56, and SEQ ID NO: 57, respectively.

An amino acid substitution of threonine to serine at a position corresponding to position 138 and/or of leucine to alanine at a position corresponding to position 140 and/or of tyrosine to threonine at a position corresponding to position 180 of canine IgG-A (SEQ ID NO: 38) or of IgG-D (SEQ ID NO: 41) (T138S, L140A, and/or Y180T); or of threonine to serine at a position corresponding to position 137 and/or of leucine to alanine at a position corresponding to position 139 and/or of tyrosine to threonine at a position corresponding to position 179 of canine IgG-B Fc (SEQ ID NO: 39) or of IgG-C (SEQ ID NO: 40) (T137S, L139A, and/or Y179T) can be introduced as a hole. Examples of amino acid sequences of a second variant canine IgG-A, IgG-B, IgG-C, and IgG-D Fc polypeptides comprising a hole mutation are SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

An amino acid substitution of threonine to tryptophan at a position corresponding to position 154 of feline IgG1a Fc (SEQ ID NO: 42 or SEQ ID NO: 43), feline IgG1b Fc (SEQ ID NO: 44 or SEQ ID NO: 45), or of feline IgG2 (SEQ ID NO: 46) (T154W) can be introduced as a knob. Examples of amino acid sequences of a first variant feline IgG1a, and IgG1b, and IgG2 Fc polypeptide comprising a knob mutation are SEQ ID NO: 66, SEQ ID NO: 67, SEQ ID NO: 68, SEQ ID NO: 69, and SEQ ID NO: 70.

An amino acid substitution of threonine to serine at a position corresponding to position 154 and/or of leucine to alanine at a position corresponding to position 156 and/or of tyrosine to threonine at a position corresponding to position 197 of feline IgG1a (SEQ ID NO: 42 or SEQ ID NO: 43), feline IgG-b Fc (SEQ ID NO: 44 or SEQ ID NO: 45), or feline IgG2 Fc (SEQ ID NO: 46) (T154S, L156A, and/or Y(197)T) can be introduced as a hole. Examples of amino acid sequences of a second variant feline IgG1a, IgG1b, IgG2 Fc polypeptide comprising a hole mutation are SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, and SEQ ID NO: 80.

An amino acid substitution of threonine to tryptophan at a position corresponding to position 130 of equine IgG1 Fc (SEQ ID NO: 47), of equine IgG2 Fc (SEQ ID NO: 48), of equine IgG3 Fc (SEQ ID NO: 49), of equine IgG4 Fc (SEQ ID NO: 50), of equine IgG5 Fc (SEQ ID NO: 51), of equine IgG6 Fc (SEQ ID NO: 52), or of equine IgG7 Fc (SEQ ID NO: 53) (T130W) can be introduced as a knob. Examples of amino acid sequences of a first variant equine IgG1, IgG2, IgG3, IgG4, IgG5, IgG6, and IgG7 Fc polypeptides comprising a knob mutation are SEQ ID NO: 81, SEQ ID NO: 82, SEQ ID NO: 83, SEQ ID NO: 84, SEQ ID NO: 85, SEQ ID NO: 86, and SEQ ID NO: 87, respectively.

An amino acid substitution of threonine to serine at a position corresponding to position 130 and/or of leucine to alanine at a position corresponding to position 132 and/or of tyrosine to threonine at a position corresponding to position 173 of equine IgG1 Fc (SEQ ID NO: 47), of equine IgG2 Fc (SEQ ID NO: 48), of equine IgG3 Fc (SEQ ID NO: 49), of equine IgG4 Fc (SEQ ID NO: 50), of equine IgG5 Fc (SEQ ID NO: 51), of equine IgG6 Fc (SEQ ID NO: 52), or of equine IgG7 Fc (SEQ ID NO: 53) (T130W, L(132)A, and/or Y(173)T) can be introduced as a hole. Examples of amino acid sequences of a second variant equine IgG1, IgG2, IgG3, IgG4, IgG5, IgG6, and IgG7 Fc polypeptides comprising a hole mutation are SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, and SEQ ID NO: 101.

Example 7

IL13R/IL4R ECD Heterodimeric Proteins

In addition to contiguous IL13R/IL4R ECD polypeptide formats, heterodimeric protein pairs may have the following formats:

Heterodimeric protein A:
  Polypeptide 1: IL13R(n)-L-Fc1 and
  Polypeptide 2: IL4R(n)-L-Fc2; or
Heterodimeric protein B:
  Polypeptide 1: IL4R(n)-L-Fc1 and
  Polypeptide 2: IL13R(n)-L-Fc2, wherein IL13R(n) is at least one IL13R extracellular domain (ECD) polypeptide derived from a companion animal species, IL4R(n) is at least one IL4R ECD polypeptide derived from a companion animal species, (n) is one, two, three, four, or more ECD polypeptides, L is an optional linker, Fc1 is a variant Fc polypeptide, such as a variant Fc polypeptide comprising knob mutation, Fc2 is a variant Fc polypeptide, such as a variant Fc polypeptide comprising a hole mutation. An optional linker could also be used between multiple ECD polypeptides. In addition, other binding partner(s) may be included before, after, and/or between any one or more ECD polypeptide(s). Other potential binding partners include: IL5, IL6, IL17, IL22, IL31, LFA-1, TNF-α, TSLP, and/or IgE.

Examples of pairs of contiguous polypeptide 1 and 2 that may form a heterodimeric protein include SEQ ID NOs 102 and 103, SEQ ID NOs: 104 and 105, SEQ ID NOs: 106 and 107, SEQ ID NOs: 108 and 109, SEQ ID NOs: 110 and 111, and SEQ ID NOs: 112 and 113. A host cell may be cotransfected with vectors expressing these contiguous polypeptide pairs to produce the heterodimeric proteins described.

---

The invention claimed is:

1. A heterodimeric protein comprising:

a) a first contiguous polypeptide comprising at least one IL13R extracellular domain (ECD) and a first Fc polypeptide, wherein the amino acid sequence of the at least one IL13R ECD is SEQ ID NO: 22, SEQ ID NO: 24, SEQ ID NO: 26, SEQ ID NO: 32, or SEQ ID NO: 34, SEQ ID NO: 36, and b) a second contiguous polypeptide comprising at least one IL4R ECD and a second Fc polypeptide, wherein the amino acid sequence of the at least one IL4R ECD is SEQ ID NO: 23, SEQ ID NO: 25, SEQ ID NO: 27, SEQ ID NO: 33, SEQ ID NO: 35, or SEQ ID NO: 37, wherein the IL13R ECD and/or the IL4R ECD are derived from a companion animal species.

2. The heterodimeric protein of claim 1, wherein the first contiguous polypeptide and/or the second contiguous polypeptide comprises one, two, three, or four IL4R ECDs and/or one, two, three, or four IL13R ECDs.

3. The heterodimeric protein of claim 1, wherein the first contiguous polypeptide and/or the second contiguous polypeptide further comprises at least one binding partner other than IL4R ECD or IL13R ECD, and wherein the at least one binding partner comprises IL5, IL6, IL17, IL22, IL31, LFA-1, TNF-α, TSLP, and/or IgE.

4. The heterodimeric protein of claim 1, wherein the heterodimeric protein binds to IL13 and/or IL4 with a dissociation constant (Kd) of less than $5\times10^{-6}$ M, less than $1\times10^{-6}$ M, less than $5\times10^{-7}$ M, less than $1\times10^{-7}$ M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, or less than $1\times10^{-12}$ M, as measured by biolayer interferometry; and/or wherein the heterodimeric protein reduces IL13 and/or IL4 signaling in a companion animal species.

5. The heterodimeric protein of claim 1, wherein the companion animal species is canine, feline, or equine.

6. The heterodimeric protein of claim 1, wherein the first Fc polypeptide and/or the second Fc polypeptide is:
a) a canine IgG-A, IgG-B, IgG-C, or IgG-D Fc polypeptide;
b) a feline IgG1a, IgG1b, or IgG2 Fc polypeptide; and/or
c) an equine IgG1, IgG2, IgG3, IgG4, IgG5, IgG6, or IgG7 Fc polypeptide.

7. The heterodimeric protein of claim 1, wherein the first Fc polypeptide or the second Fc polypeptide comprises a knob mutation; and/or wherein the first Fc polypeptide or the second Fc polypeptide comprises a hole mutation.

8. The heterodimeric protein of claim 1, wherein the first Fc polypeptide or the second Fc polypeptide comprises:
a) SEQ ID NO: 38 with an amino acid substitution at position 138, SEQ ID NO: 39 with an amino acid substitution at position 137, SEQ ID NO: 40 with an amino acid substitution at position 137, or SEQ ID NO: 41 with an amino acid substitution at position 138; and/or
b) SEQ ID NO: 42, SEQ ID NO: 43, SEQ ID NO: 44, SEQ ID NO: 45, or SEQ ID NO: 46, each with an amino acid substitution at position 154; and/or
c) SEQ ID NO: 47, SEQ ID NO: 48, SEQ ID NO: 49, SEQ ID NO: 50, SEQ ID NO: 51, SEQ ID NO: 52, or SEQ ID NO: 53, each with an amino acid substitution at position 130.

9. The heterodimeric protein of claim 1, wherein the first Fc polypeptide or the second Fc polypeptide comprises:
a) SEQ ID NO: 38 with a tryptophan at position 138, SEQ ID NO: 39 with a tryptophan at position 137, SEQ ID NO: 40 with a tryptophan at position 137, or SEQ ID NO: 41 with a tryptophan at position 138; and/or
b) SEQ ID NO: 42, SEQ ID NO: 43, SEQ ID NO: 44, SEQ ID NO: 45, or SEQ ID NO: 46, each with a tryptophan at position 154; and/or
c) SEQ ID NO: 47, SEQ ID NO: 48, SEQ ID NO: 49, SEQ ID NO: 50, SEQ ID NO: 51, SEQ ID NO: 52, or SEQ ID NO: 53, each with a tryptophan at position 130.

10. The heterodimeric protein of claim 1, wherein the first Fc polypeptide or the second Fc polypeptide comprises:
a) SEQ ID NO: 38 or SEQ ID NO: 41, each with an amino acid substitution at position 138 and/or position 140 and/or position 181; ID NO: 39 or SEQ ID NO: 40, each with an amino acid substitution at position 137 and/or position 139 and/or position 180; and/or
b) SEQ ID NO: 42, SEQ ID NO: 43, SEQ ID NO: 44, SEQ ID NO: 45, or SEQ ID NO: 46, each with an amino acid substitution at position 154 and/or position 156 and/or position 197; and/or
c) SEQ ID NO: 47, SEQ ID NO: 48, SEQ ID NO: 49, SEQ ID NO: 50, SEQ ID NO: 51, SEQ ID NO: 52, or SEQ ID NO: 53, each with an amino acid substitution at position 130 and/or position 132 and/or position 173.

11. The heterodimeric protein of claim 1, wherein the first Fc polypeptide or the second Fc polypeptide comprises:
a) SEQ ID NO: 38 with a serine at position 138 and/or an alanine at position 140 and/or a threonine at position 181; SEQ ID NO: 39 with a serine at position 137 and/or an alanine at position 139 and/or a threonine at position 180; SEQ ID NO: 40 with a serine at position 137 and/or an alanine at position 139 and/or a threonine at position 180; or SEQ ID NO: 41 with a serine at position 138 and/or an alanine at position 140 and/or a threonine at position 181; and/or
b) SEQ ID NO: 42, SEQ ID NO: 43, SEQ ID NO: 44, SEQ ID NO: 45, or SEQ ID NO: 46, each with a serine at position 154 and/or an alanine at position 156 and/or a threonine at position 197; and/or
c) SEQ ID NO: 47, SEQ ID NO: 48, SEQ ID NO: 49, SEQ ID NO: 50, SEQ ID NO: 51, SEQ ID NO: 52, or SEQ ID NO: 53, each with a serine at position 130 and/or an alanine at position 132 and/or a threonine at position 173.

12. The heterodimeric protein of claim 1, wherein the first Fc polypeptide or the second Fc polypeptide comprises the amino acid sequence of SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, or SEQ ID NO: 101.

13. The heterodimeric protein of claim 1, wherein the first contiguous polypeptide comprises the amino acid sequence of SEQ ID NO: 103, SEQ ID NO: 105, SEQ ID NO: 107, SEQ ID NO: 109, SEQ ID NO: 111, or SEQ ID NO: 113; and/or wherein the second contiguous polypeptide comprises the amino acid sequence of SEQ ID NO: 102, SEQ ID NO: 104, SEQ ID NO: 106, SEQ ID NO: 108, SEQ ID NO: 110, or SEQ ID NO: 112.

14. A pharmaceutical composition comprising the heterodimeric protein of claim 1 and a pharmaceutically acceptable carrier.

15. A heterodimeric protein comprising:
a) a first polypeptide comprising at least one IL13R extracellular domain (ECD) and a first Fc polypeptide, and
b) a second polypeptide comprising at least one IL4R ECD and a second Fc polypeptide;

wherein the IL13R ECD and/or the IL4R ECD are derived from a canine;
wherein the IL13R ECD sequence is SEQ ID NO: 22;
wherein the IL4R ECD sequence is SEQ ID NO: 23;
wherein the first polypeptide is SEQ ID NO: 103;
wherein the second polypeptide is SEQ ID NO: 102;
wherein the first Fc polypeptide is SEQ ID NO 55; and
wherein the second Fc polypeptide is SEQ ID NO 59.

16. The heterodimeric protein of claim 15, wherein the first polypeptide and/or the second polypeptide further comprises at least one binding partner other than IL4R ECD or IL13R ECD, and wherein the at least one binding partner comprises IL31.

17. The heterodimeric protein of claim 15, wherein the heterodimeric protein binds to IL13 and/or IL4 with a dissociation constant (Kd) of less than $5\times10^{-6}$ M as measured by biolayer interferometry.

18. The heterodimeric protein of claim 15, wherein the heterodimeric protein reduces IL13 and/or IL4 signaling in a companion animal species.

* * * * *

SEQUENCE LISTING

```
<160> NUMBER OF SEQ ID NOS: 113

<210> SEQ ID NO 1
<211> LENGTH: 131
<212> TYPE: PRT
<213> ORGANISM: Canis lupus
<220> FEATURE:
<221> NAME/KEY: misc_feature
<222> LOCATION: (1)..(131)
<223> OTHER INFORMATION: Canis lupus interleukin-4 precursor

<400> SEQUENCE: 1

Met Gly Leu Thr Ser Gln Leu Ile Pro Thr Leu Val Cys Leu Leu Ala
1               5                   10                  15

Leu Thr Ser Thr Phe Val His Gly His Asn Phe Asn Ile Thr Ile Lys
            20                  25                  30

Glu Ile Ile Lys Met Leu Asn Ile Leu Thr Ala Arg Asn Asp Ser Cys
        35                  40                  45

Met Glu Leu Thr Val Asp Val Phe Thr Ala Pro Lys Asn Thr Ser Asp
    50                  55                  60

Lys Glu Ile Phe Cys Arg Ala Ala Thr Val Leu Arg Gln Ile Tyr Thr
65                  70                  75                  80

His Asn Cys Ser Asn Arg Tyr Leu Arg Gly Leu Tyr Arg Asn Leu Ser
                85                  90                  95

Ser Met Ala Asn Lys Thr Cys Ser Met Asn Glu Ile Lys Lys Ser Thr
            100                 105                 110

Leu Lys Asp Phe Leu Glu Arg Leu Lys Val Ile Met Gln Lys Lys Tyr
        115                 120                 125

Tyr Arg His
    130

<210> SEQ ID NO 2
<211> LENGTH: 132
<212> TYPE: PRT
<213> ORGANISM: Felis catus
<220> FEATURE:
<221> NAME/KEY: misc_feature
<222> LOCATION: (1)..(132)
<223> OTHER INFORMATION: Felis catus interleukin-4 precursor

<400> SEQUENCE: 2

Met Asp Leu Thr Ser Gln Leu Ile Pro Ala Leu Val Cys Leu Leu Ala
1               5                   10                  15
```

```
Phe Thr Ser Thr Phe Val His Gly Gln Asn Phe Asn Asn Thr Leu Lys
                20                  25                  30

Glu Ile Ile Lys Thr Leu Asn Ile Leu Thr Ala Arg Asn Asp Ser Cys
            35                  40                  45

Met Glu Leu Thr Met Asp Val Leu Ala Ala Pro Lys Asn Thr Ser Asp
 50                  55                  60

Lys Glu Ile Phe Cys Arg Ala Thr Thr Val Leu Arg Gln Ile Tyr Thr
 65                  70                  75                  80

His His Asn Cys Ser Thr Lys Phe Leu Lys Gly Leu Asp Arg Asn Leu
                85                  90                  95

Ser Ser Met Ala Asn Arg Thr Cys Ser Val Asn Glu Val Lys Lys Cys
            100                 105                 110

Thr Leu Lys Asp Phe Leu Glu Arg Leu Lys Ala Ile Met Gln Lys Lys
        115                 120                 125

Tyr Ser Lys His
        130

<210> SEQ ID NO 3
<211> LENGTH: 137
<212> TYPE: PRT
<213> ORGANISM: Equus caballus
<220> FEATURE:
<221> NAME/KEY: misc_feature
<222> LOCATION: (1)..(137)
<223> OTHER INFORMATION: Equus caballus interleukin-4 precursor

<400> SEQUENCE: 3

Met Gly Leu Thr Tyr Gln Leu Ile Pro Ala Leu Val Cys Leu Leu Ala
 1               5                  10                  15

Cys Thr Ser Asn Phe Ile Gln Gly Cys Lys Tyr Asp Ile Thr Leu Gln
                20                  25                  30

Glu Ile Ile Lys Thr Leu Asn Asn Leu Thr Asp Gly Lys Gly Lys Asn
            35                  40                  45

Ser Cys Met Glu Leu Thr Val Ala Asp Ala Phe Ala Gly Pro Lys Asn
 50                  55                  60

Thr Asp Gly Lys Glu Ile Cys Arg Ala Ala Lys Val Leu Gln Gln Leu
65                   70                  75                  80

Tyr Lys Arg His Asp Arg Ser Leu Ile Lys Glu Cys Leu Ser Gly Leu
                85                  90                  95

Asp Arg Asn Leu Lys Gly Met Ala Asn Gly Thr Cys Cys Thr Val Asn
            100                 105                 110

Glu Ala Lys Lys Ser Thr Leu Lys Asp Phe Leu Glu Arg Leu Lys Thr
        115                 120                 125

Ile Met Lys Glu Lys Tyr Ser Lys Cys
        130                 135

<210> SEQ ID NO 4
<211> LENGTH: 131
<212> TYPE: PRT
<213> ORGANISM: Canis lupus
<220> FEATURE:
<221> NAME/KEY: misc_feature
<222> LOCATION: (1)..(131)
<223> OTHER INFORMATION: Canis lupus interleukin-13 precursor

<400> SEQUENCE: 4

Met Ala Leu Trp Leu Thr Val Val Ile Ala Leu Thr Cys Leu Gly Gly
 1               5                  10                  15

Leu Ala Ser Pro Ser Pro Val Thr Pro Ser Pro Thr Leu Lys Glu Leu
```

```
            20                  25                  30
Ile Glu Glu Leu Val Asn Ile Thr Gln Asn Gln Ala Ser Leu Cys Asn
         35                  40                  45

Gly Ser Met Val Trp Ser Val Asn Leu Thr Ala Gly Met Tyr Cys Ala
     50                  55                  60

Ala Leu Glu Ser Leu Ile Asn Val Ser Asp Cys Ser Ala Ile Gln Arg
 65                  70                  75                  80

Thr Gln Arg Met Leu Lys Ala Leu Cys Ser Gln Lys Pro Ala Ala Gly
                 85                  90                  95

Gln Ile Ser Ser Glu Arg Ser Arg Asp Thr Lys Ile Glu Val Ile Gln
            100                 105                 110

Leu Val Lys Asn Leu Leu Thr Tyr Val Arg Gly Val Tyr Arg His Gly
        115                 120                 125

Asn Phe Arg
        130

<210> SEQ ID NO 5
<211> LENGTH: 183
<212> TYPE: PRT
<213> ORGANISM: Felis catus
<220> FEATURE:
<221> NAME/KEY: misc_feature
<222> LOCATION: (1)..(183)
<223> OTHER INFORMATION: Felis catus interleukin-13 precursor

<400> SEQUENCE: 5

Met Trp Phe Leu Asp Ser Thr Arg Gln Ser Gly Asp Gln Gly Gly Arg
 1               5                  10                  15

Arg His Thr Trp Pro Ile Lys Ala Thr Ala Arg Gly Gln Gly His Lys
             20                  25                  30

Pro Leu Ser Leu Gly Gln Pro Thr Cys Pro Leu Leu Ala Pro Pro Val
         35                  40                  45

Leu Ala Leu Gly Ser Met Ala Leu Trp Leu Thr Val Val Ile Ala Leu
     50                  55                  60

Thr Cys Leu Gly Gly Leu Ala Ser Pro Gly Pro His Ser Arg Arg Glu
 65                  70                  75                  80

Leu Lys Glu Leu Ile Glu Glu Leu Val Asn Ile Thr Gln Asn Gln Val
                 85                  90                  95

Ser Leu Cys Asn Gly Ser Met Val Trp Ser Val Asn Leu Thr Thr Gly
            100                 105                 110

Met Tyr Cys Ala Ala Leu Glu Ser Leu Ile Asn Val Ser Asp Cys Thr
        115                 120                 125

Ala Ile Gln Arg Thr Gln Arg Met Leu Lys Ala Leu Cys Thr Gln Lys
    130                 135                 140

Pro Ser Ala Gly Gln Thr Ala Ser Glu Arg Ser Arg Asp Thr Lys Ile
145                 150                 155                 160

Glu Val Ile Gln Leu Val Lys Asn Leu Leu Asn His Leu Arg Arg Asn
                165                 170                 175

Phe Arg His Gly Asn Phe Lys
            180

<210> SEQ ID NO 6
<211> LENGTH: 133
<212> TYPE: PRT
<213> ORGANISM: Equus caballus
<220> FEATURE:
<221> NAME/KEY: misc_feature
<222> LOCATION: (1)..(133)
```

<223> OTHER INFORMATION: Equus caballus interleukin-13 precursor

<400> SEQUENCE: 6

Met Ala Leu Trp Leu Thr Ala Val Ile Ala Leu Ala Cys Leu Gly Gly
1               5                   10                  15

Leu Ala Ser Pro Ala Pro Leu Pro Ser Ser Met Ala Lys Glu Leu
            20                  25                  30

Ile Lys Glu Leu Val Asn Ile Thr Gln Asn Gln Ala Pro Leu Cys Asn
        35                  40                  45

Gly Ser Met Val Trp Ser Val Asn Leu Thr Ala Asp Thr Tyr Cys Arg
    50                  55                  60

Ala Leu Glu Ser Leu Ser Asn Val Ser Thr Cys Ser Ala Ile Gln Asn
65                  70                  75                  80

Thr Arg Lys Met Leu Thr Lys Leu Cys Pro His Gln Leu Ser Ala Gly
                85                  90                  95

Gln Val Ser Ser Glu Arg Ala Arg Asp Thr Lys Ile Glu Val Ile Val
            100                 105                 110

Leu Val Lys Asp Leu Leu Lys Asn Leu Arg Lys Ile Phe His Gly Gly
        115                 120                 125

Lys His Val Asp Ala
    130

<210> SEQ ID NO 7
<211> LENGTH: 823
<212> TYPE: PRT
<213> ORGANISM: Canis lupus
<220> FEATURE:
<221> NAME/KEY: misc_feature
<222> LOCATION: (1)..(823)
<223> OTHER INFORMATION: Canis lupus interleukin-4 receptor subunit
      alpha

<400> SEQUENCE: 7

Met Gly Arg Leu Cys Ser Gly Leu Thr Phe Pro Val Ser Cys Leu Val
1               5                   10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
        35                  40                  45

Asp His Pro Thr Asn Cys Ser Ala Glu Leu Arg Leu Ser Tyr Gln Leu
    50                  55                  60

Asp Phe Met Gly Ser Glu Asn His Thr Cys Val Pro Glu Asn Arg Glu
65                  70                  75                  80

Asp Ser Val Cys Val Cys Ser Met Pro Ile Asp Asp Ala Val Glu Ala
                85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
        115                 120                 125

Leu Thr Val His Pro Asn Ile Ser His Thr Trp Leu Leu Met Trp Thr
    130                 135                 140

Asn Pro Tyr Pro Thr Glu Asn His Leu His Ser Glu Leu Thr Tyr Met
145                 150                 155                 160

Val Asn Val Ser Asn Asp Asn Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

```
Ser Gly Ala Ser Tyr Ser Ala Arg Val Arg Ala Trp Ala Gln Thr Tyr
        195                 200                 205

Asn Ser Thr Trp Ser Asp Trp Ser Pro Ser Thr Thr Trp Leu Asn Tyr
210                 215                 220

Tyr Glu Pro Trp Glu Gln His Leu Pro Leu Gly Val Ser Ile Ser Cys
225                 230                 235                 240

Leu Val Ile Leu Ala Ile Cys Leu Ser Cys Tyr Phe Ser Ile Ile Lys
            245                 250                 255

Ile Lys Lys Gly Trp Trp Asp Gln Ile Pro Asn Pro Ala His Ser Pro
                260                 265                 270

Leu Val Ala Ile Val Gln Asp Ser Gln Val Ser Leu Trp Gly Lys
            275                 280                 285

Arg Ser Arg Gly Gln Glu Pro Ala Lys Cys Pro His Trp Lys Thr Cys
        290                 295                 300

Leu Thr Lys Leu Leu Pro Cys Leu Leu Glu His Gly Leu Gly Arg Glu
305                 310                 315                 320

Glu Glu Ser Pro Lys Thr Ala Lys Asn Gly Pro Leu Gln Gly Pro Gly
                325                 330                 335

Lys Pro Ala Trp Cys Pro Val Glu Val Ser Lys Thr Ile Leu Trp Pro
            340                 345                 350

Glu Ser Ile Ser Val Val Gln Cys Val Glu Leu Ser Glu Ala Pro Val
        355                 360                 365

Asp Asn Glu Glu Glu Glu Val Glu Glu Asp Lys Arg Ser Leu Cys
370                 375                 380

Pro Ser Leu Glu Gly Ser Gly Gly Ser Phe Gln Glu Gly Arg Glu Gly
385                 390                 395                 400

Ile Val Ala Arg Leu Thr Glu Ser Leu Phe Leu Asp Leu Leu Gly Gly
                405                 410                 415

Glu Asn Gly Gly Phe Cys Pro Gln Gly Leu Glu Glu Ser Cys Leu Pro
            420                 425                 430

Pro Pro Ser Gly Ser Val Gly Ala Gln Met Pro Trp Ala Gln Phe Pro
        435                 440                 445

Arg Ala Gly Pro Arg Ala Ala Pro Glu Gly Pro Glu Gln Pro Arg Arg
450                 455                 460

Pro Glu Ser Ala Leu Gln Ala Ser Pro Thr Gln Ser Ala Gly Ser Ser
465                 470                 475                 480

Ala Phe Pro Glu Pro Pro Val Val Thr Asp Asn Pro Ala Tyr Arg
            485                 490                 495

Ser Phe Gly Ser Phe Leu Gly Gln Ser Ser Asp Pro Gly Asp Gly Asp
                500                 505                 510

Ser Asp Pro Glu Leu Ala Asp Arg Pro Gly Glu Ala Asp Pro Gly Ile
            515                 520                 525

Pro Ser Ala Pro Gln Pro Pro Glu Pro Ala Ala Leu Gln Pro Glu
530                 535                 540

Pro Glu Ser Trp Glu Gln Ile Leu Arg Gln Ser Val Leu Gln His Arg
545                 550                 555                 560

Ala Ala Pro Ala Pro Gly Pro Gly Pro Gly Ser Gly Tyr Arg Glu Phe
                565                 570                 575

Thr Cys Ala Val Lys Gln Gly Ser Ala Pro Asp Ala Gly Gly Pro Gly
            580                 585                 590

Phe Gly Pro Ser Gly Glu Ala Gly Tyr Lys Ala Phe Cys Ser Leu Leu
        595                 600                 605
```

```
Pro Gly Gly Ala Thr Cys Pro Gly Thr Ser Gly Glu Ala Gly Ser
    610             615             620

Gly Glu Gly Gly Tyr Lys Pro Phe Gln Ser Leu Thr Pro Gly Cys Pro
625             630             635             640

Gly Ala Pro Thr Pro Val Pro Val Pro Leu Phe Thr Phe Gly Leu Asp
            645             650             655

Thr Glu Pro Pro Gly Ser Pro Gln Asp Ser Leu Gly Ala Gly Ser Ser
            660             665             670

Pro Glu His Leu Gly Val Glu Pro Ala Gly Lys Glu Asp Ser Arg
        675             680             685

Lys Thr Leu Leu Ala Pro Glu Gln Ala Thr Asp Pro Leu Arg Asp Asp
690             695             700

Leu Ala Ser Ser Ile Val Tyr Ser Ala Leu Thr Cys His Leu Cys Gly
705             710             715             720

His Leu Lys Gln Trp His Asp Gln Glu Arg Gly Lys Ala His Ile
            725             730             735

Val Pro Ser Pro Cys Cys Gly Cys Cys Cys Gly Asp Arg Ser Ser Leu
            740             745             750

Leu Leu Ser Pro Leu Arg Ala Pro Asn Val Leu Pro Gly Gly Val Leu
            755             760             765

Leu Glu Ala Ser Leu Ser Pro Ala Ser Leu Val Pro Ser Gly Val Ser
770             775             780

Lys Glu Gly Lys Ser Ser Pro Phe Ser Gln Pro Ala Ser Ser Ser Ala
785             790             795             800

Gln Ser Ser Ser Gln Thr Pro Lys Lys Leu Ala Val Leu Ser Thr Glu
            805             810             815

Pro Thr Cys Met Ser Ala Ser
            820

<210> SEQ ID NO 8
<211> LENGTH: 881
<212> TYPE: PRT
<213> ORGANISM: Felis catus
<220> FEATURE:
<221> NAME/KEY: misc_feature
<222> LOCATION: (1)..(881)
<223> OTHER INFORMATION: Felis catus interleukin-4 receptor subunit
      alpha

<400> SEQUENCE: 8

Met Gly Arg Leu Cys Ser Gly Leu Thr Phe Pro Val Ser Cys Leu Ile
1               5               10              15

Leu Met Trp Ala Ala Gly Ser Gly Ser Val Lys Val Leu Arg Ala Pro
            20              25              30

Thr Cys Phe Ser Asp Tyr Phe Ser Thr Ser Val Cys Gln Trp Asn Met
        35              40              45

Asp Ala Pro Thr Asn Cys Ser Ala Glu Leu Arg Leu Ser Tyr Gln Leu
    50              55              60

Asn Phe Met Gly Ser Glu Asn Arg Thr Cys Val Pro Glu Asn Gly Glu
65              70              75              80

Gly Ala Ala Cys Ala Cys Ser Met Leu Met Asp Asp Phe Val Glu Ala
            85              90              95

Asp Val Tyr Gln Leu His Leu Trp Ala Gly Thr Gln Leu Leu Trp Ser
            100             105             110

Gly Ser Phe Lys Pro Ser Ser His Val Lys Pro Arg Ala Pro Gly Asn
        115             120             125
```

```
Leu Thr Val His Pro Asn Val Ser His Thr Trp Leu Leu Arg Trp Ser
130                 135                 140

Asn Pro Tyr Pro Pro Glu Asn His Leu His Ala Glu Leu Thr Tyr Met
145                 150                 155                 160

Val Asn Ile Ser Ser Glu Asp Pro Thr Asp Val Ser Val Cys Ala
            165                 170                 175

Ser Gly Phe Leu Cys His Leu Leu Gly Leu Arg Arg Val Glu Thr Gly
            180                 185                 190

Ala Pro Gly Ala Arg Leu Pro Trp Leu Cys Ala Pro Arg Pro Arg
        195                 200                 205

Arg Val Pro Gly Ser Gln Cys Ala Val Ile Ser Cys Cys Arg Trp Val
210                 215                 220

Leu Ile Ala Leu Thr Ser Arg Gly Arg Trp Arg Leu Thr Pro Gly
225                 230                 235                 240

Leu Arg Ser Gln Thr Arg Tyr Val Ser Val Ala Glu Gly Leu Phe Gly
                245                 250                 255

Ala Thr Pro Arg Val Leu Cys Pro Gly Thr Gln Ala Gly Leu Ala Ser
            260                 265                 270

Ala Ala Arg Glu Gln Met Ser Pro Asp Pro Ser Ala Phe His Ser Ile
        275                 280                 285

Asp Tyr Glu Pro Trp Glu Gln His Leu Pro Leu Gly Val Ser Ile Ser
290                 295                 300

Cys Leu Val Ile Leu Ala Val Cys Leu Ser Cys Tyr Leu Ser Val Ile
305                 310                 315                 320

Lys Ile Lys Lys Glu Trp Trp Asp Gln Ile Pro Asn Pro Ala His Ser
                325                 330                 335

His Leu Val Ala Ile Val Ile Gln Asp Pro Gln Val Ser Leu Trp Gly
            340                 345                 350

Lys Arg Ser Arg Gly Gln Glu Pro Ala Lys Cys Pro His Trp Lys Thr
        355                 360                 365

Cys Leu Arg Lys Leu Leu Pro Cys Leu Leu Glu His Gly Met Glu Arg
        370                 375                 380

Lys Glu Asp Pro Ser Lys Ile Ala Arg Asn Gly Pro Ser Gln Cys Ser
385                 390                 395                 400

Gly Lys Ser Ala Trp Cys Pro Val Glu Val Ser Lys Thr Ile Leu Trp
                405                 410                 415

Pro Glu Ser Ile Ser Val Val Arg Cys Val Glu Leu Glu Ala Pro
            420                 425                 430

Val Glu Ser Glu Glu Glu Glu Glu Glu Asp Lys Gly Ser Phe
            435                 440                 445

Cys Pro Ser Pro Val Asn Leu Glu Asp Ser Phe Gln Glu Gly Arg Glu
450                 455                 460

Gly Ile Ala Ala Arg Leu Thr Glu Ser Leu Phe Met Asp Leu Leu Gly
465                 470                 475                 480

Val Glu Lys Gly Gly Phe Gly Pro Gln Gly Ser Leu Glu Ser Trp Phe
                485                 490                 495

Pro Pro Pro Ser Gly Ser Ala Gly Ala Gln Met Pro Trp Ala Glu Phe
            500                 505                 510

Pro Gly Pro Gly Pro Gln Glu Ala Ser Pro Gln Gly Lys Glu Gln Pro
        515                 520                 525

Phe Asp Pro Arg Ser Asp Pro Leu Ala Thr Leu Pro Gln Ser Pro Ala
530                 535                 540

Ser Pro Thr Phe Pro Glu Thr Pro Pro Val Val Thr Asp Asn Pro Ala
```

```
            545                 550                 555                 560
Tyr Arg Ser Phe Gly Thr Phe Gln Gly Arg Ser Ser Gly Pro Gly Glu
                565                 570                 575

Cys Asp Ser Gly Pro Glu Leu Ala Gly Arg Leu Gly Glu Ala Asp Pro
                580                 585                 590

Gly Ile Pro Ala Ala Pro Gln Pro Ser Glu Pro Pro Ser Ala Leu Gln
                595                 600                 605

Pro Glu Ala Glu Thr Trp Glu Gln Ile Leu Arg Gln Arg Val Leu Gln
                610                 615                 620

His Arg Gly Ala Pro Ala Pro Ala Pro Gly Ser Gly Tyr Arg Glu Phe
625                 630                 635                 640

Val Cys Ala Val Arg Gln Gly Ser Thr Gln Asp Ser Gly Val Gly Asp
                645                 650                 655

Phe Gly Pro Ser Glu Glu Ala Gly Tyr Lys Ala Phe Ser Ser Leu Leu
                660                 665                 670

Thr Ser Gly Ala Val Cys Pro Glu Ser Gly Gly Glu Ala Gly Ser Gly
                675                 680                 685

Asp Gly Gly Tyr Lys Pro Phe Gln Ser Leu Thr Pro Gly Cys Pro Gly
                690                 695                 700

Ala Pro Ala Pro Val Pro Val Pro Leu Phe Thr Phe Gly Leu Asp Ala
705                 710                 715                 720

Glu Pro Pro His Cys Pro Gln Asp Ser Pro Leu Pro Gly Ser Ser Pro
                725                 730                 735

Glu Pro Ala Gly Lys Ala Gln Asp Ser His Lys Thr Pro Pro Ala Pro
                740                 745                 750

Glu Gln Ala Ala Asp Pro Leu Arg Asp Asp Leu Ala Ser Gly Ile Val
                755                 760                 765

Tyr Ser Ala Leu Thr Cys His Leu Cys Gly His Leu Lys Gln Cys His
                770                 775                 780

Gly Gln Glu Glu Gly Glu Ala His Pro Val Ala Ser Pro Cys Cys
785                 790                 795                 800

Gly Cys Cys Cys Gly Asp Arg Ser Ser Pro Leu Val Ser Pro Leu Arg
                805                 810                 815

Ala Pro Asp Pro Leu Pro Gly Gly Val Pro Leu Glu Ala Ser Leu Ser
                820                 825                 830

Pro Ala Ser Pro Ala Pro Leu Ala Val Ser Glu Glu Gly Pro Pro Ser
                835                 840                 845

Leu Cys Phe Gln Pro Ala Leu Ser His Ala His Ser Ser Ser Gln Thr
                850                 855                 860

Pro Lys Lys Val Ala Met Leu Ser Pro Glu Pro Thr Cys Thr Met Ala
865                 870                 875                 880

Ser

<210> SEQ ID NO 9
<211> LENGTH: 809
<212> TYPE: PRT
<213> ORGANISM: Equus caballus
<220> FEATURE:
<221> NAME/KEY: misc_feature
<222> LOCATION: (1)..(809)
<223> OTHER INFORMATION: Equus caballus interleukin-4 receptor subunit
      alpha

<400> SEQUENCE: 9

Met Gly Cys Leu Cys Pro Gly Leu Thr Leu Pro Val Ser Cys Leu Ile
1               5                   10                  15
```

```
Leu Val Trp Ala Ala Gly Ser Gly Ser Val Lys Val Leu His Leu Thr
            20                  25                  30

Ala Cys Phe Ser Asp Tyr Ile Ser Ala Ser Thr Cys Glu Trp Lys Met
            35                  40                  45

Asp Arg Pro Thr Asn Cys Ser Ala Gln Leu Arg Leu Ser Tyr Gln Leu
 50                  55                  60

Asn Asp Glu Phe Ser Asp Asn Leu Thr Cys Ile Pro Glu Asn Arg Glu
65                   70                  75                  80

Asp Glu Val Cys Val Cys Arg Met Leu Met Asp Asn Ile Val Ser Glu
                85                  90                  95

Asp Val Tyr Glu Leu Asp Leu Trp Ala Gly Asn Gln Leu Leu Trp Asn
            100                 105                 110

Ser Ser Phe Lys Pro Ser Arg His Val Lys Pro Arg Ala Pro Gln Asn
            115                 120                 125

Leu Thr Val His Ala Ile Ser His Thr Trp Leu Leu Thr Trp Ser Asn
            130                 135                 140

Pro Tyr Pro Leu Lys Asn His Leu Trp Ser Glu Leu Thr Tyr Leu Val
145                 150                 155                 160

Asn Ile Ser Lys Glu Asp Asp Pro Thr Asp Phe Lys Ile Tyr Asn Val
                165                 170                 175

Thr Tyr Met Asp Pro Thr Leu Arg Val Thr Ala Ser Thr Leu Lys Ser
            180                 185                 190

Arg Ala Thr Tyr Ser Ala Arg Val Lys Ala Arg Ala Gln Asn Tyr Asn
            195                 200                 205

Ser Thr Trp Ser Glu Trp Ser Pro Ser Thr Thr Trp His Asn Tyr Tyr
            210                 215                 220

Glu Gln Pro Leu Glu Gln Arg Leu Pro Leu Gly Val Ser Ile Ser Cys
225                 230                 235                 240

Val Val Ile Leu Ala Ile Cys Leu Ser Cys Tyr Phe Ser Ile Ile Lys
                245                 250                 255

Ile Lys Lys Glu Trp Trp Asp Gln Ile Pro Asn Pro Ala His Ser Pro
            260                 265                 270

Leu Val Ala Ile Val Leu Gln Asp Ser Gln Val Ser Leu Trp Gly Lys
            275                 280                 285

Gln Ser Arg Gly Gln Glu Pro Ala Lys Cys Pro Arg Trp Lys Thr Cys
290                 295                 300

Leu Thr Lys Leu Leu Pro Cys Leu Leu Glu His Gly Leu Gln Lys Glu
305                 310                 315                 320

Glu Asp Ser Ser Lys Thr Val Arg Asn Gly Pro Phe Gln Ser Pro Gly
                325                 330                 335

Lys Ser Ala Trp His Thr Val Gly Val Asn His Thr Ile Leu Arg Pro
            340                 345                 350

Glu Ile Ile Ser Val Val Pro Cys Val Glu Leu Cys Glu Ala Gln Val
            355                 360                 365

Glu Ser Glu Glu Glu Val Glu Asp Arg Gly Ser Phe Cys Pro
            370                 375                 380

Ser Pro Glu Ser Ser Gly Ser Gly Phe Gln Glu Gly Arg Glu Gly Val
385                 390                 395                 400

Ala Ala Arg Leu Thr Glu Ser Leu Phe Leu Gly Leu Leu Gly Ala Glu
                405                 410                 415

Asn Gly Ala Leu Gly Glu Ser Cys Leu Leu Pro Pro Leu Gly Ser Ala
            420                 425                 430
```

His Met Pro Trp Ala Arg Ile Ser Ala Gly Pro Gln Glu Ala Ala
            435                 440                 445

Ser Gln Gly Glu Glu Gln Pro Leu Asn Pro Glu Ser Asn Pro Leu Ala
450                 455                 460

Thr Leu Thr Gln Ser Pro Gly Ser Leu Ala Phe Thr Glu Ala Pro Ala
465                 470                 475                 480

Val Val Ala Asp Asn Pro Ala Tyr Arg Ser Phe Ser Asn Ser Leu Ser
                485                 490                 495

Gln Pro Arg Gly Pro Gly Glu Leu Asp Ser Asp Pro Gln Leu Ala Glu
            500                 505                 510

His Leu Gly Gln Val Asp Pro Ser Ile Pro Ser Ala Pro Gln Pro Ser
        515                 520                 525

Glu Pro Pro Thr Ala Leu Gln Pro Glu Pro Glu Thr Trp Glu Gln Met
    530                 535                 540

Leu Arg Gln Ser Val Leu Gln Gln Gly Ala Ala Pro Ala Pro Ala Ser
545                 550                 555                 560

Ala Pro Thr Gly Gly Tyr Arg Glu Phe Ala Gln Ala Val Lys Gln Gly
                565                 570                 575

Gly Gly Ala Ala Gly Ser Gly Pro Ser Gly Glu Ala Gly Tyr Lys Ala
            580                 585                 590

Phe Ser Ser Leu Leu Ala Gly Ser Ala Val Cys Pro Gly Gln Ser Gly
        595                 600                 605

Val Glu Ala Ser Ser Gly Glu Gly Gly Tyr Arg Pro Tyr Glu Ser Pro
    610                 615                 620

Asp Pro Gly Ala Pro Ala Pro Val Pro Val Pro Leu Phe Thr Phe Gly
625                 630                 635                 640

Leu Asp Val Glu Pro Pro His Ser Pro Gln Asn Ser Leu Leu Pro Gly
                645                 650                 655

Gly Ser Pro Glu Leu Pro Gly Pro Glu Pro Thr Val Lys Gly Glu Asp
            660                 665                 670

Pro Arg Lys Pro Leu Leu Ser Ala Gln Gln Ala Thr Asp Ser Leu Arg
        675                 680                 685

Asp Asp Leu Gly Ser Gly Ile Val Tyr Ser Ala Leu Thr Cys His Leu
    690                 695                 700

Cys Gly His Leu Lys Gln Cys His Gly Gln Glu Glu His Gly Glu Ala
705                 710                 715                 720

His Thr Val Ala Ser Pro Cys Cys Gly Cys Cys Gly Asp Arg Ser
                725                 730                 735

Ser Pro Pro Val Ser Pro Val Arg Ala Leu Asp Pro Pro Gly Gly
            740                 745                 750

Val Pro Leu Glu Ala Gly Leu Ser Leu Ala Ser Leu Gly Ser Leu Gly
        755                 760                 765

Leu Ser Glu Glu Arg Lys Pro Ser Leu Phe Phe Gln Pro Ala Pro Gly
    770                 775                 780

Asn Ala Gln Ser Ser Ser Gln Thr Pro Leu Thr Val Ala Met Leu Ser
785                 790                 795                 800

Thr Gly Pro Thr Cys Thr Ser Ala Ser
                805

<210> SEQ ID NO 10
<211> LENGTH: 427
<212> TYPE: PRT
<213> ORGANISM: Canis lupus
<220> FEATURE:
<221> NAME/KEY: misc_feature
<222> LOCATION: (1)..(427)
<223> OTHER INFORMATION: Canis lupus interleukin-13 receptor subunit alpha-1

<400> SEQUENCE: 10

```
Met Glu Arg Pro Ala Arg Leu Cys Gly Leu Trp Ala Leu Leu Leu Cys
1               5                   10                  15

Ala Ala Gly Gly Arg Gly Gly Val Ala Ala Pro Thr Glu Thr Gln
            20                  25                  30

Pro Pro Val Thr Asn Leu Ser Val Glu Asn Leu Cys Thr Val
            35              40                  45

Ile Trp Thr Trp Asp Pro Pro Glu Gly Ala Ser Pro Asn Cys Thr Leu
50                      55                  60

Arg Tyr Phe Ser His Phe Asp Asn Lys Gln Asp Lys Lys Ile Ala Pro
65                  70                  75                  80

Glu Thr His Arg Ser Lys Glu Val Pro Leu Asn Glu Arg Ile Cys Leu
                85                  90                  95

Gln Val Gly Ser Gln Cys Ser Thr Asn Glu Ser Asp Asn Pro Ser Ile
            100                 105                 110

Leu Val Glu Lys Cys Thr Pro Pro Glu Gly Asp Pro Glu Ser Ala
        115                 120                 125

Val Thr Glu Leu Gln Cys Val Trp His Asn Leu Ser Tyr Met Lys Cys
130                 135                 140

Thr Trp Leu Pro Gly Arg Asn Thr Ser Pro Asp Thr Asn Tyr Thr Leu
145                 150                 155                 160

Tyr Tyr Trp His Ser Ser Leu Gly Lys Ile Leu Gln Cys Glu Asp Ile
                165                 170                 175

Tyr Arg Glu Gly Gln His Ile Gly Cys Ser Phe Ala Leu Thr Asn Leu
            180                 185                 190

Lys Asp Ser Ser Phe Glu Gln His Ser Val Gln Ile Val Lys Asp
        195                 200                 205

Asn Ala Gly Lys Ile Arg Pro Ser Phe Asn Ile Val Pro Leu Thr Ser
210                 215                 220

His Val Lys Pro Asp Pro Pro His Ile Lys Arg Leu Phe Phe Gln Asn
225                 230                 235                 240

Gly Asn Leu Tyr Val Gln Trp Lys Asn Pro Gln Asn Phe Tyr Ser Arg
                245                 250                 255

Cys Leu Ser Tyr Gln Val Glu Val Asn Asn Ser Gln Thr Glu Thr Asn
            260                 265                 270

Asp Ile Phe Tyr Val Glu Glu Ala Lys Cys Gln Asn Ser Glu Phe Glu
        275                 280                 285

Gly Asn Leu Glu Gly Thr Ile Cys Phe Met Val Pro Gly Val Leu Pro
290                 295                 300

Asp Thr Leu Asn Thr Val Arg Ile Arg Val Arg Thr Asn Lys Leu Cys
305                 310                 315                 320

Tyr Glu Asp Asp Lys Leu Trp Ser Asn Trp Ser Gln Ala Met Ser Ile
                325                 330                 335

Gly Glu Asn Thr Asp Pro Thr Phe Tyr Ile Thr Met Leu Leu Ala Thr
            340                 345                 350

Pro Val Ile Val Ala Gly Ala Ile Val Leu Leu Leu Tyr Leu Lys
        355                 360                 365

Arg Leu Lys Ile Ile Ile Phe Pro Pro Ile Pro Asp Pro Gly Lys Ile
370                 375                 380

Phe Lys Glu Met Phe Gly Asp Gln Asn Asp Asp Thr Leu His Trp Arg
```

```
               385                 390                 395                 400
Lys Tyr Asp Ile Tyr Glu Lys Gln Thr Lys Glu Glu Thr Asp Ser Val
                        405                 410                 415

Val Leu Ile Glu Asn Leu Lys Lys Ala Ser Gln
                    420                 425

<210> SEQ ID NO 11
<211> LENGTH: 479
<212> TYPE: PRT
<213> ORGANISM: Felis catus
<220> FEATURE:
<221> NAME/KEY: misc_feature
<222> LOCATION: (1)..(479)
<223> OTHER INFORMATION: Felis catus interleukin-13 receptor subunit
      alpha-1

<400> SEQUENCE: 11

Met Met Thr Lys Cys Ser Ser Asp Arg Asn Val Phe Lys Arg Lys Trp
1               5                   10                  15

Phe Leu Phe Pro Ala Ser Gln Tyr Thr Phe Arg Pro Ile His Gln Ala
                20                  25                  30

Arg Pro Cys Glu Val Pro Ala Val His Leu Glu Pro Ser Pro Pro Trp
            35                  40                  45

Glu Val Gly Leu Gly Leu Leu Asn Leu Glu Ser Glu Phe Arg Lys Leu
        50                  55                  60

Gly Leu Arg Gly Arg Arg Leu Ala Ala Ala Pro Pro Asp Ser Arg Ala
65                  70                  75                  80

Glu Ala Ala Ser Gln Thr Gln Pro Pro Val Thr Asn Leu Ser Val Ser
                85                  90                  95

Val Glu Asn Leu Cys Thr Val Ile Trp Thr Trp Asp Pro Pro Glu Gly
                100                 105                 110

Ala Ser Pro Asn Cys Thr Leu Arg Tyr Phe Ser His Phe Asp Asn Lys
            115                 120                 125

Gln Asp Lys Lys Ile Ala Pro Glu Thr His Arg Ser Lys Glu Val Pro
        130                 135                 140

Leu Asn Glu Arg Ile Cys Leu Gln Val Gly Ser Gln Cys Ser Thr Asn
145                 150                 155                 160

Glu Ser Asp Asn Pro Ser Ile Leu Val Glu Lys Cys Thr Pro Pro Pro
                165                 170                 175

Glu Gly Asp Pro Glu Ser Ala Val Thr Glu Leu Gln Cys Val Trp His
            180                 185                 190

Asn Leu Ser Tyr Met Lys Cys Thr Trp Leu Pro Gly Arg Asn Thr Ser
        195                 200                 205

Pro Asp Thr Asn Tyr Thr Leu Tyr Tyr Trp His Ser Ser Leu Gly Lys
            210                 215                 220

Ile Leu Gln Cys Glu Asn Ile Tyr Arg Glu Gly Gln His Ile Gly Cys
225                 230                 235                 240

Ser Phe Ala Leu Thr Asn Leu Lys Asp Ser Phe Glu Gln His Ser
                245                 250                 255

Val Gln Ile Val Val Lys Asp Asn Ala Gly Lys Ile Arg Pro Ser Phe
            260                 265                 270

Asn Ile Val Pro Leu Thr Ser His Val Lys Pro Asp Pro His Ile
        275                 280                 285

Lys Arg Leu Phe Phe Gln Asn Gly Asn Leu Tyr Val Gln Trp Lys Asn
        290                 295                 300

Pro Gln Asn Phe Tyr Ser Arg Cys Leu Ser Tyr Gln Val Glu Val Asn
```

```
                305                 310                 315                 320
Asn Ser Gln Thr Glu Thr His Asp Ile Phe Tyr Val Glu Glu Ala Lys
                    325                 330                 335

Cys Gln Asn Ser Glu Phe Glu Gly Asn Leu Glu Gly Thr Ile Cys Phe
                340                 345                 350

Met Val Pro Gly Ile Leu Pro Asp Thr Leu Asn Thr Val Arg Ile Arg
            355                 360                 365

Val Arg Thr Asn Lys Leu Cys Tyr Glu Asp Arg Leu Trp Ser Asn
        370                 375                 380

Trp Ser Gln Ala Met Ser Ile Gly Glu Asn Thr Asp Pro Thr Phe Tyr
385                 390                 395                 400

Ile Thr Met Leu Leu Ala Thr Pro Val Ile Val Ala Gly Ala Ile Ile
                405                 410                 415

Val Leu Leu Leu Tyr Leu Lys Arg Leu Lys Ile Ile Phe Pro Pro
                420                 425                 430

Ile Pro Asp Pro Gly Lys Ile Phe Lys Glu Met Phe Gly Asp Gln Asn
            435                 440                 445

Asp Asp Ser Leu His Trp Lys Lys Tyr Asp Ile Tyr Glu Lys Gln Thr
        450                 455                 460

Lys Glu Glu Thr Asp Ser Val Val Leu Ile Glu Asn Ala Ser Gln
465                 470                 475
```

<210> SEQ ID NO 12
<211> LENGTH: 407
<212> TYPE: PRT
<213> ORGANISM: Equus caballus
<220> FEATURE:
<221> NAME/KEY: misc_feature
<222> LOCATION: (1)..(407)
<223> OTHER INFORMATION: Equus caballus interleukin-13 receptor subunit
      alpha-1

<400> SEQUENCE: 12

```
Met Tyr Phe Leu Cys Leu Ile Trp Thr Glu Ser Gln Pro Pro Val Thr
1               5                   10                  15

Asn Leu Ser Val Ser Val Glu Asn Leu Cys Thr Val Ile Trp Thr Trp
                20                  25                  30

Asn Pro Pro Glu Gly Val Ser Pro Asn Cys Ser Leu Trp Tyr Phe Ser
            35                  40                  45

His Phe Gly Asn Lys Gln Asp Lys Lys Ile Ala Pro Glu Thr His Arg
        50                  55                  60

Ser Lys Glu Val Pro Leu Asn Glu Arg Ile Cys Leu Gln Val Gly Ser
65                  70                  75                  80

Gln Cys Ser Thr Asn Glu Ser Asp Asn Pro Ser Ile Leu Val Glu Lys
                85                  90                  95

Cys Ile Ser Pro Pro Glu Gly Asp Pro Glu Ser Ala Val Thr Glu Leu
            100                 105                 110

Gln Cys Val Trp His Asn Leu Ser Tyr Met Lys Cys Thr Trp Leu Pro
        115                 120                 125

Gly Lys Asn Ala Ser Pro Asp Thr Asn Tyr Thr Leu Tyr Tyr Trp His
        130                 135                 140

Ser Ser Leu Gly Lys Ile Leu Gln Cys Glu Asp Ile Tyr Arg Glu Gly
145                 150                 155                 160

Gln His Ile Gly Cys Ser Phe Ala Leu Thr Glu Val Lys Asp Ser Ile
                165                 170                 175

Phe Glu Gln His Ser Val Gln Ile Met Val Lys Asp Asn Ala Gly Lys
```

```
                180             185             190
Ile Arg Pro Phe Phe Asn Ile Val Pro Leu Thr Ser His Val Lys Pro
            195             200             205

Asp Pro Pro His Ile Lys Lys Leu Phe Phe Gln Asn Gly Asp Leu Tyr
            210             215             220

Val Gln Trp Lys Asn Pro Gln Asn Phe Tyr Ser Arg Cys Leu Ser Tyr
225             230             235             240

Gln Val Glu Val Asn Asn Ser Gln Thr Glu Thr Arg Asp Ile Phe Ser
            245             250             255

Val Glu Glu Ala Lys Cys Gln Asn Pro Glu Phe Glu Gly Asp Leu Glu
            260             265             270

Gly Thr Ile Cys Phe Met Val Pro Gly Val Leu Pro Asp Thr Val Asn
            275             280             285

Thr Val Arg Ile Arg Val Lys Thr Asn Lys Leu Cys Tyr Glu Asp Asp
            290             295             300

Lys Leu Trp Ser Asn Trp Ser Gln Ala Met Ser Ile Gly Lys Lys Ala
305             310             315             320

Asp Pro Thr Phe Tyr Ile Ala Met Leu Leu Ile Ile Pro Val Ile Val
            325             330             335

Ala Gly Ala Ile Ile Val Leu Leu Leu Tyr Leu Lys Arg Leu Lys Ile
            340             345             350

Ile Met Phe Pro Pro Ile Pro Asp Pro Gly Lys Ile Phe Lys Glu Met
            355             360             365

Phe Gly Asp Gln Asn Asp Asp Thr Leu His Trp Lys Lys Tyr Asp Ile
            370             375             380

Tyr Glu Lys Gln Thr Lys Glu Glu Thr Asp Ser Val Val Leu Ile Glu
385             390             395             400

Asn Leu Lys Arg Ala Ser Gln
            405

<210> SEQ ID NO 13
<211> LENGTH: 761
<212> TYPE: PRT
<213> ORGANISM: Artificial Sequence
<220> FEATURE:
<223> OTHER INFORMATION: Synthetic: Exemplary Canis lupus IL13RECD-
      IL4RECD-IgGA Fc (without signal sequence)

<400> SEQUENCE: 13

Thr Glu Thr Gln Pro Pro Val Thr Asn Leu Ser Val Ser Val Glu Asn
1               5              10              15

Leu Cys Thr Val Ile Trp Thr Trp Asp Pro Pro Glu Gly Ala Ser Pro
            20              25              30

Asn Cys Thr Leu Arg Tyr Phe Ser His Phe Asp Asn Lys Gln Asp Lys
            35              40              45

Lys Ile Ala Pro Glu Thr His Arg Ser Lys Glu Val Pro Leu Asn Glu
            50              55              60

Arg Ile Cys Leu Gln Val Gly Ser Gln Cys Ser Thr Asn Glu Ser Asp
65              70              75              80

Asn Pro Ser Ile Leu Val Glu Lys Cys Thr Pro Pro Glu Gly Asp
            85              90              95

Pro Glu Ser Ala Val Thr Glu Leu Gln Cys Val Trp His Asn Leu Ser
            100             105             110

Tyr Met Lys Cys Thr Trp Leu Pro Gly Arg Asn Thr Ser Pro Asp Thr
            115             120             125
```

```
Asn Tyr Thr Leu Tyr Tyr Trp His Ser Ser Leu Gly Lys Ile Leu Gln
    130                 135                 140

Cys Glu Asp Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
                165                 170                 175

Val Val Lys Asp Asn Ala Gly Lys Ile Arg Pro Ser Phe Asn Ile Val
            180                 185                 190

Pro Leu Thr Ser His Val Lys Pro Asp Pro His Ile Lys Arg Leu
        195                 200                 205

Phe Phe Gln Asn Gly Asn Leu Tyr Val Gln Trp Lys Asn Pro Gln Asn
210                 215                 220

Phe Tyr Ser Arg Cys Leu Ser Tyr Gln Val Glu Val Asn Asn Ser Gln
225                 230                 235                 240

Thr Glu Thr Asn Asp Ile Phe Tyr Val Glu Glu Ala Lys Cys Gln Asn
                245                 250                 255

Ser Glu Phe Glu Gly Asn Leu Glu Gly Thr Ile Cys Phe Met Val Pro
            260                 265                 270

Gly Val Leu Pro Asp Thr Leu Asn Thr Val Arg Ile Arg Val Arg Thr
        275                 280                 285

Asn Lys Leu Cys Tyr Glu Asp Asp Lys Leu Trp Ser Asn Trp Ser Gln
290                 295                 300

Ala Met Ser Ile Gly Glu Asn Thr Asp Pro Thr Gly Gly Gly Ser Gly
305                 310                 315                 320

Ser Gly Ser Val Lys Val Leu His Glu Pro Ser Cys Phe Ser Asp Tyr
                325                 330                 335

Ile Ser Thr Ser Val Cys Gln Trp Lys Met Asp His Pro Thr Asn Cys
            340                 345                 350

Ser Ala Glu Leu Arg Leu Ser Tyr Gln Leu Asp Phe Met Gly Ser Glu
        355                 360                 365

Asn His Thr Cys Val Pro Glu Asn Arg Glu Asp Ser Val Cys Val Cys
370                 375                 380

Ser Met Pro Ile Asp Asp Ala Val Glu Ala Asp Val Tyr Gln Leu Asp
385                 390                 395                 400

Leu Trp Ala Gly Gln Gln Leu Leu Trp Ser Gly Ser Phe Gln Pro Ser
                405                 410                 415

Lys His Val Lys Pro Arg Thr Pro Gly Asn Leu Thr Val His Pro Asn
            420                 425                 430

Ile Ser His Thr Trp Leu Leu Met Trp Thr Asn Pro Tyr Pro Thr Glu
        435                 440                 445

Asn His Leu His Ser Glu Leu Thr Tyr Met Val Asn Val Ser Asn Asp
450                 455                 460

Asn Asp Pro Glu Asp Phe Lys Val Tyr Asn Val Thr Tyr Met Gly Pro
465                 470                 475                 480

Thr Leu Arg Leu Ala Ala Ser Thr Leu Lys Ser Gly Ala Ser Tyr Ser
                485                 490                 495

Ala Arg Val Arg Ala Trp Ala Gln Thr Tyr Asn Ser Thr Trp Ser Asp
            500                 505                 510

Trp Ser Pro Ser Thr Thr Trp Leu Asn Tyr Tyr Glu Pro Lys Arg Glu
        515                 520                 525

Asn Gly Arg Val Pro Arg Pro Asp Cys Pro Lys Cys Pro Ala Pro
530                 535                 540

Glu Met Leu Gly Gly Pro Ser Val Phe Ile Phe Pro Pro Lys Pro Lys
```

```
                545                 550                 555                 560
Asp Thr Leu Leu Ile Ala Arg Thr Pro Glu Val Thr Cys Val Val Val
                565                 570                 575

Asp Leu Asp Pro Glu Asp Pro Glu Val Gln Ile Ser Trp Phe Val Asp
            580                 585                 590

Gly Lys Gln Met Gln Thr Ala Lys Thr Gln Pro Arg Glu Glu Gln Phe
            595                 600                 605

Asn Gly Thr Tyr Arg Val Val Ser Val Leu Pro Ile Gly His Gln Asp
        610                 615                 620

Trp Leu Lys Gly Lys Gln Phe Thr Cys Lys Val Asn Asn Lys Ala Leu
625                 630                 635                 640

Pro Ser Pro Ile Glu Arg Thr Ile Ser Lys Ala Arg Gly Gln Ala His
                645                 650                 655

Gln Pro Ser Val Tyr Val Leu Pro Pro Ser Arg Glu Glu Leu Ser Lys
            660                 665                 670

Asn Thr Val Ser Leu Thr Cys Leu Ile Lys Asp Phe Phe Pro Pro Asp
            675                 680                 685

Ile Asp Val Glu Trp Gln Ser Asn Gly Gln Gln Glu Pro Glu Ser Lys
        690                 695                 700

Tyr Arg Thr Thr Pro Pro Gln Leu Asp Glu Asp Gly Ser Tyr Phe Leu
705                 710                 715                 720

Tyr Ser Lys Leu Ser Val Asp Lys Ser Arg Trp Gln Arg Gly Asp Thr
                725                 730                 735

Phe Ile Cys Ala Val Met His Glu Ala Leu His Asn His Tyr Thr Gln
            740                 745                 750

Glu Ser Leu Ser His Ser Pro Gly Lys
            755                 760

<210> SEQ ID NO 14
<211> LENGTH: 758
<212> TYPE: PRT
<213> ORGANISM: Artificial Sequence
<220> FEATURE:
<223> OTHER INFORMATION: Synthetic: Exemplary canine IL4RECD-IL13RECD-
      IgGA Fc (without signal sequence)

<400> SEQUENCE: 14

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
            20                  25                  30

Ser Ala Glu Leu Arg Leu Ser Tyr Gln Leu Asp Phe Met Gly Ser Glu
        35                  40                  45

Asn His Thr Cys Val Pro Glu Asn Arg Glu Asp Ser Val Cys Val Cys
    50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
                85                  90                  95

Lys His Val Lys Pro Arg Thr Pro Gly Asn Leu Thr Val His Pro Asn
            100                 105                 110

Ile Ser His Thr Trp Leu Leu Met Trp Thr Asn Pro Tyr Pro Thr Glu
        115                 120                 125

Asn His Leu His Ser Glu Leu Thr Tyr Met Val Asn Val Ser Asn Asp
    130                 135                 140
```

-continued

```
Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
            165                 170                 175

Ala Arg Val Arg Ala Trp Ala Gln Thr Tyr Asn Ser Thr Trp Ser Asp
            180                 185                 190

Trp Ser Pro Ser Thr Thr Trp Leu Asn Tyr Tyr Glu Pro Gly Gly Gly
            195                 200                 205

Ser Gly Thr Glu Thr Gln Pro Pro Val Thr Asn Leu Ser Val Ser Val
            210                 215                 220

Glu Asn Leu Cys Thr Val Ile Trp Thr Trp Asp Pro Pro Glu Gly Ala
225                 230                 235                 240

Ser Pro Asn Cys Thr Leu Arg Tyr Phe Ser His Phe Asp Asn Lys Gln
            245                 250                 255

Asp Lys Lys Ile Ala Pro Glu Thr His Arg Ser Lys Glu Val Pro Leu
            260                 265                 270

Asn Glu Arg Ile Cys Leu Gln Val Gly Ser Gln Cys Ser Thr Asn Glu
            275                 280                 285

Ser Asp Asn Pro Ser Ile Leu Val Glu Lys Cys Thr Pro Pro Pro Glu
290                 295                 300

Gly Asp Pro Glu Ser Ala Val Thr Glu Leu Gln Cys Val Trp His Asn
305                 310                 315                 320

Leu Ser Tyr Met Lys Cys Thr Trp Leu Pro Gly Arg Asn Thr Ser Pro
            325                 330                 335

Asp Thr Asn Tyr Thr Leu Tyr Tyr Trp His Ser Ser Leu Gly Lys Ile
            340                 345                 350

Leu Gln Cys Glu Asp Ile Tyr Arg Glu Gly Gln His Ile Gly Cys Ser
            355                 360                 365

Phe Ala Leu Thr Asn Leu Lys Asp Ser Ser Phe Glu Gln His Ser Val
            370                 375                 380

Gln Ile Val Val Lys Asp Asn Ala Gly Lys Ile Arg Pro Ser Phe Asn
385                 390                 395                 400

Ile Val Pro Leu Thr Ser His Val Lys Pro Asp Pro Pro His Ile Lys
            405                 410                 415

Arg Leu Phe Phe Gln Asn Gly Asn Leu Tyr Val Gln Trp Lys Asn Pro
            420                 425                 430

Gln Asn Phe Tyr Ser Arg Cys Leu Ser Tyr Gln Val Glu Val Asn Asn
            435                 440                 445

Ser Gln Thr Glu Thr Asn Asp Ile Phe Tyr Val Glu Glu Ala Lys Cys
            450                 455                 460

Gln Asn Ser Glu Phe Glu Gly Asn Leu Glu Gly Thr Ile Cys Phe Met
465                 470                 475                 480

Val Pro Gly Val Leu Pro Asp Thr Leu Asn Thr Val Arg Ile Arg Val
            485                 490                 495

Arg Thr Asn Lys Leu Cys Tyr Glu Asp Asp Lys Leu Trp Ser Asn Trp
            500                 505                 510

Ser Gln Ala Met Ser Ile Gly Glu Asn Thr Asp Pro Thr Phe Asn Glu
            515                 520                 525

Cys Arg Cys Thr Asp Thr Pro Pro Cys Pro Val Glu Pro Leu Gly
            530                 535                 540

Gly Pro Ser Val Leu Ile Phe Pro Pro Lys Pro Lys Asp Ile Leu Arg
545                 550                 555                 560

Ile Thr Arg Thr Pro Glu Val Thr Cys Val Val Leu Asp Leu Gly Arg
```

```
                      565                 570                 575
Glu Asp Pro Glu Val Gln Ile Ser Trp Phe Val Asp Gly Lys Glu Val
            580                 585                 590

His Thr Ala Lys Thr Gln Ser Arg Glu Gln Gln Phe Asn Gly Thr Tyr
            595                 600                 605

Arg Val Val Ser Val Leu Pro Ile Glu His Gln Asp Trp Leu Thr Gly
            610                 615                 620

Lys Glu Phe Lys Cys Arg Val Asn His Ile Asp Leu Pro Ser Pro Ile
625                 630                 635                 640

Glu Arg Thr Ile Ser Lys Ala Arg Gly Arg Ala His Lys Pro Ser Val
            645                 650                 655

Tyr Val Leu Pro Pro Ser Pro Lys Glu Leu Ser Ser Ser Asp Thr Val
            660                 665                 670

Ser Ile Thr Cys Leu Ile Lys Asp Phe Tyr Pro Pro Asp Ile Asp Val
            675                 680                 685

Glu Trp Gln Ser Asn Gly Gln Gln Glu Pro Glu Arg Lys His Arg Met
            690                 695                 700

Thr Pro Pro Gln Leu Asp Glu Asp Gly Ser Tyr Phe Leu Tyr Ser Lys
705                 710                 715                 720

Leu Ser Val Asp Lys Ser Arg Trp Gln Gln Gly Asp Pro Phe Thr Cys
            725                 730                 735

Ala Val Met His Glu Thr Leu Gln Asn His Tyr Thr Asp Leu Ser Leu
            740                 745                 750

Ser His Ser Pro Gly Lys
            755

<210> SEQ ID NO 15
<211> LENGTH: 762
<212> TYPE: PRT
<213> ORGANISM: Artificial Sequence
<220> FEATURE:
<223> OTHER INFORMATION: Synthetic: Exemplary canine IL4RECD-IL13RECD-
      IgGB Fc (without signal sequence)

<400> SEQUENCE: 15

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
            20                  25                  30

Ser Ala Glu Leu Arg Leu Ser Tyr Gln Leu Asp Phe Met Gly Ser Glu
            35                  40                  45

Asn His Thr Cys Val Pro Glu Asn Arg Glu Asp Ser Val Cys Val Cys
            50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
            85                  90                  95

Lys His Val Lys Pro Arg Thr Pro Gly Asn Leu Thr Val His Pro Asn
            100                 105                 110

Ile Ser His Thr Trp Leu Leu Met Trp Thr Asn Pro Tyr Pro Thr Glu
            115                 120                 125

Asn His Leu His Ser Glu Leu Thr Tyr Met Val Asn Val Ser Asn Asp
            130                 135                 140

Asn Asp Pro Glu Asp Phe Lys Val Tyr Asn Val Thr Tyr Met Gly Pro
145                 150                 155                 160
```

-continued

Thr Leu Arg Leu Ala Ala Ser Thr Leu Lys Ser Gly Ala Ser Tyr Ser
            165                 170                 175

Ala Arg Val Arg Ala Trp Ala Gln Thr Tyr Asn Ser Thr Trp Ser Asp
            180                 185                 190

Trp Ser Pro Ser Thr Thr Trp Leu Asn Tyr Tyr Glu Pro Gly Gly Gly
            195                 200                 205

Ser Gly Thr Glu Thr Gln Pro Pro Val Thr Asn Leu Ser Val Ser Val
            210                 215                 220

Glu Asn Leu Cys Thr Val Ile Trp Thr Trp Asp Pro Glu Gly Ala
225                 230                 235                 240

Ser Pro Asn Cys Thr Leu Arg Tyr Phe Ser His Phe Asp Asn Lys Gln
            245                 250                 255

Asp Lys Lys Ile Ala Pro Glu Thr His Arg Ser Lys Glu Val Pro Leu
            260                 265                 270

Asn Glu Arg Ile Cys Leu Gln Val Gly Ser Gln Cys Ser Thr Asn Glu
            275                 280                 285

Ser Asp Asn Pro Ser Ile Leu Val Glu Lys Cys Thr Pro Pro Glu
            290                 295                 300

Gly Asp Pro Glu Ser Ala Val Thr Glu Leu Gln Cys Val Trp His Asn
305                 310                 315                 320

Leu Ser Tyr Met Lys Cys Thr Trp Leu Pro Gly Arg Asn Thr Ser Pro
            325                 330                 335

Asp Thr Asn Tyr Thr Leu Tyr Tyr Trp His Ser Ser Leu Gly Lys Ile
            340                 345                 350

Leu Gln Cys Glu Asp Ile Tyr Arg Glu Gly Gln His Ile Gly Cys Ser
            355                 360                 365

Phe Ala Leu Thr Asn Leu Lys Asp Ser Ser Phe Glu Gln His Ser Val
            370                 375                 380

Gln Ile Val Val Lys Asp Asn Ala Gly Lys Ile Arg Pro Ser Phe Asn
385                 390                 395                 400

Ile Val Pro Leu Thr Ser His Val Lys Pro Asp Pro Pro His Ile Lys
            405                 410                 415

Arg Leu Phe Phe Gln Asn Gly Asn Leu Tyr Val Gln Trp Lys Asn Pro
            420                 425                 430

Gln Asn Phe Tyr Ser Arg Cys Leu Ser Tyr Gln Val Glu Val Asn Asn
            435                 440                 445

Ser Gln Thr Glu Thr Asn Asp Ile Phe Tyr Val Glu Glu Ala Lys Cys
            450                 455                 460

Gln Asn Ser Glu Phe Glu Gly Asn Leu Glu Gly Thr Ile Cys Phe Met
465                 470                 475                 480

Val Pro Gly Val Leu Pro Asp Thr Leu Asn Thr Val Arg Ile Arg Val
            485                 490                 495

Arg Thr Asn Lys Leu Cys Tyr Glu Asp Asp Lys Leu Trp Ser Asn Trp
            500                 505                 510

Ser Gln Ala Met Ser Ile Gly Glu Asn Thr Asp Pro Thr Pro Lys Arg
            515                 520                 525

Glu Asn Gly Arg Val Pro Arg Pro Asp Cys Pro Lys Cys Pro Ala
530                 535                 540

Pro Glu Met Leu Gly Gly Pro Ser Val Phe Ile Phe Pro Pro Lys Pro
545                 550                 555                 560

Lys Asp Thr Leu Leu Ile Ala Arg Thr Pro Glu Val Thr Cys Val Val
            565                 570                 575

Val Asp Leu Asp Pro Glu Asp Pro Glu Val Gln Ile Ser Trp Phe Val

```
                    580                 585                 590
Asp Gly Lys Gln Met Gln Thr Ala Lys Thr Gln Pro Arg Glu Glu Gln
                595                 600                 605

Phe Asn Gly Thr Tyr Arg Val Ser Val Leu Pro Ile Gly His Gln
        610                 615                 620

Asp Trp Leu Lys Gly Lys Gln Phe Thr Cys Lys Val Asn Asn Lys Ala
625                 630                 635                 640

Leu Pro Ser Pro Ile Glu Arg Thr Ile Ser Lys Ala Arg Gly Gln Ala
                645                 650                 655

His Gln Pro Ser Val Tyr Val Leu Pro Pro Ser Arg Glu Glu Leu Ser
                660                 665                 670

Lys Asn Thr Val Ser Leu Thr Cys Leu Ile Lys Asp Phe Phe Pro Pro
                675                 680                 685

Asp Ile Asp Val Glu Trp Gln Ser Asn Gly Gln Gln Glu Pro Glu Ser
                690                 695                 700

Lys Tyr Arg Thr Thr Pro Pro Gln Leu Asp Glu Asp Gly Ser Tyr Phe
705                 710                 715                 720

Leu Tyr Ser Lys Leu Ser Val Asp Lys Ser Arg Trp Gln Arg Gly Asp
                725                 730                 735

Thr Phe Ile Cys Ala Val Met His Glu Ala Leu His Asn His Tyr Thr
                740                 745                 750

Gln Glu Ser Leu Ser His Ser Pro Gly Lys
                755                 760

<210> SEQ ID NO 16
<211> LENGTH: 760
<212> TYPE: PRT
<213> ORGANISM: Artificial Sequence
<220> FEATURE:
<223> OTHER INFORMATION: Synthetic: Exemplary canine IL4RECD-IL13RECD-
      IgGC (without signal sequence)

<400> SEQUENCE: 16

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
                20                  25                  30

Ser Ala Glu Leu Arg Leu Ser Tyr Gln Leu Asp Phe Met Gly Ser Glu
                35                  40                  45

Asn His Thr Cys Val Pro Glu Asn Arg Glu Asp Ser Val Cys Val Cys
        50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
                85                  90                  95

Lys His Val Lys Pro Arg Thr Pro Gly Asn Leu Thr Val His Pro Asn
                100                 105                 110

Ile Ser His Thr Trp Leu Leu Met Trp Thr Asn Pro Tyr Pro Thr Glu
                115                 120                 125

Asn His Leu His Ser Glu Leu Thr Tyr Met Val Asn Val Ser Asn Asp
        130                 135                 140

Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
                165                 170                 175
```

-continued

Ala Arg Val Arg Ala Trp Ala Gln Thr Tyr Asn Ser Thr Trp Ser Asp
        180                 185                 190

Trp Ser Pro Ser Thr Thr Trp Leu Asn Tyr Tyr Glu Pro Gly Gly Gly
        195                 200             205

Ser Gly Thr Glu Thr Gln Pro Pro Val Thr Asn Leu Ser Val Ser Val
210                 215                 220

Glu Asn Leu Cys Thr Val Ile Trp Thr Trp Asp Pro Pro Glu Gly Ala
225                 230                 235                 240

Ser Pro Asn Cys Thr Leu Arg Tyr Phe Ser His Phe Asp Asn Lys Gln
                245                 250                 255

Asp Lys Lys Ile Ala Pro Glu Thr His Arg Ser Lys Glu Val Pro Leu
            260                 265                 270

Asn Glu Arg Ile Cys Leu Gln Val Gly Ser Gln Cys Ser Thr Asn Glu
        275                 280                 285

Ser Asp Asn Pro Ser Ile Leu Val Glu Lys Cys Thr Pro Pro Glu
    290                 295                 300

Gly Asp Pro Glu Ser Ala Val Thr Glu Leu Gln Cys Val Trp His Asn
305                 310                 315                 320

Leu Ser Tyr Met Lys Cys Thr Trp Leu Pro Gly Arg Asn Thr Ser Pro
                325                 330                 335

Asp Thr Asn Tyr Thr Leu Tyr Tyr Trp His Ser Ser Leu Gly Lys Ile
                340                 345                 350

Leu Gln Cys Glu Asp Ile Tyr Arg Glu Gly Gln His Ile Gly Cys Ser
            355                 360                 365

Phe Ala Leu Thr Asn Leu Lys Asp Ser Ser Phe Glu Gln His Ser Val
370                 375                 380

Gln Ile Val Val Lys Asp Asn Ala Gly Lys Ile Arg Pro Ser Phe Asn
385                 390                 395                 400

Ile Val Pro Leu Thr Ser His Val Lys Pro Asp Pro His Ile Lys
                405                 410                 415

Arg Leu Phe Phe Gln Asn Gly Asn Leu Tyr Val Gln Trp Lys Asn Pro
                420                 425                 430

Gln Asn Phe Tyr Ser Arg Cys Leu Ser Tyr Gln Val Glu Val Asn Asn
            435                 440                 445

Ser Gln Thr Glu Thr Asn Asp Ile Phe Tyr Val Glu Glu Ala Lys Cys
    450                 455                 460

Gln Asn Ser Glu Phe Glu Gly Asn Leu Glu Gly Thr Ile Cys Phe Met
465                 470                 475                 480

Val Pro Gly Val Leu Pro Asp Thr Leu Asn Thr Val Arg Ile Arg Val
                485                 490                 495

Arg Thr Asn Lys Leu Cys Tyr Glu Asp Asp Lys Leu Trp Ser Asn Trp
                500                 505                 510

Ser Gln Ala Met Ser Ile Gly Glu Asn Thr Asp Pro Thr Ala Lys Glu
            515                 520                 525

Cys Glu Cys Lys Cys Asn Cys Asn Asn Cys Pro Cys Pro Gly Cys Gly
            530                 535                 540

Leu Leu Gly Gly Pro Ser Val Phe Ile Phe Pro Pro Lys Pro Lys Asp
545                 550                 555                 560

Ile Leu Val Thr Ala Arg Thr Pro Thr Val Thr Cys Val Val Val Asp
                565                 570                 575

Leu Asp Pro Glu Asn Pro Glu Val Gln Ile Ser Trp Phe Val Asp Ser
            580                 585                 590

Lys Gln Val Gln Thr Ala Asn Thr Gln Pro Arg Glu Glu Gln Ser Asn

```
                595                 600                 605
Gly Thr Tyr Arg Val Val Ser Val Leu Pro Ile Gly His Gln Asp Trp
        610                 615                 620

Leu Ser Gly Lys Gln Phe Lys Cys Lys Val Asn Asn Lys Ala Leu Pro
625                 630                 635                 640

Ser Pro Ile Glu Glu Ile Ile Ser Lys Thr Pro Gly Gln Ala His Gln
                645                 650                 655

Pro Asn Val Tyr Val Leu Pro Pro Ser Arg Asp Glu Met Ser Lys Asn
                660                 665                 670

Thr Val Thr Leu Thr Cys Leu Val Lys Asp Phe Phe Pro Pro Glu Ile
                675                 680                 685

Asp Val Glu Trp Gln Ser Asn Gly Gln Gln Glu Pro Glu Ser Lys Tyr
        690                 695                 700

Arg Met Thr Pro Pro Gln Leu Asp Glu Asp Gly Ser Tyr Phe Leu Tyr
705                 710                 715                 720

Ser Lys Leu Ser Val Asp Lys Ser Arg Trp Gln Arg Gly Asp Thr Phe
                725                 730                 735

Ile Cys Ala Val Met His Glu Ala Leu His Asn His Tyr Thr Gln Ile
                740                 745                 750

Ser Leu Ser His Ser Pro Gly Lys
        755                 760

<210> SEQ ID NO 17
<211> LENGTH: 758
<212> TYPE: PRT
<213> ORGANISM: Artificial Sequence
<220> FEATURE:
<223> OTHER INFORMATION: Synthetic: Exemplary canine IL4RECD-IL13RECD-
      IgGD Fc (without signal sequence)

<400> SEQUENCE: 17

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
                20                  25                  30

Ser Ala Glu Leu Arg Leu Ser Tyr Gln Leu Asp Phe Met Gly Ser Glu
        35                  40                  45

Asn His Thr Cys Val Pro Glu Asn Arg Glu Asp Ser Val Cys Val Cys
    50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
                85                  90                  95

Lys His Val Lys Pro Arg Thr Pro Gly Asn Leu Thr Val His Pro Asn
                100                 105                 110

Ile Ser His Thr Trp Leu Leu Met Trp Thr Asn Pro Tyr Pro Thr Glu
        115                 120                 125

Asn His Leu His Ser Glu Leu Thr Tyr Met Val Asn Val Ser Asn Asp
    130                 135                 140

Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
                165                 170                 175

Ala Arg Val Arg Ala Trp Ala Gln Thr Tyr Asn Ser Thr Trp Ser Asp
                180                 185                 190
```

```
Trp Ser Pro Ser Thr Thr Trp Leu Asn Tyr Tyr Glu Pro Gly Gly
        195                 200                 205
Ser Gly Thr Glu Thr Gln Pro Pro Val Thr Asn Leu Ser Val Ser Val
210                 215                 220
Glu Asn Leu Cys Thr Val Ile Trp Thr Trp Asp Pro Pro Glu Gly Ala
225                 230                 235                 240
Ser Pro Asn Cys Thr Leu Arg Tyr Phe Ser His Phe Asp Asn Lys Gln
            245                 250                 255
Asp Lys Lys Ile Ala Pro Glu Thr His Arg Ser Lys Glu Val Pro Leu
                260                 265                 270
Asn Glu Arg Ile Cys Leu Gln Val Gly Ser Gln Cys Ser Thr Asn Glu
        275                 280                 285
Ser Asp Asn Pro Ser Ile Leu Val Glu Lys Cys Thr Pro Pro Glu
    290                 295                 300
Gly Asp Pro Glu Ser Ala Val Thr Glu Leu Gln Cys Val Trp His Asn
305                 310                 315                 320
Leu Ser Tyr Met Lys Cys Thr Trp Leu Pro Gly Arg Asn Thr Ser Pro
                325                 330                 335
Asp Thr Asn Tyr Thr Leu Tyr Tyr Trp His Ser Ser Leu Gly Lys Ile
                340                 345                 350
Leu Gln Cys Glu Asp Ile Tyr Arg Glu Gly Gln His Ile Gly Cys Ser
            355                 360                 365
Phe Ala Leu Thr Asn Leu Lys Asp Ser Ser Phe Glu Gln His Ser Val
370                 375                 380
Gln Ile Val Val Lys Asp Asn Ala Gly Lys Ile Arg Pro Ser Phe Asn
385                 390                 395                 400
Ile Val Pro Leu Thr Ser His Val Lys Pro Asp Pro Pro His Ile Lys
                405                 410                 415
Arg Leu Phe Phe Gln Asn Gly Asn Leu Tyr Val Gln Trp Lys Asn Pro
                420                 425                 430
Gln Asn Phe Tyr Ser Arg Cys Leu Ser Tyr Gln Val Glu Val Asn Asn
            435                 440                 445
Ser Gln Thr Glu Thr Asn Asp Ile Phe Tyr Val Glu Glu Ala Lys Cys
450                 455                 460
Gln Asn Ser Glu Phe Glu Gly Asn Leu Glu Gly Thr Ile Cys Phe Met
465                 470                 475                 480
Val Pro Gly Val Leu Pro Asp Thr Leu Asn Thr Val Arg Ile Arg Val
                485                 490                 495
Arg Thr Asn Lys Leu Cys Tyr Glu Asp Asp Lys Leu Trp Ser Asn Trp
                500                 505                 510
Ser Gln Ala Met Ser Ile Gly Glu Asn Thr Asp Pro Thr Pro Lys Glu
            515                 520                 525
Ser Thr Cys Lys Cys Ile Ser Pro Cys Pro Val Pro Glu Ser Leu Gly
    530                 535                 540
Gly Pro Ser Val Phe Ile Phe Pro Pro Lys Pro Lys Asp Ile Leu Arg
545                 550                 555                 560
Ile Thr Arg Thr Pro Glu Ile Thr Cys Val Val Leu Asp Leu Gly Arg
                565                 570                 575
Glu Asp Pro Glu Val Gln Ile Ser Trp Phe Val Asp Gly Lys Glu Val
                580                 585                 590
His Thr Ala Lys Thr Gln Pro Arg Glu Gln Gln Phe Asn Ser Thr Tyr
                595                 600                 605
Arg Val Val Ser Val Leu Pro Ile Glu His Gln Asp Trp Leu Thr Gly
```

-continued

```
    610                 615                 620

Lys Glu Phe Lys Cys Arg Val Asn His Ile Gly Leu Pro Ser Pro Ile
625                 630                 635                 640

Glu Arg Thr Ile Ser Lys Ala Arg Gly Gln Ala His Gln Pro Ser Val
                645                 650                 655

Tyr Val Leu Pro Pro Ser Pro Lys Glu Leu Ser Ser Ser Asp Thr Val
            660                 665                 670

Thr Leu Thr Cys Leu Ile Lys Asp Phe Phe Pro Pro Glu Ile Asp Val
        675                 680                 685

Glu Trp Gln Ser Asn Gly Gln Pro Glu Pro Glu Ser Lys Tyr His Thr
    690                 695                 700

Thr Ala Pro Gln Leu Asp Glu Asp Gly Ser Tyr Phe Leu Tyr Ser Lys
705                 710                 715                 720

Leu Ser Val Asp Lys Ser Arg Trp Gln Gln Gly Asp Thr Phe Thr Cys
                725                 730                 735

Ala Val Met His Glu Ala Leu Gln Asn His Tyr Thr Asp Leu Ser Leu
            740                 745                 750

Ser His Ser Pro Gly Lys
        755

<210> SEQ ID NO 18
<211> LENGTH: 590
<212> TYPE: PRT
<213> ORGANISM: Artificial Sequence
<220> FEATURE:
<223> OTHER INFORMATION: Synthetic: Exemplary Feline IL4RECD-IL13RECD
      (without signal sequence)

<400> SEQUENCE: 18

Ser Gly Ser Val Lys Val Leu Arg Ala Pro Thr Cys Phe Ser Asp Tyr
1               5                   10                  15

Phe Ser Thr Ser Val Cys Gln Trp Asn Met Asp Ala Pro Thr Asn Cys
            20                  25                  30

Ser Ala Glu Leu Arg Leu Ser Tyr Gln Leu Asn Phe Met Gly Ser Glu
        35                  40                  45

Asn Arg Thr Cys Val Pro Glu Asn Gly Glu Gly Ala Ala Cys Ala Cys
    50                  55                  60

Ser Met Leu Met Asp Asp Phe Val Glu Ala Asp Val Tyr Gln Leu His
65                  70                  75                  80

Leu Trp Ala Gly Thr Gln Leu Leu Trp Ser Gly Ser Phe Lys Pro Ser
                85                  90                  95

Ser His Val Lys Pro Arg Ala Pro Gly Asn Leu Thr Val His Pro Asn
            100                 105                 110

Val Ser His Thr Trp Leu Leu Arg Trp Ser Asn Pro Tyr Pro Pro Glu
        115                 120                 125

Asn His Leu His Ala Glu Leu Thr Tyr Met Val Asn Ile Ser Ser Glu
    130                 135                 140

Asp Asp Pro Thr Asp Val Ser Val Cys Ala Ser Gly Phe Leu Cys His
145                 150                 155                 160

Leu Leu Gly Leu Arg Arg Val Glu Thr Gly Ala Pro Gly Ala Arg Leu
                165                 170                 175

Pro Pro Trp Leu Cys Ala Pro Arg Pro Arg Arg Val Pro Gly Ser Gln
            180                 185                 190

Cys Ala Val Ile Ser Cys Cys Arg Trp Val Leu Ile Ala Leu Thr Ser
        195                 200                 205
```

```
Arg Gly Gly Arg Trp Arg Leu Thr Pro Gly Leu Arg Ser Gln Thr Arg
    210                 215                 220

Tyr Val Ser Val Ala Glu Gly Leu Phe Gly Ala Thr Pro Arg Val Leu
225                 230                 235                 240

Cys Pro Gly Thr Gln Ala Gly Leu Ala Ser Ala Ala Arg Glu Gln Met
                245                 250                 255

Ser Pro Asp Pro Ser Ala Phe His Ser Ile Asp Tyr Glu Pro Gly Gly
                260                 265                 270

Gly Ser Gly Ser Gln Thr Gln Pro Val Thr Asn Leu Ser Val Ser
                275                 280                 285

Val Glu Asn Leu Cys Thr Val Ile Trp Thr Trp Asp Pro Pro Glu Gly
290                 295                 300

Ala Ser Pro Asn Cys Thr Leu Arg Tyr Phe Ser His Phe Asp Asn Lys
305                 310                 315                 320

Gln Asp Lys Lys Ile Ala Pro Glu Thr His Arg Ser Lys Glu Val Pro
                325                 330                 335

Leu Asn Glu Arg Ile Cys Leu Gln Val Gly Ser Gln Cys Ser Thr Asn
                340                 345                 350

Glu Ser Asp Asn Pro Ser Ile Leu Val Glu Lys Cys Thr Pro Pro
                355                 360                 365

Glu Gly Asp Pro Glu Ser Ala Val Thr Glu Leu Gln Cys Val Trp His
370                 375                 380

Asn Leu Ser Tyr Met Lys Cys Thr Trp Leu Pro Gly Arg Asn Thr Ser
385                 390                 395                 400

Pro Asp Thr Asn Tyr Thr Leu Tyr Tyr Trp His Ser Ser Leu Gly Lys
                405                 410                 415

Ile Leu Gln Cys Glu Asn Ile Tyr Arg Glu Gly Gln His Ile Gly Cys
                420                 425                 430

Ser Phe Ala Leu Thr Asn Leu Lys Asp Ser Ser Phe Glu Gln His Ser
                435                 440                 445

Val Gln Ile Val Val Lys Asp Asn Ala Gly Lys Ile Arg Pro Ser Phe
450                 455                 460

Asn Ile Val Pro Leu Thr Ser His Val Lys Pro Asp Pro Pro His Ile
465                 470                 475                 480

Lys Arg Leu Phe Phe Gln Asn Gly Asn Leu Tyr Val Gln Trp Lys Asn
                485                 490                 495

Pro Gln Asn Phe Tyr Ser Arg Cys Leu Ser Tyr Gln Val Glu Val Asn
                500                 505                 510

Asn Ser Gln Thr Glu Thr His Asp Ile Phe Tyr Val Glu Glu Ala Lys
                515                 520                 525

Cys Gln Asn Ser Glu Phe Glu Gly Asn Leu Glu Gly Thr Ile Cys Phe
530                 535                 540

Met Val Pro Gly Ile Leu Pro Asp Thr Leu Asn Thr Val Arg Ile Arg
545                 550                 555                 560

Val Arg Thr Asn Lys Leu Cys Tyr Glu Asp Asp Arg Leu Trp Ser Asn
                565                 570                 575

Trp Ser Gln Ala Met Ser Ile Gly Glu Asn Thr Asp Pro Thr
                580                 585                 590

<210> SEQ ID NO 19
<211> LENGTH: 525
<212> TYPE: PRT
<213> ORGANISM: Artificial Sequence
<220> FEATURE:
<223> OTHER INFORMATION: Synthetic: Exemplary equine IL4RECD-IL13RECD
```

-continued (without signal sequence)

<400> SEQUENCE: 19

```
Ser Gly Ser Val Lys Val Leu His Leu Thr Ala Cys Phe Ser Asp Tyr
1               5                   10                  15

Ile Ser Ala Ser Thr Cys Glu Trp Lys Met Asp Arg Pro Thr Asn Cys
            20                  25                  30

Ser Ala Gln Leu Arg Leu Ser Tyr Gln Leu Asn Asp Glu Phe Ser Asp
        35                  40                  45

Asn Leu Thr Cys Ile Pro Glu Asn Arg Glu Asp Val Cys Val Cys
    50                  55                  60

Arg Met Leu Met Asp Asn Ile Val Ser Glu Asp Val Tyr Glu Leu Asp
65                  70                  75                  80

Leu Trp Ala Gly Asn Gln Leu Leu Trp Asn Ser Ser Phe Lys Pro Ser
                85                  90                  95

Arg His Val Lys Pro Arg Ala Pro Gln Asn Leu Thr Val His Ala Ile
            100                 105                 110

Ser His Thr Trp Leu Leu Thr Trp Ser Asn Pro Tyr Pro Leu Lys Asn
            115                 120                 125

His Leu Trp Ser Glu Leu Thr Tyr Leu Val Asn Ile Ser Lys Glu Asp
        130                 135                 140

Asp Pro Thr Asp Phe Lys Ile Tyr Asn Val Thr Tyr Met Asp Pro Thr
145                 150                 155                 160

Leu Arg Val Thr Ala Ser Thr Leu Lys Ser Arg Ala Thr Tyr Ser Ala
                165                 170                 175

Arg Val Lys Ala Arg Ala Gln Asn Tyr Asn Ser Thr Trp Ser Glu Trp
            180                 185                 190

Ser Pro Ser Thr Thr Trp His Asn Tyr Tyr Glu Gln Pro Gly Gly Gly
        195                 200                 205

Ser Gly Thr Glu Ser Gln Pro Pro Val Thr Asn Leu Ser Val Ser Val
    210                 215                 220

Glu Asn Leu Cys Thr Val Ile Trp Thr Trp Asn Pro Pro Glu Gly Val
225                 230                 235                 240

Ser Pro Asn Cys Ser Leu Trp Tyr Phe Ser His Phe Gly Asn Lys Gln
                245                 250                 255

Asp Lys Lys Ile Ala Pro Glu Thr His Arg Ser Lys Glu Val Pro Leu
            260                 265                 270

Asn Glu Arg Ile Cys Leu Gln Val Gly Ser Gln Cys Ser Thr Asn Glu
        275                 280                 285

Ser Asp Asn Pro Ser Ile Leu Val Glu Lys Cys Ile Ser Pro Pro Glu
    290                 295                 300

Gly Asp Pro Glu Ser Ala Val Thr Glu Leu Gln Cys Val Trp His Asn
305                 310                 315                 320

Leu Ser Tyr Met Lys Cys Thr Trp Leu Pro Gly Lys Asn Ala Ser Pro
                325                 330                 335

Asp Thr Asn Tyr Thr Leu Tyr Tyr Trp His Ser Ser Leu Gly Lys Ile
            340                 345                 350

Leu Gln Cys Glu Asp Ile Tyr Arg Glu Gly Gln His Ile Gly Cys Ser
        355                 360                 365

Phe Ala Leu Thr Glu Val Lys Asp Ser Ile Phe Glu Gln His Ser Val
    370                 375                 380

Gln Ile Met Val Lys Asp Asn Ala Gly Lys Ile Arg Pro Phe Phe Asn
385                 390                 395                 400
```

```
Ile Val Pro Leu Thr Ser His Val Lys Pro Asp Pro His Ile Lys
                405                 410                 415

Lys Leu Phe Phe Gln Asn Gly Asp Leu Tyr Val Gln Trp Lys Asn Pro
        420                 425                 430

Gln Asn Phe Tyr Ser Arg Cys Leu Ser Tyr Gln Val Glu Val Asn Asn
        435                 440                 445

Ser Gln Thr Glu Thr Arg Asp Ile Phe Ser Val Glu Glu Ala Lys Cys
        450                 455                 460

Gln Asn Pro Glu Phe Glu Gly Asp Leu Glu Gly Thr Ile Cys Phe Met
465                 470                 475                 480

Val Pro Gly Val Leu Pro Asp Thr Val Asn Thr Val Arg Ile Arg Val
                485                 490                 495

Lys Thr Asn Lys Leu Cys Tyr Glu Asp Asp Lys Leu Trp Ser Asn Trp
                500                 505                 510

Ser Gln Ala Met Ser Ile Gly Lys Lys Ala Asp Pro Thr
        515                 520                 525

<210> SEQ ID NO 20
<211> LENGTH: 780
<212> TYPE: PRT
<213> ORGANISM: Artificial Sequence
<220> FEATURE:
<223> OTHER INFORMATION: Synthetic: Exemplary canine IL13RECD-IL4RECD-
      IgGB Fc (with signal sequence)

<400> SEQUENCE: 20

Met Ala Val Leu Gly Leu Leu Phe Cys Leu Val Thr Phe Pro Ser Cys
1               5                   10                  15

Val Leu Ser Thr Glu Thr Gln Pro Pro Val Thr Asn Leu Ser Val Ser
                20                  25                  30

Val Glu Asn Leu Cys Thr Val Ile Trp Thr Trp Asp Pro Pro Glu Gly
            35                  40                  45

Ala Ser Pro Asn Cys Thr Leu Arg Tyr Phe Ser His Phe Asp Asn Lys
        50                  55                  60

Gln Asp Lys Lys Ile Ala Pro Glu Thr His Arg Ser Lys Glu Val Pro
65                  70                  75                  80

Leu Asn Glu Arg Ile Cys Leu Gln Val Gly Ser Gln Cys Ser Thr Asn
                85                  90                  95

Glu Ser Asp Asn Pro Ser Ile Leu Val Glu Lys Cys Thr Pro Pro
            100                 105                 110

Glu Gly Asp Pro Glu Ser Ala Val Thr Glu Leu Gln Cys Val Trp His
        115                 120                 125

Asn Leu Ser Tyr Met Lys Cys Thr Trp Leu Pro Gly Arg Asn Thr Ser
130                 135                 140

Pro Asp Thr Asn Tyr Thr Leu Tyr Tyr Trp His Ser Ser Leu Gly Lys
145                 150                 155                 160

Ile Leu Gln Cys Glu Asp Ile Tyr Arg Glu Gly Gln His Ile Gly Cys
                165                 170                 175

Ser Phe Ala Leu Thr Asn Leu Lys Asp Ser Ser Phe Glu Gln His Ser
            180                 185                 190

Val Gln Ile Val Val Lys Asp Asn Ala Gly Lys Ile Arg Pro Ser Phe
        195                 200                 205

Asn Ile Val Pro Leu Thr Ser His Val Lys Pro Asp Pro His Ile
    210                 215                 220

Lys Arg Leu Phe Phe Gln Asn Gly Asn Leu Tyr Val Gln Trp Lys Asn
225                 230                 235                 240
```

```
Pro Gln Asn Phe Tyr Ser Arg Cys Leu Ser Tyr Gln Val Glu Val Asn
            245                 250                 255

Asn Ser Gln Thr Glu Thr Asn Asp Ile Phe Tyr Val Glu Glu Ala Lys
            260                 265                 270

Cys Gln Asn Ser Glu Phe Glu Gly Asn Leu Glu Gly Thr Ile Cys Phe
            275                 280                 285

Met Val Pro Gly Val Leu Pro Asp Thr Leu Asn Thr Val Arg Ile Arg
            290                 295                 300

Val Arg Thr Asn Lys Leu Cys Tyr Glu Asp Asp Lys Leu Trp Ser Asn
305                 310                 315                 320

Trp Ser Gln Ala Met Ser Ile Gly Glu Asn Thr Asp Pro Thr Gly Gly
            325                 330                 335

Gly Ser Gly Ser Gly Ser Val Lys Val Leu His Glu Pro Ser Cys Phe
            340                 345                 350

Ser Asp Tyr Ile Ser Thr Ser Val Cys Gln Trp Lys Met Asp His Pro
            355                 360                 365

Thr Asn Cys Ser Ala Glu Leu Arg Leu Ser Tyr Gln Leu Asp Phe Met
            370                 375                 380

Gly Ser Glu Asn His Thr Cys Val Pro Glu Asn Arg Glu Asp Ser Val
385                 390                 395                 400

Cys Val Cys Ser Met Pro Ile Asp Asp Ala Val Glu Ala Asp Val Tyr
            405                 410                 415

Gln Leu Asp Leu Trp Ala Gly Gln Gln Leu Leu Trp Ser Gly Ser Phe
            420                 425                 430

Gln Pro Ser Lys His Val Lys Pro Arg Thr Pro Gly Asn Leu Thr Val
            435                 440                 445

His Pro Asn Ile Ser His Thr Trp Leu Leu Met Trp Thr Asn Pro Tyr
            450                 455                 460

Pro Thr Glu Asn His Leu His Ser Glu Leu Thr Tyr Met Val Asn Val
465                 470                 475                 480

Ser Asn Asp Asn Asp Pro Glu Asp Phe Lys Val Tyr Asn Val Thr Tyr
            485                 490                 495

Met Gly Pro Thr Leu Arg Leu Ala Ala Ser Thr Leu Lys Ser Gly Ala
            500                 505                 510

Ser Tyr Ser Ala Arg Val Arg Ala Trp Ala Gln Thr Tyr Asn Ser Thr
            515                 520                 525

Trp Ser Asp Trp Ser Pro Ser Thr Thr Trp Leu Asn Tyr Tyr Glu Pro
            530                 535                 540

Lys Arg Glu Asn Gly Arg Val Pro Arg Pro Asp Cys Pro Lys Cys
545                 550                 555                 560

Pro Ala Pro Glu Met Leu Gly Gly Pro Ser Val Phe Ile Phe Pro Pro
            565                 570                 575

Lys Pro Lys Asp Thr Leu Leu Ile Ala Arg Thr Pro Glu Val Thr Cys
            580                 585                 590

Val Val Val Asp Leu Asp Pro Glu Asp Pro Glu Val Gln Ile Ser Trp
            595                 600                 605

Phe Val Asp Gly Lys Gln Met Gln Thr Ala Lys Thr Gln Pro Arg Glu
            610                 615                 620

Glu Gln Phe Asn Gly Thr Tyr Arg Val Val Ser Val Leu Pro Ile Gly
625                 630                 635                 640

His Gln Asp Trp Leu Lys Gly Lys Gln Phe Thr Cys Lys Val Asn Asn
            645                 650                 655
```

```
Lys Ala Leu Pro Ser Pro Ile Glu Arg Thr Ile Ser Lys Ala Arg Gly
            660                 665                 670

Gln Ala His Gln Pro Ser Val Tyr Val Leu Pro Ser Arg Glu Glu
            675                 680                 685

Leu Ser Lys Asn Thr Val Ser Leu Thr Cys Leu Ile Lys Asp Phe Phe
        690                 695                 700

Pro Pro Asp Ile Asp Val Glu Trp Gln Ser Asn Gly Gln Gln Glu Pro
705                 710                 715                 720

Glu Ser Lys Tyr Arg Thr Thr Pro Pro Gln Leu Asp Glu Asp Gly Ser
                725                 730                 735

Tyr Phe Leu Tyr Ser Lys Leu Ser Val Asp Lys Ser Arg Trp Gln Arg
            740                 745                 750

Gly Asp Thr Phe Ile Cys Ala Val Met His Glu Ala Leu His Asn His
            755                 760                 765

Tyr Thr Gln Glu Ser Leu Ser His Ser Pro Gly Lys
            770                 775                 780

<210> SEQ ID NO 21
<211> LENGTH: 781
<212> TYPE: PRT
<213> ORGANISM: Artificial Sequence
<220> FEATURE:
<223> OTHER INFORMATION: Synthetic: Exemplary canine IL4RECD-IL13RECD-
      IgGB Fc (with signal sequence)

<400> SEQUENCE: 21

Met Ala Val Leu Gly Leu Leu Phe Cys Leu Val Thr Phe Pro Ser Cys
1               5                   10                  15

Val Leu Ser Ser Gly Ser Val Lys Val Leu His Glu Pro Ser Cys Phe
            20                  25                  30

Ser Asp Tyr Ile Ser Thr Ser Val Cys Gln Trp Lys Met Asp His Pro
        35                  40                  45

Thr Asn Cys Ser Ala Glu Leu Arg Leu Ser Tyr Gln Leu Asp Phe Met
    50                  55                  60

Gly Ser Glu Asn His Thr Cys Val Pro Glu Asn Arg Glu Asp Ser Val
65              70                  75                  80

Cys Val Cys Ser Met Pro Ile Asp Asp Ala Val Glu Ala Asp Val Tyr
                85                  90                  95

Gln Leu Asp Leu Trp Ala Gly Gln Gln Leu Leu Trp Ser Gly Ser Phe
            100                 105                 110

Gln Pro Ser Lys His Val Lys Pro Arg Thr Pro Gly Asn Leu Thr Val
        115                 120                 125

His Pro Asn Ile Ser His Thr Trp Leu Leu Met Trp Thr Asn Pro Tyr
    130                 135                 140

Pro Thr Glu Asn His Leu His Ser Glu Leu Thr Tyr Met Val Asn Val
145                 150                 155                 160

Ser Asn Asp Asn Asp Pro Glu Asp Phe Lys Val Tyr Asn Val Thr Tyr
                165                 170                 175

Met Gly Pro Thr Leu Arg Leu Ala Ala Ser Thr Leu Lys Ser Gly Ala
            180                 185                 190

Ser Tyr Ser Ala Arg Val Arg Ala Trp Ala Gln Thr Tyr Asn Ser Thr
        195                 200                 205

Trp Ser Asp Trp Ser Pro Ser Thr Thr Trp Leu Asn Tyr Tyr Glu Pro
    210                 215                 220

Gly Gly Gly Ser Gly Thr Glu Thr Gln Pro Pro Val Thr Asn Leu Ser
225                 230                 235                 240
```

```
Val Ser Val Glu Asn Leu Cys Thr Val Ile Trp Thr Trp Asp Pro Pro
                245                 250                 255
Glu Gly Ala Ser Pro Asn Cys Thr Leu Arg Tyr Phe Ser His Phe Asp
            260                 265                 270
Asn Lys Gln Asp Lys Lys Ile Ala Pro Glu Thr His Arg Ser Lys Glu
        275                 280                 285
Val Pro Leu Asn Glu Arg Ile Cys Leu Gln Val Gly Ser Gln Cys Ser
    290                 295                 300
Thr Asn Glu Ser Asp Asn Pro Ser Ile Leu Val Glu Lys Cys Thr Pro
305                 310                 315                 320
Pro Pro Glu Gly Asp Pro Glu Ser Ala Val Thr Glu Leu Gln Cys Val
                325                 330                 335
Trp His Asn Leu Ser Tyr Met Lys Cys Thr Trp Leu Pro Gly Arg Asn
            340                 345                 350
Thr Ser Pro Asp Thr Asn Tyr Thr Leu Tyr Tyr Trp His Ser Ser Leu
        355                 360                 365
Gly Lys Ile Leu Gln Cys Glu Asp Ile Tyr Arg Glu Gly Gln His Ile
    370                 375                 380
Gly Cys Ser Phe Ala Leu Thr Asn Leu Lys Asp Ser Ser Phe Glu Gln
385                 390                 395                 400
His Ser Val Gln Ile Val Val Lys Asp Asn Ala Gly Lys Ile Arg Pro
                405                 410                 415
Ser Phe Asn Ile Val Pro Leu Thr Ser His Val Lys Pro Asp Pro Pro
            420                 425                 430
His Ile Lys Arg Leu Phe Phe Gln Asn Gly Asn Leu Tyr Val Gln Trp
        435                 440                 445
Lys Asn Pro Gln Asn Phe Tyr Ser Arg Cys Leu Ser Tyr Gln Val Glu
    450                 455                 460
Val Asn Asn Ser Gln Thr Glu Thr Asn Asp Ile Phe Tyr Val Glu Glu
465                 470                 475                 480
Ala Lys Cys Gln Asn Ser Glu Phe Glu Gly Asn Leu Glu Gly Thr Ile
                485                 490                 495
Cys Phe Met Val Pro Gly Val Leu Pro Asp Thr Leu Asn Thr Val Arg
            500                 505                 510
Ile Arg Val Arg Thr Asn Lys Leu Cys Tyr Glu Asp Asp Lys Leu Trp
        515                 520                 525
Ser Asn Trp Ser Gln Ala Met Ser Ile Gly Glu Asn Thr Asp Pro Thr
    530                 535                 540
Pro Lys Arg Glu Asn Gly Arg Val Pro Arg Pro Asp Cys Pro Lys
545                 550                 555                 560
Cys Pro Ala Pro Glu Met Leu Gly Gly Pro Ser Val Phe Ile Phe Pro
                565                 570                 575
Pro Lys Pro Lys Asp Thr Leu Leu Ile Ala Arg Thr Pro Glu Val Thr
            580                 585                 590
Cys Val Val Val Asp Leu Asp Pro Glu Asp Pro Glu Val Gln Ile Ser
        595                 600                 605
Trp Phe Val Asp Gly Lys Gln Met Gln Thr Ala Lys Thr Gln Pro Arg
    610                 615                 620
Glu Glu Gln Phe Asn Gly Thr Tyr Arg Val Val Ser Val Leu Pro Ile
625                 630                 635                 640
Gly His Gln Asp Trp Leu Lys Gly Lys Gln Phe Thr Cys Lys Val Asn
                645                 650                 655
```

```
Asn Lys Ala Leu Pro Ser Pro Ile Glu Arg Thr Ile Ser Lys Ala Arg
            660                 665                 670

Gly Gln Ala His Gln Pro Ser Val Tyr Val Leu Pro Ser Arg Glu
        675                 680                 685

Glu Leu Ser Lys Asn Thr Val Ser Leu Thr Cys Leu Ile Lys Asp Phe
    690                 695                 700

Phe Pro Pro Asp Ile Asp Val Glu Trp Gln Ser Asn Gly Gln Gln Glu
705                 710                 715                 720

Pro Glu Ser Lys Tyr Arg Thr Thr Pro Gln Leu Asp Glu Asp Gly
                725                 730                 735

Ser Tyr Phe Leu Tyr Ser Lys Leu Ser Val Asp Lys Ser Arg Trp Gln
        740                 745                 750

Arg Gly Asp Thr Phe Ile Cys Ala Val Met His Glu Ala Leu His Asn
            755                 760                 765

His Tyr Thr Gln Glu Ser Leu Ser His Ser Pro Gly Lys
            770                 775                 780

<210> SEQ ID NO 22
<211> LENGTH: 315
<212> TYPE: PRT
<213> ORGANISM: Artificial Sequence
<220> FEATURE:
<223> OTHER INFORMATION: Synthetic: Exemplary canine IL13R extracellular
      domain (without signal sequence)

<400> SEQUENCE: 22

Thr Glu Thr Gln Pro Pro Val Thr Asn Leu Ser Val Ser Val Glu Asn
1               5                   10                  15

Leu Cys Thr Val Ile Trp Thr Trp Asp Pro Pro Glu Gly Ala Ser Pro
            20                  25                  30

Asn Cys Thr Leu Arg Tyr Phe Ser His Phe Asp Asn Lys Gln Asp Lys
        35                  40                  45

Lys Ile Ala Pro Glu Thr His Arg Ser Lys Glu Val Pro Leu Asn Glu
    50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Glu Gly Asp
            85                  90                  95

Pro Glu Ser Ala Val Thr Glu Leu Gln Cys Val Trp His Asn Leu Ser
        100                 105                 110

Tyr Met Lys Cys Thr Trp Leu Pro Gly Arg Asn Thr Ser Pro Asp Thr
            115                 120                 125

Asn Tyr Thr Leu Tyr Tyr Trp His Ser Ser Leu Gly Lys Ile Leu Gln
        130                 135                 140

Cys Glu Asp Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
            165                 170                 175

Val Val Lys Asp Asn Ala Gly Lys Ile Arg Pro Ser Phe Asn Ile Val
        180                 185                 190

Pro Leu Thr Ser His Val Lys Pro Asp Pro His Ile Lys Arg Leu
            195                 200                 205

Phe Phe Gln Asn Gly Asn Leu Tyr Val Gln Trp Lys Asn Pro Gln Asn
    210                 215                 220

Phe Tyr Ser Arg Cys Leu Ser Tyr Gln Val Glu Val Asn Asn Ser Gln
225                 230                 235                 240
```

```
Thr Glu Thr Asn Asp Ile Phe Tyr Val Glu Glu Ala Lys Cys Gln Asn
            245                 250                 255

Ser Glu Phe Glu Gly Asn Leu Glu Gly Thr Ile Cys Phe Met Val Pro
            260                 265                 270

Gly Val Leu Pro Asp Thr Leu Asn Thr Val Arg Ile Arg Val Arg Thr
            275                 280                 285

Asn Lys Leu Cys Tyr Glu Asp Asp Lys Leu Trp Ser Asn Trp Ser Gln
            290                 295                 300

Ala Met Ser Ile Gly Glu Asn Thr Asp Pro Thr
305                 310                 315

<210> SEQ ID NO 23
<211> LENGTH: 205
<212> TYPE: PRT
<213> ORGANISM: Artificial Sequence
<220> FEATURE:
<223> OTHER INFORMATION: Synthetic: Exemplary canine IL4R extracellular
      domain (ECD; without signal sequence)

<400> SEQUENCE: 23

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
            20                  25                  30

Ser Ala Glu Leu Arg Leu Ser Tyr Gln Leu Asp Phe Met Gly Ser Glu
            35                  40                  45

Asn His Thr Cys Val Pro Glu Asn Arg Glu Asp Ser Val Cys Val Cys
50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
            85                  90                  95

Lys His Val Lys Pro Arg Thr Pro Gly Asn Leu Thr Val His Pro Asn
            100                 105                 110

Ile Ser His Thr Trp Leu Leu Met Trp Thr Asn Pro Tyr Pro Thr Glu
            115                 120                 125

Asn His Leu His Ser Glu Leu Thr Tyr Met Val Asn Val Ser Asn Asp
            130                 135                 140

Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
            165                 170                 175

Ala Arg Val Arg Ala Trp Ala Gln Thr Tyr Asn Ser Thr Trp Ser Asp
            180                 185                 190

Trp Ser Pro Ser Thr Thr Trp Leu Asn Tyr Tyr Glu Pro
            195                 200                 205

<210> SEQ ID NO 24
<211> LENGTH: 315
<212> TYPE: PRT
<213> ORGANISM: Artificial Sequence
<220> FEATURE:
<223> OTHER INFORMATION: Synthetic: Exemplary feline IL13R extracellular
      domain (ECD; without signal sequence)

<400> SEQUENCE: 24

Ser Gln Thr Gln Pro Pro Val Thr Asn Leu Ser Val Ser Val Glu Asn
1               5                   10                  15
```

Leu Cys Thr Val Ile Trp Thr Trp Asp Pro Pro Glu Gly Ala Ser Pro
            20                  25                  30

Asn Cys Thr Leu Arg Tyr Phe Ser His Phe Asp Asn Lys Gln Asp Lys
            35                  40                  45

Lys Ile Ala Pro Glu Thr His Arg Ser Lys Glu Val Pro Leu Asn Glu
 50                  55                  60

Arg Ile Cys Leu Gln Val Gly Ser Gln Cys Ser Thr Asn Glu Ser Asp
 65                  70                  75                  80

Asn Pro Ser Ile Leu Val Glu Lys Cys Thr Pro Pro Glu Gly Asp
            85                  90                  95

Pro Glu Ser Ala Val Thr Glu Leu Gln Cys Val Trp His Asn Leu Ser
            100                 105                 110

Tyr Met Lys Cys Thr Trp Leu Pro Gly Arg Asn Thr Ser Pro Asp Thr
            115                 120                 125

Asn Tyr Thr Leu Tyr Tyr Trp His Ser Ser Leu Gly Lys Ile Leu Gln
130                 135                 140

Cys Glu Asn Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
            165                 170                 175

Val Val Lys Asp Asn Ala Gly Lys Ile Arg Pro Ser Phe Asn Ile Val
            180                 185                 190

Pro Leu Thr Ser His Val Lys Pro Asp Pro His Ile Lys Arg Leu
            195                 200                 205

Phe Phe Gln Asn Gly Asn Leu Tyr Val Gln Trp Lys Asn Pro Gln Asn
            210                 215                 220

Phe Tyr Ser Arg Cys Leu Ser Tyr Gln Val Glu Val Asn Asn Ser Gln
225                 230                 235                 240

Thr Glu Thr His Asp Ile Phe Tyr Val Glu Glu Ala Lys Cys Gln Asn
                245                 250                 255

Ser Glu Phe Glu Gly Asn Leu Glu Gly Thr Ile Cys Phe Met Val Pro
            260                 265                 270

Gly Ile Leu Pro Asp Thr Leu Asn Thr Val Arg Ile Arg Val Arg Thr
            275                 280                 285

Asn Lys Leu Cys Tyr Glu Asp Asp Arg Leu Trp Ser Asn Trp Ser Gln
            290                 295                 300

Ala Met Ser Ile Gly Glu Asn Thr Asp Pro Thr
305                 310                 315

<210> SEQ ID NO 25
<211> LENGTH: 270
<212> TYPE: PRT
<213> ORGANISM: Artificial Sequence
<220> FEATURE:
<223> OTHER INFORMATION: Synthetic: Exemplary feline IL4R extracellular
      domain (ECD; without signal sequence)

<400> SEQUENCE: 25

Ser Gly Ser Val Lys Val Leu Arg Ala Pro Thr Cys Phe Ser Asp Tyr
 1               5                  10                  15

Phe Ser Thr Ser Val Cys Gln Trp Asn Met Asp Ala Pro Thr Asn Cys
            20                  25                  30

Ser Ala Glu Leu Arg Leu Ser Tyr Gln Leu Asn Phe Met Gly Ser Glu
            35                  40                  45

Asn Arg Thr Cys Val Pro Glu Asn Gly Glu Gly Ala Ala Cys Ala Cys

```
                        50                  55                  60
Ser Met Leu Met Asp Asp Phe Val Glu Ala Asp Val Tyr Gln Leu His
 65                  70                  75                  80

Leu Trp Ala Gly Thr Gln Leu Leu Trp Ser Gly Ser Phe Lys Pro Ser
                 85                  90                  95

Ser His Val Lys Pro Arg Ala Pro Gly Asn Leu Thr Val His Pro Asn
                100                 105                 110

Val Ser His Thr Trp Leu Leu Arg Trp Ser Asn Pro Tyr Pro Pro Glu
            115                 120                 125

Asn His Leu His Ala Glu Leu Thr Tyr Met Val Asn Ile Ser Ser Glu
            130                 135                 140

Asp Asp Pro Thr Asp Val Ser Val Cys Ala Ser Gly Phe Leu Cys His
145                 150                 155                 160

Leu Leu Gly Leu Arg Arg Val Glu Thr Gly Ala Pro Gly Ala Arg Leu
                165                 170                 175

Pro Pro Trp Leu Cys Ala Pro Arg Pro Arg Val Pro Gly Ser Gln
                180                 185                 190

Cys Ala Val Ile Ser Cys Cys Arg Trp Val Leu Ile Ala Leu Thr Ser
            195                 200                 205

Arg Gly Gly Arg Trp Arg Leu Thr Pro Gly Leu Arg Ser Gln Thr Arg
210                 215                 220

Tyr Val Ser Val Ala Glu Gly Leu Phe Gly Ala Thr Pro Arg Val Leu
225                 230                 235                 240

Cys Pro Gly Thr Gln Ala Gly Leu Ala Ser Ala Ala Arg Glu Gln Met
                245                 250                 255

Ser Pro Asp Pro Ser Ala Phe His Ser Ile Asp Tyr Glu Pro
                260                 265                 270

<210> SEQ ID NO 26
<211> LENGTH: 315
<212> TYPE: PRT
<213> ORGANISM: Artificial Sequence
<220> FEATURE:
<223> OTHER INFORMATION: Synthetic: Exemplary equine IL13R extracellular
      domain (ECD; without signal sequence)

<400> SEQUENCE: 26

Thr Glu Ser Gln Pro Pro Val Thr Asn Leu Ser Val Ser Val Glu Asn
 1               5                  10                  15

Leu Cys Thr Val Ile Trp Thr Trp Asn Pro Pro Glu Gly Val

```
Cys Glu Asp Ile Tyr Arg Glu Gly Gln His Ile Gly Cys Ser Phe Ala
145                 150                 155                 160

Leu Thr Glu Val Lys Asp Ser Ile Phe Glu Gln His Ser Val Gln Ile
                165                 170                 175

Met Val Lys Asp Asn Ala Gly Lys Ile Arg Pro Phe Asn Ile Val
            180                 185                 190

Pro Leu Thr Ser His Val Lys Pro Asp Pro His Ile Lys Lys Leu
            195                 200                 205

Phe Phe Gln Asn Gly Asp Leu Tyr Val Gln Trp Lys Asn Pro Gln Asn
210                 215                 220

Phe Tyr Ser Arg Cys Leu Ser Tyr Gln Val Glu Val Asn Asn Ser Gln
225                 230                 235                 240

Thr Glu Thr Arg Asp Ile Phe Ser Val Glu Glu Ala Lys Cys Gln Asn
                245                 250                 255

Pro Glu Phe Glu Gly Asp Leu Glu Gly Thr Ile Cys Phe Met Val Pro
            260                 265                 270

Gly Val Leu Pro Asp Thr Val Asn Thr Val Arg Ile Arg Val Lys Thr
            275                 280                 285

Asn Lys Leu Cys Tyr Glu Asp Asp Lys Leu Trp Ser Asn Trp Ser Gln
290                 295                 300

Ala Met Ser Ile Gly Lys Lys Ala Asp Pro Thr
305                 310                 315

<210> SEQ ID NO 27
<211> LENGTH: 205
<212> TYPE: PRT
<213> ORGANISM: Artificial Sequence
<220> FEATURE:
<223> OTHER INFORMATION: Synthetic: Exemplary equine IL4R extracellular
      domain (ECD; without signal sequence)

<400> SEQUENCE: 27

Ser Gly Ser Val Lys Val Leu His Leu Thr Ala Cys Phe Ser Asp Tyr
1               5                   10                  15

Ile Ser Ala Ser Thr Cys Glu Trp Lys Met Asp Arg Pro Thr Asn Cys
            20                  25                  30

Ser Ala Gln Leu Arg Leu Ser Tyr Gln Leu Asn Asp Glu Phe Ser Asp
        35                  40                  45

Asn Leu Thr Cys Ile Pro Glu Asn Arg Glu Asp Glu Val Cys Val Cys
50                  55                  60

Arg Met Leu Met Asp Asn Ile Val Ser Glu Asp Val Tyr Glu Leu Asp
65                  70                  75                  80

Leu Trp Ala Gly Asn Gln Leu Leu Trp Asn Ser Ser Phe Lys Pro Ser
                85                  90                  95

Arg His Val Lys Pro Arg Ala Pro Gln Asn Leu Thr Val His Ala Ile
            100                 105                 110

Ser His Thr Trp Leu Leu Thr Trp Ser Asn Pro Tyr Pro Leu Lys Asn
        115                 120                 125

His Leu Trp Ser Glu Leu Thr Tyr Leu Val Asn Ile Ser Lys Glu Asp
130                 135                 140

Asp Pro Thr Asp Phe Lys Ile Tyr Asn Val Thr Tyr Met Asp Pro Thr
145                 150                 155                 160

Leu Arg Val Thr Ala Ser Thr Leu Lys Ser Arg Ala Thr Tyr Ser Ala
                165                 170                 175

Arg Val Lys Ala Arg Ala Gln Asn Tyr Asn Ser Thr Trp Ser Glu Trp
            180                 185                 190
```

Ser Pro Ser Thr Thr Trp His Asn Tyr Tyr Glu Gln Pro
        195                 200                 205

<210> SEQ ID NO 28
<211> LENGTH: 829
<212> TYPE: PRT
<213> ORGANISM: Artificial Sequence
<220> FEATURE:
<223> OTHER INFORMATION: Synthetic: Exemplary feline IL13RECD-IL4RECD-
      IgG2 Fc (without signal sequence)

<400> SEQUENCE: 28

Ser Gln Thr Gln Pro Pro Val Thr Asn Leu Ser Val Ser Val Glu Asn
1               5                   10                  15

Leu Cys Thr Val Ile Trp Thr Trp Asp Pro Glu Gly Ala Ser Pro
                20                  25                  30

Asn Cys Thr Leu Arg Tyr Phe Ser His Phe Asp Asn Lys Gln Asp Lys
            35                  40                  45

Lys Ile Ala Pro Glu Thr His Arg Ser Lys Glu Val Pro Leu Asn Glu
50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Gly Asp
                85                  90                  95

Pro Glu Ser Ala Val Thr Glu Leu Gln Cys Val Trp His Asn Leu Ser
                100                 105                 110

Tyr Met Lys Cys Thr Trp Leu Pro Gly Arg Asn Thr Ser Pro Asp Thr
            115                 120                 125

Asn Tyr Thr Leu Tyr Tyr Trp His Ser Ser Leu Gly Lys Ile Leu Gln
130                 135                 140

Cys Glu Asn Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
                165                 170                 175

Val Val Lys Asp Asn Ala Gly Lys Ile Arg Pro Ser Phe Asn Ile Val
            180                 185                 190

Pro Leu Thr Ser His Val Lys Pro Asp Pro Pro His Ile Lys Arg Leu
195                 200                 205

Phe Phe Gln Asn Gly Asn Leu Tyr Val Gln Trp Lys Asn Pro Gln Asn
210                 215                 220

Phe Tyr Ser Arg Cys Leu Ser Tyr Gln Val Glu Val Asn Asn Ser Gln
225                 230                 235                 240

Thr Glu Thr His Asp Ile Phe Tyr Val Glu Glu Ala Lys Cys Gln Asn
                245                 250                 255

Ser Glu Phe Glu Gly Asn Leu Glu Gly Thr Ile Cys Phe Met Val Pro
            260                 265                 270

Gly Ile Leu Pro Asp Thr Leu Asn Thr Val Arg Ile Arg Val Arg Thr
        275                 280                 285

Asn Lys Leu Cys Tyr Glu Asp Asp Arg Leu Trp Ser Asn Trp Ser Gln
290                 295                 300

Ala Met Ser Ile Gly Glu Asn Thr Asp Pro Thr Gly Gly Gly Ser Gly
305                 310                 315                 320

Ser Ser Gly Ser Val Lys Val Leu Arg Ala Pro Thr Cys Phe Ser Asp
                325                 330                 335

Tyr Phe Ser Thr Ser Val Cys Gln Trp Asn Met Asp Ala Pro Thr Asn

-continued

```
                340                 345                 350
Cys Ser Ala Glu Leu Arg Leu Ser Tyr Gln Leu Asn Phe Met Gly Ser
            355                 360                 365
Glu Asn Arg Thr Cys Val Pro Glu Asn Gly Glu Gly Ala Ala Cys Ala
            370                 375             380
Cys Ser Met Leu Met Asp Asp Phe Val Glu Ala Asp Val Tyr Gln Leu
385                 390                 395                 400
His Leu Trp Ala Gly Thr Gln Leu Leu Trp Ser Gly Ser Phe Lys Pro
                405                 410                 415
Ser Ser His Val Lys Pro Arg Ala Pro Gly Asn Leu Thr Val His Pro
            420                 425                 430
Asn Val Ser His Thr Trp Leu Leu Arg Trp Ser Asn Pro Tyr Pro Pro
            435                 440                 445
Glu Asn His Leu His Ala Glu Leu Thr Tyr Met Val Asn Ile Ser Ser
        450                 455                 460
Glu Asp Asp Pro Thr Asp Val Ser Val Cys Ala Ser Gly Phe Leu Cys
465                 470                 475                 480
His Leu Leu Gly Leu Arg Arg Val Glu Thr Gly Ala Pro Gly Ala Arg
                485                 490                 495
Leu Pro Pro Trp Leu Cys Ala Pro Arg Pro Arg Val Pro Gly Ser
                500                 505                 510
Gln Cys Ala Val Ile Ser Cys Cys Arg Trp Val Leu Ile Ala Leu Thr
            515                 520                 525
Ser Arg Gly Gly Arg Trp Arg Leu Thr Pro Gly Leu Arg Ser Gln Thr
            530                 535                 540
Arg Tyr Val Ser Val Ala Glu Gly Leu Phe Gly Ala Thr Pro Arg Val
545                 550                 555                 560
Leu Cys Pro Gly Thr Gln Ala Gly Leu Ala Ser Ala Ala Arg Glu Gln
                565                 570                 575
Met Ser Pro Asp Pro Ser Ala Phe His Ser Ile Asp Tyr Glu Pro Ser
            580                 585                 590
Pro Lys Thr Ala Ser Thr Ile Glu Ser Lys Thr Gly Glu Cys Pro Lys
            595                 600                 605
Cys Pro Val Pro Glu Ile Pro Gly Ala Pro Ser Val Phe Ile Phe Pro
    610                 615                 620
Pro Lys Pro Lys Asp Thr Leu Ser Ile Ser Arg Thr Pro Glu Val Thr
625                 630                 635                 640
Cys Leu Val Val Asp Leu Gly Pro Asp Asp Ser Asn Val Gln Ile Thr
                645                 650                 655
Trp Phe Val Asp Asn Thr Glu Met His Thr Ala Lys Thr Arg Pro Arg
            660                 665                 670
Glu Glu Gln Phe Asn Ser Thr Tyr Arg Val Val Ser Val Leu Pro Ile
            675                 680                 685
Leu His Gln Asp Trp Leu Lys Gly Lys Glu Phe Lys Cys Lys Val Asn
        690                 695                 700
Ser Lys Ser Leu Pro Ser Ala Met Glu Arg Thr Ile Ser Lys Ala Lys
705                 710                 715                 720
Gly Gln Pro His Glu Pro Gln Val Tyr Val Leu Pro Pro Thr Gln Glu
                725                 730                 735
Glu Leu Ser Glu Asn Lys Val Ser Val Thr Cys Leu Ile Lys Gly Phe
            740                 745                 750
His Pro Pro Asp Ile Ala Val Glu Trp Glu Ile Thr Gly Gln Pro Glu
            755                 760                 765
```

```
Pro Glu Asn Asn Tyr Gln Thr Thr Pro Pro Gln Leu Asp Ser Asp Gly
    770                 775                 780

Thr Tyr Phe Leu Tyr Ser Arg Leu Ser Val Asp Arg Ser His Trp Gln
785                 790                 795                 800

Arg Gly Asn Thr Tyr Thr Cys Ser Val Ser His Glu Ala Leu His Ser
            805                 810                 815

His His Thr Gln Lys Ser Leu Thr Gln Ser Pro Gly Lys
            820                 825

<210> SEQ ID NO 29
<211> LENGTH: 829
<212> TYPE: PRT
<213> ORGANISM: Artificial Sequence
<220> FEATURE:
<223> OTHER INFORMATION: Synthetic: Exemplary feline IL4RECD-IL13RECD-
      IgG2 (without signal sequence)

<400> SEQUENCE: 29

Ser Gly Ser Val Lys Val Leu Arg Ala Pro Thr Cys Phe Ser Asp Tyr
1               5                   10                  15

Phe Ser Thr Ser Val Cys Gln Trp Asn Met Asp Ala Pro Thr Asn Cys
            20                  25                  30

Ser Ala Glu Leu Arg Leu Ser Tyr Gln Leu Asn Phe Met Gly Ser Glu
        35                  40                  45

Asn Arg Thr Cys Val Pro Glu Asn Gly Glu Gly Ala Ala Cys Ala Cys
    50                  55                  60

Ser Met Leu Met Asp Asp Phe Val Glu Ala Asp Val Tyr Gln Leu His
65                  70                  75                  80

Leu Trp Ala Gly Thr Gln Leu Leu Trp Ser Gly Ser Phe Lys Pro Ser
                85                  90                  95

Ser His Val Lys Pro Arg Ala Pro Gly Asn Leu Thr Val His Pro Asn
            100                 105                 110

Val Ser His Thr Trp Leu Leu Arg Trp Ser Asn Pro Tyr Pro Pro Glu
        115                 120                 125

Asn His Leu His Ala Glu Leu Thr Tyr Met Val Asn Ile Ser Ser Glu
130                 135                 140

Asp Pro Thr Asp Val Ser Val Cys Ala Ser Gly Phe Leu Cys His
145                 150                 155                 160

Leu Leu Gly Leu Arg Arg Val Glu Thr Gly Ala Pro Gly Ala Arg Leu
                165                 170                 175

Pro Pro Trp Leu Cys Ala Pro Arg Pro Arg Val Pro Gly Ser Gln
            180                 185                 190

Cys Ala Val Ile Ser Cys Cys Arg Trp Val Leu Ile Ala Leu Thr Ser
        195                 200                 205

Arg Gly Gly Arg Trp Arg Leu Thr Pro Gly Leu Arg Ser Gln Thr Arg
210                 215                 220

Tyr Val Ser Val Ala Glu Gly Leu Phe Gly Ala Thr Pro Arg Val Leu
225                 230                 235                 240

Cys Pro Gly Thr Gln Ala Gly Leu Ala Ser Ala Ala Arg Glu Gln Met
                245                 250                 255

Ser Pro Asp Pro Ser Ala Phe His Ser Ile Asp Tyr Glu Pro Gly Gly
            260                 265                 270

Gly Ser Gly Ser Ser Gln Thr Gln Pro Pro Val Thr Asn Leu Ser Val
        275                 280                 285

Ser Val Glu Asn Leu Cys Thr Val Ile Trp Thr Trp Asp Pro Pro Glu
```

```
                290                 295                 300
Gly Ala Ser Pro Asn Cys Thr Leu Arg Tyr Phe Ser His Phe Asp Asn
305                 310                 315                 320

Lys Gln Asp Lys Lys Ile Ala Pro Glu Thr His Arg Ser Lys Glu Val
                325                 330                 335

Pro Leu Asn Glu Arg Ile Cys Leu Gln Val Gly Ser Gln Cys Ser Thr
                340                 345                 350

Asn Glu Ser Asp Asn Pro Ser Ile Leu Val Glu Lys Cys Thr Pro Pro
                355                 360                 365

Pro Glu Gly Asp Pro Glu Ser Ala Val Thr Glu Leu Gln Cys Val Trp
370                 375                 380

His Asn Leu Ser Tyr Met Lys Cys Thr Trp Leu Pro Gly Arg Asn Thr
385                 390                 395                 400

Ser Pro Asp Thr Asn Tyr Thr Leu Tyr Tyr Trp His Ser Ser Leu Gly
                405                 410                 415

Lys Ile Leu Gln Cys Glu Asn Ile Tyr Arg Glu Gly Gln His Ile Gly
                420                 425                 430

Cys Ser Phe Ala Leu Thr Asn Leu Lys Asp Ser Ser Phe Glu Gln His
                435                 440                 445

Ser Val Gln Ile Val Val Lys Asp Asn Ala Gly Lys Ile Arg Pro Ser
                450                 455                 460

Phe Asn Ile Val Pro Leu Thr Ser His Val Lys Pro Asp Pro Pro His
465                 470                 475                 480

Ile Lys Arg Leu Phe Phe Gln Asn Gly Asn Leu Tyr Val Gln Trp Lys
                485                 490                 495

Asn Pro Gln Asn Phe Tyr Ser Arg Cys Leu Ser Tyr Gln Val Glu Val
                500                 505                 510

Asn Asn Ser Gln Thr Glu Thr His Asp Ile Phe Tyr Val Glu Glu Ala
                515                 520                 525

Lys Cys Gln Asn Ser Glu Phe Glu Gly Asn Leu Glu Gly Thr Ile Cys
                530                 535                 540

Phe Met Val Pro Gly Ile Leu Pro Asp Thr Leu Asn Thr Val Arg Ile
545                 550                 555                 560

Arg Val Arg Thr Asn Lys Leu Cys Tyr Glu Asp Asp Arg Leu Trp Ser
                565                 570                 575

Asn Trp Ser Gln Ala Met Ser Ile Gly Glu Asn Thr Asp Pro Thr Ser
                580                 585                 590

Pro Lys Thr Ala Ser Thr Ile Glu Ser Lys Thr Gly Glu Cys Pro Lys
                595                 600                 605

Cys Pro Val Pro Glu Ile Pro Gly Ala Pro Ser Val Phe Ile Phe Pro
610                 615                 620

Pro Lys Pro Lys Asp Thr Leu Ser Ile Ser Arg Thr Pro Glu Val Thr
625                 630                 635                 640

Cys Leu Val Val Asp Leu Gly Pro Asp Asp Ser Asn Val Gln Ile Thr
                645                 650                 655

Trp Phe Val Asp Asn Thr Glu Met His Thr Ala Lys Thr Arg Pro Arg
                660                 665                 670

Glu Glu Gln Phe Asn Ser Thr Tyr Arg Val Val Ser Val Leu Pro Ile
                675                 680                 685

Leu His Gln Asp Trp Leu Lys Gly Lys Glu Phe Lys Cys Lys Val Asn
                690                 695                 700

Ser Lys Ser Leu Pro Ser Ala Met Glu Arg Thr Ile Ser Lys Ala Lys
705                 710                 715                 720
```

-continued

Gly Gln Pro His Glu Pro Gln Val Tyr Val Leu Pro Pro Thr Gln Glu
725 730 735

Glu Leu Ser Glu Asn Lys Val Ser Val Thr Cys Leu Ile Lys Gly Phe
740 745 750

His Pro Pro Asp Ile Ala Val Glu Trp Glu Ile Thr Gly Gln Pro Glu
755 760 765

Pro Glu Asn Asn Tyr Gln Thr Thr Pro Pro Gln Leu Asp Ser Asp Gly
770 775 780

Thr Tyr Phe Leu Tyr Ser Arg Leu Ser Val Asp Arg Ser His Trp Gln
785 790 795 800

Arg Gly Asn Thr Tyr Thr Cys Ser Val Ser His Glu Ala Leu His Ser
805 810 815

His His Thr Gln Lys Ser Leu Thr Gln Ser Pro Gly Lys
820 825

<210> SEQ ID NO 30
<211> LENGTH: 754
<212> TYPE: PRT
<213> ORGANISM: Artificial Sequence
<220> FEATURE:
<223> OTHER INFORMATION: Synthetic: Exemplary equine IL13RECD-IL4RECD-IgG2 Fc (without signal sequence)

<400> SEQUENCE: 30

Thr Glu Ser Gln Pro Pro Val Thr Asn Leu Ser Val Ser Val Glu Asn
1 5 10 15

Leu Cys Thr Val Ile Trp Thr Trp Asn Pro Pro Glu Gly Val Ser Pro
20 25 30

Asn Cys Ser Leu Trp Tyr Phe Ser His Phe Gly Asn Lys Gln Asp Lys
35 40 45

Lys Ile Ala Pro Glu Thr His Arg Ser Lys Glu Val Pro Leu Asn Glu
50 55 60

Arg Ile Cys Leu Gln Val Gly Ser Gln Cys Ser Thr Asn Glu Ser Asp
65 70 75 80

Asn Pro Ser Ile Leu Val Glu Lys Cys Ile Ser Pro Pro Glu Gly Asp
85 90 95

Pro Glu Ser Ala Val Thr Glu Leu Gln Cys Val Trp His Asn Leu Ser
100 105 110

Tyr Met Lys Cys Thr Trp Leu Pro Gly Lys Asn Ala Ser Pro Asp Thr
115 120 125

Asn Tyr Thr Leu Tyr Tyr Trp His Ser Ser Leu Gly Lys Ile Leu Gln
130 135 140

Cys Glu Asp Ile Tyr Arg Glu Gly Gln His Ile Gly Cys Ser Phe Ala
145 150 155 160

Leu Thr Glu Val Lys Asp Ser Ile Phe Glu Gln His Ser Val Gln Ile
165 170 175

Met Val Lys Asp Asn Ala Gly Lys Ile Arg Pro Phe Phe Asn Ile Val
180 185 190

Pro Leu Thr Ser His Val Lys Pro Asp Pro Pro His Ile Lys Lys Leu
195 200 205

Phe Phe Gln Asn Gly Asp Leu Tyr Val Gln Trp Lys Asn Pro Gln Asn
210 215 220

Phe Tyr Ser Arg Cys Leu Ser Tyr Gln Val Glu Val Asn Asn Ser Gln
225 230 235 240

Thr Glu Thr Arg Asp Ile Phe Ser Val Glu Glu Ala Lys Cys Gln Asn

```
                    245                 250                 255
Pro Glu Phe Glu Gly Asp Leu Glu Gly Thr Ile Cys Phe Met Val Pro
                260                 265                 270

Gly Val Leu Pro Asp Thr Val Asn Thr Val Arg Ile Arg Val Lys Thr
            275                 280                 285

Asn Lys Leu Cys Tyr Glu Asp Asp Lys Leu Trp Ser Asn Trp Ser Gln
        290                 295                 300

Ala Met Ser Ile Gly Lys Lys Ala Asp Pro Thr Gly Gly Ser Gly
305                 310                 315                 320

Ser Ser Gly Ser Val Lys Val Leu His Leu Thr Ala Cys Phe Ser Asp
                325                 330                 335

Tyr Ile Ser Ala Ser Thr Cys Glu Trp Lys Met Asp Arg Pro Thr Asn
                340                 345                 350

Cys Ser Ala Gln Leu Arg Leu Ser Tyr Gln Leu Asn Asp Glu Phe Ser
                355                 360                 365

Asp Asn Leu Thr Cys Ile Pro Glu Asn Arg Glu Asp Glu Val Cys Val
        370                 375                 380

Cys Arg Met Leu Met Asp Asn Ile Val Ser Glu Asp Val Tyr Glu Leu
385                 390                 395                 400

Asp Leu Trp Ala Gly Asn Gln Leu Leu Trp Asn Ser Ser Phe Lys Pro
                405                 410                 415

Ser Arg His Val Lys Pro Arg Ala Pro Gln Asn Leu Thr Val His Ala
                420                 425                 430

Ile Ser His Thr Trp Leu Leu Thr Trp Ser Asn Pro Tyr Pro Leu Lys
                435                 440                 445

Asn His Leu Trp Ser Glu Leu Thr Tyr Leu Val Asn Ile Ser Lys Glu
        450                 455                 460

Asp Asp Pro Thr Asp Phe Lys Ile Tyr Asn Val Thr Tyr Met Asp Pro
465                 470                 475                 480

Thr Leu Arg Val Thr Ala Ser Thr Leu Lys Ser Arg Ala Thr Tyr Ser
                485                 490                 495

Ala Arg Val Lys Ala Arg Ala Gln Asn Tyr Asn Ser Thr Trp Ser Glu
                500                 505                 510

Trp Ser Pro Ser Thr Thr Trp His Asn Tyr Tyr Glu Gln Pro Asp Met
        515                 520                 525

Ser Lys Cys Pro Lys Cys Pro Ala Pro Glu Leu Leu Gly Gly Pro Ser
        530                 535                 540

Val Phe Ile Phe Pro Pro Asn Pro Lys Asp Thr Leu Met Ile Ser Arg
545                 550                 555                 560

Thr Pro Val Val Thr Cys Val Val Asn Leu Ser Asp Gln Tyr Pro
                565                 570                 575

Asp Val Gln Phe Ser Trp Tyr Val Asp Asn Thr Glu Val His Ser Ala
                580                 585                 590

Ile Thr Lys Gln Arg Glu Ala Gln Phe Asn Ser Thr Tyr Arg Val Val
                595                 600                 605

Ser Val Leu Pro Ile Gln His Gln Asp Trp Leu Ser Gly Lys Glu Phe
        610                 615                 620

Lys Cys Ser Val Thr Asn Val Gly Val Pro Gln Pro Ile Ser Arg Ala
625                 630                 635                 640

Ile Ser Arg Gly Lys Gly Pro Ser Arg Val Pro Gln Val Tyr Val Leu
                645                 650                 655

Pro Pro His Pro Asp Glu Leu Ala Lys Ser Lys Val Ser Val Thr Cys
                660                 665                 670
```

```
Leu Val Lys Asp Phe Tyr Pro Pro Asp Ile Ser Val Glu Trp Gln Ser
            675                 680                 685

Asn Arg Trp Pro Glu Leu Glu Gly Lys Tyr Ser Thr Thr Pro Ala Gln
        690                 695                 700

Leu Asp Gly Asp Gly Ser Tyr Phe Leu Tyr Ser Lys Leu Ser Leu Glu
705                 710                 715                 720

Thr Ser Arg Trp Gln Gln Val Glu Ser Phe Thr Cys Ala Val Met His
                725                 730                 735

Glu Ala Leu His Asn His Tyr Thr Lys Thr Asp Ile Ser Glu Ser Leu
            740                 745                 750

Gly Lys

<210> SEQ ID NO 31
<211> LENGTH: 754
<212> TYPE: PRT
<213> ORGANISM: Artificial Sequence
<220> FEATURE:
<223> OTHER INFORMATION: Synthetic: Exemplary equine IL4RECD-IL13RECD-
      IgG2 Fc (without signal sequence)

<400> SEQUENCE: 31

Ser Gly Ser Val Lys Val Leu His Leu Thr Ala Cys Phe Ser Asp Tyr
1               5                   10                  15

Ile Ser Ala Ser Thr Cys Glu Trp Lys Met Asp Arg Pro Thr Asn Cys
            20                  25                  30

Ser Ala Gln Leu Arg Leu Ser Tyr Gln Leu Asn Asp Glu Phe Ser Asp
        35                  40                  45

Asn Leu Thr Cys Ile Pro Glu Asn Arg Glu Asp Glu Val Cys Val Cys
50                  55                  60

Arg Met Leu Met Asp Asn Ile Val Ser Glu Asp Val Tyr Glu Leu Asp
65                  70                  75                  80

Leu Trp Ala Gly Asn Gln Leu Leu Trp Asn Ser Ser Phe Lys Pro Ser
                85                  90                  95

Arg His Val Lys Pro Arg Ala Pro Gln Asn Leu Thr Val His Ala Ile
            100                 105                 110

Ser His Thr Trp Leu Leu Thr Trp Ser Asn Pro Tyr Pro Leu Lys Asn
        115                 120                 125

His Leu Trp Ser Glu Leu Thr Tyr Leu Val Asn Ile Ser Lys Glu Asp
    130                 135                 140

Asp Pro Thr Asp Phe Lys Ile Tyr Asn Val Thr Tyr Met Asp Pro Thr
145                 150                 155                 160

Leu Arg Val Thr Ala Ser Thr Leu Lys Ser Arg Ala Thr Tyr Ser Ala
                165                 170                 175

Arg Val Lys Ala Arg Ala Gln Asn Tyr Asn Ser Thr Trp Ser Glu Trp
            180                 185                 190

Ser Pro Ser Thr Thr Trp His Asn Tyr Glu Gln Pro Gly Gly Gly
        195                 200                 205

Ser Gly Ser Thr Glu Ser Gln Pro Val Thr Asn Leu Ser Val Ser
    210                 215                 220

Val Glu Asn Leu Cys Thr Val Ile Trp Thr Trp Asn Pro Pro Glu Gly
225                 230                 235                 240

Val Ser Pro Asn Cys Ser Leu Trp Tyr Phe Ser His Phe Gly Asn Lys
                245                 250                 255

Gln Asp Lys Lys Ile Ala Pro Glu Thr His Arg Ser Lys Glu Val Pro
            260                 265                 270
```

```
Leu Asn Glu Arg Ile Cys Leu Gln Val Gly Ser Gln Cys Ser Thr Asn
            275                 280                 285

Glu Ser Asp Asn Pro Ser Ile Leu Val Glu Lys Cys Ile Ser Pro Pro
        290                 295                 300

Glu Gly Asp Pro Glu Ser Ala Val Thr Glu Leu Gln Cys Val Trp His
305                 310                 315                 320

Asn Leu Ser Tyr Met Lys Cys Thr Trp Leu Pro Gly Lys Asn Ala Ser
                325                 330                 335

Pro Asp Thr Asn Tyr Thr Leu Tyr Tyr Trp His Ser Ser Leu Gly Lys
            340                 345                 350

Ile Leu Gln Cys Glu Asp Ile Tyr Arg Glu Gly Gln His Ile Gly Cys
            355                 360                 365

Ser Phe Ala Leu Thr Glu Val Lys Asp Ser Ile Phe Glu Gln His Ser
        370                 375                 380

Val Gln Ile Met Val Lys Asp Asn Ala Gly Lys Ile Arg Pro Phe Phe
385                 390                 395                 400

Asn Ile Val Pro Leu Thr Ser His Val Lys Pro Asp Pro Pro His Ile
                405                 410                 415

Lys Lys Leu Phe Phe Gln Asn Gly Asp Leu Tyr Val Gln Trp Lys Asn
            420                 425                 430

Pro Gln Asn Phe Tyr Ser Arg Cys Leu Ser Tyr Gln Val Glu Val Asn
        435                 440                 445

Asn Ser Gln Thr Glu Thr Arg Asp Ile Phe Ser Val Glu Glu Ala Lys
    450                 455                 460

Cys Gln Asn Pro Glu Phe Glu Gly Asp Leu Glu Gly Thr Ile Cys Phe
465                 470                 475                 480

Met Val Pro Gly Val Leu Pro Asp Thr Val Asn Thr Val Arg Ile Arg
                485                 490                 495

Val Lys Thr Asn Lys Leu Cys Tyr Glu Asp Asp Lys Leu Trp Ser Asn
            500                 505                 510

Trp Ser Gln Ala Met Ser Ile Gly Lys Lys Ala Asp Pro Thr Asp Met
        515                 520                 525

Ser Lys Cys Pro Lys Cys Pro Ala Pro Glu Leu Leu Gly Gly Pro Ser
    530                 535                 540

Val Phe Ile Phe Pro Pro Asn Pro Lys Asp Thr Leu Met Ile Ser Arg
545                 550                 555                 560

Thr Pro Val Val Thr Cys Val Val Asn Leu Ser Asp Gln Tyr Pro
                565                 570                 575

Asp Val Gln Phe Ser Trp Tyr Val Asp Asn Thr Glu Val His Ser Ala
        580                 585                 590

Ile Thr Lys Gln Arg Glu Ala Gln Phe Asn Ser Thr Tyr Arg Val Val
    595                 600                 605

Ser Val Leu Pro Ile Gln His Gln Asp Trp Leu Ser Gly Lys Glu Phe
        610                 615                 620

Lys Cys Ser Val Thr Asn Val Gly Val Pro Gln Pro Ile Ser Arg Ala
625                 630                 635                 640

Ile Ser Arg Gly Lys Gly Pro Ser Arg Val Pro Gln Val Tyr Val Leu
                645                 650                 655

Pro Pro His Pro Asp Glu Leu Ala Lys Ser Lys Val Ser Val Thr Cys
            660                 665                 670

Leu Val Lys Asp Phe Tyr Pro Pro Asp Ile Ser Val Glu Trp Gln Ser
            675                 680                 685
```

```
Asn Arg Trp Pro Glu Leu Glu Gly Lys Tyr Ser Thr Thr Pro Ala Gln
    690             695                 700
Leu Asp Gly Asp Gly Ser Tyr Phe Leu Tyr Ser Lys Leu Ser Leu Glu
705             710                 715                 720
Thr Ser Arg Trp Gln Gln Val Glu Ser Phe Thr Cys Ala Val Met His
            725                 730                 735
Glu Ala Leu His Asn His Tyr Thr Lys Thr Asp Ile Ser Glu Ser Leu
            740                 745                 750
Gly Lys

<210> SEQ ID NO 32
<211> LENGTH: 305
<212> TYPE: PRT
<213> ORGANISM: Artificial Sequence
<220> FEATURE:
<223> OTHER INFORMATION: Synthetic: Exemplary canine mini-IL13R ECD

<400> SEQUENCE: 32

Gln Pro Pro Val Thr Asn Leu Ser Val Ser Val Glu Asn Leu Cys Thr
1               5                   10                  15
Val Ile Trp Thr Trp Asp Pro Pro Glu Gly Ala Ser Pro Asn Cys Thr
            20                  25                  30
Leu Arg Tyr Phe Ser His Phe Asp Asn Lys Gln Asp Lys Lys Ile Ala
        35                  40                  45
Pro Glu Thr His Arg Ser Lys Glu Val Pro Leu Asn Glu Arg Ile Cys
    50                  55                  60
Leu Gln Val Gly Ser Gln Cys Ser Thr Asn Glu Ser Asp Asn Pro Ser
65                  70                  75                  80
Ile Leu Val Glu Lys Cys Thr Pro Pro Glu Gly Asp Pro Glu Ser
                85                  90                  95
Ala Val Thr Glu Leu Gln Cys Val Trp His Asn Leu Ser Tyr Met Lys
            100                 105                 110
Cys Thr Trp Leu Pro Gly Arg Asn Thr Ser Pro Asp Thr Asn Tyr Thr
        115                 120                 125
Leu Tyr Tyr Trp His Ser Ser Leu Gly Lys Ile Leu Gln Cys Glu Asp
    130                 135                 140
Ile Tyr Arg Glu Gly Gln His Ile Gly Cys Ser Phe Ala Leu Thr Asn
145                 150                 155                 160
Leu Lys Asp Ser Ser Phe Glu Gln His Ser Val Gln Ile Val Val Lys
                165                 170                 175
Asp Asn Ala Gly Lys Ile Arg Pro Ser Phe Asn Ile Val Pro Leu Thr
            180                 185                 190
Ser His Val Lys Pro Asp Pro Pro His Ile Lys Arg Leu Phe Phe Gln
        195                 200                 205
Asn Gly Asn Leu Tyr Val Gln Trp Lys Asn Pro Gln Asn Phe Tyr Ser
    210                 215                 220
Arg Cys Leu Ser Tyr Gln Val Glu Val Asn Asn Ser Gln Thr Glu Thr
225                 230                 235                 240
Asn Asp Ile Phe Tyr Val Glu Glu Ala Lys Cys Gln Asn Ser Glu Phe
                245                 250                 255
Glu Gly Asn Leu Glu Gly Thr Ile Cys Phe Met Val Pro Gly Val Leu
            260                 265                 270
Pro Asp Thr Leu Asn Thr Val Arg Ile Arg Val Arg Thr Asn Lys Leu
        275                 280                 285
Cys Tyr Glu Asp Asp Lys Leu Trp Ser Asn Trp Ser Gln Ala Met Ser
```

```
            290                 295                 300

Ile
305

<210> SEQ ID NO 33
<211> LENGTH: 184
<212> TYPE: PRT
<213> ORGANISM: Artificial Sequence
<220> FEATURE:
<223> OTHER INFORMATION: Synthetic: Exemplary canine mini-IL4R ECD

<400> SEQUENCE: 33

Lys Val Leu His Glu Pro Ser Cys Phe Ser Asp Tyr Ile Ser Thr Ser
1               5                   10                  15

Val Cys Gln Trp Lys Met Asp His Pro Thr Asn Cys Ser Ala Glu Leu
            20                  25                  30

Arg Leu Ser Tyr Gln Leu Asp Phe Met Gly Ser Glu Asn His Thr Cys
        35                  40                  45

Val Pro Glu Asn Arg Glu Asp Ser Val Cys Val Cys Ser Met Pro Ile
    50                  55                  60

Asp Asp Ala Val Glu Ala Asp Val Tyr Gln Leu Asp Leu Trp Ala Gly
65                  70                  75                  80

Gln Gln Leu Leu Trp Ser Gly Ser Phe Gln Pro Ser Lys His Val Lys
                85                  90                  95

Pro Arg Thr Pro Gly Asn Leu Thr Val His Pro Asn Ile Ser His Thr
            100                 105                 110

Trp Leu Leu Met Trp Thr Asn Pro Tyr Pro Thr Glu Asn His Leu His
        115                 120                 125

Ser Glu Leu Thr Tyr Met Val Asn Val Ser Asn Asp Asn Asp Pro Glu
    130                 135                 140

Asp Phe Lys Val Tyr Asn Val Thr Tyr Met Gly Pro Thr Leu Arg Leu
145                 150                 155                 160

Ala Ala Ser Thr Leu Lys Ser Gly Ala Ser Tyr Ser Ala Arg Val Arg
                165                 170                 175

Ala Trp Ala Gln Thr Tyr Asn Ser
            180

<210> SEQ ID NO 34
<211> LENGTH: 305
<212> TYPE: PRT
<213> ORGANISM: Artificial Sequence
<220> FEATURE:
<223> OTHER INFORMATION: Synthetic: Exemplary feline mini-IL13R ECD

<400> SEQUENCE: 34

Gln Pro Pro Val Thr Asn Leu Ser Val Ser Val Glu Asn Leu Cys Thr
1               5                   10                  15

Val Ile Trp Thr Trp Asp Pro Pro Glu Gly Ala Ser Pro Asn Cys Thr
            20                  25                  30

Leu Arg Tyr Phe Ser His Phe Asp Asn Lys Gln Asp Lys Ile Ala
        35                  40                  45

Pro Glu Thr His Arg Ser Lys Glu Val Pro Leu Asn Glu Arg Ile Cys
    50                  55                  60

Leu Gln Val Gly Ser Gln Cys Ser Thr Asn Glu Ser Asp Asn Pro Ser
65                  70                  75                  80

Ile Leu Val Glu Lys Cys Thr Pro Pro Glu Gly Asp Pro Glu Ser
                85                  90                  95
```

```
Ala Val Thr Glu Leu Gln Cys Val Trp His Asn Leu Ser Tyr Met Lys
            100                 105                 110

Cys Thr Trp Leu Pro Gly Arg Asn Thr Ser Pro Asp Thr Asn Tyr Thr
            115                 120                 125

Leu Tyr Tyr Trp His Ser Ser Leu Gly Lys Ile Leu Gln Cys Glu Asn
        130                 135                 140

Ile Tyr Arg Glu Gly Gln His Ile Gly Cys Ser Phe Ala Leu Thr Asn
145                 150                 155                 160

Leu Lys Asp Ser Ser Phe Glu Gln His Ser Val Gln Ile Val Val Lys
                165                 170                 175

Asp Asn Ala Gly Lys Ile Arg Pro Ser Phe Asn Ile Val Pro Leu Thr
            180                 185                 190

Ser His Val Lys Pro Asp Pro His Ile Lys Arg Leu Phe Phe Gln
            195                 200                 205

Asn Gly Asn Leu Tyr Val Gln Trp Lys Asn Pro Gln Asn Phe Tyr Ser
        210                 215                 220

Arg Cys Leu Ser Tyr Gln Val Glu Val Asn Asn Ser Gln Thr Glu Thr
225                 230                 235                 240

His Asp Ile Phe Tyr Val Glu Glu Ala Lys Cys Gln Asn Ser Glu Phe
                245                 250                 255

Glu Gly Asn Leu Glu Gly Thr Ile Cys Phe Met Val Pro Gly Ile Leu
            260                 265                 270

Pro Asp Thr Leu Asn Thr Val Arg Ile Arg Val Arg Thr Asn Lys Leu
            275                 280                 285

Cys Tyr Glu Asp Asp Arg Leu Trp Ser Asn Trp Ser Gln Ala Met Ser
        290                 295                 300

Ile
305

<210> SEQ ID NO 35
<211> LENGTH: 266
<212> TYPE: PRT
<213> ORGANISM: Artificial Sequence
<220> FEATURE:
<223> OTHER INFORMATION: Synthetic: Exemplary feline mini-IL4R ECD

<400> SEQUENCE: 35

Lys Val Leu Arg Ala Pro Thr Cys Phe Ser Asp Tyr Phe Ser Thr Ser
1               5                   10                  15

Val Cys Gln Trp Asn Met Asp Ala Pro Thr Asn Cys Ser Ala Glu Leu
            20                  25                  30

Arg Leu Ser Tyr Gln Leu Asn Phe Met Gly Ser Glu Asn Arg Thr Cys
        35                  40                  45

Val Pro Glu Asn Gly Glu Gly Ala Ala Cys Ala Cys Ser Met Leu Met
    50                  55                  60

Asp Asp Phe Val Glu Ala Asp Val Tyr Gln Leu His Leu Trp Ala Gly
65                  70                  75                  80

Thr Gln Leu Leu Trp Ser Gly Ser Phe Lys Pro Ser Ser His Val Lys
                85                  90                  95

Pro Arg Ala Pro Gly Asn Leu Thr Val His Pro Asn Val Ser His Thr
            100                 105                 110

Trp Leu Leu Arg Trp Ser Asn Pro Tyr Pro Pro Glu Asn His Leu His
            115                 120                 125

Ala Glu Leu Thr Tyr Met Val Asn Ile Ser Ser Glu Asp Asp Pro Thr
        130                 135                 140
```

```
Asp Val Ser Val Cys Ala Ser Gly Phe Leu Cys His Leu Leu Gly Leu
145                 150                 155                 160

Arg Arg Val Glu Thr Gly Ala Pro Gly Ala Arg Leu Pro Pro Trp Leu
                165                 170                 175

Cys Ala Pro Arg Pro Arg Val Pro Gly Ser Gln Cys Ala Val Ile
                180                 185                 190

Ser Cys Cys Arg Trp Val Leu Ile Ala Leu Thr Ser Arg Gly Gly Arg
            195                 200                 205

Trp Arg Leu Thr Pro Gly Leu Arg Ser Gln Thr Arg Tyr Val Ser Val
    210                 215                 220

Ala Glu Gly Leu Phe Gly Ala Thr Pro Arg Val Leu Cys Pro Gly Thr
225                 230                 235                 240

Gln Ala Gly Leu Ala Ser Ala Ala Arg Glu Gln Met Ser Pro Asp Pro
                245                 250                 255

Ser Ala Phe His Ser Ile Asp Tyr Glu Pro
                260                 265

<210> SEQ ID NO 36
<211> LENGTH: 305
<212> TYPE: PRT
<213> ORGANISM: Artificial Sequence
<220> FEATURE:
<223> OTHER INFORMATION: Synthetic: Exemplary equine mini-IL13R ECD

<400> SEQUENCE: 36

Gln Pro Pro Val Thr Asn Leu Ser Val Ser Val Glu Asn Leu Cys Thr
1               5                   10                  15

Val Ile Trp Thr Trp Asn Pro Pro Glu Gly Val Ser Pro Asn Cys Ser
                20                  25                  30

Leu Trp Tyr Phe Ser His Phe Gly Asn Lys Gln Asp Lys Lys Ile Ala
            35                  40                  45

Pro Glu Thr His Arg Ser Lys Glu Val Pro Leu Asn Glu Arg Ile Cys
        50                  55                  60

Leu Gln Val Gly Ser Gln Cys Ser Thr Asn Glu Ser Asp Asn Pro Ser
65                  70                  75                  80

Ile Leu Val Glu Lys Cys Ile Ser Pro Pro Gly Asp Pro Glu Ser
                85                  90                  95

Ala Val Thr Glu Leu Gln Cys Val Trp His Asn Leu Ser Tyr Met Lys
                100                 105                 110

Cys Thr Trp Leu Pro Gly Lys Asn Ala Ser Pro Asp Thr Asn Tyr Thr
            115                 120                 125

Leu Tyr Tyr Trp His Ser Ser Leu Gly Lys Ile Leu Gln Cys Glu Asp
        130                 135                 140

Ile Tyr Arg Glu Gly Gln His Ile Gly Cys Ser Phe Ala Leu Thr Glu
145                 150                 155                 160

Val Lys Asp Ser Ile Phe Glu Gln His Ser Val Gln Ile Met Val Lys
                165                 170                 175

Asp Asn Ala Gly Lys Ile Arg Pro Phe Phe Asn Ile Val Pro Leu Thr
            180                 185                 190

Ser His Val Lys Pro Asp Pro His Ile Lys Lys Leu Phe Phe Gln
        195                 200                 205

Asn Gly Asp Leu Tyr Val Gln Trp Lys Asn Pro Gln Asn Phe Tyr Ser
    210                 215                 220

Arg Cys Leu Ser Tyr Gln Val Glu Val Asn Asn Ser Gln Thr Glu Thr
225                 230                 235                 240
```

```
Arg Asp Ile Phe Ser Val Glu Glu Ala Lys Cys Gln Asn Pro Glu Phe
                245                 250                 255

Glu Gly Asp Leu Glu Gly Thr Ile Cys Phe Met Val Pro Gly Val Leu
            260                 265                 270

Pro Asp Thr Val Asn Thr Val Arg Ile Arg Val Lys Thr Asn Lys Leu
        275                 280                 285

Cys Tyr Glu Asp Lys Leu Trp Ser Asn Trp Ser Gln Ala Met Ser
    290                 295                 300

Ile
305

<210> SEQ ID NO 37
<211> LENGTH: 201
<212> TYPE: PRT
<213> ORGANISM: Artificial Sequence
<220> FEATURE:
<223> OTHER INFORMATION: Synthetic: Exemplary equine mini-IL4R ECD

<400> SEQUENCE: 37

Lys Val Leu His Leu Thr Ala Cys Phe Ser Asp Tyr Ile Ser Ala Ser
1               5                   10                  15

Thr Cys Glu Trp Lys Met Asp Arg Pro Thr Asn Cys Ser Ala Gln Leu
            20                  25                  30

Arg Leu Ser Tyr Gln Leu Asn Asp Glu Phe Ser Asp Asn Leu Thr Cys
        35                  40                  45

Ile Pro Glu Asn Arg Glu Asp Glu Val Cys Val Cys Arg Met Leu Met
    50                  55                  60

Asp Asn Ile Val Ser Glu Asp Val Tyr Glu Leu Asp Leu Trp Ala Gly
65                  70                  75                  80

Asn Gln Leu Leu Trp Asn Ser Ser Phe Lys Pro Ser Arg His Val Lys
                85                  90                  95

Pro Arg Ala Pro Gln Asn Leu Thr Val His Ala Ile Ser His Thr Trp
            100                 105                 110

Leu Leu Thr Trp Ser Asn Pro Tyr Pro Leu Lys Asn His Leu Trp Ser
        115                 120                 125

Glu Leu Thr Tyr Leu Val Asn Ile Ser Lys Glu Asp Asp Pro Thr Asp
    130                 135                 140

Phe Lys Ile Tyr Asn Val Thr Tyr Met Asp Pro Thr Leu Arg Val Thr
145                 150                 155                 160

Ala Ser Thr Leu Lys Ser Arg Ala Thr Tyr Ser Ala Arg Val Lys Ala
                165                 170                 175

Arg Ala Gln Asn Tyr Asn Ser Thr Trp Ser Glu Trp Ser Pro Ser Thr
            180                 185                 190

Thr Trp His Asn Tyr Tyr Glu Gln Pro
        195                 200

<210> SEQ ID NO 38
<211> LENGTH: 221
<212> TYPE: PRT
<213> ORGANISM: Artificial Sequence
<220> FEATURE:
<223> OTHER INFORMATION: Synthetic: Exemplary wild-type canine IgG-A Fc

<400> SEQUENCE: 38

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30
```

```
Val Val Leu Asp Leu Gly Arg Glu Asp Pro Glu Val Gln Ile Ser Trp
         35                  40                  45

Phe Val Asp Gly Lys Glu Val His Thr Ala Lys Thr Gln Ser Arg Glu
 50                  55                  60

Gln Gln Phe Asn Gly Thr Tyr Arg Val Val Ser Val Leu Pro Ile Glu
 65                  70                  75                  80

His Gln Asp Trp Leu Thr Gly Lys Glu Phe Lys Cys Arg Val Asn His
             85                  90                  95

Ile Asp Leu Pro Ser Pro Ile Glu Arg Thr Ile Ser Lys Ala Arg Gly
             100                 105                 110

Arg Ala His Lys Pro Ser Val Tyr Val Leu Pro Pro Ser Pro Lys Glu
             115                 120                 125

Leu Ser Ser Ser Asp Thr Val Ser Ile Thr Cys Leu Ile Lys Asp Phe
 130                 135                 140

Tyr Pro Pro Asp Ile Asp Val Glu Trp Gln Ser Asn Gly Gln Gln Glu
 145                 150                 155                 160

Pro Glu Arg Lys His Arg Met Thr Pro Pro Gln Leu Asp Glu Asp Gly
             165                 170                 175

Ser Tyr Phe Leu Tyr Ser Lys Leu Ser Val Asp Lys Ser Arg Trp Gln
             180                 185                 190

Gln Gly Asp Pro Phe Thr Cys Ala Val Met His Glu Thr Leu Gln Asn
             195                 200                 205

His Tyr Thr Asp Leu Ser Leu Ser His Ser Pro Gly Lys
             210                 215                 220

<210> SEQ ID NO 39
<211> LENGTH: 220
<212> TYPE: PRT
<213> ORGANISM: Artificial Sequence
<220> FEATURE:
<223> OTHER INFORMATION: Synthetic: Exemplary wild-type canine IgG-B Fc

<400> SEQUENCE: 39

Pro Ala Pro Glu Met Leu Gly Gly Pro Ser Val Phe Ile Phe Pro Pro
1                5                  10                  15

Lys Pro Lys Asp Thr Leu Leu Ile Ala Arg Thr Pro Glu Val Thr Cys
             20                  25                  30

Val Val Val Asp Leu Asp Pro Glu Asp Pro Glu Val Gln Ile Ser Trp
         35                  40                  45

Phe Val Asp Gly Lys Gln Met Gln Thr Ala Lys Thr Gln Pro Arg Glu
 50                  55                  60

Glu Gln Phe Asn Gly Thr Tyr Arg Val Val Ser Val Leu Pro Ile Gly
 65                  70                  75                  80

His Gln Asp Trp Leu Lys Gly Lys Gln Phe Thr Cys Lys Val Asn Asn
             85                  90                  95

Lys Ala Leu Pro Ser Pro Ile Glu Arg Thr Ile Ser Lys Ala Arg Gly
             100                 105                 110

Gln Ala His Gln Pro Ser Val Tyr Val Leu Pro Pro Ser Arg Glu Glu
             115                 120                 125

Leu Ser Lys Asn Thr Val Ser Leu Thr Cys Leu Ile Lys Asp Phe Phe
 130                 135                 140

Pro Pro Asp Ile Asp Val Glu Trp Gln Ser Asn Gly Gln Gln Glu Pro
 145                 150                 155                 160

Glu Ser Lys Tyr Arg Thr Thr Pro Pro Gln Leu Asp Glu Asp Gly Ser
             165                 170                 175
```

```
Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 40
<211> LENGTH: 220
<212> TYPE: PRT
<213> ORGANISM: Artificial Sequence
<220> FEATURE:
<223> OTHER INFORMATION: Synthetic: Exemplary wild-type canine IgG-C Fc

<400> SEQUENCE: 40

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
    210                 215                 220

<210> SEQ ID NO 41
<211> LENGTH: 221
<212> TYPE: PRT
<213> ORGANISM: Artificial Sequence
<220> FEATURE:
<223> OTHER INFORMATION: Synthetic: Exemplary wild-type canine IgG-D Fc

<400> SEQUENCE: 41

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
```

```
                    35                  40                  45
Phe Val Asp Gly Lys Glu Val His Thr Ala Lys Thr Gln Pro Arg Glu
 50                  55                  60

Gln Gln Phe Asn Ser Thr Tyr Arg Val Val Ser Val Leu Pro Ile Glu
 65                  70                  75                  80

His Gln Asp Trp Leu Thr Gly Lys Glu Phe Lys Cys Arg Val Asn His
                     85                  90                  95

Ile Gly Leu Pro Ser Pro Ile Glu Arg Thr Ile Ser Lys Ala Arg Gly
                100                 105                 110

Gln Ala His Gln Pro Ser Val Tyr Val Leu Pro Pro Ser Pro Lys Glu
            115                 120                 125

Leu Ser Ser Asp Thr Val Thr Leu Thr Cys Leu Ile Lys Asp Phe
130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Thr Phe Thr Cys Ala Val Met His Glu Ala Leu Gln Asn
            195                 200                 205

His Tyr Thr Asp Leu Ser Leu Ser His Ser Pro Gly Lys
            210                 215                 220

<210> SEQ ID NO 42
<211> LENGTH: 237
<212> TYPE: PRT
<213> ORGANISM: Artificial Sequence
<220> FEATURE:
<223> OTHER INFORMATION: Synthetic: Exemplary wild-type feline IgG1a Fc

<400> SEQUENCE: 42

Arg Lys Thr Asp His Pro Pro Gly Pro Lys Pro Cys Asp Cys Pro Lys
  1               5                  10                  15

Cys Pro Pro Pro Glu Met Leu Gly Gly Pro Ser Ile Phe Ile Phe Pro
                 20                  25                  30

Pro Lys Pro Lys Asp Thr Leu Ser Ile Ser Arg Thr Pro Glu Val Thr
             35                  40                  45

Cys Leu Val Val Asp Leu Gly Pro Asp Asp Ser Asp Val Gln Ile Thr
 50                  55                  60

Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
            115                 120                 125

Gly Gln Pro His Glu Pro Gln Val Tyr Val Leu Pro Pro Ala Gln Glu
        130                 135                 140

Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
```

```
                  180               185               190
Thr Tyr Phe Val Tyr Ser Lys Leu Ser Val Asp Arg Ser His Trp Gln
            195               200               205
Arg Gly Asn Thr Tyr Thr Cys Ser Val Ser His Glu Ala Leu His Ser
        210               215               220
His His Thr Gln Lys Ser Leu Thr Gln Ser Pro Gly Lys
225               230               235

<210> SEQ ID NO 43
<211> LENGTH: 237
<212> TYPE: PRT
<213> ORGANISM: Artificial Sequence
<220> FEATURE:
<223> OTHER INFORMATION: Synthetic: Exemplary wild-type feline IgG1a Fc

<400> SEQUENCE: 43

Arg Lys Thr Asp His Pro Pro Gly Pro Lys Thr Gly Glu Gly Pro Lys
1               5                   10                  15
Cys Pro Pro Pro Glu Met Leu Gly Gly Pro Ser Ile Phe Ile Phe Pro
            20                  25                  30
Pro Lys Pro Lys Asp Thr Leu Ser Ile Ser Arg Thr Pro Glu Val Thr
        35                  40                  45
Cys Leu Val Val Asp Leu Gly Pro Asp Asp Ser Asp Val Gln Ile Thr
    50                  55                  60
Trp Phe Val Asp Asn Thr Gln Val Tyr Thr Ala Lys Thr Ser Pro Arg
65                  70                  75                  80
Glu Glu Gln Phe Asn Ser Thr Tyr Arg Val Val Ser Val Leu Pro Ile
                85                  90                  95
Leu His Gln Asp Trp Leu Lys Gly Lys Glu Phe Lys Cys Lys Val Asn
            100                 105                 110
Ser Lys Ser Leu Pro Ser Pro Ile Glu Arg Thr Ile Ser Lys Ala Lys
        115                 120                 125
Gly Gln Pro His Glu Pro Gln Val Tyr Val Leu Pro Pro Ala Gln Glu
    130                 135                 140
Glu Leu Ser Glu Asn Lys Val Ser Val Thr Cys Leu Ile Lys Ser Phe
145                 150                 155                 160
His Pro Pro Asp Ile Ala Val Glu Trp Glu Ile Thr Gly Gln Pro Glu
                165                 170                 175
Pro Glu Asn Asn Tyr Arg Thr Thr Pro Pro Gln Leu Asp Ser Asp Gly
            180                 185                 190
Thr Tyr Phe Val Tyr Ser Lys Leu Ser Val Asp Arg Ser His Trp Gln
        195                 200                 205
Arg Gly Asn Thr Tyr Thr Cys Ser Val Ser His Glu Ala Leu His Ser
    210                 215                 220
His His Thr Gln Lys Ser Leu Thr Gln Ser Pro Gly Lys
225                 230                 235

<210> SEQ ID NO 44
<211> LENGTH: 237
<212> TYPE: PRT
<213> ORGANISM: Artificial Sequence
<220> FEATURE:
<223> OTHER INFORMATION: Synthetic: Exemplary wild-type feline IgG1b Fc

<400> SEQUENCE: 44

Arg Lys Thr Asp His Pro Pro Gly Pro Lys Pro Cys Asp Cys Pro Lys
1               5                   10                  15
```

```
Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 45
<211> LENGTH: 237
<212> TYPE: PRT
<213> ORGANISM: Artificial Sequence
<220> FEATURE:
<223> OTHER INFORMATION: Synthetic: Exemplary wild-type feline IgG1b Fc

<400> SEQUENCE: 45

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140
```

```
Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 46
<211> LENGTH: 237
<212> TYPE: PRT
<213> ORGANISM: Artificial Sequence
<220> FEATURE:
<223> OTHER INFORMATION: Synthetic: Exemplary wild-type feline IgG2 Fc

<400> SEQUENCE: 46

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
        50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 47
<211> LENGTH: 213
<212> TYPE: PRT
<213> ORGANISM: Artificial Sequence
<220> FEATURE:
```

<223> OTHER INFORMATION: Synthetic: Exemplary wild-type equine IgG1 Fc

<400> SEQUENCE: 47

```
Gly Pro Ser Val Phe Ile Phe Pro Pro Asn Pro Lys Asp Thr Leu Met
1               5                   10                  15
Ile Thr Arg Thr Pro Glu Val Thr Cys Val Val Val Asp Val Ser Gln
            20                  25                  30
Glu Asn Pro Asp Val Lys Phe Asn Trp Tyr Met Asp Gly Val Glu Val
        35                  40                  45
Arg Thr Ala Thr Thr Arg Pro Lys Glu Glu Gln Phe Asn Ser Thr Tyr
    50                  55                  60
Arg Val Val Ser Val Leu Arg Ile Gln His Gln Asp Trp Leu Ser Gly
65                  70                  75                  80
Lys Glu Phe Lys Cys Lys Val Asn Asn Gln Ala Leu Pro Gln Pro Ile
                85                  90                  95
Glu Arg Thr Ile Thr Lys Thr Lys Gly Arg Ser Gln Glu Pro Gln Val
            100                 105                 110
Tyr Val Leu Ala Pro His Pro Asp Glu Leu Ser Lys Ser Lys Val Ser
        115                 120                 125
Val Thr Cys Leu Val Lys Asp Phe Tyr Pro Pro Glu Ile Asn Ile Glu
    130                 135                 140
Trp Gln Ser Asn Gly Gln Pro Glu Leu Glu Thr Lys Tyr Ser Thr Thr
145                 150                 155                 160
Gln Ala Gln Gln Asp Ser Asp Gly Ser Tyr Phe Leu Tyr Ser Lys Leu
                165                 170                 175
Ser Val Asp Arg Asn Arg Trp Gln Gln Gly Thr Thr Phe Thr Cys Gly
            180                 185                 190
Val Met His Glu Ala Leu His Asn His Tyr Thr Gln Lys Asn Val Ser
        195                 200                 205
Lys Asn Pro Gly Lys
    210
```

<210> SEQ ID NO 48
<211> LENGTH: 213
<212> TYPE: PRT
<213> ORGANISM: Artificial Sequence
<220> FEATURE:
<223> OTHER INFORMATION: Synthetic: Exemplary wild-type equine IgG2 Fc

<400> SEQUENCE: 48

```
Gly Pro Ser Val Phe Ile Phe Pro Pro Asn Pro Lys Asp Ala Leu Met
1               5                   10                  15
Ile Ser Arg Thr Pro Val Val Thr Cys Val Val Val Asn Leu Ser Asp
            20                  25                  30
Gln Tyr Pro Asp Val Gln Phe Ser Trp Tyr Val Asp Asn Thr Glu Val
        35                  40                  45
His Ser Ala Ile Thr Lys Gln Arg Glu Ala Gln Phe Asn Ser Thr Tyr
    50                  55                  60
Arg Val Val Ser Val Leu Pro Ile Gln His Gln Asp Trp Leu Ser Gly
65                  70                  75                  80
Lys Glu Phe Lys Cys Ser Val Thr Asn Val Gly Val Pro Gln Pro Ile
                85                  90                  95
Ser Arg Ala Ile Ser Arg Gly Lys Gly Pro Ser Arg Val Pro Gln Val
            100                 105                 110
Tyr Val Leu Pro Pro His Pro Asp Glu Leu Ala Lys Ser Lys Val Ser
        115                 120                 125
```

```
Val Thr Cys Leu Val Lys Asp Phe Tyr Pro Pro Asp Ile Ser Val Glu
            130                 135                 140

Trp Gln Ser Asn Arg Trp Pro Glu Leu Glu Gly Lys Tyr Ser Thr Thr
145                 150                 155                 160

Pro Ala Gln Leu Asp Gly Asp Gly Ser Tyr Phe Leu Tyr Ser Lys Leu
                165                 170                 175

Ser Leu Glu Thr Ser Arg Trp Gln Gln Val Glu Ser Phe Thr Cys Ala
            180                 185                 190

Val Met His Glu Ala Leu His Asn His Phe Thr Lys Thr Asp Ile Ser
            195                 200                 205

Glu Ser Leu Gly Lys
        210

<210> SEQ ID NO 49
<211> LENGTH: 213
<212> TYPE: PRT
<213> ORGANISM: Artificial Sequence
<220> FEATURE:
<223> OTHER INFORMATION: Synthetic: Exemplary wild-type equine IgG3 Fc

<400> SEQUENCE: 49

Gly Pro Ser Val Phe Ile Phe Pro Pro Lys Pro Lys Asp Val Leu Met
1               5                   10                  15

Ile Thr Arg Met Pro Glu Val Thr Cys Leu Val Val Asp Val Ser His
            20                  25                  30

Asp Ser Ser Asp Val Leu Phe Thr Trp Tyr Val Asp Gly Thr Glu Val
        35                  40                  45

Lys Thr Ala Lys Thr Met Pro Asn Glu Glu Gln Asn Asn Ser Thr Tyr
50                  55                  60

Arg Val Val Ser Val Leu Arg Ile Gln His Gln Asp Trp Leu Asn Gly
65                  70                  75                  80

Lys Lys Phe Lys Cys Lys Val Asn Asn Gln Ala Leu Pro Ala Pro Val
                85                  90                  95

Glu Arg Thr Ile Ser Lys Ala Thr Gly Gln Thr Arg Val Pro Gln Val
            100                 105                 110

Tyr Val Leu Ala Pro His Pro Asp Glu Leu Ser Lys Asn Lys Val Ser
        115                 120                 125

Val Thr Cys Leu Val Lys Asp Phe Tyr Pro Pro Asp Ile Thr Val Glu
            130                 135                 140

Trp Gln Ser Asn Glu His Pro Glu Pro Glu Gly Lys Tyr Arg Thr Thr
145                 150                 155                 160

Glu Ala Gln Lys Asp Ser Asp Gly Ser Tyr Phe Leu Tyr Ser Lys Leu
                165                 170                 175

Thr Val Glu Lys Asp Arg Trp Gln Gln Gly Thr Thr Phe Thr Cys Val
            180                 185                 190

Val Met His Glu Ala Leu His Asn His Val Met Gln Lys Asn Ile Ser
            195                 200                 205

Lys Asn Pro Gly Lys
        210

<210> SEQ ID NO 50
<211> LENGTH: 213
<212> TYPE: PRT
<213> ORGANISM: Artificial Sequence
<220> FEATURE:
<223> OTHER INFORMATION: Synthetic: Exemplary wild-type equine IgG4 Fc
```

<400> SEQUENCE: 50

```
Gly Pro Ser Val Phe Ile Phe Pro Pro Lys Pro Lys Asp Val Leu Met
1               5                   10                  15

Ile Ser Arg Thr Pro Thr Val Thr Cys Val Val Asp Val Gly His
                20                  25                  30

Asp Phe Pro Asp Val Gln Phe Asn Trp Tyr Val Asp Gly Val Glu Thr
                35                  40                  45

His Thr Ala Thr Thr Glu Pro Lys Gln Glu Gln Phe Asn Ser Thr Tyr
            50                  55                  60

Arg Val Val Ser Val Leu Pro Ile Gln His Lys Asp Trp Leu Ser Gly
65                  70                  75                  80

Lys Glu Phe Lys Cys Lys Val Asn Asn Lys Ala Leu Pro Ala Pro Val
                85                  90                  95

Glu Arg Thr Ile Ser Ala Pro Thr Gly Gln Pro Arg Glu Pro Gln Val
                100                 105                 110

Tyr Val Leu Ala Pro His Arg Asp Glu Leu Ser Lys Asn Lys Val Ser
            115                 120                 125

Val Thr Cys Leu Val Lys Asp Phe Tyr Pro Pro Asp Ile Asp Ile Glu
        130                 135                 140

Trp Lys Ser Asn Gly Gln Pro Glu Pro Glu Thr Lys Tyr Ser Thr Thr
145                 150                 155                 160

Pro Ala Gln Leu Asp Ser Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
                180                 185                 190

Val Met His Glu Ala Leu His Asn His Tyr Thr Glu Lys Ser Val Ser
            195                 200                 205

Lys Ser Pro Gly Lys
        210
```

<210> SEQ ID NO 51
<211> LENGTH: 213
<212> TYPE: PRT
<213> ORGANISM: Artificial Sequence
<220> FEATURE:
<223> OTHER INFORMATION: Synthetic: Exemplary wild-type equine IgG5 Fc

<400> SEQUENCE: 51

```
Gly Pro Ser Val Phe Ile Phe Pro Pro Lys Pro Lys Asp Val Leu Met
1               5                   10                  15

Ile Ser Arg Lys Pro Glu Val Thr Cys Val Val Asp Leu Gly His
                20                  25                  30

Asp Asp Pro Asp Val Gln Phe Thr Trp Phe Val Asp Gly Val Glu Thr
                35                  40                  45

His Thr Ala Thr Thr Glu Pro Lys Glu Glu Gln Phe Asn Ser Thr Tyr
            50                  55                  60

Arg Val Val Ser Val Leu Pro Ile Gln His Gln Asp Trp Leu Ser Gly
65                  70                  75                  80

Lys Glu Phe Lys Cys Ser Val Thr Ser Lys Ala Leu Pro Ala Pro Val
                85                  90                  95

Glu Arg Thr Ile Ser Lys Ala Lys Gly Gln Leu Arg Val Pro Gln Val
                100                 105                 110

Tyr Val Leu Ala Pro His Pro Asp Glu Leu Ala Lys Asn Thr Val Ser
            115                 120                 125

Val Thr Cys Leu Val Lys Asp Phe Tyr Pro Pro Glu Ile Asp Val Glu
```

```
                130                 135                 140
Trp Gln Ser Asn Glu His Pro Glu Pro Glu Gly Lys Tyr Ser Thr Thr
145                 150                 155                 160

Pro Ala Gln Leu Asn Ser Asp Gly Ser Tyr Phe Leu Tyr Ser Lys Leu
                165                 170                 175

Ser Val Glu Thr Ser Arg Trp Lys Gln Gly Ser Phe Thr Cys Gly
                180                 185                 190

Val Met His Glu Ala Val Glu Asn His Tyr Thr Gln Lys Asn Val Ser
                195                 200                 205

His Ser Pro Gly Lys
        210

<210> SEQ ID NO 52
<211> LENGTH: 214
<212> TYPE: PRT
<213> ORGANISM: Artificial Sequence
<220> FEATURE:
<223> OTHER INFORMATION: Synthetic: Exemplary wild-type equine IgG6 Fc

<400> SEQUENCE: 52

Gly Arg Pro Ser Val Phe Ile Phe Pro Pro Asn Pro Lys Asp Thr Leu
1               5                   10                  15

Met Ile Ser Arg Thr Pro Glu Val Thr Cys Val Val Val Asp Val Ser
                20                  25                  30

Gln Glu Asn Pro Asp Val Lys Phe Asn Trp Tyr Val Asp Gly Val Glu
            35                  40                  45

Ala His Thr Ala Thr Thr Lys Ala Lys Glu Lys Gln Asp Asn Ser Thr
    50                  55                  60

Tyr Arg Val Val Ser Val Leu Pro Ile Gln His Gln Asp Trp Arg Arg
65                  70                  75                  80

Gly Lys Glu Phe Lys Cys Lys Val Asn Asn Arg Ala Leu Pro Ala Pro
                85                  90                  95

Val Glu Arg Thr Ile Thr Lys Ala Lys Gly Leu Gln Asp Pro Lys
                100                 105                 110

Val Tyr Ile Leu Ala Pro His Arg Glu Glu Val Thr Lys Asn Thr Val
                115                 120                 125

Ser Val Thr Cys Leu Val Lys Asp Phe Tyr Pro Pro Asp Ile Asn Val
            130                 135                 140

Glu Trp Gln Ser Asn Glu Glu Pro Glu Pro Glu Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
                180                 185                 190

Val Val Met His Glu Ala Ile Arg His Thr Tyr Arg Gln Lys Ser Ile
                195                 200                 205

Thr Asn Phe Pro Gly Lys
        210

<210> SEQ ID NO 53
<211> LENGTH: 213
<212> TYPE: PRT
<213> ORGANISM: Artificial Sequence
<220> FEATURE:
<223> OTHER INFORMATION: Synthetic: Exemplary wild-type equine IgG7 Fc

<400> SEQUENCE: 53
```

```
Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Asn Asn Ser Thr Tyr
    50                  55                  60

Arg Val Val Ser Ile Leu Ala Ile Gln His Lys Asp Trp Leu Ser Gly
65                  70                  75                  80

Lys Glu Phe Lys Cys Lys Val Asn Asn Gln Ala Leu Pro Ala Pro Val
                85                  90                  95

Gln Lys Thr Ile Ser Lys Pro Thr Gly Gln Pro Arg Glu Pro Gln Val
            100                 105                 110

Tyr Val Leu Ala Pro His Pro Asp Glu Leu Ser Lys Asn Lys Val Ser
            115                 120                 125

Val Thr Cys Leu Val Lys Asp Phe Tyr Pro Pro Asp Ile Asp Ile Glu
        130                 135                 140

Trp Lys Ser Asn Gly Gln Pro Glu Pro Glu Thr Lys Tyr Ser Thr Thr
145                 150                 155                 160

Pro Ala Gln Leu Asp Gly Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
        210

<210> SEQ ID NO 54
<211> LENGTH: 221
<212> TYPE: PRT
<213> ORGANISM: Artificial Sequence
<220> FEATURE:
<223> OTHER INFORMATION: Synthetic: Exemplary variant canine IgG-A Fc
      Heterodimer knob T(138)W

<400> SEQUENCE: 54

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Trp Cys Leu Ile Lys Asp Phe
        130                 135                 140
```

```
Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220

<210> SEQ ID NO 55
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc
      Heterodimer knob T(137)W

<400> SEQUENCE: 55

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Trp Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
210                 215                 220

<210> SEQ ID NO 56
<211> LENGTH: 220
<212> TYPE: PRT
<213> ORGANISM: Artificial Sequence
<220> FEATURE:
<223> OTHER INFORMATION: Synthetic: Exemplary variant canine IgG-C Fc
      Heterodimer knob T(137)W

<400> SEQUENCE: 56
```

Pro Gly Cys Gly Leu Leu Gly Pro Ser Val Phe Ile Phe Pro Pro
1               5                   10                  15

Lys Pro Lys Asp Ile Leu Val Thr Ala Arg Thr Pro Val Thr Cys
                20                  25                  30

Val Val Val Asp Leu Asp Pro Glu Asn Pro Glu Val Gln Ile Ser Trp
                35                  40                  45

Phe Val Asp Ser Lys Gln Val Gln Thr Ala Asn Thr Gln Pro Arg Glu
        50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
                100                 105                 110

Gln Ala His Gln Pro Asn Val Tyr Val Leu Pro Pro Ser Arg Asp Glu
        115                 120                 125

Met Ser Lys Asn Thr Val Thr Leu Trp Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
    210                 215                 220

<210> SEQ ID NO 57
<211> LENGTH: 221
<212> TYPE: PRT
<213> ORGANISM: Artificial Sequence
<220> FEATURE:
<223> OTHER INFORMATION: Synthetic: Exemplary variant canine IgG-D Fc
      Heterodimer knob T(138)W

<400> SEQUENCE: 57

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
                20                  25                  30

Val Val Leu Asp Leu Gly Arg Glu Asp Pro Glu Val Gln Ile Ser Trp
                35                  40                  45

Phe Val Asp Gly Lys Glu Val His Thr Ala Lys Thr Gln Pro Arg Glu
        50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
                100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Trp Cys Leu Ile Lys Asp Phe

```
                130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Thr Phe Thr Cys Ala Val Met His Glu Ala Leu Gln Asn
                195                 200                 205

His Tyr Thr Asp Leu Ser Leu Ser His Ser Pro Gly Lys
                210                 215                 220

<210> SEQ ID NO 58
<211> LENGTH: 221
<212> TYPE: PRT
<213> ORGANISM: Artificial Sequence
<220> FEATURE:
<223> OTHER INFORMATION: Synthetic: Exemplary variant canine IgG-A Fc
      Heterodimer hole T(138)S L(140)A

<400> SEQUENCE: 58

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
                20                  25                  30

Val Val Leu Asp Leu Gly Arg Glu Asp Pro Glu Val Gln Ile Ser Trp
                35                  40                  45

Phe Val Asp Gly Lys Glu Val His Thr Ala Lys Thr Gln Ser Arg Glu
50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
                100                 105                 110

Arg Ala His Lys Pro Ser Val Tyr Val Leu Pro Pro Ser Pro Lys Glu
                115                 120                 125

Leu Ser Ser Ser Asp Thr Val Ser Ile Ser Cys Ala Ile Lys Asp Phe
130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Pro Phe Thr Cys Ala Val Met His Glu Thr Leu Gln Asn
                195                 200                 205

His Tyr Thr Asp Leu Ser Leu Ser His Ser Pro Gly Lys
                210                 215                 220

<210> SEQ ID NO 59
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc
      Heterodimer hole T(137)S L(139)A
```

-continued

<400> SEQUENCE: 59

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Ser Cys Ala Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 60
<211> LENGTH: 220
<212> TYPE: PRT
<213> ORGANISM: Artificial Sequence
<220> FEATURE:
<223> OTHER INFORMATION: Synthetic: Exemplary variant canine IgG-C Fc
      Heterodimer hole T(137)S L(139)A

<400> SEQUENCE: 60

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Ser Cys Ala Val Lys Asp Phe Phe
            130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
210                 215                 220

<210> SEQ ID NO 61
<211> LENGTH: 221
<212> TYPE: PRT
<213> ORGANISM: Artificial Sequence
<220> FEATURE:
<223> OTHER INFORMATION: Synthetic: Exemplary variant canine IgG-D Fc
      Heterodimer hole T(138)S L(140)A

<400> SEQUENCE: 61

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
            35                  40                  45

Phe Val Asp Gly Lys Glu Val His Thr Ala Lys Thr Gln Pro Arg Glu
50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
            85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
            115                 120                 125

Leu Ser Ser Ser Asp Thr Val Thr Leu Ser Cys Ala Ile Lys Asp Phe
            130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
            195                 200                 205

His Tyr Thr Asp Leu Ser Leu Ser His Ser Pro Gly Lys
210                 215                 220

<210> SEQ ID NO 62
<211> LENGTH: 221
<212> TYPE: PRT
<213> ORGANISM: Artificial Sequence
<220> FEATURE:
<223> OTHER INFORMATION: Synthetic: Exemplary variant canine IgG-A Fc
      Heterodimer hole T(138)S L(140)A Y(181)T

<400> SEQUENCE: 62

```
Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Ser Cys Ala Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Thr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220
```

<210> SEQ ID NO 63
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc Heterodimer hole T(137)S L(139)A Y(180)T

<400> SEQUENCE: 63

```
Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125
```

```
Leu Ser Lys Asn Thr Val Ser Leu Ser Cys Ala Ile Lys Asp Phe Phe
            130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Thr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Glu Ser Leu Ser His Ser Pro Gly Lys
            210                 215                 220

<210> SEQ ID NO 64
<211> LENGTH: 220
<212> TYPE: PRT
<213> ORGANISM: Artificial Sequence
<220> FEATURE:
<223> OTHER INFORMATION: Synthetic: Exemplary variant canine IgG-C Fc
      Heterodimer hole T(137)S L(139)A Y(180)T

<400> SEQUENCE: 64

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
                20                  25                  30

Val Val Val Asp Leu Asp Pro Glu Asn Pro Glu Val Gln Ile Ser Trp
            35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Ser Cys Ala Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Thr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Ile Ser Leu Ser His Ser Pro Gly Lys
            210                 215                 220

<210> SEQ ID NO 65
<211> LENGTH: 221
<212> TYPE: PRT
<213> ORGANISM: Artificial Sequence
<220> FEATURE:
<223> OTHER INFORMATION: Synthetic: Exemplary variant canine IgG-D Fc
```

Heterodimer hole T(138)S L(140)A Y(181)T

<400> SEQUENCE: 65

```
Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Ser Cys Ala Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Thr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220
```

<210> SEQ ID NO 66
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc Heterodimer knob T(154)W

<400> SEQUENCE: 66

```
Arg Lys Thr Asp His Pro Pro Gly Pro Lys Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
```

```
                115                 120                 125
Gly Gln Pro His Glu Pro Gln Val Tyr Val Leu Pro Pro Ala Gln Glu
    130                 135                 140
Glu Leu Ser Glu Asn Lys Val Ser Val Trp Cys Leu Ile Lys Ser Phe
145                 150                 155                 160
His Pro Pro Asp Ile Ala Val Glu Trp Glu Ile Thr Gly Gln Pro Glu
                165                 170                 175
Pro Glu Asn Asn Tyr Arg Thr Thr Pro Pro Gln Leu Asp Ser Asp Gly
                180                 185                 190
Thr Tyr Phe Val Tyr Ser Lys Leu Ser Val Asp Arg Ser His Trp Gln
                195                 200                 205
Arg Gly Asn Thr Tyr Thr Cys Ser Val Ser His Glu Ala Leu His Ser
    210                 215                 220
His His Thr Gln Lys Ser Leu Thr Gln Ser Pro Gly Lys
225                 230                 235

<210> SEQ ID NO 67
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc
      Heterodimer knob T(154)W

<400> SEQUENCE: 67

Arg Lys Thr Asp His Pro Pro Gly Pro Lys Thr Gly Glu Gly Pro Lys
1               5                   10                  15
Cys Pro Pro Pro Glu Met Leu Gly Gly Pro Ser Ile Phe Ile Phe Pro
                20                  25                  30
Pro Lys Pro Lys Asp Thr Leu Ser Ile Ser Arg Thr Pro Glu Val Thr
            35                  40                  45
Cys Leu Val Val Asp Leu Gly Pro Asp Asp Ser Asp Val Gln Ile Thr
        50                  55                  60
Trp Phe Val Asp Asn Thr Gln Val Tyr Thr Ala Lys Thr Ser Pro Arg
65                  70                  75                  80
Glu Glu Gln Phe Asn Ser Thr Tyr Arg Val Val Ser Val Leu Pro Ile
                85                  90                  95
Leu His Gln Asp Trp Leu Lys Gly Lys Glu Phe Lys Cys Lys Val Asn
                100                 105                 110
Ser Lys Ser Leu Pro Ser Pro Ile Glu Arg Thr Ile Ser Lys Ala Lys
            115                 120                 125
Gly Gln Pro His Glu Pro Gln Val Tyr Val Leu Pro Pro Ala Gln Glu
    130                 135                 140
Glu Leu Ser Glu Asn Lys Val Ser Val Trp Cys Leu Ile Lys Ser Phe
145                 150                 155                 160
His Pro Pro Asp Ile Ala Val Glu Trp Glu Ile Thr Gly Gln Pro Glu
                165                 170                 175
Pro Glu Asn Asn Tyr Arg Thr Thr Pro Pro Gln Leu Asp Ser Asp Gly
                180                 185                 190
Thr Tyr Phe Val Tyr Ser Lys Leu Ser Val Asp Arg Ser His Trp Gln
                195                 200                 205
Arg Gly Asn Thr Tyr Thr Cys Ser Val Ser His Glu Ala Leu His Ser
    210                 215                 220
His His Thr Gln Lys Ser Leu Thr Gln Ser Pro Gly Lys
225                 230                 235
```

<210> SEQ ID NO 68
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc Heterodimer knob T(154)W

<400> SEQUENCE: 68

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Trp Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 69
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc Heterodimer knob T(154)W

<400> SEQUENCE: 69

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
50                  55                  60

```
Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Trp Cys Leu Ile Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
                180                 185                 190

Thr Tyr Phe Leu Tyr Ser Arg Leu Ser Val Asp Arg Ser Arg Trp Gln
            195                 200                 205

Arg Gly Asn Thr Tyr Thr Cys Ser Val Ser His Glu Ala Leu His Ser
        210                 215                 220

His His Thr Gln Lys Ser Leu Thr Gln Ser Pro Gly Lys
225                 230                 235

<210> SEQ ID NO 70
<211> LENGTH: 237
<212> TYPE: PRT
<213> ORGANISM: Artificial Sequence
<220> FEATURE:
<223> OTHER INFORMATION: Synthetic: Exemplary variant feline IgG2 Fc
      Heterodimer knob T(154)W

<400> SEQUENCE: 70

Pro Lys Thr Ala Ser Thr Ile Glu Ser Lys Thr Gly Glu Gly Pro Lys
 1               5                  10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
        50                  55                  60

Trp Phe Val Asp Asn Thr Glu Met His Thr Ala Lys Thr Arg Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Trp Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
                180                 185                 190
```

```
Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 71
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc
      Heterodimer hole T(154)S L(156)A

<400> SEQUENCE: 71

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Ser Cys Ala Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 72
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc
      Heterodimer hole T(154)S L(156)A

<400> SEQUENCE: 72

Arg Lys Thr Asp His Pro Pro Gly Pro Lys Thr Gly Glu Gly Pro Lys
1               5                   10                  15
```

Cys Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
            115                 120                 125

Gly Gln Pro His Glu Pro Gln Val Tyr Val Leu Pro Pro Ala Gln Glu
130                 135                 140

Glu Leu Ser Glu Asn Lys Val Ser Val Ser Cys Ala Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
            195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 73
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc
      Heterodimer hole T(154)S L(156)A

<400> SEQUENCE: 73

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
            115                 120                 125

Gly Gln Pro His Glu Pro Gln Val Tyr Val Leu Pro Pro Ala Gln Glu

```
            130                 135                 140
Glu Leu Ser Glu Asn Lys Val Ser Val Ser Cys Ala Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
            195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 74
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc
      Heterodimer hole T(154)S L(156)A

<400> SEQUENCE: 74

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
            115                 120                 125

Gly Gln Pro His Glu Pro Gln Val Tyr Val Leu Pro Pro Ala Gln Glu
            130                 135                 140

Glu Leu Ser Glu Asn Lys Val Ser Val Ser Cys Ala Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
            195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 75
<211> LENGTH: 237
```

```
<212> TYPE: PRT
<213> ORGANISM: Artificial Sequence
<220> FEATURE:
<223> OTHER INFORMATION: Synthetic: Exemplary variant feline IgG2 Fc
      Heterodimer hole T(154)S L(156)A

<400> SEQUENCE: 75

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
130                 135                 140

Glu Leu Ser Glu Asn Lys Val Ser Val Ser Cys Ala Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 76
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc
      Heterodimer hole T(154)S L(156)A Y(197)T

<400> SEQUENCE: 76

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80
```

```
Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Ser Cys Ala Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Thr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 77
<211> LENGTH: 237
<212> TYPE: PRT
<213> ORGANISM: Artificial Sequence
<220> FEATURE:
<223> OTHER INFORMATION: Synthetic: Exemplary variant feline IgG1a Fc
      Heterodimer hole T(154)S L(156)A Y(197)T

<400> SEQUENCE: 77

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Ser Cys Ala Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Thr Ser Lys Leu Ser Val Asp Arg Ser His Trp Gln
        195                 200                 205
```

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 78
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc
      Heterodimer hole T(154)S L(156)A Y(197)T

<400> SEQUENCE: 78

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
130                 135                 140

Glu Leu Ser Glu Asn Lys Val Ser Val Ser Cys Ala Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Thr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 79
<211> LENGTH: 237
<212> TYPE: PRT
<213> ORGANISM: Artificial Sequence
<220> FEATURE:
<223> OTHER INFORMATION: Synthetic: Exemplary variant feline IgG1b Fc
      Heterodimer hole T(154)S L(156)A Y(197)T

<400> SEQUENCE: 79

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
                20                  25                  30

```
Pro Lys Pro Lys Asp Thr Leu Ser Ile Ser Arg Thr Pro Glu Val Thr
        35                  40                  45

Cys Leu Val Val Asp Leu Gly Pro Asp Ser Asp Val Gln Ile Thr
 50                  55                  60

Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
                100                 105                 110

Ser Lys Ser Leu Pro Ser Pro Ile Glu Arg Thr Ile Ser Lys Asp Lys
            115                 120                 125

Gly Gln Pro His Glu Pro Gln Val Tyr Val Leu Pro Pro Ala Gln Glu
        130                 135                 140

Glu Leu Ser Glu Asn Lys Val Ser Val Ser Cys Ala Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Thr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 80
<211> LENGTH: 237
<212> TYPE: PRT
<213> ORGANISM: Artificial Sequence
<220> FEATURE:
<223> OTHER INFORMATION: Synthetic: Exemplary variant feline IgG2 Fc
      Heterodimer hole T(154)S L(156)A Y(197)T

<400> SEQUENCE: 80

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                 20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Ser Asn Val Gln Ile Thr
 50                  55                  60

Trp Phe Val Asp Asn Thr Glu Met His Thr Ala Lys Thr Arg Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
                100                 105                 110

Ser Lys Ser Leu Pro Ser Ala Met Glu Arg Thr Ile Ser Lys Ala Lys
            115                 120                 125

Gly Gln Pro His Glu Pro Gln Val Tyr Val Leu Pro Pro Thr Gln Glu
        130                 135                 140

Glu Leu Ser Glu Asn Lys Val Ser Val Ser Cys Ala Ile Lys Gly Phe
```

```
                145                 150                 155                 160
His Pro Pro Asp Ile Ala Val Glu Trp Glu Ile Thr Gly Gln Pro Glu
                    165                 170                 175

Pro Glu Asn Asn Tyr Gln Thr Thr Pro Pro Gln Leu Asp Ser Asp Gly
                    180                 185                 190

Thr Tyr Phe Leu Thr Ser Arg Leu Ser Val Asp Arg Ser His Trp Gln
                    195                 200                 205

Arg Gly Asn Thr Tyr Thr Cys Ser Val Ser His Glu Ala Leu His Ser
                    210                 215                 220

His His Thr Gln Lys Ser Leu Thr Gln Ser Pro Gly Lys
225                 230                 235

<210> SEQ ID NO 81
<211> LENGTH: 213
<212> TYPE: PRT
<213> ORGANISM: Artificial Sequence
<220> FEATURE:
<223> OTHER INFORMATION: Synthetic: Exemplary variant equine IgG1 Fc
      Heterodimer knob T(130)W

<400> SEQUENCE: 81

Gly Pro Ser Val Phe Ile Phe Pro Pro Asn Pro Lys Asp Thr Leu Met
1               5                   10                  15

Ile Thr Arg Thr Pro Glu Val Thr Cys Val Val Val Asp Val Ser Gln
                20                  25                  30

Glu Asn Pro Asp Val Lys Phe Asn Trp Tyr Met Asp Gly Val Glu Val
            35                  40                  45

Arg Thr Ala Thr Thr Arg Pro Lys Glu Glu Gln Phe Asn Ser Thr Tyr
50                  55                  60

Arg Val Val Ser Val Leu Arg Ile Gln His Gln Asp Trp Leu Ser Gly
65                  70                  75                  80

Lys Glu Phe Lys Cys Lys Val Asn Asn Gln Ala Leu Pro Gln Pro Ile
                85                  90                  95

Glu Arg Thr Ile Thr Lys Thr Lys Gly Arg Ser Gln Glu Pro Gln Val
            100                 105                 110

Tyr Val Leu Ala Pro His Pro Asp Glu Leu Ser Lys Ser Lys Val Ser
        115                 120                 125

Val Trp Cys Leu Val Lys Asp Phe Tyr Pro Pro Glu Ile Asn Ile Glu
    130                 135                 140

Trp Gln Ser Asn Gly Gln Pro Glu Leu Glu Thr Lys Tyr Ser Thr Thr
145                 150                 155                 160

Gln Ala Gln Gln Asp Ser Asp Gly Ser Tyr Phe Leu Tyr Ser Lys Leu
                165                 170                 175

Ser Val Asp Arg Asn Arg Trp Gln Gln Gly Thr Thr Phe Thr Cys Gly
            180                 185                 190

Val Met His Glu Ala Leu His Asn His Tyr Thr Gln Lys Asn Val Ser
        195                 200                 205

Lys Asn Pro Gly Lys
    210

<210> SEQ ID NO 82
<211> LENGTH: 213
<212> TYPE: PRT
<213> ORGANISM: Artificial Sequence
<220> FEATURE:
<223> OTHER INFORMATION: Synthetic: Exemplary variant equine IgG2 Fc
      Heterodimer knob T(130)W
```

<400> SEQUENCE: 82

```
Gly Pro Ser Val Phe Ile Phe Pro Pro Asn Pro Lys Asp Ala Leu Met
1               5                   10                  15

Ile Ser Arg Thr Pro Val Val Thr Cys Val Val Asn Leu Ser Asp
                20                  25                  30

Gln Tyr Pro Asp Val Gln Phe Ser Trp Tyr Val Asp Asn Thr Glu Val
                35                  40                  45

His Ser Ala Ile Thr Lys Gln Arg Glu Ala Gln Phe Asn Ser Thr Tyr
        50                  55                  60

Arg Val Val Ser Val Leu Pro Ile Gln His Gln Asp Trp Leu Ser Gly
65                  70                  75                  80

Lys Glu Phe Lys Cys Ser Val Thr Asn Val Gly Val Pro Gln Pro Ile
                85                  90                  95

Ser Arg Ala Ile Ser Arg Gly Lys Gly Pro Ser Arg Val Pro Gln Val
                100                 105                 110

Tyr Val Leu Pro Pro His Pro Asp Glu Leu Ala Lys Ser Lys Val Ser
                115                 120                 125

Val Trp Cys Leu Val Lys Asp Phe Tyr Pro Asp Ile Ser Val Glu
    130                 135                 140

Trp Gln Ser Asn Arg Trp Pro Glu Leu Glu Gly Lys Tyr Ser Thr Thr
145                 150                 155                 160

Pro Ala Gln Leu Asp Gly Asp Gly Ser Tyr Phe Leu Tyr Ser Lys Leu
                165                 170                 175

Ser Leu Glu Thr Ser Arg Trp Gln Gln Val Glu Ser Phe Thr Cys Ala
                180                 185                 190

Val Met His Glu Ala Leu His Asn His Phe Thr Lys Thr Asp Ile Ser
        195                 200                 205

Glu Ser Leu Gly Lys
        210
```

<210> SEQ ID NO 83
<211> LENGTH: 213
<212> TYPE: PRT
<213> ORGANISM: Artificial Sequence
<220> FEATURE:
<223> OTHER INFORMATION: Synthetic: Exemplary variant equine IgG3 Fc Heterodimer knob T(130)W

<400> SEQUENCE: 83

```
Gly Pro Ser Val Phe Ile Phe Pro Pro Lys Pro Lys Asp Val Leu Met
1               5                   10                  15

Ile Thr Arg Met Pro Glu Val Thr Cys Leu Val Val Asp Val Ser His
                20                  25                  30

Asp Ser Ser Asp Val Leu Phe Thr Trp Tyr Val Asp Gly Thr Glu Val
                35                  40                  45

Lys Thr Ala Lys Thr Met Pro Asn Glu Glu Gln Asn Asn Ser Thr Tyr
        50                  55                  60

Arg Val Val Ser Val Leu Arg Ile Gln His Gln Asp Trp Leu Asn Gly
65                  70                  75                  80

Lys Lys Phe Lys Cys Lys Val Asn Asn Gln Ala Leu Pro Ala Pro Val
                85                  90                  95

Glu Arg Thr Ile Ser Lys Ala Thr Gly Gln Thr Arg Val Pro Gln Val
                100                 105                 110

Tyr Val Leu Ala Pro His Pro Asp Glu Leu Ser Lys Asn Lys Val Ser
                115                 120                 125
```

```
Val Trp Cys Leu Val Lys Asp Phe Tyr Pro Pro Asp Ile Thr Val Glu
    130                 135                 140

Trp Gln Ser Asn Glu His Pro Glu Pro Glu Gly Lys Tyr Arg Thr Thr
145                 150                 155                 160

Glu Ala Gln Lys Asp Ser Asp Gly Ser Tyr Phe Leu Tyr Ser Lys Leu
                165                 170                 175

Thr Val Glu Lys Asp Arg Trp Gln Gln Gly Thr Thr Phe Thr Cys Val
            180                 185                 190

Val Met His Glu Ala Leu His Asn His Val Met Gln Lys Asn Ile Ser
        195                 200                 205

Lys Asn Pro Gly Lys
    210

<210> SEQ ID NO 84
<211> LENGTH: 213
<212> TYPE: PRT
<213> ORGANISM: Artificial Sequence
<220> FEATURE:
<223> OTHER INFORMATION: Synthetic: Exemplary variant equine IgG4 Fc
      Heterodimer knob T(130)W

<400> SEQUENCE: 84

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Phe Asn Ser Thr Tyr
    50                  55                  60

Arg Val Val Ser Val Leu Pro Ile Gln His Lys Asp Trp Leu Ser Gly
65                  70                  75                  80

Lys Glu Phe Lys Cys Lys Val Asn Asn Lys Ala Leu Pro Ala Pro Val
                85                  90                  95

Glu Arg Thr Ile Ser Ala Pro Thr Gly Gln Pro Arg Glu Pro Gln Val
            100                 105                 110

Tyr Val Leu Ala Pro His Arg Asp Glu Leu Ser Lys Asn Lys Val Ser
        115                 120                 125

Val Trp Cys Leu Val Lys Asp Phe Tyr Pro Pro Asp Ile Asp Ile Glu
    130                 135                 140

Trp Lys Ser Asn Gly Gln Pro Glu Pro Glu Thr Lys Tyr Ser Thr Thr
145                 150                 155                 160

Pro Ala Gln Leu Asp Ser Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
    210

<210> SEQ ID NO 85
<211> LENGTH: 213
<212> TYPE: PRT
<213> ORGANISM: Artificial Sequence
<220> FEATURE:
<223> OTHER INFORMATION: Synthetic: Exemplary variant equine IgG5 Fc
      Heterodimer knob T(130)W
```

<400> SEQUENCE: 85

```
Gly Pro Ser Val Phe Ile Phe Pro Pro Lys Pro Asp Val Leu Met
1               5                   10                  15

Ile Ser Arg Lys Pro Glu Val Thr Cys Val Val Asp Leu Gly His
            20                  25                  30

Asp Asp Pro Asp Val Gln Phe Thr Trp Phe Val Asp Gly Val Glu Thr
            35                  40                  45

His Thr Ala Thr Thr Glu Pro Lys Glu Glu Gln Phe Asn Ser Thr Tyr
    50                  55                      60

Arg Val Val Ser Val Leu Pro Ile Gln His Gln Asp Trp Leu Ser Gly
65                  70                  75                  80

Lys Glu Phe Lys Cys Ser Val Thr Ser Lys Ala Leu Pro Ala Pro Val
                85                  90                  95

Glu Arg Thr Ile Ser Lys Ala Lys Gly Gln Leu Arg Val Pro Gln Val
                100                 105                 110

Tyr Val Leu Ala Pro His Pro Asp Glu Leu Ala Lys Asn Thr Val Ser
            115                 120                 125

Val Trp Cys Leu Val Lys Asp Phe Tyr Pro Pro Glu Ile Asp Val Glu
130                 135                 140

Trp Gln Ser Asn Glu His Pro Glu Pro Glu Gly Lys Tyr Ser Thr Thr
145                 150                 155                 160

Pro Ala Gln Leu Asn Ser Asp Gly Ser Tyr Phe Leu Tyr Ser Lys Leu
                165                 170                 175

Ser Val Glu Thr Ser Arg Trp Lys Gln Gly Val Ser Phe Thr Cys Gly
                180                 185                 190

Val Met His Glu Ala Val Glu Asn His Tyr Thr Gln Lys Asn Val Ser
            195                 200                 205

His Ser Pro Gly Lys
            210
```

<210> SEQ ID NO 86
<211> LENGTH: 213
<212> TYPE: PRT
<213> ORGANISM: Artificial Sequence
<220> FEATURE:
<223> OTHER INFORMATION: Synthetic: Exemplary variant equine IgG6 Fc Heterodimer knob T(130)W

<400> SEQUENCE: 86

```
Arg Pro Ser Val Phe Ile Phe Pro Pro Asn Pro Lys Asp Thr Leu Met
1               5                   10                  15

Ile Ser Arg Thr Pro Glu Val Thr Cys Val Val Asp Val Ser Gln
            20                  25                  30

Glu Asn Pro Asp Val Lys Phe Asn Trp Tyr Val Asp Gly Val Glu Ala
            35                  40                  45

His Thr Ala Thr Thr Lys Ala Lys Glu Lys Gln Asp Asn Ser Thr Tyr
    50                  55                      60

Arg Val Val Ser Val Leu Pro Ile Gln His Gln Asp Trp Arg Arg Gly
65                  70                  75                  80

Lys Glu Phe Lys Cys Lys Val Asn Asn Arg Ala Leu Pro Ala Pro Val
                85                  90                  95

Glu Arg Thr Ile Thr Lys Ala Lys Gly Glu Leu Gln Asp Pro Lys Val
                100                 105                 110

Tyr Ile Leu Ala Pro His Arg Glu Glu Val Thr Lys Asn Thr Val Ser
            115                 120                 125
```

```
Val Trp Cys Leu Val Lys Asp Phe Tyr Pro Pro Asp Ile Asn Val Glu
    130                 135                 140

Trp Gln Ser Asn Glu Glu Pro Glu Pro Glu Val Lys Tyr Ser Thr Thr
145                 150                 155                 160

Pro Ala Gln Leu Asp Gly Asp Gly Ser Tyr Phe Leu Tyr Ser Lys Leu
                165                 170                 175

Thr Val Glu Thr Asp Arg Trp Glu Gln Gly Glu Ser Phe Thr Cys Val
            180                 185                 190

Val Met His Glu Ala Ile Arg His Thr Tyr Arg Gln Lys Ser Ile Thr
        195                 200                 205

Asn Phe Pro Gly Lys
    210

<210> SEQ ID NO 87
<211> LENGTH: 213
<212> TYPE: PRT
<213> ORGANISM: Artificial Sequence
<220> FEATURE:
<223> OTHER INFORMATION: Synthetic: Exemplary variant equine IgG7 Fc
      Heterodimer knob T(130)W

<400> SEQUENCE: 87

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Asn Asn Ser Thr Tyr
    50                  55                  60

Arg Val Val Ser Ile Leu Ala Ile Gln His Lys Asp Trp Leu Ser Gly
65                  70                  75                  80

Lys Glu Phe Lys Cys Lys Val Asn Asn Gln Ala Leu Pro Ala Pro Val
                85                  90                  95

Gln Lys Thr Ile Ser Lys Pro Thr Gly Gln Pro Arg Glu Pro Gln Val
            100                 105                 110

Tyr Val Leu Ala Pro His Pro Asp Glu Leu Ser Lys Asn Lys Val Ser
        115                 120                 125

Val Trp Cys Leu Val Lys Asp Phe Tyr Pro Pro Asp Ile Asp Ile Glu
    130                 135                 140

Trp Lys Ser Asn Gly Gln Pro Glu Pro Glu Thr Lys Tyr Ser Thr Thr
145                 150                 155                 160

Pro Ala Gln Leu Asp Gly Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
    210

<210> SEQ ID NO 88
<211> LENGTH: 213
<212> TYPE: PRT
<213> ORGANISM: Artificial Sequence
<220> FEATURE:
<223> OTHER INFORMATION: Synthetic: Exemplary variant equine IgG1 Fc
```

Heterodimer hole T(130)S L(132)A

<400> SEQUENCE: 88

```
Gly Pro Ser Val Phe Ile Phe Pro Pro Asn Pro Lys Asp Thr Leu Met
1               5                   10                  15
Ile Thr Arg Thr Pro Glu Val Thr Cys Val Val Val Asp Val Ser Gln
            20                  25                  30
Glu Asn Pro Asp Val Lys Phe Asn Trp Tyr Met Asp Gly Val Glu Val
        35                  40                  45
Arg Thr Ala Thr Thr Arg Pro Lys Glu Glu Gln Phe Asn Ser Thr Tyr
    50                  55                  60
Arg Val Val Ser Val Leu Arg Ile Gln His Gln Asp Trp Leu Ser Gly
65                  70                  75                  80
Lys Glu Phe Lys Cys Lys Val Asn Asn Gln Ala Leu Pro Gln Pro Ile
                85                  90                  95
Glu Arg Thr Ile Thr Lys Thr Lys Gly Arg Ser Gln Glu Pro Gln Val
            100                 105                 110
Tyr Val Leu Ala Pro His Pro Asp Glu Leu Ser Lys Ser Lys Val Ser
        115                 120                 125
Val Ser Cys Ala Val Lys Asp Phe Tyr Pro Pro Glu Ile Asn Ile Glu
    130                 135                 140
Trp Gln Ser Asn Gly Gln Pro Glu Leu Glu Thr Lys Tyr Ser Thr Thr
145                 150                 155                 160
Gln Ala Gln Gln Asp Ser Asp Gly Ser Tyr Phe Leu Tyr Ser Lys Leu
                165                 170                 175
Ser Val Asp Arg Asn Arg Trp Gln Gln Gly Thr Thr Phe Thr Cys Gly
            180                 185                 190
Val Met His Glu Ala Leu His Asn His Tyr Thr Gln Lys Asn Val Ser
        195                 200                 205
Lys Asn Pro Gly Lys
    210
```

<210> SEQ ID NO 89
<211> LENGTH: 213
<212> TYPE: PRT
<213> ORGANISM: Artificial Sequence
<220> FEATURE:
<223> OTHER INFORMATION: Synthetic: Exemplary variant equine IgG2 Fc
      Heterodimer hole T(130)S L(132)A

<400> SEQUENCE: 89

```
Gly Pro Ser Val Phe Ile Phe Pro Pro Asn Pro Lys Asp Ala Leu Met
1               5                   10                  15
Ile Ser Arg Thr Pro Val Val Thr Cys Val Val Val Asn Leu Ser Asp
            20                  25                  30
Gln Tyr Pro Asp Val Gln Phe Ser Trp Tyr Val Asp Asn Thr Glu Val
        35                  40                  45
His Ser Ala Ile Thr Lys Gln Arg Glu Ala Gln Phe Asn Ser Thr Tyr
    50                  55                  60
Arg Val Val Ser Val Leu Pro Ile Gln His Gln Asp Trp Leu Ser Gly
65                  70                  75                  80
Lys Glu Phe Lys Cys Ser Val Thr Asn Val Gly Val Pro Gln Pro Ile
                85                  90                  95
Ser Arg Ala Ile Ser Arg Gly Lys Gly Pro Ser Arg Val Pro Gln Val
            100                 105                 110
Tyr Val Leu Pro Pro His Pro Asp Glu Leu Ala Lys Ser Lys Val Ser
```

```
             115                 120                 125
Val Ser Cys Ala Val Lys Asp Phe Tyr Pro Pro Asp Ile Ser Val Glu
        130                 135                 140

Trp Gln Ser Asn Arg Trp Pro Glu Leu Glu Gly Lys Tyr Ser Thr Thr
145                 150                 155                 160

Pro Ala Gln Leu Asp Gly Asp Gly Ser Tyr Phe Leu Tyr Ser Lys Leu
                165                 170                 175

Ser Leu Glu Thr Ser Arg Trp Gln Gln Val Glu Ser Phe Thr Cys Ala
            180                 185                 190

Val Met His Glu Ala Leu His Asn His Phe Thr Lys Thr Asp Ile Ser
        195                 200                 205

Glu Ser Leu Gly Lys
        210
```

<210> SEQ ID NO 90
<211> LENGTH: 213
<212> TYPE: PRT
<213> ORGANISM: Artificial Sequence
<220> FEATURE:
<223> OTHER INFORMATION: Synthetic: Exemplary variant equine IgG3 Fc
      Heterodimer hole T(130)S L(132)A

<400> SEQUENCE: 90

```
Gly Pro Ser Val Phe Ile Phe Pro Pro Lys Pro Lys Asp Val Leu Met
1               5                   10                  15

Ile Thr Arg Met Pro Glu Val Thr Cys Leu Val Val Asp Val Ser His
            20                  25                  30

Asp Ser Ser Asp Val Leu Phe Thr Trp Tyr Val Asp Gly Thr Glu Val
        35                  40                  45

Lys Thr Ala Lys Thr Met Pro Asn Glu Glu Gln Asn Asn Ser Thr Tyr
    50                  55                  60

Arg Val Val Ser Val Leu Arg Ile Gln His Gln Asp Trp Leu Asn Gly
65                  70                  75                  80

Lys Lys Phe Lys Cys Lys Val Asn Asn Gln Ala Leu Pro Ala Pro Val
                85                  90                  95

Glu Arg Thr Ile Ser Lys Ala Thr Gly Gln Thr Arg Val Pro Gln Val
            100                 105                 110

Tyr Val Leu Ala Pro His Pro Asp Glu Leu Ser Lys Asn Lys Val Ser
        115                 120                 125

Val Ser Cys Ala Val Lys Asp Phe Tyr Pro Pro Asp Ile Thr Val Glu
    130                 135                 140

Trp Gln Ser Asn Glu His Pro Glu Pro Glu Gly Lys Tyr Arg Thr Thr
145                 150                 155                 160

Glu Ala Gln Lys Asp Ser Asp Gly Ser Tyr Phe Leu Tyr Ser Lys Leu
                165                 170                 175

Thr Val Glu Lys Asp Arg Trp Gln Gln Gly Thr Thr Phe Thr Cys Val
            180                 185                 190

Val Met His Glu Ala Leu His Asn His Val Met Gln Lys Asn Ile Ser
        195                 200                 205

Lys Asn Pro Gly Lys
        210
```

<210> SEQ ID NO 91
<211> LENGTH: 213
<212> TYPE: PRT
<213> ORGANISM: Artificial Sequence
<220> FEATURE:

<223> OTHER INFORMATION: Synthetic: Exemplary variant equine IgG4 Fc
      Heterodimer hole T(130)S L(132)A

<400> SEQUENCE: 91

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Phe Asn Ser Thr Tyr
    50                  55                  60

Arg Val Val Ser Val Leu Pro Ile Gln His Lys Asp Trp Leu Ser Gly
65                  70                  75                  80

Lys Glu Phe Lys Cys Lys Val Asn Asn Lys Ala Leu Pro Ala Pro Val
                85                  90                  95

Glu Arg Thr Ile Ser Ala Pro Thr Gly Gln Pro Arg Glu Pro Gln Val
            100                 105                 110

Tyr Val Leu Ala Pro His Arg Asp Glu Leu Ser Lys Asn Lys Val Ser
        115                 120                 125

Val Ser Cys Ala Val Lys Asp Phe Tyr Pro Pro Asp Ile Asp Ile Glu
    130                 135                 140

Trp Lys Ser Asn Gly Gln Pro Glu Pro Glu Thr Lys Tyr Ser Thr Thr
145                 150                 155                 160

Pro Ala Gln Leu Asp Ser Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
    210

<210> SEQ ID NO 92
<211> LENGTH: 213
<212> TYPE: PRT
<213> ORGANISM: Artificial Sequence
<220> FEATURE:
<223> OTHER INFORMATION: Synthetic: Exemplary variant equine IgG5 Fc
      Heterodimer hole T(130)S L(132)A

<400> SEQUENCE: 92

Gly Pro Ser Val Phe Ile Phe Pro Pro Lys Pro Lys Asp Val Leu Met
1               5                   10                  15

Ile Ser Arg Lys Pro Glu Val Thr Cys Val Val Val Asp Leu Gly His
            20                  25                  30

Asp Asp Pro Asp Val Gln Phe Thr Trp Phe Val Asp Gly Val Glu Thr
        35                  40                  45

His Thr Ala Thr Thr Glu Pro Lys Glu Glu Gln Phe Asn Ser Thr Tyr
    50                  55                  60

Arg Val Val Ser Val Leu Pro Ile Gln His Gln Asp Trp Leu Ser Gly
65                  70                  75                  80

Lys Glu Phe Lys Cys Ser Val Thr Ser Lys Ala Leu Pro Ala Pro Val
                85                  90                  95

Glu Arg Thr Ile Ser Lys Ala Lys Gly Gln Leu Arg Val Pro Gln Val
            100                 105                 110

```
Tyr Val Leu Ala Pro His Pro Asp Glu Leu Ala Lys Asn Thr Val Ser
            115                 120                 125

Val Ser Cys Ala Val Lys Asp Phe Tyr Pro Pro Glu Ile Asp Val Glu
        130                 135                 140

Trp Gln Ser Asn Glu His Pro Glu Pro Glu Gly Lys Tyr Ser Thr Thr
145                 150                 155                 160

Pro Ala Gln Leu Asn Ser Asp Gly Ser Tyr Phe Leu Tyr Ser Lys Leu
                165                 170                 175

Ser Val Glu Thr Ser Arg Trp Lys Gln Gly Ser Phe Thr Cys Gly
            180                 185                 190

Val Met His Glu Ala Val Glu Asn His Tyr Thr Gln Lys Asn Val Ser
        195                 200                 205

His Ser Pro Gly Lys
    210
```

<210> SEQ ID NO 93
<211> LENGTH: 213
<212> TYPE: PRT
<213> ORGANISM: Artificial Sequence
<220> FEATURE:
<223> OTHER INFORMATION: Synthetic: Exemplary variant equine IgG6 Fc Heterodimer hole T(130)S L(132)A

<400> SEQUENCE: 93

```
Arg Pro Ser Val Phe Ile Phe Pro Pro Asn Pro Lys Asp Thr Leu Met
1               5                   10                  15

Ile Ser Arg Thr Pro Glu Val Thr Cys Val Val Val Asp Val Ser Gln
            20                  25                  30

Glu Asn Pro Asp Val Lys Phe Asn Trp Tyr Val Asp Gly Val Glu Ala
        35                  40                  45

His Thr Ala Thr Thr Lys Ala Lys Glu Lys Gln Asp Asn Ser Thr Tyr
    50                  55                  60

Arg Val Val Ser Val Leu Pro Ile Gln His Gln Asp Trp Arg Arg Gly
65                  70                  75                  80

Lys Glu Phe Lys Cys Lys Val Asn Asn Arg Ala Leu Pro Ala Pro Val
                85                  90                  95

Glu Arg Thr Ile Thr Lys Ala Lys Gly Glu Leu Gln Asp Pro Lys Val
            100                 105                 110

Tyr Ile Leu Ala Pro His Arg Glu Glu Val Thr Lys Asn Thr Val Ser
        115                 120                 125

Val Ser Cys Ala Val Lys Asp Phe Tyr Pro Pro Asp Ile Asn Val Glu
    130                 135                 140

Trp Gln Ser Asn Glu Glu Pro Glu Pro Glu Val Lys Tyr Ser Thr Thr
145                 150                 155                 160

Pro Ala Gln Leu Asp Gly Asp Gly Ser Tyr Phe Leu Tyr Ser Lys Leu
                165                 170                 175

Thr Val Glu Thr Asp Arg Trp Leu Gln Gly Glu Ser Phe Thr Cys Val
            180                 185                 190

Val Met His Glu Ala Ile Arg His Thr Tyr Arg Gln Lys Ser Ile Thr
        195                 200                 205

Asn Phe Pro Gly Lys
    210
```

<210> SEQ ID NO 94
<211> LENGTH: 213
<212> TYPE: PRT
<213> ORGANISM: Artificial Sequence
<220> FEATURE:
<223> OTHER INFORMATION: Synthetic: Exemplary variant equine IgG7 Fc
       Heterodimer hole T(130)S L(132)A

<400> SEQUENCE: 94

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Asn Asn Ser Thr Tyr
    50                  55                  60

Arg Val Val Ser Ile Leu Ala Ile Gln His Lys Asp Trp Leu Ser Gly
65                  70                  75                  80

Lys Glu Phe Lys Cys Lys Val Asn Asn Gln Ala Leu Pro Ala Pro Val
                85                  90                  95

Gln Lys Thr Ile Ser Lys Pro Thr Gly Gln Pro Arg Glu Pro Gln Val
            100                 105                 110

Tyr Val Leu Ala Pro His Pro Asp Glu Leu Ser Lys Asn Lys Val Ser
        115                 120                 125

Val Ser Cys Ala Val Lys Asp Phe Tyr Pro Pro Asp Ile Asp Ile Glu
130                 135                 140

Trp Lys Ser Asn Gly Gln Pro Glu Pro Glu Thr Lys Tyr Ser Thr Thr
145                 150                 155                 160

Pro Ala Gln Leu Asp Gly Asp Gly Ser Tyr Phe Leu Tyr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
        210

<210> SEQ ID NO 95
<211> LENGTH: 213
<212> TYPE: PRT
<213> ORGANISM: Artificial Sequence
<220> FEATURE:
<223> OTHER INFORMATION: Synthetic: Exemplary variant equine IgG1 Fc
       Heterodimer hole T(130)S L(132)A Y(173)T

<400> SEQUENCE: 95

Gly Pro Ser Val Phe Ile Phe Pro Pro Asn Pro Lys Asp Thr Leu Met
1               5                   10                  15

Ile Thr Arg Thr Pro Glu Val Thr Cys Val Val Val Asp Val Ser Gln
            20                  25                  30

Glu Asn Pro Asp Val Lys Phe Asn Trp Tyr Met Asp Gly Val Glu Val
        35                  40                  45

Arg Thr Ala Thr Thr Arg Pro Lys Glu Glu Gln Phe Asn Ser Thr Tyr
    50                  55                  60

Arg Val Val Ser Val Leu Arg Ile Gln His Gln Asp Trp Leu Ser Gly
65                  70                  75                  80

Lys Glu Phe Lys Cys Lys Val Asn Asn Gln Ala Leu Pro Gln Pro Ile
                85                  90                  95

Glu Arg Thr Ile Thr Lys Thr Lys Gly Arg Ser Gln Glu Pro Gln Val
            100                 105                 110

Tyr Val Leu Ala Pro His Pro Asp Glu Leu Ser Lys Ser Lys Val Ser
            115                 120                 125

Val Ser Cys Ala Val Lys Asp Phe Tyr Pro Pro Glu Ile Asn Ile Glu
    130                 135                 140

Trp Gln Ser Asn Gly Gln Pro Glu Leu Glu Thr Lys Tyr Ser Thr Thr
145                 150                 155                 160

Gln Ala Gln Gln Asp Ser Asp Gly Ser Tyr Phe Leu Thr Ser Lys Leu
                165                 170                 175

Ser Val Asp Arg Asn Arg Trp Gln Gln Gly Thr Thr Phe Thr Cys Gly
            180                 185                 190

Val Met His Glu Ala Leu His Asn His Tyr Thr Gln Lys Asn Val Ser
            195                 200                 205

Lys Asn Pro Gly Lys
            210

<210> SEQ ID NO 96
<211> LENGTH: 213
<212> TYPE: PRT
<213> ORGANISM: Artificial Sequence
<220> FEATURE:
<223> OTHER INFORMATION: Synthetic: Exemplary variant equine IgG2 Fc
      Heterodimer hole T(130)S L(132)A Y(173)T

<400> SEQUENCE: 96

Gly Pro Ser Val Phe Ile Phe Pro Pro Asn Pro Lys Asp Ala Leu Met
1               5                   10                  15

Ile Ser Arg Thr Pro Val Val Thr Cys Val Val Asn Leu Ser Asp
            20                  25                  30

Gln Tyr Pro Asp Val Gln Phe Ser Trp Tyr Val Asp Asn Thr Glu Val
                35                  40                  45

His Ser Ala Ile Thr Lys Gln Arg Glu Ala Gln Phe Asn Ser Thr Tyr
    50                  55                  60

Arg Val Val Ser Val Leu Pro Ile Gln His Gln Asp Trp Leu Ser Gly
65                  70                  75                  80

Lys Glu Phe Lys Cys Ser Val Thr Asn Val Gly Val Pro Gln Pro Ile
                85                  90                  95

Ser Arg Ala Ile Ser Arg Gly Lys Gly Pro Ser Arg Val Pro Gln Val
            100                 105                 110

Tyr Val Leu Pro Pro His Pro Asp Glu Leu Ala Lys Ser Lys Val Ser
            115                 120                 125

Val Ser Cys Ala Val Lys Asp Phe Tyr Pro Pro Asp Ile Ser Val Glu
    130                 135                 140

Trp Gln Ser Asn Arg Trp Pro Glu Leu Glu Gly Lys Tyr Ser Thr Thr
145                 150                 155                 160

Pro Ala Gln Leu Asp Gly Asp Gly Ser Tyr Phe Leu Thr Ser Lys Leu
                165                 170                 175

Ser Leu Glu Thr Ser Arg Trp Gln Gln Val Glu Ser Phe Thr Cys Ala
            180                 185                 190

Val Met His Glu Ala Leu His Asn His Phe Thr Lys Thr Asp Ile Ser
            195                 200                 205

Glu Ser Leu Gly Lys
            210

<210> SEQ ID NO 97
<211> LENGTH: 213
<212> TYPE: PRT

<213> ORGANISM: Artificial Sequence
<220> FEATURE:
<223> OTHER INFORMATION: Synthetic: Exemplary variant equine IgG3 Fc
      Heterodimer hole T(130)S L(132)A Y(173)T

<400> SEQUENCE: 97

Gly Pro Ser Val Phe Ile Phe Pro Pro Lys Pro Lys Asp Val Leu Met
1               5                   10                  15

Ile Thr Arg Met Pro Glu Val Thr Cys Leu Val Val Asp Val Ser His
            20                  25                  30

Asp Ser Ser Asp Val Leu Phe Thr Trp Tyr Val Asp Gly Thr Glu Val
        35                  40                  45

Lys Thr Ala Lys Thr Met Pro Asn Glu Glu Gln Asn Asn Ser Thr Tyr
50                  55                  60

Arg Val Val Ser Val Leu Arg Ile Gln His Gln Asp Trp Leu Asn Gly
65                  70                  75                  80

Lys Lys Phe Lys Cys Lys Val Asn Asn Gln Ala Leu Pro Ala Pro Val
            85                  90                  95

Glu Arg Thr Ile Ser Lys Ala Thr Gly Gln Thr Arg Val Pro Gln Val
            100                 105                 110

Tyr Val Leu Ala Pro His Pro Asp Glu Leu Ser Lys Asn Lys Val Ser
        115                 120                 125

Val Ser Cys Ala Val Lys Asp Phe Tyr Pro Pro Asp Ile Thr Val Glu
130                 135                 140

Trp Gln Ser Asn Glu His Pro Glu Pro Glu Gly Lys Tyr Arg Thr Thr
145                 150                 155                 160

Glu Ala Gln Lys Asp Ser Asp Gly Ser Tyr Phe Leu Thr Ser Lys Leu
            165                 170                 175

Thr Val Glu Lys Asp Arg Trp Gln Gln Gly Thr Thr Phe Thr Cys Val
            180                 185                 190

Val Met His Glu Ala Leu His Asn His Val Met Gln Lys Asn Ile Ser
        195                 200                 205

Lys Asn Pro Gly Lys
    210

<210> SEQ ID NO 98
<211> LENGTH: 213
<212> TYPE: PRT
<213> ORGANISM: Artificial Sequence
<220> FEATURE:
<223> OTHER INFORMATION: Synthetic: Exemplary variant equine IgG4 Fc
      Heterodimer hole T(130)S L(132)A Y(173)T

<400> SEQUENCE: 98

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Phe Asn Ser Thr Tyr
50                  55                  60

Arg Val Val Ser Val Leu Pro Ile Gln His Lys Asp Trp Leu Ser Gly
65                  70                  75                  80

Lys Glu Phe Lys Cys Lys Val Asn Asn Lys Ala Leu Pro Ala Pro Val
            85                  90                  95

Glu Arg Thr Ile Ser Ala Pro Thr Gly Gln Pro Arg Glu Pro Gln Val

```
              100                 105                 110
Tyr Val Leu Ala Pro His Arg Asp Glu Leu Ser Lys Asn Lys Val Ser
            115                 120                 125

Val Ser Cys Ala Val Lys Asp Phe Tyr Pro Asp Ile Asp Ile Glu
130                 135                 140

Trp Lys Ser Asn Gly Gln Pro Glu Pro Glu Thr Lys Tyr Ser Thr Thr
145                 150                 155                 160

Pro Ala Gln Leu Asp Ser Asp Gly Ser Tyr Phe Leu Thr Ser Lys Leu
            165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
            195                 200                 205

Lys Ser Pro Gly Lys
            210
```

<210> SEQ ID NO 99
<211> LENGTH: 213
<212> TYPE: PRT
<213> ORGANISM: Artificial Sequence
<220> FEATURE:
<223> OTHER INFORMATION: Synthetic: Exemplary variant equine IgG5 Fc
      Heterodimer hole T(130)S L(132)A Y(173)T

<400> SEQUENCE: 99

```
Gly Pro Ser Val Phe Ile Phe Pro Pro Lys Pro Lys Asp Val Leu Met
1               5                   10                  15

Ile Ser Arg Lys Pro Glu Val Thr Cys Val Val Val Asp Leu Gly His
            20                  25                  30

Asp Asp Pro Asp Val Gln Phe Thr Trp Phe Val Asp Gly Val Glu Thr
            35                  40                  45

His Thr Ala Thr Thr Glu Pro Lys Glu Glu Gln Phe Asn Ser Thr Tyr
        50                  55                  60

Arg Val Val Ser Val Leu Pro Ile Gln His Gln Asp Trp Leu Ser Gly
65                  70                  75                  80

Lys Glu Phe Lys Cys Ser Val Thr Ser Lys Ala Leu Pro Ala Pro Val
                85                  90                  95

Glu Arg Thr Ile Ser Lys Ala Lys Gly Gln Leu Arg Val Pro Gln Val
            100                 105                 110

Tyr Val Leu Ala Pro His Pro Asp Glu Leu Ala Lys Asn Thr Val Ser
            115                 120                 125

Val Ser Cys Ala Val Lys Asp Phe Tyr Pro Glu Ile Asp Val Glu
130                 135                 140

Trp Gln Ser Asn Glu His Pro Glu Pro Glu Gly Lys Tyr Ser Thr Thr
145                 150                 155                 160

Pro Ala Gln Leu Asn Ser Asp Gly Ser Tyr Phe Leu Thr Ser Lys Leu
            165                 170                 175

Ser Val Glu Thr Ser Arg Trp Lys Gln Gly Glu Ser Phe Thr Cys Gly
            180                 185                 190

Val Met His Glu Ala Val Glu Asn His Tyr Thr Gln Lys Asn Val Ser
            195                 200                 205

His Ser Pro Gly Lys
            210
```

<210> SEQ ID NO 100
<211> LENGTH: 213

-continued

```
<212> TYPE: PRT
<213> ORGANISM: Artificial Sequence
<220> FEATURE:
<223> OTHER INFORMATION: Synthetic: Exemplary variant equine IgG6 Fc
      Heterodimer hole T(130)S L(132)A Y(173)T

<400> SEQUENCE: 100
```

Arg Pro Ser Val Phe Ile Phe Pro Pro Asn Pro Lys Asp Thr Leu Met
1               5                   10                  15

Ile Ser Arg Thr Pro Glu Val Thr Cys Val Val Val Asp Val Ser Gln
            20                  25                  30

Glu Asn Pro Asp Val Lys Phe Asn Trp Tyr Val Asp Gly Val Glu Ala
        35                  40                  45

His Thr Ala Thr Thr Lys Ala Lys Glu Lys Gln Asp Asn Ser Thr Tyr
    50                  55                  60

Arg Val Val Ser Val Leu Pro Ile Gln His Gln Asp Trp Arg Arg Gly
65                  70                  75                  80

Lys Glu Phe Lys Cys Lys Val Asn Asn Arg Ala Leu Pro Ala Pro Val
                85                  90                  95

Glu Arg Thr Ile Thr Lys Ala Lys Gly Glu Leu Gln Asp Pro Lys Val
            100                 105                 110

Tyr Ile Leu Ala Pro His Arg Glu Glu Val Thr Lys Asn Thr Val Ser
        115                 120                 125

Val Ser Cys Ala Val Lys Asp Phe Tyr Pro Pro Asp Ile Asn Val Glu
    130                 135                 140

Trp Gln Ser Asn Glu Glu Pro Glu Pro Glu Val Lys Tyr Ser Thr Thr
145                 150                 155                 160

Pro Ala Gln Leu Asp Gly Asp Gly Ser Tyr Phe Leu Thr Ser Lys Leu
                165                 170                 175

Thr Val Glu Thr Asp Arg Trp Glu Gln Gly Glu Ser Phe Thr Cys Val
            180                 185                 190

Val Met His Glu Ala Ile Arg His Thr Tyr Arg Gln Lys Ser Ile Thr
        195                 200                 205

Asn Phe Pro Gly Lys
    210

```
<210> SEQ ID NO 101
<211> LENGTH: 213
<212> TYPE: PRT
<213> ORGANISM: Artificial Sequence
<220> FEATURE:
<223> OTHER INFORMATION: Synthetic: Exemplary variant equine IgG7 Fc
      Heterodimer hole T(130)S L(132)A Y(173)T

<400> SEQUENCE: 101
```

Gly Pro Ser Val Phe Ile Phe Pro Pro Lys Pro Lys Asp Val Leu Met
1               5                   10                  15

Ile Ser Arg Thr Pro Thr Val Thr Cys Val Val Val Asp Val Gly His
            20                  25                  30

Asp Phe Pro Asp Val Gln Phe Asn Trp Tyr Val Asp Gly Val Glu Thr
        35                  40                  45

His Thr Ala Thr Thr Glu Pro Lys Gln Glu Gln Asn Asn Ser Thr Tyr
    50                  55                  60

Arg Val Val Ser Ile Leu Ala Ile Gln His Lys Asp Trp Leu Ser Gly
65                  70                  75                  80

Lys Glu Phe Lys Cys Lys Val Asn Asn Gln Ala Leu Pro Ala Pro Val
                85                  90                  95

```
Gln Lys Thr Ile Ser Lys Pro Thr Gly Gln Pro Arg Glu Pro Gln Val
                100                 105                 110

Tyr Val Leu Ala Pro His Pro Asp Glu Leu Ser Lys Asn Lys Val Ser
            115                 120                 125

Val Ser Cys Ala Val Lys Asp Phe Tyr Pro Pro Asp Ile Asp Ile Glu
        130                 135                 140

Trp Lys Ser Asn Gly Gln Pro Glu Pro Glu Thr Lys Tyr Ser Thr Thr
145                 150                 155                 160

Pro Ala Gln Leu Asp Gly Asp Gly Ser Tyr Phe Leu Thr Ser Lys Leu
                165                 170                 175

Thr Val Glu Thr Asn Arg Trp Gln Gln Gly Thr Thr Phe Thr Cys Ala
            180                 185                 190

Val Met His Glu Ala Leu His Asn His Tyr Thr Glu Lys Ser Val Ser
        195                 200                 205

Lys Ser Pro Gly Lys
    210
```

<210> SEQ ID NO 102
<211> LENGTH: 450
<212> TYPE: PRT
<213> ORGANISM: Artificial Sequence
<220> FEATURE:
<223> OTHER INFORMATION: Synthetic: Canine IL4R ECD canine IgG-B Fc knob

<400> SEQUENCE: 102

```
Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
            20                  25                  30

Ser Ala Glu Leu Arg Leu Ser Tyr Gln Leu Asp Phe Met Gly Ser Glu
        35                  40                  45

Asn His Thr Cys Val Pro Glu Asn Arg Glu Asp Ser Val Cys Val Cys
    50                  55                  60

Ser Met Pro Ile Asp Asp Ala Val Glu Ala Asp Val Tyr Gln Leu Asp
65                  70                  75                  80

Leu Trp Ala Gly Gln Gln Leu Leu Trp Ser Gly Ser Phe Gln Pro Ser
                85                  90                  95

Lys His Val Lys Pro Arg Thr Pro Gly Asn Leu Thr Val His Pro Asn
                100                 105                 110

Ile Ser His Thr Trp Leu Leu Met Trp Thr Asn Pro Tyr Pro Thr Glu
            115                 120                 125

Asn His Leu His Ser Glu Leu Thr Tyr Met Val Asn Val Ser Asn Asp
        130                 135                 140

Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
                165                 170                 175

Ala Arg Val Arg Ala Trp Ala Gln Thr Tyr Asn Ser Thr Trp Ser Asp
            180                 185                 190

Trp Ser Pro Ser Thr Thr Trp Leu Asn Tyr Tyr Glu Pro Gly Gly Gly
        195                 200                 205

Ser Gly Gly Gly Gly Ser Gly Gly Gly Ser Gly Gly Gly Gly Ser
    210                 215                 220

Gly Gly Gly Gly Ser Gly Pro Ala Pro Glu Met Leu Gly Gly Pro Ser
225                 230                 235                 240
```

```
Val Phe Ile Phe Pro Pro Lys Pro Lys Asp Thr Leu Leu Ile Ala Arg
                245                 250                 255

Thr Pro Glu Val Thr Cys Val Val Asp Leu Asp Pro Glu Asp Pro
            260                 265                 270

Glu Val Gln Ile Ser Trp Phe Val Asp Gly Lys Gln Met Gln Thr Ala
        275                 280                 285

Lys Thr Gln Pro Arg Glu Gln Phe Asn Gly Thr Tyr Arg Val Val
    290                 295                 300

Ser Val Leu Pro Ile Gly His Gln Asp Trp Leu Lys Gly Lys Gln Phe
305                 310                 315                 320

Thr Cys Lys Val Asn Asn Lys Ala Leu Pro Ser Pro Ile Glu Arg Thr
                325                 330                 335

Ile Ser Lys Ala Arg Gly Gln Ala His Gln Pro Ser Val Tyr Val Leu
            340                 345                 350

Pro Pro Ser Arg Glu Glu Leu Ser Lys Asn Thr Val Ser Leu Trp Cys
        355                 360                 365

Leu Ile Lys Asp Phe Phe Pro Pro Asp Ile Asp Val Glu Trp Gln Ser
    370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Arg Gly Asp Thr Phe Ile Cys Ala Val Met His
            420                 425                 430

Glu Ala Leu His Asn His Tyr Thr Gln Glu Ser Leu Ser His Ser Pro
        435                 440                 445

Gly Lys
    450

<210> SEQ ID NO 103
<211> LENGTH: 560
<212> TYPE: PRT
<213> ORGANISM: Artificial Sequence
<220> FEATURE:
<223> OTHER INFORMATION: Synthetic: Canine IL13R ECD canine IgG-B Fc
      hole

<400> SEQUENCE: 103

Thr Glu Thr Gln Pro Pro Val Thr Asn Leu Ser Val Ser Val Glu Asn
1               5                   10                  15

Leu Cys Thr Val Ile Trp Thr Trp Asp Pro Pro Glu Gly Ala Ser Pro
            20                  25                  30

Asn Cys Thr Leu Arg Tyr Phe Ser His Phe Asp Asn Lys Gln Asp Lys
        35                  40                  45

Lys Ile Ala Pro Glu Thr His Arg Ser Lys Glu Val Pro Leu Asn Glu
    50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Glu Gly Asp
                85                  90                  95

Pro Glu Ser Ala Val Thr Glu Leu Gln Cys Val Trp His Asn Leu Ser
            100                 105                 110

Tyr Met Lys Cys Thr Trp Leu Pro Gly Arg Asn Thr Ser Pro Asp Thr
        115                 120                 125

Asn Tyr Thr Leu Tyr Tyr Trp His Ser Ser Leu Gly Lys Ile Leu Gln
    130                 135                 140
```

```
Cys Glu Asp Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
            165                 170                 175

Val Val Lys Asp Asn Ala Gly Lys Ile Arg Pro Ser Phe Asn Ile Val
            180                 185                 190

Pro Leu Thr Ser His Val Lys Pro Asp Pro His Ile Lys Arg Leu
            195                 200                 205

Phe Phe Gln Asn Gly Asn Leu Tyr Val Gln Trp Lys Asn Pro Gln Asn
210                 215                 220

Phe Tyr Ser Arg Cys Leu Ser Tyr Gln Val Glu Val Asn Asn Ser Gln
225                 230                 235                 240

Thr Glu Thr Asn Asp Ile Phe Tyr Val Glu Glu Ala Lys Cys Gln Asn
            245                 250                 255

Ser Glu Phe Glu Gly Asn Leu Glu Gly Thr Ile Cys Phe Met Val Pro
            260                 265                 270

Gly Val Leu Pro Asp Thr Leu Asn Thr Val Arg Ile Arg Val Arg Thr
            275                 280                 285

Asn Lys Leu Cys Tyr Glu Asp Asp Lys Leu Trp Ser Asn Trp Ser Gln
290                 295                 300

Ala Met Ser Ile Gly Glu Asn Thr Asp Pro Thr Gly Gly Ser Gly
305                 310                 315                 320

Gly Gly Gly Ser Gly Gly Gly Ser Gly Gly Gly Ser Gly Gly
            325                 330                 335

Gly Gly Ser Gly Pro Ala Pro Glu Met Leu Gly Gly Pro Ser Val Phe
            340                 345                 350

Ile Phe Pro Pro Lys Pro Lys Asp Thr Leu Leu Ile Ala Arg Thr Pro
            355                 360                 365

Glu Val Thr Cys Val Val Val Asp Leu Asp Pro Glu Asp Pro Glu Val
            370                 375                 380

Gln Ile Ser Trp Phe Val Asp Gly Lys Gln Met Gln Thr Ala Lys Thr
385                 390                 395                 400

Gln Pro Arg Glu Glu Gln Phe Asn Gly Thr Tyr Arg Val Val Ser Val
            405                 410                 415

Leu Pro Ile Gly His Gln Asp Trp Leu Lys Gly Lys Gln Phe Thr Cys
            420                 425                 430

Lys Val Asn Asn Lys Ala Leu Pro Ser Pro Ile Glu Arg Thr Ile Ser
            435                 440                 445

Lys Ala Arg Gly Gln Ala His Gln Pro Ser Val Tyr Val Leu Pro Pro
450                 455                 460

Ser Arg Glu Glu Leu Ser Lys Asn Thr Val Ser Leu Ser Cys Ala Ile
465                 470                 475                 480

Lys Asp Phe Phe Pro Pro Asp Ile Asp Val Glu Trp Gln Ser Asn Gly
            485                 490                 495

Gln Gln Glu Pro Glu Ser Lys Tyr Arg Thr Thr Pro Gln Leu Asp
            500                 505                 510

Glu Asp Gly Ser Tyr Phe Leu Thr Ser Lys Leu Ser Val Asp Lys Ser
            515                 520                 525

Arg Trp Gln Arg Gly Asp Thr Phe Ile Cys Ala Val Met His Glu Ala
            530                 535                 540

Leu His Asn His Tyr Thr Gln Glu Ser Leu Ser His Ser Pro Gly Lys
545                 550                 555                 560
```

```
<210> SEQ ID NO 104
<211> LENGTH: 450
<212> TYPE: PRT
<213> ORGANISM: Artificial Sequence
<220> FEATURE:
<223> OTHER INFORMATION: Synthetic: Canine IL4R ECD canine IgG-B Fc hole

<400> SEQUENCE: 104

Ser Gly Ser Val Lys Val Leu His Glu Pro Ser Cys Phe Ser Asp Tyr
1               5                   10                  15

Ile Ser Thr Ser Val Cys Gln Trp Lys Met Asp His Pro Thr Asn Cys
            20                  25                  30

Ser Ala Glu Leu Arg Leu Ser Tyr Gln Leu Asp Phe Met Gly Ser Glu
        35                  40                  45

Asn His Thr Cys Val Pro Glu Asn Arg Glu Asp Ser Val Cys Val Cys
    50                  55                  60

Ser Met Pro Ile Asp Asp Ala Val Glu Ala Asp Val Tyr Gln Leu Asp
65              70                  75                  80

Leu Trp Ala Gly Gln Gln Leu Leu Trp Ser Gly Ser Phe Gln Pro Ser
            85                  90                  95

Lys His Val Lys Pro Arg Thr Pro Gly Asn Leu Thr Val His Pro Asn
        100                 105                 110

Ile Ser His Thr Trp Leu Leu Met Trp Thr Asn Pro Tyr Pro Thr Glu
    115                 120                 125

Asn His Leu His Ser Glu Leu Thr Tyr Met Val Asn Val Ser Asn Asp
130                 135                 140

Asn Asp Pro Glu Asp Phe Lys Val Tyr Asn Val Thr Tyr Met Gly Pro
145                 150                 155                 160

Thr Leu Arg Leu Ala Ala Ser Thr Leu Lys Ser Gly Ala Ser Tyr Ser
            165                 170                 175

Ala Arg Val Arg Ala Trp Ala Gln Thr Tyr Asn Ser Thr Trp Ser Asp
        180                 185                 190

Trp Ser Pro Ser Thr Thr Trp Leu Asn Tyr Tyr Glu Pro Gly Gly Gly
    195                 200                 205

Ser Gly Gly Gly Gly Ser Gly Gly Gly Ser Gly Gly Gly Gly Gly Ser
    210                 215                 220

Gly Gly Gly Gly Ser Gly Pro Ala Pro Glu Met Leu Gly Gly Pro Ser
225                 230                 235                 240

Val Phe Ile Phe Pro Pro Lys Pro Lys Asp Thr Leu Leu Ile Ala Arg
                245                 250                 255

Thr Pro Glu Val Thr Cys Val Val Val Asp Leu Asp Pro Glu Asp Pro
            260                 265                 270

Glu Val Gln Ile Ser Trp Phe Val Asp Gly Lys Gln Met Gln Thr Ala
        275                 280                 285

Lys Thr Gln Pro Arg Glu Glu Gln Phe Asn Gly Thr Tyr Arg Val Val
    290                 295                 300

Ser Val Leu Pro Ile Gly His Gln Asp Trp Leu Lys Gly Lys Gln Phe
305                 310                 315                 320

Thr Cys Lys Val Asn Asn Lys Ala Leu Pro Ser Pro Ile Glu Arg Thr
                325                 330                 335

Ile Ser Lys Ala Arg Gly Gln Ala His Gln Pro Ser Val Tyr Val Leu
            340                 345                 350

Pro Pro Ser Arg Glu Glu Leu Ser Lys Asn Thr Val Ser Leu Ser Cys
        355                 360                 365
```

```
Ala Ile Lys Asp Phe Phe Pro Pro Asp Ile Asp Val Glu Trp Gln Ser
    370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Thr Ser Lys Leu Ser Val Asp
                405                 410                 415

Lys Ser Arg Trp Gln Arg Gly Asp Thr Phe Ile Cys Ala Val Met His
                420                 425                 430

Glu Ala Leu His Asn His Tyr Thr Gln Glu Ser Leu Ser His Ser Pro
            435                 440                 445

Gly Lys
    450

<210> SEQ ID NO 105
<211> LENGTH: 560
<212> TYPE: PRT
<213> ORGANISM: Artificial Sequence
<220> FEATURE:
<223> OTHER INFORMATION: Synthetic: Canine IL13R ECD canine IgG-B Fc
      knob

<400> SEQUENCE: 105

Thr Glu Thr Gln Pro Pro Val Thr Asn Leu Ser Val Ser Val Glu Asn
1               5                   10                  15

Leu Cys Thr Val Ile Trp Thr Trp Asp Pro Glu Gly Ala Ser Pro
                20                  25                  30

Asn Cys Thr Leu Arg Tyr Phe Ser His Phe Asp Asn Lys Gln Asp Lys
            35                  40                  45

Lys Ile Ala Pro Glu Thr His Arg Ser Lys Glu Val Pro Leu Asn Glu
50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Glu Gly Asp
                85                  90                  95

Pro Glu Ser Ala Val Thr Glu Leu Gln Cys Val Trp His Asn Leu Ser
                100                 105                 110

Tyr Met Lys Cys Thr Trp Leu Pro Gly Arg Asn Thr Ser Pro Asp Thr
            115                 120                 125

Asn Tyr Thr Leu Tyr Tyr Trp His Ser Ser Leu Gly Lys Ile Leu Gln
            130                 135                 140

Cys Glu Asp Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
                165                 170                 175

Val Val Lys Asp Asn Ala Gly Lys Ile Arg Pro Ser Phe Asn Ile Val
                180                 185                 190

Pro Leu Thr Ser His Val Lys Pro Asp Pro His Ile Lys Arg Leu
            195                 200                 205

Phe Phe Gln Asn Gly Asn Leu Tyr Val Gln Trp Lys Asn Pro Gln Asn
    210                 215                 220

Phe Tyr Ser Arg Cys Leu Ser Tyr Gln Val Glu Val Asn Asn Ser Gln
225                 230                 235                 240

Thr Glu Thr Asn Asp Ile Phe Tyr Val Glu Glu Ala Lys Cys Gln Asn
                245                 250                 255

Ser Glu Phe Glu Gly Asn Leu Glu Gly Thr Ile Cys Phe Met Val Pro
                260                 265                 270
```

-continued

```
Gly Val Leu Pro Asp Thr Leu Asn Thr Val Arg Ile Arg Val Arg Thr
            275                 280                 285

Asn Lys Leu Cys Tyr Glu Asp Lys Leu Trp Ser Asn Trp Ser Gln
    290                 295                 300

Ala Met Ser Ile Gly Glu Asn Thr Asp Pro Thr Gly Gly Ser Gly
305                 310                 315                 320

Gly Gly Gly Ser Gly Gly Gly Ser Gly Gly Gly Ser Gly Gly
            325                 330                 335

Gly Gly Ser Gly Pro Ala Pro Glu Met Leu Gly Gly Pro Ser Val Phe
            340                 345                 350

Ile Phe Pro Pro Lys Pro Lys Asp Thr Leu Leu Ile Ala Arg Thr Pro
            355                 360                 365

Glu Val Thr Cys Val Val Val Asp Leu Asp Pro Glu Asp Pro Glu Val
370                 375                 380

Gln Ile Ser Trp Phe Val Asp Gly Lys Gln Met Gln Thr Ala Lys Thr
385                 390                 395                 400

Gln Pro Arg Glu Glu Gln Phe Asn Gly Thr Tyr Arg Val Val Ser Val
            405                 410                 415

Leu Pro Ile Gly His Gln Asp Trp Leu Lys Gly Lys Gln Phe Thr Cys
            420                 425                 430

Lys Val Asn Asn Lys Ala Leu Pro Ser Pro Ile Glu Arg Thr Ile Ser
            435                 440                 445

Lys Ala Arg Gly Gln Ala His Gln Pro Ser Val Tyr Val Leu Pro Pro
450                 455                 460

Ser Arg Glu Glu Leu Ser Lys Asn Thr Val Ser Leu Trp Cys Leu Ile
465                 470                 475                 480

Lys Asp Phe Phe Pro Asp Ile Asp Val Glu Trp Gln Ser Asn Gly
            485                 490                 495

Gln Gln Glu Pro Glu Ser Lys Tyr Arg Thr Thr Pro Gln Leu Asp
            500                 505                 510

Glu Asp Gly Ser Tyr Phe Leu Tyr Ser Lys Leu Ser Val Asp Lys Ser
            515                 520                 525

Arg Trp Gln Arg Gly Asp Thr Phe Ile Cys Ala Val Met His Glu Ala
            530                 535                 540

Leu His Asn His Tyr Thr Gln Glu Ser Leu Ser His Ser Pro Gly Lys
545                 550                 555                 560

<210> SEQ ID NO 106
<211> LENGTH: 532
<212> TYPE: PRT
<213> ORGANISM: Artificial Sequence
<220> FEATURE:
<223> OTHER INFORMATION: Synthetic: Feline IL4R ECD feline IgG-2 Fc knob

<400> SEQUENCE: 106

Ser Gly Ser Val Lys Val Leu Arg Ala Pro Thr Cys Phe Ser Asp Tyr
1               5                   10                  15

Phe Ser Thr Ser Val Cys Gln Trp Asn Met Asp Ala Pro Thr Asn Cys
            20                  25                  30

Ser Ala Glu Leu Arg Leu Ser Tyr Gln Leu Asn Phe Met Gly Ser Glu
        35                  40                  45

Asn Arg Thr Cys Val Pro Glu Asn Gly Glu Gly Ala Ala Cys Ala Cys
    50                  55                  60

Ser Met Leu Met Asp Asp Phe Val Glu Ala Asp Val Tyr Gln Leu His
65                  70                  75                  80
```

```
Leu Trp Ala Gly Thr Gln Leu Leu Trp Ser Gly Ser Phe Lys Pro Ser
                 85                  90                  95

Ser His Val Lys Pro Arg Ala Pro Gly Asn Leu Thr Val His Pro Asn
                100                 105                 110

Val Ser His Thr Trp Leu Leu Arg Trp Ser Asn Pro Tyr Pro Pro Glu
                115                 120                 125

Asn His Leu His Ala Glu Leu Thr Tyr Met Val Asn Ile Ser Ser Glu
                130                 135                 140

Asp Asp Pro Thr Asp Val Ser Val Cys Ala Ser Gly Phe Leu Cys His
145                 150                 155                 160

Leu Leu Gly Leu Arg Arg Val Glu Thr Gly Ala Pro Gly Ala Arg Leu
                165                 170                 175

Pro Pro Trp Leu Cys Ala Pro Arg Pro Arg Arg Val Pro Gly Ser Gln
                180                 185                 190

Cys Ala Val Ile Ser Cys Cys Arg Trp Val Leu Ile Ala Leu Thr Ser
                195                 200                 205

Arg Gly Gly Arg Trp Arg Leu Thr Pro Gly Leu Arg Ser Gln Thr Arg
210                 215                 220

Tyr Val Ser Val Ala Glu Gly Leu Phe Gly Ala Thr Pro Arg Val Leu
225                 230                 235                 240

Cys Pro Gly Thr Gln Ala Gly Leu Ala Ser Ala Ala Arg Glu Gln Met
                245                 250                 255

Ser Pro Asp Pro Ser Ala Phe His Ser Ile Asp Tyr Glu Pro Gly Gly
                260                 265                 270

Gly Ser Gly Gly Gly Ser Gly Gly Gly Ser Gly Gly Gly Gly
                275                 280                 285

Ser Gly Gly Gly Gly Ser Gly Pro Lys Thr Ala Ser Thr Ile Glu Ser
                290                 295                 300

Lys Thr Gly Glu Gly Pro Lys Cys Pro Val Pro Glu Ile Pro Gly Ala
305                 310                 315                 320

Pro Ser Val Phe Ile Phe Pro Pro Lys Pro Lys Asp Thr Leu Ser Ile
                325                 330                 335

Ser Arg Thr Pro Glu Val Thr Cys Leu Val Val Asp Leu Gly Pro Asp
                340                 345                 350

Asp Ser Asn Val Gln Ile Thr Trp Phe Val Asp Asn Thr Glu Met His
                355                 360                 365

Thr Ala Lys Thr Arg Pro Arg Glu Glu Gln Phe Asn Ser Thr Tyr Arg
                370                 375                 380

Val Val Ser Val Leu Pro Ile Leu His Gln Asp Trp Leu Lys Gly Lys
385                 390                 395                 400

Glu Phe Lys Cys Lys Val Asn Ser Lys Ser Leu Pro Ser Ala Met Glu
                405                 410                 415

Arg Thr Ile Ser Lys Ala Lys Gly Gln Pro His Glu Pro Gln Val Tyr
                420                 425                 430

Val Leu Pro Pro Thr Gln Glu Glu Leu Ser Glu Asn Lys Val Ser Val
                435                 440                 445

Trp Cys Leu Ile Lys Gly Phe His Pro Pro Asp Ile Ala Val Glu Trp
                450                 455                 460

Glu Ile Thr Gly Gln Pro Glu Pro Glu Asn Asn Tyr Gln Thr Thr Pro
465                 470                 475                 480

Pro Gln Leu Asp Ser Asp Gly Thr Tyr Phe Leu Tyr Ser Arg Leu Ser
                485                 490                 495
```

-continued

```
Val Asp Arg Ser His Trp Gln Arg Gly Asn Thr Tyr Thr Cys Ser Val
            500                 505                 510

Ser His Glu Ala Leu His Ser His His Thr Gln Lys Ser Leu Thr Gln
        515                 520                 525

Ser Pro Gly Lys
    530

<210> SEQ ID NO 107
<211> LENGTH: 577
<212> TYPE: PRT
<213> ORGANISM: Artificial Sequence
<220> FEATURE:
<223> OTHER INFORMATION: Synthetic: Feline IL13R ECD feline IgG-2 Fc
      hole

<400> SEQUENCE: 107

Ser Gln Thr Gln Pro Pro Val Thr Asn Leu Ser Val Ser Val Glu Asn
1               5                   10                  15

Leu Cys Thr Val Ile Trp Thr Trp Asp Pro Glu Gly Ala Ser Pro
            20                  25                  30

Asn Cys Thr Leu Arg Tyr Phe Ser His Phe Asp Asn Lys Gln Asp Lys
        35                  40                  45

Lys Ile Ala Pro Glu Thr His Arg Ser Lys Glu Val Pro Leu Asn Glu
    50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Glu Gly Asp
            85                  90                  95

Pro Glu Ser Ala Val Thr Glu Leu Gln Cys Val Trp His Asn Leu Ser
            100                 105                 110

Tyr Met Lys Cys Thr Trp Leu Pro Gly Arg Asn Thr Ser Pro Asp Thr
        115                 120                 125

Asn Tyr Thr Leu Tyr Tyr Trp His Ser Ser Leu Gly Lys Ile Leu Gln
    130                 135                 140

Cys Glu Asn Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
            165                 170                 175

Val Val Lys Asp Asn Ala Gly Lys Ile Arg Pro Ser Phe Asn Ile Val
        180                 185                 190

Pro Leu Thr Ser His Val Lys Pro Asp Pro Pro His Ile Lys Arg Leu
    195                 200                 205

Phe Phe Gln Asn Gly Asn Leu Tyr Val Gln Trp Lys Asn Pro Gln Asn
    210                 215                 220

Phe Tyr Ser Arg Cys Leu Ser Tyr Gln Val Val Asn Asn Ser Gln
225                 230                 235                 240

Thr Glu Thr His Asp Ile Phe Tyr Val Glu Glu Ala Lys Cys Gln Asn
            245                 250                 255

Ser Glu Phe Glu Gly Asn Leu Glu Gly Thr Ile Cys Phe Met Val Pro
        260                 265                 270

Gly Ile Leu Pro Asp Thr Leu Asn Thr Val Arg Ile Arg Val Arg Thr
    275                 280                 285

Asn Lys Leu Cys Tyr Glu Asp Asp Arg Leu Trp Ser Asn Trp Ser Gln
    290                 295                 300

Ala Met Ser Ile Gly Glu Asn Thr Asp Pro Thr Gly Gly Gly Ser Gly
305                 310                 315                 320
```

```
Gly Gly Gly Ser Gly Gly Gly Ser Gly Gly Gly Ser Gly Gly
                325                 330                 335

Gly Gly Ser Gly Pro Lys Thr Ala Ser Thr Ile Glu Ser Lys Thr Gly
        340                 345                 350

Glu Gly Pro Lys Cys Pro Val Pro Glu Ile Pro Gly Ala Pro Ser Val
    355                 360                 365

Phe Ile Phe Pro Pro Lys Pro Lys Asp Thr Leu Ser Ile Ser Arg Thr
370                 375                 380

Pro Glu Val Thr Cys Leu Val Val Asp Leu Gly Pro Asp Asp Ser Asn
385                 390                 395                 400

Val Gln Ile Thr Trp Phe Val Asp Asn Thr Glu Met His Thr Ala Lys
                405                 410                 415

Thr Arg Pro Arg Glu Glu Gln Phe Asn Ser Thr Tyr Arg Val Val Ser
            420                 425                 430

Val Leu Pro Ile Leu His Gln Asp Trp Leu Lys Gly Lys Glu Phe Lys
        435                 440                 445

Cys Lys Val Asn Ser Lys Ser Leu Pro Ser Ala Met Glu Arg Thr Ile
    450                 455                 460

Ser Lys Ala Lys Gly Gln Pro His Glu Pro Gln Val Tyr Val Leu Pro
465                 470                 475                 480

Pro Thr Gln Glu Glu Leu Ser Glu Asn Lys Val Ser Val Ser Cys Ala
                485                 490                 495

Ile Lys Gly Phe His Pro Pro Asp Ile Ala Val Glu Trp Glu Ile Thr
            500                 505                 510

Gly Gln Pro Glu Pro Glu Asn Asn Tyr Gln Thr Thr Pro Pro Gln Leu
        515                 520                 525

Asp Ser Asp Gly Thr Tyr Phe Leu Thr Ser Arg Leu Ser Val Asp Arg
    530                 535                 540

Ser His Trp Gln Arg Gly Asn Thr Tyr Thr Cys Ser Val Ser His Glu
545                 550                 555                 560

Ala Leu His Ser His His Thr Gln Lys Ser Leu Thr Gln Ser Pro Gly
                565                 570                 575

Lys

<210> SEQ ID NO 108
<211> LENGTH: 532
<212> TYPE: PRT
<213> ORGANISM: Artificial Sequence
<220> FEATURE:
<223> OTHER INFORMATION: Synthetic: Feline IL4R ECD feline IgG-2 Fc hole

<400> SEQUENCE: 108

Ser Gly Ser Val Lys Val Leu Arg Ala Pro Thr Cys Phe Ser Asp Tyr
1               5                   10                  15

Phe Ser Thr Ser Val Cys Gln Trp Asn Met Asp Ala Pro Thr Asn Cys
            20                  25                  30

Ser Ala Glu Leu Arg Leu Ser Tyr Gln Leu Asn Phe Met Gly Ser Glu
        35                  40                  45

Asn Arg Thr Cys Val Pro Glu Asn Gly Glu Gly Ala Ala Cys Ala Cys
    50                  55                  60

Ser Met Leu Met Asp Asp Phe Val Glu Ala Asp Val Tyr Gln Leu His
65                  70                  75                  80

Leu Trp Ala Gly Thr Gln Leu Leu Trp Ser Gly Ser Phe Lys Pro Ser
                85                  90                  95
```

```
Ser His Val Lys Pro Arg Ala Pro Gly Asn Leu Thr Val His Pro Asn
            100                 105                 110

Val Ser His Thr Trp Leu Leu Arg Trp Ser Asn Pro Tyr Pro Pro Glu
        115                 120                 125

Asn His Leu His Ala Glu Leu Thr Tyr Met Val Asn Ile Ser Ser Glu
    130                 135                 140

Asp Asp Pro Thr Asp Val Ser Val Cys Ala Ser Gly Phe Leu Cys His
145                 150                 155                 160

Leu Leu Gly Leu Arg Arg Val Glu Thr Gly Ala Pro Gly Ala Arg Leu
                165                 170                 175

Pro Pro Trp Leu Cys Ala Pro Arg Pro Arg Val Pro Gly Ser Gln
                180                 185                 190

Cys Ala Val Ile Ser Cys Cys Arg Trp Val Leu Ile Ala Leu Thr Ser
        195                 200                 205

Arg Gly Gly Arg Trp Arg Leu Thr Pro Gly Leu Arg Ser Gln Thr Arg
    210                 215                 220

Tyr Val Ser Val Ala Glu Gly Leu Phe Gly Ala Thr Pro Arg Val Leu
225                 230                 235                 240

Cys Pro Gly Thr Gln Ala Gly Leu Ala Ser Ala Ala Arg Glu Gln Met
                245                 250                 255

Ser Pro Asp Pro Ser Ala Phe His Ser Ile Asp Tyr Glu Pro Gly Gly
            260                 265                 270

Gly Ser Gly Gly Gly Gly Ser Gly Gly Gly Ser Gly Gly Gly
        275                 280                 285

Ser Gly Gly Gly Gly Ser Gly Pro Lys Thr Ala Ser Thr Ile Glu Ser
290                 295                 300

Lys Thr Gly Glu Gly Pro Lys Cys Pro Val Pro Glu Ile Pro Gly Ala
305                 310                 315                 320

Pro Ser Val Phe Ile Phe Pro Pro Lys Pro Lys Asp Thr Leu Ser Ile
                325                 330                 335

Ser Arg Thr Pro Glu Val Thr Cys Leu Val Val Asp Leu Gly Pro Asp
            340                 345                 350

Asp Ser Asn Val Gln Ile Thr Trp Phe Val Asp Asn Thr Glu Met His
        355                 360                 365

Thr Ala Lys Thr Arg Pro Arg Glu Glu Gln Phe Asn Ser Thr Tyr Arg
    370                 375                 380

Val Val Ser Val Leu Pro Ile Leu His Gln Asp Trp Leu Lys Gly Lys
385                 390                 395                 400

Glu Phe Lys Cys Lys Val Asn Ser Lys Ser Leu Pro Ser Ala Met Glu
                405                 410                 415

Arg Thr Ile Ser Lys Ala Lys Gly Gln Pro His Glu Pro Gln Val Tyr
            420                 425                 430

Val Leu Pro Pro Thr Gln Glu Glu Leu Ser Glu Asn Lys Val Ser Val
        435                 440                 445

Ser Cys Ala Ile Lys Gly Phe His Pro Pro Asp Ile Ala Val Glu Trp
    450                 455                 460

Glu Ile Thr Gly Gln Pro Glu Pro Glu Asn Asn Tyr Gln Thr Thr Pro
465                 470                 475                 480

Pro Gln Leu Asp Ser Asp Gly Thr Tyr Phe Leu Thr Ser Arg Leu Ser
                485                 490                 495

Val Asp Arg Ser His Trp Gln Arg Gly Asn Thr Tyr Thr Cys Ser Val
            500                 505                 510

Ser His Glu Ala Leu His Ser His His Thr Gln Lys Ser Leu Thr Gln
```

```
                515                 520                 525

Ser Pro Gly Lys
        530

<210> SEQ ID NO 109
<211> LENGTH: 577
<212> TYPE: PRT
<213> ORGANISM: Artificial Sequence
<220> FEATURE:
<223> OTHER INFORMATION: Synthetic: Feline IL13R ECD feline IgG-2 Fc
      knob

<400> SEQUENCE: 109

Ser Gln Thr Gln Pro Val Thr Asn Leu Ser Val Ser Val Glu Asn
1               5                   10                  15

Leu Cys Thr Val Ile Trp Thr Trp Asp Pro Glu Gly Ala Ser Pro
                20                  25                  30

Asn Cys Thr Leu Arg Tyr Phe Ser His Phe Asp Asn Lys Gln Asp Lys
            35                  40                  45

Lys Ile Ala Pro Glu Thr His Arg Ser Lys Glu Val Pro Leu Asn Glu
        50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Thr Pro Pro Glu Gly Asp
                85                  90                  95

Pro Glu Ser Ala Val Thr Glu Leu Gln Cys Val Trp His Asn Leu Ser
            100                 105                 110

Tyr Met Lys Cys Thr Trp Leu Pro Gly Arg Asn Thr Ser Pro Asp Thr
        115                 120                 125

Asn Tyr Thr Leu Tyr Tyr Trp His Ser Ser Leu Gly Lys Ile Leu Gln
                130                 135                 140

Cys Glu Asn Ile Tyr Arg Glu Gly Gln His Ile Gly Cys Ser Phe Ala
145                 150                 155                 160

Leu Thr Asn Leu Lys Asp Ser Ser Phe Glu Gln His Ser Val Gln Ile
                165                 170                 175

Val Val Lys Asp Asn Ala Gly Lys Ile Arg Pro Ser Phe Asn Ile Val
            180                 185                 190

Pro Leu Thr Ser His Val Lys Pro Asp Pro Pro His Ile Lys Arg Leu
        195                 200                 205

Phe Phe Gln Asn Gly Asn Leu Tyr Val Gln Trp Lys Asn Pro Gln Asn
                210                 215                 220

Phe Tyr Ser Arg Cys Leu Ser Tyr Gln Val Glu Val Asn Asn Ser Gln
225                 230                 235                 240

Thr Glu Thr His Asp Ile Phe Tyr Val Glu Glu Ala Lys Cys Gln Asn
                245                 250                 255

Ser Glu Phe Glu Gly Asn Leu Glu Gly Thr Ile Cys Phe Met Val Pro
            260                 265                 270

Gly Ile Leu Pro Asp Thr Leu Asn Thr Val Arg Ile Arg Val Arg Thr
        275                 280                 285

Asn Lys Leu Cys Tyr Glu Asp Asp Arg Leu Trp Ser Asn Trp Ser Gln
        290                 295                 300

Ala Met Ser Ile Gly Glu Asn Thr Asp Pro Thr Gly Gly Ser Gly
305                 310                 315                 320

Gly Gly Gly Ser Gly Gly Gly Ser Gly Gly Gly Ser Gly Gly
                325                 330                 335
```

```
Gly Gly Ser Gly Pro Lys Thr Ala Ser Thr Ile Glu Ser Lys Thr Gly
                340                 345                 350

Glu Gly Pro Lys Cys Pro Val Pro Glu Ile Pro Gly Ala Pro Ser Val
            355                 360                 365

Phe Ile Phe Pro Pro Lys Pro Lys Asp Thr Leu Ser Ile Ser Arg Thr
        370                 375                 380

Pro Glu Val Thr Cys Leu Val Val Asp Leu Gly Pro Asp Asp Ser Asn
385                 390                 395                 400

Val Gln Ile Thr Trp Phe Val Asp Asn Thr Glu Met His Thr Ala Lys
                405                 410                 415

Thr Arg Pro Arg Glu Glu Gln Phe Asn Ser Thr Tyr Arg Val Val Ser
            420                 425                 430

Val Leu Pro Ile Leu His Gln Asp Trp Leu Lys Gly Lys Glu Phe Lys
        435                 440                 445

Cys Lys Val Asn Ser Lys Ser Leu Pro Ser Ala Met Glu Arg Thr Ile
450                 455                 460

Ser Lys Ala Lys Gly Gln Pro His Glu Pro Gln Val Tyr Val Leu Pro
465                 470                 475                 480

Pro Thr Gln Glu Glu Leu Ser Glu Asn Lys Val Ser Val Trp Cys Leu
                485                 490                 495

Ile Lys Gly Phe His Pro Pro Asp Ile Ala Val Glu Trp Glu Ile Thr
            500                 505                 510

Gly Gln Pro Glu Pro Glu Asn Asn Tyr Gln Thr Thr Pro Pro Gln Leu
        515                 520                 525

Asp Ser Asp Gly Thr Tyr Phe Leu Tyr Ser Arg Leu Ser Val Asp Arg
530                 535                 540

Ser His Trp Gln Arg Gly Asn Thr Tyr Thr Cys Ser Val Ser His Glu
545                 550                 555                 560

Ala Leu His Ser His His Thr Gln Lys Ser Leu Thr Gln Ser Pro Gly
                565                 570                 575

Lys

<210> SEQ ID NO 110
<211> LENGTH: 443
<212> TYPE: PRT
<213> ORGANISM: Artificial Sequence
<220> FEATURE:
<223> OTHER INFORMATION: Synthetic: Equine IL4R ECD equine IgG-2 Fc knob

<400> SEQUENCE: 110

Ser Gly Ser Val Lys Val Leu His Leu Thr Ala Cys Phe Ser Asp Tyr
1               5                   10                  15

Ile Ser Ala Ser Thr Cys Glu Trp Lys Met Asp Arg Pro Thr Asn Cys
            20

```
            115                 120                 125
His Leu Trp Ser Glu Leu Thr Tyr Leu Val Asn Ile Ser Lys Gl

-continued

```
Asn Cys Ser Leu Trp Tyr Phe Ser His Phe Gly Asn Lys Gln Asp Lys
         35                  40                  45

Lys Ile Ala Pro Glu Thr His Arg Ser Lys Glu Val Pro Leu Asn Glu
 50                  55                  60

Arg Ile Cys Leu Gln Val Gly Ser Gln Cys Ser Thr Asn Glu Ser Asp
 65                  70                  75                  80

Asn Pro Ser Ile Leu Val Glu Lys Cys Ile Ser Pro Glu Gly Asp
                 85                  90                  95

Pro Glu Ser Ala Val Thr Glu Leu Gln Cys Val Trp His Asn Leu Ser
                100                 105                 110

Tyr Met Lys Cys Thr Trp Leu Pro Gly Lys Asn Ala Ser Pro Asp Thr
            115                 120                 125

Asn Tyr Thr Leu Tyr Tyr Trp His Ser Ser Leu Gly Lys Ile Leu Gln
    130                 135                 140

Cys Glu Asp Ile Tyr Arg Glu Gly Gln His Ile Gly Cys Ser Phe Ala
145                 150                 155                 160

Leu Thr Glu Val Lys Asp Ser Ile Phe Glu Gln His Ser Val Gln Ile
                165                 170                 175

Met Val Lys Asp Asn Ala Gly Lys Ile Arg Pro Phe Phe Asn Ile Val
            180                 185                 190

Pro Leu Thr Ser His Val Lys Pro Asp Pro His Ile Lys Lys Leu
    195                 200                 205

Phe Phe Gln Asn Gly Asp Leu Tyr Val Gln Trp Lys Asn Pro Gln Asn
    210                 215                 220

Phe Tyr Ser Arg Cys Leu Ser Tyr Gln Val Glu Val Asn Asn Ser Gln
225                 230                 235                 240

Thr Glu Thr Arg Asp Ile Phe Ser Val Glu Glu Ala Lys Cys Gln Asn
                245                 250                 255

Pro Glu Phe Glu Gly Asp Leu Glu Gly Thr Ile Cys Phe Met Val Pro
                260                 265                 270

Gly Val Leu Pro Asp Thr Val Asn Thr Val Arg Ile Arg Val Lys Thr
                275                 280                 285

Asn Lys Leu Cys Tyr Glu Asp Asp Lys Leu Trp Ser Asn Trp Ser Gln
    290                 295                 300

Ala Met Ser Ile Gly Lys Lys Ala Asp Pro Thr Gly Gly Ser Gly
305                 310                 315                 320

Gly Gly Gly Ser Gly Gly Gly Ser Gly Gly Gly Ser Gly Gly
                325                 330                 335

Gly Gly Ser Gly Gly Pro Ser Val Phe Ile Phe Pro Asn Pro Lys
            340                 345                 350

Asp Ala Leu Met Ile Ser Arg Thr Pro Val Val Thr Cys Val Val Val
            355                 360                 365

Asn Leu Ser Asp Gln Tyr Pro Asp Val Gln Phe Ser Trp Tyr Val Asp
    370                 375                 380

Asn Thr Glu Val His Ser Ala Ile Thr Lys Gln Arg Glu Ala Gln Phe
385                 390                 395                 400

Asn Ser Thr Tyr Arg Val Val Ser Val Leu Pro Ile Gln His Gln Asp
                405                 410                 415

Trp Leu Ser Gly Lys Glu Phe Lys Cys Ser Val Thr Asn Val Gly Val
            420                 425                 430

Pro Gln Pro Ile Ser Arg Ala Ile Ser Arg Gly Lys Gly Pro Ser Arg
    435                 440                 445

Val Pro Gln Val Tyr Val Leu Pro Pro His Pro Asp Glu Leu Ala Lys
```

```
                    450                 455                 460
Ser Lys Val Ser Val Ser Cys Ala Val Lys Asp Phe Tyr Pro Pro Asp
465                 470                 475                 480

Ile Ser Val Glu Trp Gln Ser Asn Arg Trp Pro Glu Leu Glu Gly Lys
                    485                 490                 495

Tyr Ser Thr Thr Pro Ala Gln Leu Asp Gly Asp Gly Ser Tyr Phe Leu
                    500                 505                 510

Thr Ser Lys Leu Ser Leu Glu Thr Ser Arg Trp Gln Gln Val Glu Ser
                515                 520                 525

Phe Thr Cys Ala Val Met His Glu Ala Leu His Asn His Phe Thr Lys
                530                 535                 540

Thr Asp Ile Ser Glu Ser Leu Gly Lys
545                 550

<210> SEQ ID NO 112
<211> LENGTH: 443
<212> TYPE: PRT
<213> ORGANISM: Artificial Sequence
<220> FEATURE:
<223> OTHER INFORMATION: Synthetic: Equine IL4R ECD equine IgG-2 Fc hole

<400> SEQUENCE: 112

Ser Gly Ser Val Lys Val Leu His Leu Thr Ala Cys Phe Ser Asp Tyr
1               5                   10                  15

Ile Ser Ala Ser Thr Cys Glu Trp Lys Met Asp Arg Pro Thr Asn Cys
                20                  25                  30

Ser Ala Gln Leu Arg Leu Ser Tyr Gln Leu Asn Asp Glu Phe Ser Asp
            35                  40                  45

Asn Leu Thr Cys Ile Pro Glu Asn Arg Glu Asp Glu Val Cys Val Cys
50              55                  60

Arg Met Leu Met Asp Asn Ile Val Ser Glu Asp Val Tyr Glu Leu Asp
65                  70                  75                  80

Leu Trp Ala Gly Asn Gln Leu Leu Trp Asn Ser Ser Phe Lys Pro Ser
                85                  90                  95

Arg His Val Lys Pro Arg Ala Pro Gln Asn Leu Thr Val His Ala Ile
                100                 105                 110

Ser His Thr Trp Leu Leu Thr Trp Ser Asn Pro Tyr Pro Leu Lys Asn
            115                 120                 125

His Leu Trp Ser Glu Leu Thr Tyr Leu Val Asn Ile Ser Lys Glu Asp
130                 135                 140

Asp Pro Thr Asp Phe Lys Ile Tyr Asn Val Thr Tyr Met Asp Pro Thr
145                 150                 155                 160

Leu Arg Val Thr Ala Ser Thr Leu Lys Ser Arg Ala Thr Tyr Ser Ala
                165                 170                 175

Arg Val Lys Ala Arg Ala Gln Asn Tyr Asn Ser Thr Trp Ser Glu Trp
                180                 185                 190

Ser Pro Ser Thr Thr Trp His Asn Tyr Tyr Glu Gln Pro Gly Gly Gly
            195                 200                 205

Ser Gly Gly Gly Gly Ser Gly Gly Gly Ser Gly Gly Gly Gly Ser
210                 215                 220

Gly Gly Gly Gly Ser Gly Gly Pro Ser Val Phe Ile Phe Pro Pro Asn
225                 230                 235                 240

Pro Lys Asp Ala Leu Met Ile Ser Arg Thr Pro Val Val Thr Cys Val
                245                 250                 255

Val Val Asn Leu Ser Asp Gln Tyr Pro Asp Val Gln Phe Ser Trp Tyr
```

```
            260                 265                 270
Val Asp Asn Thr Glu Val His Ser Ala Ile Thr Lys Gln Arg Glu Ala
            275                 280                 285

Gln Phe Asn Ser Thr Tyr Arg Val Val Ser Val Leu Pro Ile Gln His
        290                 295                 300

Gln Asp Trp Leu Ser Gly Lys Glu Phe Lys Cys Ser Val Thr Asn Val
305                 310                 315                 320

Gly Val Pro Gln Pro Ile Ser Arg Ala Ile Ser Arg Gly Lys Gly Pro
                325                 330                 335

Ser Arg Val Pro Gln Val Tyr Val Leu Pro Pro His Pro Asp Glu Leu
            340                 345                 350

Ala Lys Ser Lys Val Ser Val Ser Cys Ala Val Lys Asp Phe Tyr Pro
        355                 360                 365

Pro Asp Ile Ser Val Glu Trp Gln Ser Asn Arg Trp Pro Glu Leu Glu
    370                 375                 380

Gly Lys Tyr Ser Thr Thr Pro Ala Gln Leu Asp Gly Asp Gly Ser Tyr
385                 390                 395                 400

Phe Leu Thr Ser Lys Leu Ser Leu Glu Thr Ser Arg Trp Gln Gln Val
                405                 410                 415

Glu Ser Phe Thr Cys Ala Val Met His Glu Ala Leu His Asn His Phe
            420                 425                 430

Thr Lys Thr Asp Ile Ser Glu Ser Leu Gly Lys
        435                 440

<210> SEQ ID NO 113
<211> LENGTH: 553
<212> TYPE: PRT
<213> ORGANISM: Artificial Sequence
<220> FEATURE:
<223> OTHER INFORMATION: Synthetic: Equine IL13R ECD equine IgG-2 Fc
      knob

<400> SEQUENCE: 113

Thr Glu Ser Gln Pro Pro Val Thr Asn Leu Ser Val Ser Val Glu Asn
1               5                   10                  15

Leu Cys Thr Val Ile Trp Thr Trp Asn Pro Glu Gly Val Ser Pro
            20                  25                  30

Asn Cys Ser Leu Trp Tyr Phe Ser His Phe Gly Asn Lys Gln Asp Lys
        35                  40                  45

Lys Ile Ala Pro Glu Thr His Arg Ser Lys Glu Val Pro Leu Asn Glu
    50                  55                  60

Arg Ile Cys Leu Gln Val Gly Ser Gln Cys Ser Thr Asn Glu Ser Asp
65                  70                  75                  80

Asn Pro Ser Ile Leu Val Glu Lys Cys Ile Ser Pro Pro Glu Gly Asp
                85                  90                  95

Pro Glu Ser Ala Val Thr Glu Leu Gln Cys Val Trp His Asn Leu Ser
            100                 105                 110

Tyr Met Lys Cys Thr Trp Leu Pro Gly Lys Asn Ala Ser Pro Asp Thr
        115                 120                 125

Asn Tyr Thr Leu Tyr Tyr Trp His Ser Ser Leu Gly Lys Ile Leu Gln
    130                 135                 140

Cys Glu Asp Ile Tyr Arg Glu Gly Gln His Ile Gly Cys Ser Phe Ala
145                 150                 155                 160

Leu Thr Glu Val Lys Asp Ser Ile Phe Glu Gln His Ser Val Gln Ile
                165                 170                 175
```

-continued

```
Met Val Lys Asp Asn Ala Gly Lys Ile Arg Pro Phe Phe Asn Ile Val
            180                 185                 190
Pro Leu Thr Ser His Val Lys Pro Asp Pro His Ile Lys Lys Leu
        195                 200                 205
Phe Phe Gln Asn Gly Asp Leu Tyr Val Gln Trp Lys Asn Pro Gln Asn
        210                 215                 220
Phe Tyr Ser Arg Cys Leu Ser Tyr Gln Val Glu Val Asn Asn Ser Gln
225                 230                 235                 240
Thr Glu Thr Arg Asp Ile Phe Ser Val Glu Glu Ala Lys Cys Gln Asn
                245                 250                 255
Pro Glu Phe Glu Gly Asp Leu Glu Gly Thr Ile Cys Phe Met Val Pro
                260                 265                 270
Gly Val Leu Pro Asp Thr Val Asn Thr Val Arg Ile Arg Val Lys Thr
            275                 280                 285
Asn Lys Leu Cys Tyr Glu Asp Asp Lys Leu Trp Ser Asn Trp Ser Gln
        290                 295                 300
Ala Met Ser Ile Gly Lys Lys Ala Asp Pro Thr Gly Gly Gly Ser Gly
305                 310                 315                 320
Gly Gly Gly Ser Gly Gly Gly Ser Gly Gly Gly Ser Gly Gly
                325                 330                 335
Gly Gly Ser Gly Gly Pro Ser Val Phe Ile Phe Pro Pro Asn Pro Lys
            340                 345                 350
Asp Ala Leu Met Ile Ser Arg Thr Pro Val Val Thr Cys Val Val Val
                355                 360                 365
Asn Leu Ser Asp Gln Tyr Pro Asp Val Gln Phe Ser Trp Tyr Val Asp
        370                 375                 380
Asn Thr Glu Val His Ser Ala Ile Thr Lys Gln Arg Glu Ala Gln Phe
385                 390                 395                 400
Asn Ser Thr Tyr Arg Val Val Ser Val Leu Pro Ile Gln His Gln Asp
                405                 410                 415
Trp Leu Ser Gly Lys Glu Phe Lys Cys Ser Val Thr Asn Val Gly Val
                420                 425                 430
Pro Gln Pro Ile Ser Arg Ala Ile Ser Arg Gly Lys Gly Pro Ser Arg
            435                 440                 445
Val Pro Gln Val Tyr Val Leu Pro Pro His Pro Asp Glu Leu Ala Lys
        450                 455                 460
Ser Lys Val Ser Val Trp Cys Leu Val Lys Asp Phe Tyr Pro Pro Asp
465                 470                 475                 480
Ile Ser Val Glu Trp Gln Ser Asn Arg Trp Pro Glu Leu Glu Gly Lys
                485                 490                 495
Tyr Ser Thr Thr Pro Ala Gln Leu Asp Gly Asp Gly Ser Tyr Phe Leu
                500                 505                 510
Tyr Ser Lys Leu Ser Leu Glu Thr Ser Arg Trp Gln Gln Val Glu Ser
            515                 520                 525
Phe Thr Cys Ala Val Met His Glu Ala Leu His Asn His Phe Thr Lys
        530                 535                 540
Thr Asp Ile Ser Glu Ser Leu Gly Lys
545                 550
```